United States Patent
Takakura et al.

(10) Patent No.: US 9,238,639 B2
(45) Date of Patent: Jan. 19, 2016

(54) AROMATIC RING COMPOUND

(71) Applicant: TAKEDA PHARMACEUTICAL COMPANY LIMITED, Osaka (JP)

(72) Inventors: Nobuyuki Takakura, Kanagawa (JP); Yoshihiro Banno, Kanagawa (JP); Yoshito Terao, Kanagawa (JP); Atsuko Ochida, Kanagawa (JP); Sachie Morimoto, Kanagawa (JP); Tsuneo Yasuma, Osaka (JP); Minoru Ikoma, Kanagawa (JP); Kei Masuda, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/380,215

(22) PCT Filed: Feb. 22, 2013

(86) PCT No.: PCT/JP2013/055605
§ 371 (c)(1),
(2) Date: Aug. 21, 2014

(87) PCT Pub. No.: WO2013/125732
PCT Pub. Date: Aug. 29, 2013

(65) Prior Publication Data
US 2015/0018547 A1    Jan. 15, 2015

Related U.S. Application Data

(60) Provisional application No. 61/602,888, filed on Feb. 24, 2012.

(51) Int. Cl.
| | | |
|---|---|---|
| C07D 333/60 | (2006.01) |
| C07D 417/12 | (2006.01) |
| C07D 495/04 | (2006.01) |
| C07D 333/54 | (2006.01) |
| C07D 405/04 | (2006.01) |
| C07D 405/12 | (2006.01) |
| C07D 409/06 | (2006.01) |
| C07D 409/12 | (2006.01) |
| C07D 307/79 | (2006.01) |
| C07D 307/80 | (2006.01) |
| C07D 307/81 | (2006.01) |
| C07D 307/84 | (2006.01) |
| C07D 333/64 | (2006.01) |
| C07D 333/70 | (2006.01) |

(52) U.S. Cl.
CPC .......... *C07D 333/60* (2013.01); *C07D 307/79* (2013.01); *C07D 307/80* (2013.01); *C07D 307/81* (2013.01); *C07D 307/84* (2013.01); *C07D 333/54* (2013.01); *C07D 333/64* (2013.01); *C07D 333/70* (2013.01); *C07D 405/04* (2013.01); *C07D 405/12* (2013.01); *C07D 409/06* (2013.01); *C07D 409/12* (2013.01); *C07D 417/12* (2013.01); *C07D 495/04* (2013.01)

(58) Field of Classification Search
CPC ....................................................... C07D 333/60
USPC .......................................................... 544/146
See application file for complete search history.

(56) References Cited

U.S. PATENT DOCUMENTS

| | | |
|---|---|---|
| 2004/0209936 A1 | 10/2004 | Bratton et al. |
| 2006/0014785 A1 | 1/2006 | Zhu et al. |
| 2006/0258722 A1 | 11/2006 | Yasuma et al. |
| 2009/0012093 A1 | 1/2009 | Fukatsu et al. |
| 2010/0004312 A1 | 1/2010 | Yasuma et al. |
| 2010/0197761 A1 | 8/2010 | Yasuma et al. |
| 2012/0172351 A1 | 7/2012 | Negoro et al. |

FOREIGN PATENT DOCUMENTS

| | | |
|---|---|---|
| EP | 1 630 152 | 3/2006 |
| WO | 95/02402 | 1/1995 |
| WO | 00/69844 | 11/2000 |
| WO | 2008/001931 | 1/2008 |
| WO | 2009/137500 | 11/2009 |
| WO | 2010/143733 | 12/2010 |

OTHER PUBLICATIONS

King, Med. Chem. Principle and Practice (1994), pp. 206-208.*
International Search Report issued Apr. 24, 2013 in International (PCT) Application No. PCT/JP2013/055605.
Filzen et al., "Synthesis and SAR of selective benzothiophene, benzofuran, and indole-based peroxisome proliferator-activated receptor δ agonists", Bioorganic & Medicinal Chemistry Letters, vol. 17, No. 13, Apr. 2007, pp. 3630-3635.

\* cited by examiner

*Primary Examiner* — Taofiq A Solola
(74) *Attorney, Agent, or Firm* — Wenderoth, Lind & Ponack, L.L.P.

(57) ABSTRACT

The present invention provides a compound having a GOAT inhibitory action, which is useful for the prophylaxis or treatment of obesity and the like, and has superior efficacy. The present invention is a compound represented by the formula (I): wherein each symbol is as defined in the specification, or a salt thereof.

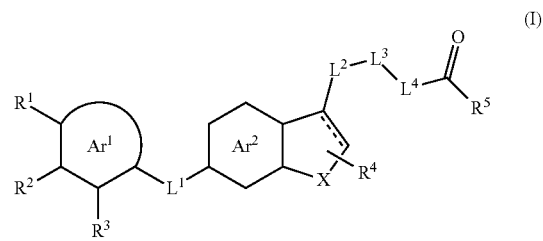

8 Claims, No Drawings

AROMATIC RING COMPOUND

TECHNICAL FIELD

The present invention relates to a compound having a ghrelin O-acyltransferase (in the present specification, sometimes to be abbreviated as GOAT) inhibitory activity, which is useful for the prophylaxis or treatment of obesity, diabetes, hyperlipidemia, metabolic syndrome, non-alcoholic fatty liver, steatohepatitis, sarcopenia, appetite control, alcohol/ narcotic dependence, Alzheimer's disease, Parkinson's disease, cerebrovascular dementia, cerebral apoplexy, cerebral infarction, cardiac disease, some kind of tumors (e.g., prostate cancer, breast cancer etc.) and the like.

BACKGROUND OF THE INVENTION

Ghrelin is a physiologically active substance consisting of 28 amino acids, and is mainly produced in the stomach. Ghrelin includes active type (acyl form) and inactive type (des-acyl form), and the active type is produced by the addition, by GOAT, of fatty acid to the serine residue at the 3-position of ghrelin [non-patent document 1]. The fatty acid to be added to ghrelin by GOAT includes octanoic acid, decanoylic acid and the like. The target of the active type ghrelin is mainly a growth hormone secretagogue receptor (GHSR) in the stomach, and the activation of signal causes promoted food ingestion and low energy consumption. Therefore, GOAT plays a key role in the control of food ingestion and energy metabolism.

The decrease of active type ghrelin due to the inhibition of GOAT leads to a promoted energy consumption [non-patent document 2] and promoted utilization of lipid as an energy source thereof. Promotion of such systemically lipid utilization brings about lower fat content of adipose tissues, and further, decreased weight of adipose tissues [non-patent document 3]. That is, since a GOAT inhibitor acts on an environment, which permits increase of obesity formation factors such as excess fat ingestion, in the direction toward suppression thereof, it can be used as an antiobesity drug for the treatment of obesity. Furthermore, since ghrelin increases along with a weight loss therapy of obese patients, a GOAT inhibitor provides a further antiobesity effect as a medicament that decreases ghrelin [non-patent document 4]. In addition, promoted utilization of lipid is also expected to improve lipid abnormality. Moreover, since it may also have a sugar metabolism improving effect [non-patent document 5], a GOAT inhibitor is expected to be effective for the prophylaxis or suppression of metabolic disorders including metabolic syndrome.

GOAT inhibition increases des-acyl ghrelin in the inactive type. This has also been confirmed in genetically-altered animals wherein GOAT has been knocked out [non-patent document 6]. Since des-acyl ghrelin suppresses activation of microglia by β-amyloid, it is expected to be a therapeutic drug for Alzheimer's disease [non-patent document 7]. Furthermore, since des-acyl ghrelin suppresses nerve cell death due to low oxygen and low glucose, it is expected to be a therapeutic drug for ischemic cerebral dysfunctions such as cerebrovascular dementia, cerebral apoplexy, cerebral infarction and the like and neurodegenerative diseases such as Parkinson's disease and the like [non-patent document 8]. In addition, a heart protecting action including suppression of ischemic cardiac diseases and cardiac hypertrophy is also expected [non-patent document 9]. Therefore, the compound of the present invention has a potential of a therapeutic drug for a metabolic disease with a heart protecting action.

Ghrelin is also involved in the preference control mechanism, and activates consumption of rewarding substances (alcohol, sweetener, narcotic etc.) [non-patent document 10]. Therefore, decrease of ghrelin by inhibition of GOAT is an effective treatment method of alcohol dependence [non-patent document 11], stimulant dependence or narcotic dependence [non-patent document 12].

It has been reported that ghrelin and a receptor thereof are expressed in proliferative tumors such as prostate cancer and breast cancer [non-patent document 13]. An antitumor effect may be exhibited by controlling ghrelin in charge of cell proliferation signals.

Accordingly, a compound having a GOAT inhibitory activity is extremely useful for the prophylaxis or treatment of metabolic diseases (e.g., obesity, metabolic syndrome, diabetes etc.); the treatment of cardiovascular diseases (e.g., hypertension [non-patent document 14], cardiac failure etc.); and the treatment of neurodegenerative diseases (e.g., Alzheimer's disease, Parkinson's disease etc.), ischemic cerebral dysfunctions (e.g., cerebrovascular dementia, cerebral apoplexy, cerebral infarction etc.), alcohol/stimulant dependence, narcotic dependence, proliferative tumors including' prostate cancer and breast cancer.

WO 2008/001931 (patent document 1) has reported, as a GPR40 agonist, the following compound

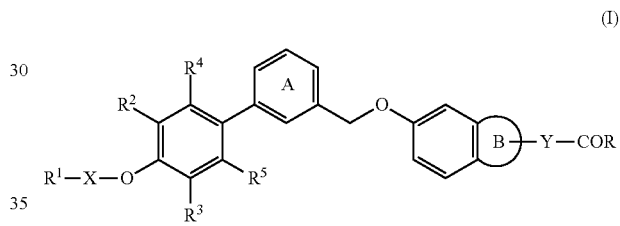

$R^1$ is $R^6$—$SO_2$— (wherein $R^6$ is a substituent) or an optionally substituted 1,1-dioxidotetrahydrothiopyranyl group;
X is a bond or a divalent hydrocarbon group;
$R^2$ and $R^3$ are the same or different and each is a hydrogen atom, a halogen atom, an optionally substituted hydrocarbon group or an optionally substituted hydroxy group;
$R^4$ and $R^5$ are the same or different and each is a $C_{1-6}$ alkyl group optionally substituted by hydroxy group(s);
ring A is a benzene ring optionally further having substituent(s) selected from a halogen atom, an optionally substituted hydrocarbon group, an optionally substituted hydroxy group and an optionally substituted amino group;
ring B is a 5- to 7-membered ring;
Y is a bond or $CH_2$; and
R is an optionally substituted hydroxy group.

WO 2010/143733 (patent document 2) has reported, as a GPR40 agonist, the following compound

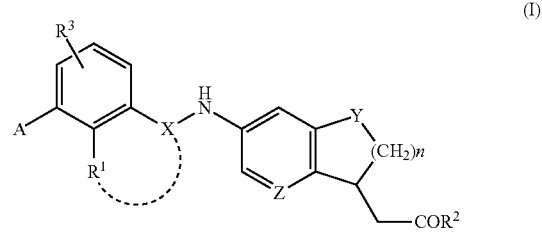

wherein
$R^1$ is a halogen atom, hydroxy, optionally substituted $C_{1-6}$ alkyl or optionally substituted $C_{1-6}$ alkoxy,
$R^2$ is optionally substituted hydroxy,
$R^3$ is a hydrogen atom, a halogen atom or optionally substituted $C_{1-6}$ alkyl,
X is $CH_2$ wherein $R^1$ and X in combination optionally form a optionally substituted ring,
Y is $CH_2$, NH or O,
Z is CH or N,
n is an integer selected from 1 to 3, and
A is a halogen atom, optionally substituted amino, or a 4- to 13-membered cyclic group optionally substituted by 1 to 5 substituents selected from
(1) a halogen atom,
(2) optionally substituted amino,
(3) optionally substituted $C_{1-6}$ alkylthio,
(4) optionally substituted $C_{1-6}$ alkyl,
(5) optionally substituted $C_{3-10}$ cycloalkyl,
(6) optionally substituted $C_{1-6}$ alkoxy,
(7) optionally substituted $C_{6-14}$ aryl,
(8) optionally substituted 4- to 7-membered heterocyclic group, and
(9) optionally substituted 4- to 7-membered heterocyclyloxy.

WO 2009/137500 (patent document 3) has reported, as a hepatitis C polymerase inhibitor, the following compound

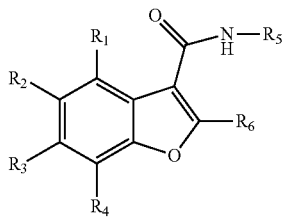

wherein
$R_1$ is hydrogen, halogen, cyano or alkyl;
$R^2$ is halogen, optionally substituted alkyl, optionally substituted alkoxy or the like;
$R_3$ is $-NR_{10}SO_2R_{11}$, $-NR_wCOOR_z$, $-NR_xR_y$, (particular substituent)-ring, or the like;
$R_4$ is hydrogen, halogen, cyano, alkyl or the like;
$R_5$ is alkyl, cycloalkyl or the like;
$R_6$ is optionally substituted aryl;
$R_{10}$ is H, $-SO_2$-alkyl or the like;
$R_{11}$ is optionally substituted alkyl or the like;
$R_w$ is hydrogen, alkyl or the like;
$R_z$ is alkyl or the like; and
$R_x$ and $R_y$ are each independently optionally substituted alkyl or the like.

WO 00/69844 (patent document 4) has reported, as a PDEIV inhibitor, the following compound

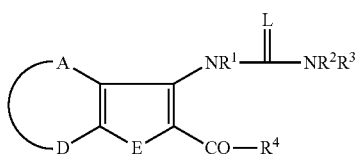

wherein
A and D in combination form phenyl, pyridyl, pyrimidinyl or the like, wherein the ring is optionally substituted by $-OR^5$;

$R^5$ is $C_{1-15}$ alkyl optionally substituted by OH, $C_{1-6}$ alkoxy, phenyl or the like;
E is O or S;
$R^1$ is hydrogen, $C_{1-4}$ alkyl or the like;
$R^2$ and $R^3$ are each independently hydrogen, $C_{3-6}$ cycloalkyl or the like; and
$R^4$ is optionally substituted $C_{6-10}$ aryl, or optionally substituted 5- to 7-membered heterocycle which is optionally fused with benzene.

WO 95/02402 (patent document 5) has reported as a 5-lipoxygenase inhibitor, the following compound

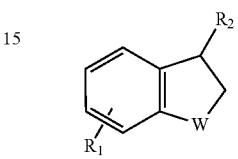

wherein

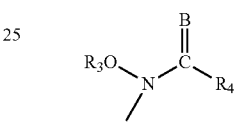

$R_3$ is hydrogen, cation, aroyl or $C_{1-12}$ alkanoyl;
B is O or S;
$R_4$ is $NR_5R_6$ or the like;
$R_5$ is hydrogen or $C_{1-6}$ alkyl;
$R_6$ is hydrogen, $C_{1-6}$ alkyl or the like;
W is $-O-(CH_2)_s-$;
S is 0-1;
$R_1$ is $(CH_2)_m-Ar-(X)_v$, $O(CH_2)_m-Ar-(X)_v$ or $S(CH_2)_m-A_r-(X)_v$;
m is 0-3;
v is 1-3;
Ar is, phenyl or naphthyl; and
X is F.

DOCUMENT LIST

Patent Documents

Patent Document 1: WO 2008/001931
Patent Document 2: WO 2010/143733
Patent Document 3: WO 2009/137500
Patent Document 4: WO 00/69844
Patent Document 5: WO 95/02402

Non-Patent Documents

Non-Patent Document 1: Cell 2008; 132: 387-396
Non-Patent Document 2: Nature Medicine 2009; 15: 741-745
Non-Patent Document 3: Proc Natl Acad Sci USA 2004; 101: 8227-8232
Non-Patent Document 4: The New England Journal of Medicine 2011; 365: 1597-1604
Non-Patent Document 5: Science 2010; 330: 1689-1692
Non-Patent Document 6: Proc Natl Acad Sci USA 2010; 107: 7467-7472
Non-Patent Document 7: J Neurosci Res 2009; 87: 2718-2727

Non-Patent Document 8: J Endocrinol 2008; 198: 511-521
Non-Patent Document 9: Endocrinology 2010; 151: 3286-3298
Non-Patent Document 10: ProS One 2011; 6: e18170
Non-Patent Document 11: Addict Biol 2011; March 11
Non-Patent Document 12: Psychopharmacology 2010; 211: 415-422
Non-Patent Document 13: Vitamins and Hormones 2008; 77: 301-324
Non-Patent Document 14: J Hypertens. 2010; 28: 560-567

SUMMARY OF THE INVENTION

Problems to be Solved by the Invention

There is a demand for the development of a compound having a GOAT inhibitory activity, which is useful for the prophylaxis or treatment of obesity, diabetes, hyperlipidemia, metabolic syndrome, non-alcoholic fatty liver, steatohepatitis, sarcopenia, appetite control, alcohol/narcotic dependence, Alzheimer's disease, Parkinson's disease, cerebrovascular dementia, cerebral apoplexy, cerebral infarction, cardiac disease, some kind of tumors (e.g., prostate cancer, breast cancer etc.) and the like, and has superior efficacy.

Means of Solving the Problems

The present inventors have found for the first time that a compound represented by the formula (I):

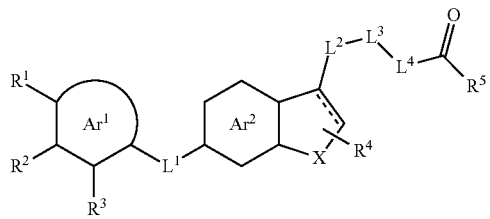

wherein
ring $Ar^1$ is a 5- or 6-membered aromatic ring optionally further substituted by 1 or 2 substituents selected from a halogen atom, an optionally substituted $C_{1-6}$ alkyl group and an optionally substituted $C_{1-6}$ alkoxy group;
ring $Ar^2$ is an optionally further substituted 6-membered aromatic ring;
------ is a single bond or a double bond;
$L^1$ is a group represented by the formula: (wherein $L^{1A}$ optionally substituted $CH_2$; and $L^{1B}$ is O, S, SO, $SO_2$ or optionally substituted $CH_2$), optionally substituted —CH=CH—, or —C≡C—;
$L^2$ and $L^4$ are each independently a bond or an optionally substituted $C_{1-3}$ alkylene group;
$L^3$ is a bond, O, S, SO, $SO_2$ or $NR^6$;
X is O, S, SO or $SO_2$;
$R^1$ and $R^3$ are each independently a halogen atom, an optionally substituted $C_{1-6}$ alkyl group, an optionally substituted $C_{1-10}$ alkoxy group, an optionally substituted amino group, an optionally substituted $C_{3-10}$ cycloalkyl group, or an optionally substituted nitrogen-containing heterocyclic group which is bonded to ring $Ar^1$ via a nitrogen atom thereof;
$R^2$ is a hydrogen atom, a halogen atom, an optionally substituted $C_{1-6}$ alkyl group or an optionally substituted $C_{1-6}$ alkoxy group, or absent;
$R^4$ is a hydrogen atom, a halogen atom, a cyano group, an optionally substituted $C_{1-6}$ alkyl group, an optionally substituted hydroxy group or —CO—$R^7$;
$R^5$ is —$OR^{8A}$ or —$NR^{8B}R^{8C}$;
$R^6$ is a hydrogen atom or an optionally substituted $C_{1-6}$ alkyl group;
$R^7$ is an optionally substituted hydroxy group, an optionally substituted amino group, or an optionally substituted nitrogen-containing heterocyclic group which is bonded to —CO— via a nitrogen atom thereof;
$R^{8A}$ is a hydrogen atom or an optionally substituted $C_{1-6}$ alkyl group;
$R^{8B}$ is a hydrogen atom, an optionally substituted $C_{1-6}$ alkyl group or —$SO_2$—$R^9$;
$R^{8C}$ is a hydrogen atom or an optionally substituted $C_{1-6}$ alkyl group, or
$R^{8B}$ and $R^{8C}$ in combination optionally form, together with the adjacent nitrogen atom, an optionally substituted ring; and
$R^9$ is an optionally substituted $C_{1-6}$ alkyl group,
or a salt thereof [hereinafter, sometimes to be referred to as compound (I)] has a superior GOAT inhibitory activity, which is useful for the prophylaxis or treatment of obesity, diabetes, hyperlipidemia, metabolic syndrome, non-alcoholic fatty liver, steatohepatitis, sarcopenia, appetite control, alcohol/narcotic dependence, Alzheimer's disease, Parkinson's disease, cerebrovascular dementia, cerebral apoplexy, cerebral infarction, cardiac disease, some kind of tumors (e.g., prostate cancer, breast cancer etc.) and the like, and has superior efficacy. Based on this finding, the present inventors have conducted intensive studies and completed the present invention.

Accordingly, the present invention relates to
[1] compound (I);
[2] compound (I) wherein $L^1$ is a group represented by the formula: (wherein each symbol is as defined above), and $R^1$ and $R^3$ are each independently a halogen atom, an optionally substituted $C_{1-6}$ alkyl group, an optionally substituted $C_{1-10}$ alkoxy group or an optionally substituted amino group;
[3] a medicament comprising compound (I);
[4] the medicament of the above-mentioned [3], which is a ghrelin O-acyltransferase inhibitor;
[5] the medicament of the above-mentioned [3], which is a body weight-lowering agent;
[6] the medicament of the above-mentioned [3], which is an agent for the prophylaxis or treatment of obesity; and the like.

Effect of the Invention

Compound (I) has a GOAT inhibitory activity, which is useful for the prophylaxis or treatment of obesity, diabetes, hyperlipidemia, metabolic syndrome, non-alcoholic fatty liver, steatohepatitis, sarcopenia, appetite control, alcohol/narcotic dependence, Alzheimer's disease, Parkinson's disease, cerebrovascular dementia, cerebral apoplexy, cerebral infarction, cardiac disease, some kind of tumors (e.g., prostate cancer, breast cancer etc.) and the like, and has superior efficacy.

DETAILED DESCRIPTION OF THE INVENTION

The definition of each symbol in the formula (I) is described in detail in the following.
The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

Examples of the "optionally substituted $C_{6-14}$ arylsulfonyloxy group" in the present specification include a benzenesulfonyloxy group, a p-toluenesulfonyloxy group and the like.

Examples of the "optionally substituted $C_{1-6}$ alkylsulfonyloxy group" in the present specification include a methanesulfonyloxy group, trifluoromethanesulfonyloxy group and the like.

$R^1$ and $R^3$ are each independently a halogen atom, an optionally substituted $C_{1-6}$ alkyl group, an optionally substituted $C_{1-10}$ alkoxy group, an optionally substituted amino group, an optionally substituted $C_{3-10}$ cycloalkyl group, or an optionally substituted nitrogen-containing heterocyclic group which is bonded to ring $Ar^1$ via a nitrogen atom thereof.

$R^2$ is a hydrogen atom, a halogen atom, an optionally substituted $C_{1-6}$ alkyl group or an optionally substituted $C_{1-6}$ alkoxy group, or absent.

$R^4$ is a hydrogen atom, a halogen atom, a cyano group, an optionally substituted $C_{1-6}$ alkyl group, an optionally substituted hydroxy group or —CO—$R^7$.

$R^7$ is an optionally substituted hydroxy group, an optionally substituted amino group, or an optionally substituted nitrogen-containing heterocyclic group which is bonded to —CO— via a nitrogen atom thereof.

The "$C_{1-6}$ alkyl group" of the "optionally substituted $C_{1-6}$ alkyl group" for $R^1$, $R^2$, $R^3$ or $R^4$ optionally has 1 to 7 (preferably 1 to 3) substituents at substitutable positions. Examples of the substituent include (1) a $C_{3-10}$ cycloalkyl group (e.g., cyclopropyl, cyclohexyl);
(2) a 06-14 aryl group (e.g., phenyl, naphthyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(4) a non-aromatic heterocyclic group (e.g., tetrahydrofuryl, morpholinyl, thiomorpholinyl, piperidyl, pyrrolidinyl, piperazinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) an oxo group;
(5) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 halogen atoms,
   (c) a $C_{1-6}$ alkoxy-carbonyl group optionally substituted by 1 to 3 halogen atoms,
   (d) a $C_{1-6}$ alkylsulfonyl group (e.g., methylsulfonyl) optionally substituted by 1 to 3 halogen atoms,
   (e) a carbamoyl group optionally mono- or di-substituted by $C_{1-6}$ alkyl group(s) optionally substituted by 1 to 3 halogen atoms, and
   (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
   (a) a halogen atom,
   (b) a carboxy group,
   (c) a $C_{1-6}$ alkoxy group,
   (d) a $C_{1-6}$ alkoxy-carbonyl group optionally substituted by 1 to 3 $C_{6-14}$ aryl groups (e.g., phenyl),
   (e) an amino group optionally mono- or di-substituted by substituent(s) selected from a $C_{1-6}$ alkyl group and a $C_{1-6}$ alkoxy-carbonyl group,
   (f) a heterocyclic group (e.g., tetrahydrofuryl), and
   (g) a $C_{3-10}$ cycloalkyl group (e.g., cyclopropyl, cyclohexyl);
(15) a $C_{2-6}$ alkenyloxy group (e.g., ethenyloxy) optionally substituted by 1 to 3 halogen atoms;

(16) a $C_{7-13}$ aralkyloxy group (e.g., benzyloxy);

(17) a $C_{6-14}$ aryloxy group (e.g., phenyloxy, naphthyloxy);

(18) a $C_{1-6}$ alkyl-carbonyloxy group (e.g., acetyloxy, tert-butylcarbonyloxy);

(19) a $C_{6-14}$ aryl-carbonyl group (e.g., benzoyl) optionally substituted by 1 to 3 substituents selected from
(a) a halogen atom, and
(b) a $C_{1-6}$ alkyl group optionally substituted by 1 to 3 halogen atoms;

(20) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;

(21) a sulfanyl group;

(22) a $C_{1-6}$ alkylsulfanyl group (e.g., methylsulfanyl, ethylsulfanyl) optionally substituted by 1 to 3 substituents selected from
(a) a halogen atom, and
(b) a $C_{1-6}$ alkoxy-carbonyl group;

(23) a $C_{7-13}$ aralkylsulfanyl group (e.g., benzylsulfanyl);

(24) a $C_{6-14}$ arylsulfanyl group (e.g., phenylsulfanyl, naphthylsulfanyl);

(25) a cyano group;

(26) a nitro group;

(27) a halogen atom;

(28) a $C_{1-3}$ alkylenedioxy group;

(29) a $C_{1-3}$ alkyleneoxy group (e.g., methyleneoxy, ethyleneoxy);

(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;

(31) a $C_{3-10}$ cycloalkoxy group (e.g., cyclopropoxy, cyclopentyloxy) optionally substituted by 1 to 3 substituents selected from
(a) a halogen atom (e.g., a fluorine atom), and
(b) a $C_{1-6}$ alkoxy group (e.g., methoxy) and the like. When the number of the substituents is not less than 2, the respective substituents may be the same or different.

Examples of the "$C_{1-10}$ alkoxy group" of the "optionally substituted $C_{1-10}$ alkoxy group" for $R^1$ or $R^3$ include methoxy, ethoxy, propoxy, isopropoxy, butoxy, isobutoxy, sec-butoxy, tert-butoxy, pentyloxy, isopentyloxy, neopentyloxy, 1-ethylpropoxy, hexyloxy, isohexyloxy, 1,1-dimethylbutoxy, 2,2-dimethylbutoxy, 3,3-dimethylbutoxy, 2-ethylbutoxy, heptyloxy, octyloxy, nonyloxy, decyloxy and the like.

The "$C_{1-10}$ alkoxy group" of the "optionally substituted $C_{1-10}$ alkoxy group" for $R^1$ or $R^3$ optionally has 1 to 7 (preferably 1 to 3) substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has.

The "$C_{1-6}$ alkoxy group" of the "optionally substituted $C_{1-6}$ alkoxy group" for $R^2$ optionally has 1 to 7 (preferably 1 to 3) substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has.

The "$C_{3-10}$ cycloalkyl group" of the "optionally substituted $C_{3-10}$ cycloalkyl group" for $R^1$ or $R^3$ optionally has 1 to 7 (preferably 1 to 3) substituents at substitutable positions. Examples of such substituent include (1) the groups exemplified as the substituents that the "$C_{1-6}$ alkyl group" of the "optionally substituted $C_{1-6}$ alkyl group" for $R^1$, $R^2$, $R^3$ or $R^4$ optionally has;

(2) a $C_{1-6}$ alkyl group optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s);

(3) a $C_{2-6}$ alkenyl group (e.g., ethenyl, 1-propenyl) optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s);

(4) a $C_{7-13}$ aralkyl group (e.g., benzyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
and the like. When the number of the substituents is not less than 2, the respective substituents may be the same or different.

Examples of the "optionally substituted hydroxy group" for $R^4$ or $R^7$ include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the $C_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Among them, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Among them, a $C_{2-6}$ alkenyl group is preferable.

Examples of the $C_{3-10}$ cycloalkyl group include cyclopropyl, cyclobutyl, cyclopentyl, cyclohexyl, cycloheptyl, cyclooctyl and the like. Among them, a $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Among them, a $C_{3-6}$ cycloalkenyl group is preferable.

The above-mentioned $C_{3-40}$ cycloalkyl group and $C_{3-10}$ cycloalkenyl group are each optionally fused with a benzene ring to form a fused ring group. Examples of the fused ring group include indanyl, dihydronaphthyl, tetrahydronaphthyl, fluorenyl and the like.

In addition, the above-mentioned $C_{3-10}$ cycloalkyl group and $C_{3-10}$ cycloalkenyl group may be each a $C_{7-10}$ bridged hydrocarbon group. Examples of the $C_{7-10}$ bridged hydrocarbon group include bicyclo[2.2.1]heptyl(norbornyl), bicyclo

[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group and $C_{3-10}$ cycloalkenyl group each optionally forms a spiro ring group together with a $C_{3-10}$ cycloalkane, a $C_{3-10}$ cycloalkene or a $C_{4-10}$ cycloalkadiene. Examples of the $C_{3-10}$ cycloalkane and $C_{3-10}$ cycloalkene include rings corresponding to the above-mentioned $C_{3-10}$ cycloalkyl group and $C_{3-10}$ cycloalkenyl group. Examples of the $C_{4-10}$ cycloalkadiene include 2,4-cyclopentadiene, 2,4-cyclohexadiene, 2,5-cyclohexadiene and the like. Among them, a $C_{4-6}$ cycloalkadiene is preferable. Examples of the Spiro ring group include spiro[4.5]decan-8-yl and the like.

Examples of the $C_{6-14}$ aryl group include phenyl, naphthyl, anthryl, phenanthryl, acenaphthylenyl, biphenylyl and the like. Among them, a $C_{6-12}$ aryl group is preferable.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

Examples of the "heterocyclic group" include an aromatic heterocyclic group and a non-aromatic heterocyclic group.

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridyl (e.g., pyrido[2,3-b]pyridin-3-yl), thienopyridyl (e.g., thieno[2,3-b]pyridin-3-yl) and the like;
and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused non-aromatic aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially saturated, and the like.

Preferable examples of the non-aromatic heterocyclic group include monocyclic non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;

fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like; and the like.

The above-mentioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group each optionally has 1 to 3 substituent at substitutable positions. When the number of the substituents is not less than 2, the respective substituents may be the same or different.

Examples of the substituent for the $C_{1-10}$ alkyl group, $C_{2-10}$ alkenyl group and $C_{1-6}$ alkyl-carbonyl group include those similar to the substituents that the "$C_{1-5}$ alkyl group" of the "optionally substituted $C_{1-6}$ alkyl group" for $R^1$, $R^2$, $R^3$ or $R^4$ optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituents that the "$C_{3-10}$ cycloalkyl group" of the "optionally substituted $C_{3-10}$ cycloalkyl group" for $R^1$ or $R^3$ optionally has.

Examples of the substituent for the heterocyclic group include those similar to the substituents that the "$C_{3-10}$ cycloalkyl group" of the "optionally substituted $C_{3-10}$ cycloalkyl group" for $R^1$ or $R^3$ optionally has. When the heterocyclic group is a "non-aromatic heterocyclic group", the substituent further includes an oxo group.

Examples of the "optionally substituted amino group" for $R^1$, $R^3$ or $R^7$ include an amino group optionally mono- or di-substituted by substituent (s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each of which is optionally substituted; an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group include those exemplified as the substituents for "optionally substituted hydroxy group" for $R^4$ or $R^7$.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group each optionally have 1 to 3 substituents at substitutable positions. When the number of the substituents is not less than 2, the respective substituents may be the same or different.

Examples of the substituent for the $C_{1-10}$ alkyl group and $C_{2-10}$ alkenyl group include those similar to the substituents that the "$C_{1-6}$ alkyl group" of the "optionally substituted $C_{1-6}$ alkyl group" for $R^1$, $R^2$, $R^3$ or $R^4$ optionally has.

Examples of the substituent for the $C_{3-10}$ cycloalkyl group, $C_{3-10}$ cycloalkenyl group, $C_{8-14}$ aryl group, $C_{7-13}$ aralkyl group and $C_{8-13}$ arylalkenyl group include those similar to the substituents that the "$C_{3-10}$ cycloalkyl group" of the "optionally substituted $C_{3-10}$ cycloalkyl group" for $R^1$ or $R^3$ optionally has.

Examples of the substituent for the heterocyclic group include those similar to the substituents that the "$C_{3-10}$ cycloalkyl group" of the "optionally substituted $C_{3-10}$ cycloalkyl group" for $R^1$ or $R^3$ optionally has. When the heterocyclic group is a "non-aromatic heterocyclic group", the substituent further includes an oxo group.

Examples of the "acyl group" exemplified as the substituent for the "optionally substituted amino group" include a group represented by the formula: —$COR^A$, —CO—$OR^A$, —$SO_3R^A$, —$S(O)_2R^A$, —$SOR^A$, —CO—$NR^{A'}R^{B'}$, —CS—$NR^{A'}R^{B'}$ or —$S(O)_2NPR'R^{B'}$ wherein $R^A$ is a hydrogen atom, an optionally substituted hydrocarbon group or an optionally substituted heterocyclic group, $R^{A'}$ and $R^{B'}$ are the same or different and each is a hydrogen atom, an optionally substituted hydrocarbon group or an optionally substituted heterocyclic group, or $R^{A'}$ and $R^{B'}$ optionally form, together with the adjacent nitrogen atom, an optionally substituted nitrogen-containing heterocycle, and the like.

Examples of the "hydrocarbon group" of the "optionally substituted hydrocarbon group for $R^A$, $R^{A'}$ or $R^{B'}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the substituents for the "optionally substituted hydroxy group" for $R^4$ or $R^7$.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Among them, a $C_{2-6}$ alkynyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Among them, a $C_{4-6}$ cycloalkadienyl group is preferable.

The $C_{1-10}$ alkyl group, $C_{2-10}$ alkenyl group, $C_{2-10}$ alkynyl group, $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group each optionally have 1 to 3 substituents at substitutable positions. When the number of the substituents is not less than 2, the respective substituents may be the same or different.

Examples of the substituent for the $C_{1-10}$ alkyl group, $C_{2-10}$ alkenyl group and $C_{2-10}$ alkynyl group include those similar to the substituents that the "$C_{1-6}$ alkyl group" of the "optionally substituted $C_{1-6}$ alkyl group" for $R^1$, $R^2$, $R^3$ or $R^4$ optionally has.

Examples of the substituent for the $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group include those similar to the substituents that the "$C_{3-10}$ cycloalkyl group" of the "optionally substituted $C_{3-10}$ cycloalkyl group" for $R^1$ or $R^3$ optionally has.

Examples of the "heterocyclic group" of the "optionally substituted heterocyclic group" for $R^A$, $R^{A'}$ or $R^{B'}$ include those exemplified as the substituents for "optionally substituted hydroxy group" for $R^4$ or $R^7$.

The "heterocyclic group" of the "optionally substituted heterocyclic group" for $R^A$, $R^{A'}$ or $R^{B'}$ optionally has 1 to 3 substituents at substitutable positions. Examples of the substituent include those similar to the substituents that the "$C_{3-10}$ cycloalkyl group" of the "optionally substituted $C_{3-10}$ cycloalkyl group" for $R^1$ or $R^3$ optionally has. When the heterocyclic group is a "non-aromatic heterocyclic group", the substituent further includes an oxo group. When the number of the substituents is not less than 2, the respective substituents may be the same or different.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The "nitrogen-containing heterocycle" of the "optionally substituted nitrogen-containing heterocycle" formed by $R^{A'}$ and $R^{B'}$ together with the adjacent nitrogen atom optionally has 1 to 5 (preferably 1 or 2) substituents at substitutable positions. Examples of the substituent include those similar to the substituents that the "$C_{3-10}$ cycloalkyl group" of the "optionally substituted $C_{3-10}$ cycloalkyl group" for $R^1$ or $R^3$ optionally has. When the number of the substituents is not less than 2, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
  (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms; and the like.

Examples of the "nitrogen-containing heterocyclic group m which is bonded to ring $Ar^1$ via a nitrogen atom thereof" of the "optionally substituted nitrogen-containing heterocyclic group which is bonded to ring $Ar^1$ via a nitrogen atom thereof" for $R^1$ or $R^3$ include a 5- to 7-membered nitrogen-containing heterocyclic group which is bonded to ring $Ar^1$ via a nitrogen atom thereof, which contains, as a ring-constituting atom besides carbon atoms, at least one nitrogen atom and optionally further contains one or two hetero atoms selected from an oxygen atom, a sulfur atom and a nitrogen atom. Preferable examples thereof include aromatic nitrogen-containing heterocyclic groups such as 1-pyrrolyl, 1-imidazolyl, 1-pyrazolyl, 1,2,4-triazol-1-yl, 1,2,3-triazol-1-yl and the like; non-aromatic nitrogen-containing heterocyclic groups such as 1-aziridinyl, 1-azetidinyl, 1-pyrrolidinyl, piperidino, morpholino, thiomorpholino, 1-piperazinyl, hexamethylenimin-1-yl, oxazolidin-3-yl, thiazolidin-3-yl, imidazolidin-1-yl, 2,3-dihydrooxazol-3-yl, 2,3-dihydrothiazol-3-yl, 2,3-dihydroimidazol-1-yl, 4,5-dihydroimidazol-1-yl, 1,5-dihydroimidazol-1-yl, 2,3-dihydropyrazol-1-yl, 3,4-dihydropyrazol-1-yl, 4,5-dihydropyrazol-1-yl and the like. Among them, a 5- or 6-membered nitrogen-containing non-aromatic heterocyclic group which is bonded to ring $Ar^1$ via a nitrogen atom thereof is preferable, and 1-pyrrolidinyl is particularly preferable.

Examples of the "nitrogen-containing heterocyclic group which is bonded to —CO— via a nitrogen atom thereof" of the "optionally substituted nitrogen-containing heterocyclic group which is bonded to —CO— via a nitrogen atom thereof" for $R^7$ include a 5- to 7-membered nitrogen-containing heterocyclic group which is bonded to —CO— via a nitrogen atom thereof, which contains, as a ring-constituting atom besides carbon atoms, at least one nitrogen atom and optionally further contains one or two hetero atoms selected from an oxygen atom, a sulfur atom and a nitrogen atom. Preferable examples thereof include aromatic nitrogen-containing heterocyclic groups such as 1-pyrrolyl, 1-imidazolyl, 1-pyrazolyl, 1,2,4-triazol-1-yl, 1,2,3-triazol-1-yl and the like; non-aromatic nitrogen-containing heterocyclic groups such as 1-aziridinyl, 1-azetidinyl, 1-pyrrolidinyl, piperidino, morpholino, thiomorpholino, 1-piperazinyl, hexamethylenimin-1-yl, oxazolidin-3-yl, thiazolidin-3-yl, imidazolidin-1-yl, 2,3-dihydrooxazol-3-yl, 2,3-dihydrothiazol-3-yl, 2,3-dihydroimidazol-1-yl, 4,5-dihydroimidazol-1-yl, 1,5-dihydroimidazol-1-yl, 2,3-dihydropyrazol-1-yl, 3,4-dihydropyrazol-1-yl, 4,5-dihydropyrazol-1-yl and the like. Among them, a 5- or 6-membered nitrogen-containing non-aromatic heterocyclic group which is bonded to —CO— via a nitrogen atom thereof is preferable, and 1-pyrrolidinyl is particularly preferable.

The "nitrogen-containing heterocyclic group which is bonded to ring $Ar^1$ via a nitrogen atom thereof" of the "optionally substituted nitrogen-containing heterocyclic group which is bonded to ring $Ar^1$ via a nitrogen atom thereof" for $R^1$ or $R^3$ optionally has 1 to 5 (preferably 1 or 2) substituents at substitutable positions. Examples of the substituent include those similar to the substituents that the "$C_{3-10}$ cycloalkyl group" of the "optionally substituted $C_{3-10}$ cycloalkyl group" for $R^1$ or $R^3$ optionally has. When the number of the substituents is not less than 2, the respective substituents may be the same or different.

The "nitrogen-containing heterocyclic group which is bonded to —CO— via a nitrogen atom thereof" of the "optionally substituted nitrogen-containing heterocyclic group which is bonded to —CO— via a nitrogen atom thereof" for $R^7$ optionally has 1 to 5 (preferably 1 or 2) substituents at substitutable positions. Examples of the substituent include those similar to the substituents that the "$C_{3-10}$ cycloalkyl group" of the "optionally substituted $C_{3-10}$ cycloalkyl group" for $R^1$ or $R^3$ optionally has. When the number of the substituents is not less than 2, the respective substituents may be the same or different.

$R^1$ is preferably a halogen atom, an optionally substituted $C_{1-6}$ alkyl group, an optionally substituted $C_{1-10}$ alkoxy group or an optionally substituted amino group.

$R^1$ is more preferably a halogen atom, an optionally substituted $C_{1-6}$ alkyl group or an optionally substituted $C_{1-10}$ alkoxy group.

Specifically, $R^1$ is more preferably
(1) a halogen atom (e.g., a fluorine atom, a chlorine atom, an iodine atom),
(2) a $C_{1-6}$ alkyl group (e.g., methyl, ethyl, isopropyl) optionally substituted by 1 to 3 halogen atoms (e.g., a fluorine atom), or
(3) a $C_{1-10}$ alkoxy group (e.g., methoxy, ethoxy, propoxy, butoxy, 2,5-dimethylhexyl-3-oxy) optionally substituted by 1 to 3 substituents selected from (i) a $C_{1-6}$ alkoxy group (e.g., methoxy),
(ii) a $C_{6-14}$ aryl group (e.g., phenyl),
(iii) a $C_{3-10}$ cycloalkyl group (e.g., cyclopropyl), and
(iv) an aromatic heterocyclic group (e.g., pyridyl).

$R^2$ is preferably a hydrogen atom, or absent.

$R^3$ is preferably a halogen atom, an optionally substituted $C_{1-6}$ alkyl group, an optionally substituted $C_{1-10}$ alkoxy group (preferably a $C_{1-6}$ alkoxy group), an optionally substituted amino group, or an optionally substituted nitrogen-containing heterocyclic group which is bonded to ring $Ar^1$ via a nitrogen atom thereof.

Specifically, $R^3$ is preferably
(1) a halogen atom (e.g., a fluorine atom, a chlorine atom),
(2) a $C_{1-6}$ alkyl group (e.g., methyl, ethyl) optionally substituted by 1 to 3 halogen atoms (e.g., a fluorine atom),
(3) a $C_{1-10}$ alkoxy group (preferably a $C_{1-6}$ alkoxy group (e.g., methoxy, ethoxy)),
(4) an amino group, or
(5) a 5- or 6-membered nitrogen-containing heterocyclic group (preferably a 5- or 6-membered nitrogen-containing non-aromatic heterocyclic group (e.g., 1-pyrrolidinyl)) which is bonded to ring $Ar^1$ via a nitrogen atom thereof.

$R^3$ is more preferably a halogen atom, an optionally substituted $C_{1-6}$ alkyl group, an optionally substituted $C_{1-10}$ alkoxy group (preferably a $C_{1-6}$ alkoxy group) or an optionally substituted amino group.

Specifically, $R^3$ is more preferably
(1) a halogen atom (e.g., a fluorine atom, a chlorine atom),
(2) a $C_{1-6}$ alkyl group (e.g., methyl, ethyl) optionally substituted by 1 to 3 halogen atoms (e.g., a fluorine atom),
(3) a $C_{1-10}$ alkoxy group (preferably a $C_{1-6}$ alkoxy group (e.g., methoxy, ethoxy)), or
(4) an amino group.

$R^4$ is preferably a hydrogen atom, an optionally substituted $C_{1-6}$ alkyl group, an optionally substituted hydroxy group or —CO—$R^7$ wherein $R^7$ is an optionally substituted hydroxy group or an optionally substituted amino group.

$R^4$ is more preferably
(1) a hydrogen atom,
(2) a $C_{1-6}$ alkyl group (e.g., methyl) optionally substituted by 1 to 3 substituents selected from
  (i) a hydroxy group, and
  (ii) a $C_{1-6}$ alkoxy group (e.g., methoxy),
(3) a hydroxy group, or
(4) —CO—$R^7$ wherein
  $R^7$ is
  (1) a hydroxy group,
  (2) a $C_{1-6}$ alkoxy group (e.g., methoxy, ethoxy), or
  (3) an amino group optionally mono- or di-substituted by $C_{1-6}$ alkyl group(s) (e.g., ethyl) optionally substituted by 1 to 3 $C_{1-6}$ alkoxy groups (e.g., methoxy).

$R^5$ is —$OR^{8A}$ or —$NR^{8B}R^{8C}$.

$R^{8A}$ is a hydrogen atom or an optionally substituted $C_{1-6}$ alkyl group.

$R^{8B}$ is a hydrogen atom, an optionally substituted $C_{1-6}$ alkyl group or —$SO_2$—$R^9$.

$R^{8C}$ is a hydrogen atom or an optionally substituted $C_{1-6}$ alkyl group.

Or, $R^{8B}$ and $R^{8C}$ in combination optionally form, together with the adjacent nitrogen atom, an optionally substituted ring.

$R^9$ is an optionally substituted $C_{1-6}$ alkyl group.

The "$C_{1-6}$ alkyl group" of the "optionally substituted $C_{1-6}$ alkyl group" for $R^{8A}$, $R^{8B}$, $R^{8C}$ or $R^9$ optionally has 1 to 7 (preferably 1 to 3) substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has. When the number of the substituents is not less than 2, the respective substituents may be the same or different.

Examples of the "ring" of the "optionally substituted ring" formed by $R^{8B}$ and $R^{8C}$ in combination together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The "ring" of the "optionally substituted ring" formed by $R^{8B}$ and $R^{8C}$ in combination together with the adjacent nitrogen atom optionally has 1 to 5 (preferably 1 or 2) substituents at substitutable positions. Examples of the substituent include those similar to the substituents that the "$C_{3-10}$ cycloalkyl group" of the "optionally substituted $C_{3-10}$ cycloalkyl group" for $R^1$ or $R^3$ optionally has. When the number of the substituents is not less than 2, the respective substituents may be the same or different.

$R^{8A}$ is preferably a hydrogen atom or a $C_{1-6}$ alkyl group.

$R^{8B}$ is preferably a hydrogen atom, an optionally substituted $C_{1-6}$ alkyl group or —$SO_2$—$R^9$ wherein $R^9$ is a $C_{1-6}$ alkyl group.

Or, preferably $R^{8B}$ and $R^{8C}$ in combination form, together with the adjacent nitrogen atom, a 5- or 6-membered nitrogen-containing heterocycle (preferably a 5- or 6-membered nitrogen-containing non-aromatic heterocycle).

$R^5$ is preferably
(1) —$OR^{8A}$ wherein $R^{8A}$ is a hydrogen atom or a $C_{1-6}$ alkyl group (e.g., methyl, ethyl), or
(2) —$NR^{8B}R^{8C}$
wherein
$R^{8B}$ is
  (1) a hydrogen atom,
  (2) a $C_{1-6}$ alkyl group (e.g., methyl, ethyl) optionally substituted by 1 to 3 substituents selected from a carboxy group, a hydroxy group and a $C_{1-6}$ alkoxy-carbonyl group (e.g., methoxycarbonyl, ethoxycarbonyl), or
  (3) —$SO_2$—$R^9$ wherein $R^9$ is a $C_{1-6}$ alkyl group (e.g., methyl, ethyl), and
$R^{8C}$ is
  (1) a hydrogen atom, or
  (2) a $C_{1-6}$ alkyl group (e.g., methyl, ethyl) optionally substituted by 1 to 3 substituents selected from a carboxy group, a hydroxy group and a $C_{1-6}$ alkoxy-carbonyl group (e.g., methoxycarbonyl, ethoxycarbonyl), or
$R^{8B}$ and $R_{8C}$ in combination form, together with the adjacent nitrogen atom, a 5- or 6-membered nitrogen-containing heterocycle (preferably a 5- or 6-membered nitrogen-containing non-aromatic heterocycle (e.g., pyrrolidine, morpholine)).

Ring $Ar^1$ is a 5- or 6-membered aromatic ring optionally further substituted by 1 or 2 substituents selected from a halogen atom, an optionally substituted $C_{1-6}$ alkyl group and an optionally substituted $C_{1-6}$ alkoxy group.

Examples of the "5- or 6-membered aromatic ring" in ring $Ar^1$ include benzene and a 5- or 6-membered aromatic heterocycle.

Examples of the 5- or 6-membered aromatic heterocycle include a 5- or 6-membered aromatic heterocycle containing, as a ring constituting atom besides carbon atom, 1 to 4 hetero atoms selected from an oxygen atom, a sulfur atom and a nitrogen atom. Preferable examples thereof include furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

The "$C_{1-6}$ alkyl group" of the "optionally substituted $C_{1-6}$ alkyl group" which is a substituent for ring $Ar^1$ optionally has 1 to 7 (preferably 1 to 3) substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has. When the number of the substituents is not less than 2, the respective substituents may be the same or different.

The "$C_{1-6}$ alkoxy group" of the "optionally substituted $C_{1-6}$ alkoxy group" which is a substituent for ring $Ar^1$ optionally has 1 to 7 (preferably 1 to 3) substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has. When the number of the substituents is not less than 2, the respective substituents may be the same or different.

Ring $Ar^1$ is preferably a 5- or 6-membered aromatic ring optionally further substituted by 1 or 2 substituents selected from a halogen atom and a $C_{1-6}$ alkyl group.

Specifically, ring $Ar^1$ is preferably benzene or a 5- or 6-membered aromatic heterocycle (e.g., furan, pyrazole, oxazole, thiazole, pyridine, pyrimidine, pyrazine), each of which is optionally further substituted by 1 or 2 substituents selected from (1) a halogen atom (e.g., a fluorine atom, a chlorine atom), and
(2) a $C_{1-6}$ alkyl group (e.g., methyl).

Ring $Ar^2$ is an optionally further substituted 6-membered aromatic ring.

Examples of the "6-membered aromatic ring" of the "optionally further substituted 6-membered aromatic ring" for ring $Ar^2$ include benzene and a 6-membered aromatic heterocycle.

Examples of the 6-membered aromatic heterocycle include a 6-membered aromatic heterocycle containing, as a ring constituting atom besides carbon atom, 1 to 4 hetero atoms selected from an oxygen atom, a sulfur atom and a nitrogen atom. Preferable examples thereof include pyridine, pyrimidine, pyridazine, pyrazine, triazine and the like.

The "6-membered aromatic ring" of the "optionally further substituted 6-membered aromatic ring" for ring $Ar^2$ optionally has 1 to 5 (preferably 1 or 2) substituents at substitutable positions. Examples of the substituent include those similar to the substituents that the "$C_{3-10}$ cycloalkyl group" of the "optionally substituted $C_{3-10}$ cycloalkyl group" for $R^1$ or $R^3$ optionally has. When the number of the substituents is not less than 2, the respective substituents may be the same or different.

Ring $Ar^2$ is preferably benzene or a 6-membered aromatic heterocycle (e.g., pyridine), each of which is optionally further substituted by 1 or 2 substituents selected from (1) a halogen atom (e.g., a fluorine atom, a chlorine atom, a bromine atom),
(2) a cyano group,
(3) a $C_{1-6}$ alkyl group (e.g., methyl, ethyl, propyl) optionally substituted by 1 to 3 substituents selected from a halogen atom (e.g., a fluorine atom) and a hydroxy group,
(4) a $C_{1-6}$ alkoxy group (e.g., methoxy),
(5) a $C_{2-6}$ alkenyl group (e.g., vinyl),
(6) a $C_{3-10}$ cycloalkyl group (e.g., cyclopropyl),
(7) a formyl group,
(8) a $C_{1-6}$ alkyl-carbonyl group (e.g., acetyl),
(9) a carbamoyl group optionally mono- or di-substituted by $C_{1-6}$ alkyl group(s) (e.g., methyl),
(10) a $C_{6-10}$ aryl group (e.g., phenyl) optionally substituted by 1 to 3 halogen atoms (e.g., a chlorine atom), and
(11) an aromatic heterocyclic group (e.g., pyrazolyl) optionally substituted by 1 to 3 $C_{1-6}$ alkyl groups (e.g., methyl).

------ is a single bond or a double bond.

------ is preferably a double bond.

$L^1$ is a group represented by the formula: $-L^{1A}-L^{1B}-$ (wherein $L^{1A}$ is optionally substituted $CH_2$; and $L^{1B}$ is O, S, SO, $SO_2$ or optionally substituted $CH_2$), optionally substituted $-CH=CH-$, or $-C\equiv C-$.

The "$CH_2$" of the "optionally substituted $CH_2$" for $L^{1A}$ or $L^{1B}$ optionally has 1 or 2 substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has. When the number of the substituents is not less than 2, the respective substituents may be the same or different.

The "$-CH=CH-$" of the "optionally substituted $-CH=CH-$" for $L^1$ optionally has 1 or 2 substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has. When the number of the substituents is not less than 2, the respective substituents may be the same or different.

$L^1$ is preferably a group represented by the formula: $-L^{1A}-L^{1B}-$ (wherein $L^{1A}$ is an optionally substituted $CH_2$, and $L^{1B}$ is O, S, SO, $SO_2$ or optionally substituted $CH_2$) or optionally substituted $-CH=CH-$.

$L^1$ is more preferably a group represented by the formula: $-L^{1A}-L^{1B}-$ (wherein $L^{1A}$ is $CH_2$ optionally substituted by $C_{1-3}$ alkyl group(s), and $L^{1B}$ is O, S, SO, $SO_2$ or $CH_2$) or $-CH=CH-$.

Specifically, $L^1$ is more preferably $-CH_2O-$, $-CH(CH_3)O-$, $-CH_2S-$, $-CH_2SO-$, $-CH_2SO_2-$, $-CH_2CH_2-$ or $-CH=CH-$.

As another embodiment, $L^1$ is preferably a group represented by the formula: $-L^{1A}-L_{1B}-$ (wherein $L^{1A}$ is an optionally substituted $CH_2$, and $L^{1B}$ is O, S, SO, $SO_2$ or optionally substituted $CH_2$).

$L^1$ is more preferably a group represented by the formula: $-L^{1A}-L^{1B}-$ (wherein $L^{1A}$ is $CH_2$ optionally substituted by $C_{1-3}$ alkyl group(s), and $L^{1B}$ is O, S, SO, $SO_2$ or $CH_2$).

$L^1$ is more preferably $-CH_2O-$, $-CH(CH_3)O-$, $-CH_2S-$, $-CH_2SO-$, $-CH_2SO_2-$ or $-CH_2CH_2-$.

$L^1$ is particularly preferably $-CH_2O-$.

$L^2$ and $L^4$ are each independently a bond or an optionally substituted $C_{1-3}$ alkylene group.

$L^3$ is a bond, O, S, SO, $SO_2$ or $NR^6$.

$R^6$ is a hydrogen atom or an optionally substituted $C_{1-6}$ alkyl group.

The "$C_{1-3}$ alkylene group" of the "optionally substituted $C_{1-3}$ alkylene group" for $L^2$ or $L^4$ is a straight or branched chain $C_{1-3}$ alkylene group, and examples thereof include $-CH_2-$, $-CH(CH_3)-$, $-CH_2CH_2-$, $-CH(CH_3)CH_2-$, $-CH_2CH(CH_3)-$, $-CH_2CH_2CH_2-$ and the like.

The "$C_{1-3}$ alkylene group" of the "optionally substituted $C_{1-3}$ alkylene group" for $L^2$ or $L^4$ optionally has 1 to 7 (preferably 1 to 3) substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has.

The "$C_{1-6}$ alkyl group" of the "optionally substituted $C_{1-6}$ alkyl group" for $R^6$ optionally has 1 to 7 (preferably 1 to 3) substituents at substitutable positions. Examples of the substituent include those similar to the substituents that the "$C_{1-6}$ alkyl group" of the "optionally substituted $C_{1-6}$ alkyl group" for $R^1$, $R^2$, $R^3$ or $R^4$ optionally has.

$L^2$ and $L^4$ are preferably each independently a bond or a $C_{1-3}$ alkylene group (e.g., —$CH_2$—, —$CH_2CH_2$—, —CH($CH_3$)—) optionally substituted by hydroxy group(s).

$L^3$ is preferably a bond, O, S or $NR^6$ wherein $R^6$ is a hydrogen atom or an optionally substituted $C_{1-6}$ alkyl group.

$L^3$ is more preferably a bond, O, S or NH.

$-L^2-L^3-L^4-$ is preferably a bond, —$CH_2$—, —$CH_2CH_2$—, —CH($CH_3$)—, —CH($CH_2OH$)—, —$OCH_2$—, —$SCH_2$—, —$CH_2CH_2SCH_2$—, —$NHCH_2$—, —$CH_2NH$— or —NH—.

X is O, S, SO or $SO_2$.

X is preferably O, S or $SO_2$.

X is more preferably O or S.

The bond of $R^1$, $R^2$, $R^3$ or $L^1$ to ring $Ar^1$ in the partial structure of the formula (I)

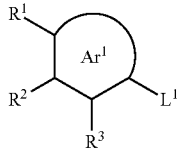

shows only the bonding position of $R^1$, $R^2$, $R^3$ or $L^1$ to ring $Ar^1$, and the atom on ring $Ar^1$ to which $R^1$, $R^2$, $R^3$ or $L^1$ is bond is not limited to a carbon atom.

The atom on ring $Ar^1$ to which $R^1$ is bond is a carbon atom or a nitrogen atom.

The atom on ring $Ar^1$ to which $R^2$ is bond is a carbon atom, a nitrogen atom, an oxygen atom and a sulfur atom.

The atom on ring $Ar^1$ to which $R^3$ is bond is a carbon atom or a nitrogen atom.

The atom on ring $Ar^1$ to which $L^1$ is bond is a carbon atom or a nitrogen atom.

Preferable examples of compound (I) include the following compounds.

[Compound A]

Compound (I) wherein ring $Ar^1$ is a 5- or 6-membered aromatic ring optionally further substituted by 1 or 2 substituents selected from a halogen atom and a $C_{1-6}$ alkyl group;

ring $Ar^2$ is an optionally further substituted 6-membered aromatic ring;

------ is a single bond or a double bond;

$L^1$ is a group represented by the formula: $L^{1A}-L^{1B}-$ (wherein $L^{1A}$ is an optionally substituted $CH_2$, and $L^{1B}$ is O, S, SO, $SO_2$ or optionally substituted $CH_2$) or optionally substituted —CH=CH—; $L^2$ and $L^4$ are each independently a bond or an optionally substituted $C_{1-3}$ alkylene group;

$L^3$ is a bond, O, S, SO, $SO_2$ or $NR^6$;

X is O, S, SO or $SO_2$;

$R^1$ and $R^3$ are each independently a halogen atom, an optionally substituted $C_{1-6}$ alkyl group, an optionally substituted $C_{1-10}$ alkoxy group, an optionally substituted amino group, or an optionally substituted nitrogen-containing heterocyclic group which is bonded to ring $Ar^1$ via a nitrogen atom thereof (preferably $R^1$ is a halogen atom, an optionally substituted $C_{1-6}$ alkyl group or an optionally substituted $C_{1-10}$ alkoxy group;

$R^3$ is a halogen atom, an optionally substituted $C_{1-6}$ alkyl group, an optionally substituted $C_{1-10}$ alkoxy group (preferably a $C_{1-6}$ alkoxy group), an optionally substituted amino group, or an optionally substituted nitrogen-containing heterocyclic group which is bonded to ring $Ar^1$ via a nitrogen atom thereof);

$R^2$ is a hydrogen atom, or absent;

$R^4$ is a hydrogen atom, an optionally substituted $C_{1-6}$ alkyl group, an optionally substituted hydroxy group or —CO—$R^7$;

$R^5$ is —$OR^{8A}$ or —$NR^{8B}R^{8C}$;

$R^6$ is a hydrogen atom or an optionally substituted $C_{1-6}$ alkyl group;

$R^7$ is an optionally substituted hydroxy group or an optionally substituted amino group;

$R^{8A}$ is a hydrogen atom or an optionally substituted $C_{1-6}$ alkyl group;

$R^{8B}$ is a hydrogen atom, an optionally substituted $C_{1-6}$ alkyl group or —$SO_2$—$R^9$;

$R^{8C}$ is a hydrogen atom or an optionally substituted $C_{1-6}$ alkyl group; or $R^{8B}$ and $R^{8C}$ in combination form, together with the adjacent nitrogen atom, an optionally substituted 5- or 6-membered nitrogen-containing heterocycle; and $R^9$ is an optionally substituted $C_{1-6}$ alkyl group.

[Compound B]

Compound (I) wherein ring $Ar^1$ is benzene or a 5- or 6-membered aromatic heterocycle (e.g., furan, pyrazole, oxazole, thiazole, pyridine, pyrimidine, pyrazine), each of which is optionally further substituted by 1 or 2 substituents selected from (1) a halogen atom (e.g., a fluorine atom, a chlorine atom), and (2) a $C_{1-6}$ alkyl group (e.g., methyl);

ring $Ar^2$ is benzene or a 6-membered aromatic heterocycle (e.g., pyridine), each of which is optionally further substituted by 1 or 2 substituents selected from (1) a halogen atom (e.g., a fluorine atom, a chlorine atom, a bromine atom), (2) a cyano group, (3) a $C_{1-6}$ alkyl group (e.g., methyl, ethyl, propyl) optionally substituted by 1 to 3 substituents selected from a halogen atom (e.g., a fluorine atom) and a hydroxy group, (4) a $C_{1-6}$ alkoxy group (e.g., methoxy), (5) a $C_{2-6}$ alkenyl group (e.g., vinyl), (6) a $C_{3-10}$ cycloalkyl group (e.g., cyclopropyl), (7) a formyl group, (8) a $C_{1-6}$ alkyl-carbonyl group (e.g., acetyl), (9) a carbamoyl group optionally mono- or di-substituted by $C_{1-6}$ alkyl group(s) (e.g., methyl),

(10) a $C_{6-10}$ aryl group (e.g., phenyl) optionally substituted by 1 to 3 halogen atoms (e.g., a chlorine atom), and

(11) an aromatic heterocyclic group (e.g., pyrazolyl) optionally substituted by 1 to 3 $C_{1-6}$ alkyl groups (e.g., methyl);

------ is a single bond or a double bond;

$L^1$ is a group represented by the formula: -$L^{1A}$-$L^{1B}$- (wherein $L^{1A}$ is $CH_2$ optionally substituted by $C_{1-3}$ alkyl group(s), and $L^{1B}$ is O, S, SO, $SO_2$ or $CH_2$) or —CH=CH— (specifically —$CH_2O$—, —CH($CH_3$)O—, —$CH_2S$—, —$CH_2SO$—, —$CH_2SO_2$—, —$CH_2CH_2$— or —CH=CH—);

$L^2$ and $L^4$ are each independently a bond or a $C_{1-3}$ alkylene group (e.g., —$CH_2$—, —$CH_2CH_2$—, —CH($CH_3$)—) optionally substituted by hydroxy group(s);

$L^3$ is a bond, O, S or $NR^6$ wherein $R^6$ is a hydrogen atom or an optionally substituted $C_{1-6}$ alkyl group;
(specific examples of -$L^2$-$L^3$-$L^4$- include a bond, —$CH_2$—, —$CH_2CH_2$—, —$CH(CH_3)$—, —$CH(CH_2OH)$—, —$SCH_2$—, —$CH_2CH_2SCH_2$—, —$NHCH_2$—, —$CH_2NH$— and —NH—)
X is O, S or $SO_2$;
$R^1$ is
(1) a halogen atom (e.g., a fluorine atom, a chlorine atom, an iodine atom),
(2) a $C_{1-6}$ alkyl group (e.g., methyl, ethyl, isopropyl) optionally substituted by 1 to 3 halogen atoms (e.g., a fluorine atom), or
(3) a $C_{1-10}$ alkoxy group (e.g., methoxy, ethoxy, propoxy, butoxy, 2,5-dimethylhexyl-3-oxy) optionally substituted by 1 to 3 substituents selected from
  (i) a $C_{1-6}$ alkoxy group (e.g., methoxy),
  (ii) a $C_{6-14}$ aryl group (e.g., phenyl),
  (iii) a $C_{3-10}$ cycloalkyl group (e.g., cyclopropyl), and
  (iv) an aromatic heterocyclic group (e.g., pyridyl);
$R^2$ is a hydrogen atom, or absent;
$R^3$ is
(1) a halogen atom (e.g., a fluorine atom, a chlorine atom),
(2) a $C_{1-6}$ alkyl group (e.g., methyl, ethyl) optionally substituted by 1 to 3 halogen atoms (e.g., a fluorine atom),
(3) a $C_{1-10}$ alkoxy group (preferably a $C_{1-6}$ alkoxy group (e.g., methoxy, ethoxy)),
(4) an amino group, or
(5) a 5- or 6-membered nitrogen-containing heterocyclic group (preferably a 5- or 6-membered nitrogen-containing non-aromatic heterocyclic group (e.g., 1-pyrrolidinyl)) which is bonded to ring $Ar^1$ via a nitrogen atom thereof;
$R^4$ is
(1) a hydrogen atom,
(2) a $C_{1-6}$ alkyl group (e.g., methyl) optionally substituted by 1 to 3 substituents selected from
  (i) a hydroxy group, and
  (ii) a $C_{1-6}$ alkoxy group (e.g., methoxy),
(3) a hydroxy group, or
(4) —CO—$R^7$ wherein
  $R^7$ is
  (1) a hydroxy group,
  (2) a $C_{1-6}$ alkoxy group (e.g., methoxy, ethoxy), or
  (3) an amino group optionally mono- or di-substituted by $C_{1-6}$ alkyl group(s) (e.g., ethyl) optionally substituted by 1 to 3 $C_{1-6}$ alkoxy groups (e.g., methoxy); and
$R^5$ is
(1) —$OR^{9A}$ wherein $R^{8A}$ is a hydrogen atom or a $C_{1-6}$ alkyl group (e.g., methyl, ethyl), or
(2) —$NR^{8B}R^{8C}$
wherein
$R^{8B}$ is
(1) a hydrogen atom,
(2) a $C_{1-6}$ alkyl group (e.g., methyl, ethyl) optionally substituted by 1 to 3 substituents selected from a carboxy group, a hydroxy group and a $C_{1-6}$ alkoxy-carbonyl group (e.g., methoxycarbonyl, ethoxycarbonyl), or
(3) —$SO_2$—$R^9$ wherein $R^9$ is a $C_{1-6}$ alkyl group (e.g., methyl, ethyl), and
$R^{8C}$ is
(1) a hydrogen atom, or
(2) a $C_{1-6}$ alkyl group (e.g., methyl, ethyl) optionally substituted by 1 to 3 substituents selected from a carboxy group, a hydroxy group and a $C_{1-6}$ alkoxy-carbonyl group (e.g., methoxycarbonyl, ethoxycarbonyl), or
$R^{8B}$ and $R^{8C}$ in combination form, together with the adjacent nitrogen atom, a 5- or 6-membered nitrogen-containing heterocycle (preferably a 5- or 6-membered nitrogen-containing non-aromatic heterocycle (e.g., pyrrolidine, morpholine)).

[Compound A']
Compound (I) wherein
ring $Ar^1$ is a 5- or 6-membered aromatic ring optionally further substituted by 1 or 2 substituents selected from a halogen atom and a $C_{1-6}$ alkyl group; ring $Ar^2$ is an optionally further substituted 6-membered aromatic ring;
- - - - - is a single bond or a double bond;
$L^1$ is a group represented by the formula: -$L^{1A}$-$L^{1B}$- (wherein $L^{1A}$ is an optionally substituted $CH_2$, and $L^{1B}$ is O, S, SO, $SO_2$ or optionally substituted $CH_2$);
$L^2$ and $L^4$ are each independently a bond or an optionally substituted $C_{1-3}$ alkylene group;
$L^3$ is a bond, O, S, SO, $SO_2$ or $NR^6$;
X is O, S, SO or $SO_2$;
$R^1$ and $R^3$ are each independently a halogen atom, an optionally substituted $C_{1-6}$ alkyl group, an optionally substituted $C_{1-10}$ alkoxy group or an optionally substituted amino group;
$R^2$ is a hydrogen atom, or absent;
$R^4$ is a hydrogen atom, an optionally substituted $C_{1-6}$ alkyl group, an optionally substituted hydroxy group or —CO—$R^7$;
$R^5$ is —$OR^{8A}$ or —$NR^{8B}R^{8C}$;
$R^6$ is a hydrogen atom or an optionally substituted $C_{1-6}$ alkyl group;
$R^7$ is an optionally substituted hydroxy group or an optionally substituted amino group;
$R^{8A}$ is a hydrogen atom or an optionally substituted $C_{1-6}$ alkyl group;
$R^{8B}$ is a hydrogen atom, an optionally substituted $C_{1-6}$ alkyl group or —$SO_2$—$R^9$;
$R^{8C}$ is a hydrogen atom or an optionally substituted $C_{1-6}$ alkyl group; or
$R^{8B}$ and $R^{8C}$ in combination form, together with the adjacent nitrogen atom, an optionally substituted 5- or 6-membered nitrogen-containing heterocycle; and
$R^9$ is an optionally substituted $C_{1-6}$ alkyl group.

[Compound B']
Compound (I) wherein
ring $Ar^1$ is benzene or a 5- or 6-membered aromatic heterocycle (e.g., furan, pyrazole, oxazole, thiazole, pyridine, pyrimidine, pyrazine), each of which is optionally further substituted by 1 or 2 substituents selected from
  (1) a halogen atom (e.g., a fluorine atom, a chlorine atom), and
  (2) a $C_{1-6}$ alkyl group (e.g., methyl); ring $Ar^2$ is benzene or a 6-membered aromatic heterocycle (e.g., pyridine), each of which is optionally further substituted by 1 or 2 substituents selected from
  (1) a halogen atom (e.g., a fluorine atom, a chlorine atom, a bromine atom),
  (2) a cyano group,
  (3) a $C_{1-6}$ alkyl group (e.g., methyl, ethyl, propyl) optionally substituted by 1 to 3 substituents selected from a halogen atom (e.g., a fluorine atom) and a hydroxy group,
  (4) a $C_{1-6}$ alkoxy group (e.g., methoxy),
  (5) a $C_{2-6}$ alkenyl group (e.g., vinyl),
  (6) a $C_{3-10}$ cycloalkyl group (e.g., cyclopropyl),
  (7) a formyl group,
  (8) a $C_{1-6}$ alkyl-carbonyl group (e.g., acetyl),
  (9) a carbamoyl group optionally mono- or di-substituted by $C_{1-6}$ alkyl group(s) (e.g., methyl),

(10) a $C_{6-10}$ aryl group (e.g., phenyl) optionally substituted by 1 to 3 halogen atoms (e.g., a chlorine atom), and
(11) an aromatic heterocyclic group (e.g., pyrazolyl) optionally substituted by 1 to 3 $C_{1-6}$ alkyl groups (e.g., methyl);

------ is a single bond or a double bond;
$L^1$ is a group represented by the formula: -$L^{1A}$-$L^{1B}$- (wherein $L^{1A}$ is $CH_2$ optionally substituted by $C_{1-3}$ alkyl group(s), and $L^{1B}$ is O, S, SO, $SO_2$ or $CH_2$) (specifically —$CH_2O$—, —CH($CH_3$)O—, —$CH_2S$—, —$CH_2SO$—, —$CH_2SO_2$— or —$CH_2CH_2$—);
$L^2$ and $L^4$ are each independently a bond or a $C_{1-3}$ alkylene group (e.g., —$CH_2$—, —$CH_2CH_2$—, —CH($CH_3$)—) optionally substituted by hydroxy group(s).
$L^3$ is a bond, O, S or $NR^6$ wherein $R^6$ is a hydrogen atom or an optionally substituted $C_{1-6}$ alkyl group;
(specific examples of -$L^2$-$L^3$-$L^4$- include a bond, —$CH_2$—, —$CH_2CH_2$—, —CH($CH_3$)—, —CH($CH_2OH$)—, —$SCH_2$—, —$CH_2CH_2SCH_2$—, —$NHCH_2$—, —$CH_2NH$— and —NH—)
X is O, S or $SO_2$;
$R^1$ is
(1) a halogen atom (e.g., a fluorine atom, a chlorine atom, an iodine atom),
(2) a $C_{1-6}$ alkyl group (e.g., methyl, ethyl, isopropyl) optionally substituted by 1 to 3 halogen atoms (e.g., a fluorine atom), or
(3) a $C_{1-10}$ alkoxy group (e.g., methoxy, ethoxy, propoxy, butoxy, 2,5-dimethylhexyl-3-oxy) optionally substituted by 1 to 3 substituents selected from
  (i) a $C_{1-6}$ alkoxy group (e.g., methoxy),
  (ii) a $C_{6-14}$ aryl group (e.g., phenyl),
  (iii) a $C_{3-10}$ cycloalkyl group (e.g., cyclopropyl), and
  (iv) an aromatic heterocyclic group (e.g., pyridyl);
$R^2$ is a hydrogen atom, or absent;
$R^3$ is
(1) a halogen atom (e.g., a fluorine atom, a chlorine atom),
(2) a $C_{1-6}$ alkyl group (e.g., methyl, ethyl) optionally substituted by 1 to 3 halogen atoms (e.g., a fluorine atom),
(3) a $C_{1-10}$ alkoxy group (preferably a $C_{1-6}$ alkoxy group (e.g., methoxy, ethoxy)), or
(4) an amino group;
$R^4$ is
(1) a hydrogen atom,
(2) a $C_{1-6}$ alkyl group (e.g., methyl) optionally substituted by 1 to 3 substituents selected from
  (i) a hydroxy group, and
  (ii) a $C_{1-6}$ alkoxy group (e.g., methoxy),
(3) a hydroxy group, or
(4) —CO—$R^7$ wherein
  $R^7$ is
  (1) a hydroxy group,
  (2) a $C_{1-6}$ alkoxy group (e.g., methoxy, ethoxy), or
  (3) an amino group optionally mono- or di-substituted by $C_{1-6}$ alkyl group(s) (e.g., ethyl) optionally substituted by 1 to 3 $C_{1-6}$ alkoxy groups (e.g., methoxy); and
$R^5$ is
(1) —$OR^{8A}$ wherein $R^{8A}$ is a hydrogen atom or a $C_{1-6}$ alkyl group (e.g., methyl, ethyl), or
(2) —$NR^{8B}R^{8C}$
wherein
  $R^{8B}$ is
  (1) a hydrogen atom,
  (2) a $C_{1-6}$ alkyl group (e.g., methyl, ethyl) optionally substituted by 1 to 3 substituents selected from a carboxy group, a hydroxy group and a $C_{1-6}$ alkoxy-carbonyl group (e.g., methoxycarbonyl, ethoxycarbonyl), or
  (3) —$SO_2$—$R^9$ wherein $R^9$ is a $C_{1-6}$ alkyl group (e.g., methyl, ethyl), and
  $R^{8C}$ is
  (1) a hydrogen atom, or
  (2) a $C_{1-6}$ alkyl group (e.g., methyl, ethyl) optionally substituted by 1 to 3 substituents selected from a carboxy group, a hydroxy group and a $C_{1-6}$ alkoxy-carbonyl group (e.g., methoxycarbonyl, ethoxycarbonyl), or
  $R^{8B}$ and $R^{8C}$ in combination form, together with the adjacent nitrogen atom, a 5- or 6-membered nitrogen-containing heterocycle (preferably a 5- or 6-membered nitrogen-containing non-aromatic heterocycle (e.g., pyrrolidine, morpholine)).

A salt of the compound represented by the formula (I) is preferably a pharmacologically acceptable salt. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (I) may be used as a prodrug.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. due to an enzyme; a compound which is converted to compound (I) by hydrolysis etc. due to gastric acid, etc.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

Compound (I) may be labeled with an isotope (e.g., $^3$H, $^{13}$C, $^{14}$C, $^{125}$I) and the like.

Compound (I) may be a hydrate or a non-hydrate, and a solvate or a non-solvate.

Compound (I) also encompasses a deuterium conversion form wherein $^1$H is converted to $^2$H(D).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., (3-carotene, chlorophyll, ferric oxide red).

Preferable examples of the sweetening agent include sodium saccharin, dipotassium glycyrrhizinate, aspartame and *stevia*.

The medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be a controlled release preparation such as an immediate-release preparation, an sustained-release preparation and the like (e.g., sustained-release microcapsule).

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, pneumotoxicity, carcinogenicity) and a few side effects. Therefore, it can be used as an agent for the prophylaxis or treatment or a diagnostic of various diseases in a mammal.

Since the compound of the present invention has a superior GOAT inhibitory activity, it can be used as a GOAT inhibitor.

The compound of the present invention can be used for the prophylaxis or treatment of diseases involving ghrelin.

Examples of the diseases involving ghrelin including obesity, visceral fat syndrome, non-alcoholic fatty liver, non-alcoholic steatohepatitis, metabolic syndrome, diabetes (e.g., type 1 diabetes, type 2 diabetes, gestational diabetes, obese diabetes), postprandial hyperglycemia, hyperlipidemia (e.g., hypertriglyceridemia, hypercholesterolemia, high LDL-cholesterolemia, low HDL-cholesterolemia, postprandial hyperlipemia), diabetic complications [e.g., neuropathy, nephropathy, retinopathy, cardiomyopathy, macroangiopathy, osteopenia, hyperosmolar coma, gangrene, xerostomia, hypacusis, cerebrovascular disorder, peripheral blood circulation disorder, infections (e.g., respiratory infection, urinary tract infection, gastrointestinal infection, dermal soft tissue infections, inferior limb infection), diabetic gangrene], digestive diseases (e.g., irritable bowel syndrome, acute or chronic diarrhea, functional gastrointestinal tract disease, ulcerative colitis, acute corrosive esophagitis, acute corrosive gastritis, Crohn's disease, acute pancreatitis, chronic pancreatitis), renal diseases (e.g., chronic nephritis, diabetic nephropathy, glomerulonephritis, glomerulosclerosis, renal failure, end-stage renal disorder, hypertensive nephrosclerosis, pyelonephritis, water nephropathy), circulatory diseases (e.g., ischemic cardiac diseases (myocardial infarction, angina pectoris), cardiac hypertrophy, cardiomyopathy, hypertension, arteriosclerosis, arrhythmia, cardiac failure, coronary heart disease, endocarditis, aneurysm, prolapse of mitral valve, venous thromboembolism, valvular involvement), autoimmune diseases (e.g., rheumatoid arthritis, multiple sclerosis, psoriasis, systemic lupus erythematosus, Sjogren's syndrome) and the like, as well as growth disorders (e.g., acromegaly, giantism), chronic obstructive pulmonary diseases, pneumonia, alcohol dependence, stimulant dependence, narcotic dependence, tobacco dependence, gamble dependence, eating disorders (e.g., hyperorexia, neurotic hyperorexia, Binge eating disorder, Prader-Willi syndrome), prostate cancer, breast cancer, hypophysis tumor, ovary tumor, uterine body cancer, cervical cancer and the like.

The compound of the present invention can be used for the protection from or regenerative repair of severe eczema/dermatitis, and various types of dermatitis.

Since the compound of the present invention has a muscle protective action, it can be used for the prophylaxis of muscular atrophy, and for the prophylaxis or treatment of sarcopenia, muscular dystrophy or myasthenia gravis, for the purpose of maintaining or regeneration of muscular tissues. In addition, it can be used for the protection of neuropathy such as spinal injury and the like.

Since the compound of the present invention has a protective action on central neurological disease, it can be used for the prophylaxis or treatment of cognitive impairment (e.g., Alzheimer's disease, Parkinson's disease, cerebrovascular dementia), cerebral apoplexy, cerebral infarction and the like.

The compound of the present invention can be used for improving symptoms such as abdominal pain, nausea, vomiting, discomfort in the upper abdomen, and the like, which are associated with peptic ulcer, acute or chronic gastritis, cholecystitis and the like, and the like.

Since the compound of the present invention has a pancreatic β cells protective action, it can be used for improving prognosis of pancreatic islet transplantation, and the like. In addition, since it also as cardio-angiogenesis promoting action, it can be used for cardiovascular tissue regeneration and the like.

The compound of the present invention is useful for the prophylaxis or treatment of obesity, diabetes, hyperlipidemia, metabolic syndrome, non-alcoholic fatty liver, steatohepatitis, sarcopenia, appetite control, alcohol/narcotic dependence, Alzheimer's disease, Parkinson's disease, cerebrovascular dementia, cerebral apoplexy, cerebral infarction, cardiac disease, cardiovascular disease, some kind of tumors (e.g., prostate cancer, breast cancer etc.) and the like.

The compound of the present invention is particularly useful for the prophylaxis or treatment of obesity, metabolic syndrome, diabetes, hypertension, cardiac failure, Alzheimer's disease, Parkinson's disease, cerebrovascular dementia, cerebral apoplexy, cerebral infarction, alcohol/stimulant dependence, narcotic dependence, prostate cancer, breast cancer and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test, (75 g OGTT) 2 hr level (glucose concentration of intravenous plasma) of less than 140 mg/dl" (normal type) is called a "borderline type".

In addition, ADA (American Diabetes Association) in 1997 and WHO (World Health Organization) in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

Since the compound of the present invention has a body weight-lowering action, it can be used as a body weight-lowering agent to mammals. Target mammals may be any mammals of which body weight is to be lowered. The mammals may have a risk of body weight gain genetically or may be suffering from lifestyle-related diseases such as diabetes, hypertension and/or hyperlipidemia and the like. The body weight gain may be caused by excessive feeding or diet without nutrient balance, or may be derived from concomitant drug (e.g., agents for enhancing insulin sensitivity having PPARγ-agonistic activity such as troglitazone, rosiglitazone, englitazone, ciglitazone, pioglitazone and the like). In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

The compound of the present invention is also useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is extremely important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

While the dose of the compound of the present invention varies depending on the subject of administration, administration route, target disease, symptom and the like, for example, for oral administration to an adult obese patient, it is generally about 0.01 to 100 mg/kg body weight, preferably 0.05 to 30 mg/kg body weight, further preferably 0.5 to 10 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and these concomitant drugs may be low-molecular-weight compounds or high-molecular-weight protein, polypeptide, antibody, vaccine and the like. They may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin, Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO 2004/041266, WO 2004/106276, WO 2005/063729, WO 2005/063725, WO 2005/087710, WO 2005/095338, WO 2007/013689 or WO 2008/001931), GLP-1 receptor agonists [e.g., GLP-1, GLP-1MR preparation, Liraglutide, Exenatide, AVE-0010, BIM-51077, Aib(8,35)hGLP-1(7,37)NH$_2$, CJC-1131, Albiglutide], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP355, compound described in WO 2006/112549, WO 2007/028135, WO 2008/047821, WO 2008/050821, WO 2008/136428 or WO2008/156757), GIP (Glucose-dependent insulinotropic peptide) and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neurotrophic factors and increasing drugs thereof (e.g., 4-(4-chlorophenyl)-2-(2-methyl-1-imidazolyl)-5-[3-(2-methylphenoxy)propyl]oxazole) described in WO 01/14372, a compound described in WO 2004/039365), nerve regeneration promoters (e.g., Y-128), PKC inhibitors (e.g., ruboxistaurin mesylate), AGE inhibitors (e.g., ALT946, pyratoxanthine, N-phenacylthiazolium bromide (ALT766), ALT-711, EXO-226, Pyridorin, pyridoxamine), GABA receptor agonists (e.g., gabapentin, Pregabalin), serotonin noradrenaline re-uptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like.

Examples of the therapeutic agent for hyperlipidemia include statin compounds (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO 97/10224, for example, N-[[(3R,5S)-1-(3-acetoxy-2,2-dimethylpropyl)-7-chloro-5-(2,3-dimethoxyphenyl)-2-oxo-1,2, 3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterols (e.g., soysterol), γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, efonidipine, nicardipine, amlodipine, cilnidipine and the like), β blockers (e.g., metoprolol, atenolol, propranolol, carvedilol, pindolol), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulators (e.g., topiramate), MCH receptor antagonists (e.g., SB-568849; SNAP-7941; compound described in WO 01/82925 or WO 01/87834), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine and pig; human FGF21 preparations genetically synthesized using *Escherichia coli* or yeast; fragments or derivatives of FGF21)), a combination agent of naltrexone hydrochloride sustained-release preparation and bupropion hydrochloride sustained-release preparation, anorexigenic agents (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, enoxaparin sodium, dalteparin sodium), warfarins (e.g., warfarin potassium), anti-thrombin drugs (e.g., argatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride, prasugrel, E5555, SHC530348), FXa inhibitors (e.g., rivaroxaban, apixaban, edoxaban, YM150, compound described in WO 02/06234, WO 2004/048363, WO 2005/030740, WO 2005/058823 or WO 2005/113504) and the like.

The administration time of the aforementioned concomitant drug is not limited, and the compound of the present invention and the concomitant drug may be administered to an administration subject simultaneously, or may be administered at different times. The dosage of the concomitant drug may be determined according to the dosage clinically used, and can be appropriately selected depending on the administration subject, administration route, diseases, combination thereof and the like.

The administration mode of the concomitant drug is not particularly limited, and the compound of the present invention and the concomitant drug only need to be combined on administration. Examples of such administration mode include the following:

1) administration of a single preparation obtained by simultaneously processing the compound of the present invention and the concomitant drug,
2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

The production method of the compound of the present invention is explained in the following.

As examples of the production methods of compound (I) (including compound (1a) to compound (1z)) or a salt thereof, representative production methods are described below, which are not to be construed as limitative.

In the following Reaction Schemes, starting compounds may be each in the form of a salt as long as it does not inhibit the reaction. Examples of the salt include those exemplified as the above-mentioned salt of the compound represented by formula (I).

When a specific production method is not described, the starting compound may be easily commercially available, or can also be produced according to a method known per se, or a method analogous thereto.

The resultant product obtained by each reaction can be used directly as the reaction mixture or as a crude product for the next reaction, or can be isolated from the reaction mixture according a conventional method, and can be purified according to separation means such as recrystallization, distillation, chromatography and HPLC and the like. When the resultant product is a mixture of stereoisomers, the mixture can be purified by separation means (e.g., diastereomer salt method, chromatography, HPLC or SFC (supercritical fluid chromatography) and the like), for example, the method described in Example or a method analogous thereto and the like.

When alkylation reaction, hydrolysis, amination reaction, esterification reaction, amidation reaction, esterification reaction, etherification reaction, oxidation reaction, reduction reaction and the like are to be performed in the following Reaction Schemes, these reactions are performed according to a method known per se. Examples of such method include the methods described in ORGANIC FUNCTIONAL GROUP PREPARATIONS, 2nd ed., ACADEMIC PRESS, INC., 1989; Comprehensive Organic Transformations: A Guide to Functional Group Preparations, 2nd ed., Wiley-VCH, 1999 and the like, and the like.

The following are explanations of the solvents in generic terms, which are used for the following reactions.

Examples of the "nitrile solvents" include acetonitrile, propionitrile and the like.

Examples of the "amide solvents" include N,N-dimethylformamide (DMF), N,N-dimethylacetamide, N-methylpyrrolidone and the like.

Examples of the "halogenated hydrocarbon solvents" include dichloromethane, chloroform, 1,2-dichloroethane, carbon tetrachloride and the like.

Examples of the "ether solvents" include diethyl ether, diisopropyl ether, tert-butyl methyl ether, tetrahydrofuran (THF), 1,4-dioxane, 1,2-dimethoxyethane and the like.

Examples of the "aromatic solvents" include benzene, toluene, xylene, chlorobenzene, (trifluoromethyl)benzene, pyridine and the like.

Examples of the "aliphatic hydrocarbon solvents" include hexane, pentane, cyclohexane and the like.

Examples of the "sulfoxide solvents" include dimethyl sulfoxide (DMSO) and the like.

Examples of the "alcohol solvents" include methanol, ethanol, propanol, 2-propanol, butanol, isobutanol, tert-butanol and the like.

Examples of the "ester solvents" include methyl acetate, ethyl acetate, n-butyl acetate, tert-butyl acetate and the like.

Examples of the "ketone solvents" include acetone, methyl ethyl ketone and the like.

Examples of the "organic acid solvents" include formic acid, acetic acid, propionic acid, trifluoroacetic acid, methanesulfonic acid and the like.

In each reaction, when the starting compound has an amino group, a carboxyl group, a hydroxy group, a carbonyl group or a sulfanyl group as a substituent, a protecting group generally used in peptide chemistry and the like may be introduced into these groups. By removing the protecting group as necessary after the reaction, the object compound can be obtained.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-10}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting, group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

Examples of the "carbonyl-protecting group" include cyclic acetal (e.g., 1,3-dioxane), non-cyclic acetal (e.g., di-$C_{1-6}$ alkylacetal) and the like.

Examples of the sulfanyl-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The introduction and removal of the above-mentioned protecting group can be performed according to a method known per se, for example, the method described in Protective Groups in Organic Synthesis, John Wiley and Sons (1980) or a method analogous thereto.

Compound (I) (including compound (1a) to compound (1z)) can be produced according to, for example, the method shown in the following Reaction Schemes 1 to 16 or a method analogous thereto. In the following reaction scheme, each symbol is as defined above unless otherwise specified.

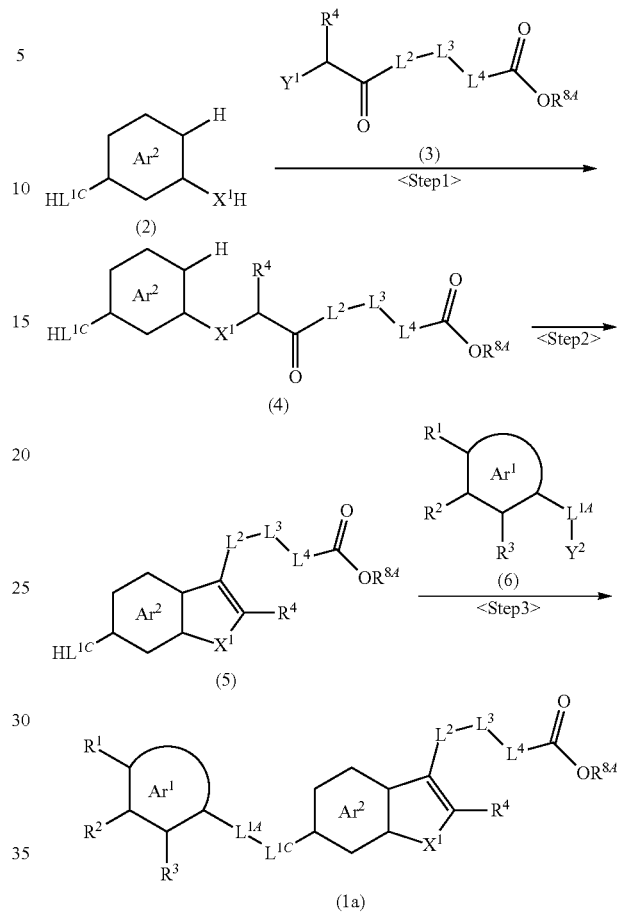

wherein $L^{1C}$ and $X^1$ are each independently an oxygen atom or a sulfur atom, $Y^1$ is a leaving group, $Y^2$ is a hydroxyl group or a leaving group, and the other symbols are as defined above.

Examples of the leaving group for $Y^1$ or $Y^2$ include a halogen atom (e.g., fluorine, chlorine, bromine, iodine), optionally halogenated $C_{1-6}$ alkylsulfonyloxy (e.g., methanesulfonyloxy, ethanesulfonyloxy, trichloromethanesulfonyloxy, trifluoromethanesulfonyloxy), $C_{6-10}$ arylsulfonyloxy optionally having substituent(s) (e.g., $C_{6-10}$ arylsulfonyloxy optionally having 1 to 3 substituents selected from a $C_{1-6}$ alkyl group (e.g., methyl, ethyl), a $C_{1-6}$ alkoxy group (e.g., methoxy, ethoxy) and a nitro group (e.g., phenylsulfonyloxy, naphthylsulfonyloxy) and the like; specific examples include phenylsulfonyloxy, m-nitrophenylsulfonyloxy, p-toluenesulfonyloxy and the like), acyloxy (e.g., trichloroacetoxy, trifluoroacetoxy etc.) and the like.

<Step 1>

Compound (4) can be produced by subjecting compound (2) to an alkylation reaction with compound (3).

This reaction is carried out in the presence of a base, in an inert solvent.

The amount of compound (3) to be used is generally 0.5 to 10 equivalents, preferably 1 to 5 equivalents, relative to compound (2).

Examples of the base include alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal phosphates such as sodium phosphate, potassium phosphate and the like; alkali metal alkoxides having 1 to 6 carbon atoms such as sodium methoxide, sodium ethoxide, sodium tert-butoxide and the like; organic bases such as trimethylamine, triethylamine, N,N-diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithiumdiisopropylamide and the like, and the like.

The amount of the base to be used is generally 1 to 10 equivalents, preferably 1 to 5 equivalents, relative to compound (2).

Examples of the inert solvent include nitrile solvents, amide solvents, halogenated hydrocarbon solvents, hydrocarbon solvents, ether solvents and the like. They may be used in a mixture of two or more kinds thereof in an appropriate ratio. Among them, THF, DMF and the like are preferable.

The reaction temperature is generally –100° C. to 150° C., preferably 0° C. to 100° C.

The reaction time is generally 5 min to 48 hr, preferably 30 min to 24 hr.

<Step 2>

Compound (5) can be produced by reacting compound (4).

This reaction is carried out in the presence of an acid, without solvent or in an inert solvent.

Examples of the acid include polyphosphoric acid, methanesulfonic acid, diphosphorus pentoxide, Eaton reagent and the like.

The amount of the acid to be used is generally 1 to 1000 equivalents, preferably 1 to 10 equivalents, relative to compound (4).

Examples of the inert solvent include halogenated hydrocarbon solvents, hydrocarbon solvents, ether solvents and the like. They may be used in a mixture of two or more kinds thereof in an appropriate ratio. Among them, halogenated hydrocarbon solvents and the like are preferable.

The reaction temperature is generally –100° C. to 150° C., preferably 0° C. to 100° C.

The reaction time is generally 5 min to 48 hr, preferably 10 min to 24 hr.

<Step 3>

Compound (1a) can be produced by subjecting compound (5) to an alkylation reaction (in the case of $Y^2$ is a leaving group) or the Mitsunobu reaction ($Y^2$ is a hydroxyl group) with compound (6).

The alkylation reaction can be carried out according to the method exemplified in Step 1 or a method analogous thereto. The Mitsunobu reaction can be carried out, for example, according to the method described in Synthesis, pages 1-27, 1981, Tetrahedron Lett., vol. 36, pages 6373-6374, 1995, Tetrahedron Lett., vol. 38, pages 5831-5834, 1997 or the like, or a method analogous thereto.

To be specific, the reaction is carried out by reacting compound (5) with compound (6) in the presence of an azodicarboxylate (e.g., diethyl azodicarboxylate, diisopropyl azodicarboxylate, 1,1'-(azodicarbonyl)dipiperidine etc.) and a phosphine (e.g., triphenylphosphine, tributylphosphine etc.).

The amount of compound (6) to be used is 0.5 to 5 mol, preferably 1 to 2 mol, per 1 mol of compound (5).

The amount of the azodicarboxylate to be used is 1 to 10 mol, preferably 1 to 5 mol, per 1 mol of compound (5).

The amount of the phosphine to be used is 1 to 10 mol, preferably 1 to 5 mol, per 1 mol of compound (5).

The reaction is advantageously carried out in a solvent inert to the reaction. While the solvent is not particularly limited as long as the reaction proceeds, preferable examples thereof include nitrile solvents, amide solvents, halogenated hydrocarbon solvents, hydrocarbon solvents, ether solvents, a mixed solvent thereof and the like.

The reaction time is generally 5 min to 100 hr, preferably 30 min to 72 hr.

The reaction temperature is generally –20 to 200° C., preferably 0 to 100° C.

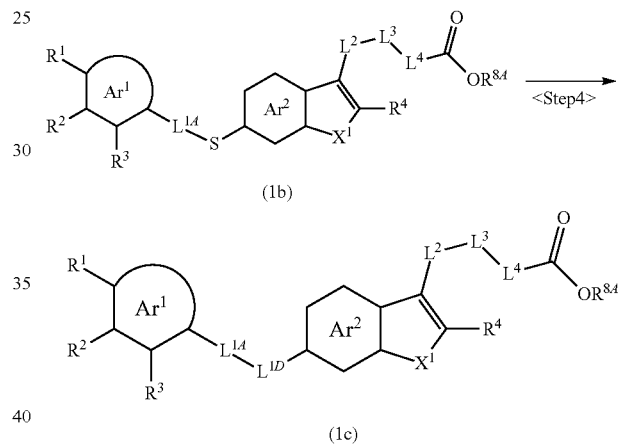

<Reaction Scheme 2> wherein $L''$ is SO or $SO_2$, and the other symbols are as defined above.

<Step 4>

Compound (1c) can be produced by subjecting compound (1b) to an oxidation reaction.

This reaction is carried out in the presence of an oxidant, in an inert solvent.

Examples of the oxidant include OXONE (registered trade mark) ($2KHSO_5 \cdot KHSO_4 \cdot K_2SO_4$), $H_2O_2$, PhIO, $LiClO_4$, $NaClO_4$, 3-chloroperbenzoic acid and the like.

The amount of the oxidant to be used is generally 1 to 100 equivalents, preferably 1 to 5 equivalents, relative to compound (1b).

Examples of the inert solvent include halogenated hydrocarbon solvents, hydrocarbon solvents, ether solvents and the like. They may be used in a mixture of two or more kinds thereof in an appropriate ratio. Among them, halogenated hydrocarbon solvents, toluene and the like are preferable.

The reaction temperature is generally –100° C. to 150° C., preferably 0° C. to 100° C.

The reaction time is generally 5 min to 48 hr, preferably 30 min to 24 hr.

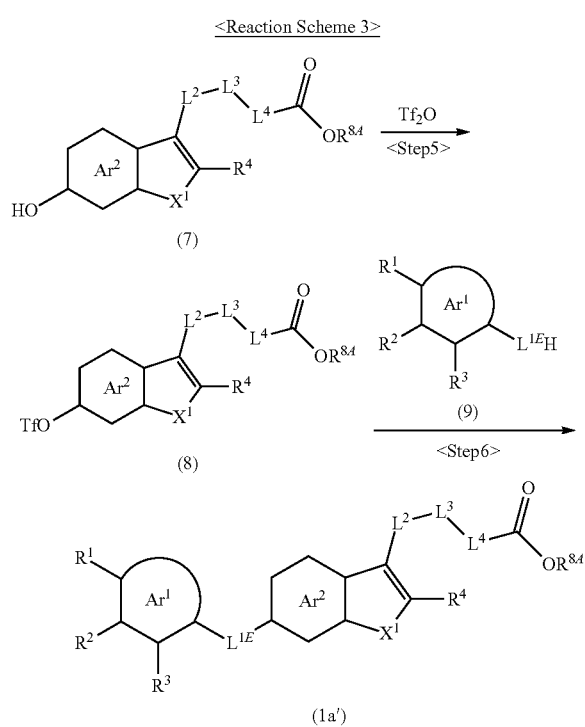

<Reaction Scheme 3> wherein $L^{1E}$ is a formula: -$L^{1A}$-$L^{1C}$- optionally substituted —CH=CH—, or —C≡C—, and the other symbols are as defined above.

<Step 5>

Compound (8) can be produced by reacting compound (7) with trifluoromethanesulfonic anhydride.

This reaction is carried out generally in the presence of a base, in an inert solvent.

The amount of the trifluoromethanesulfonic anhydride to be used is generally 1 to 10 equivalents, preferably 1 to 5 equivalents, relative to compound (7).

Preferable examples of the base include aromatic amines, tertiary amines and the like.

The amount of the base to be used is generally 1 to 100 equivalents, preferably 1 to 1.5 equivalents, relative to compound (7).

Examples of the inert solvent include aromatic solvents, aliphatic hydrocarbon solvents, ether solvents, ester solvents, amide solvents and the like. They may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 40 hr.

<Step 6>

Compound (1a') can be produced by reacting compound (8) with compound (9).

This reaction is carried out generally in the presence of a base, in an inert solvent.

The amount of compound (9) to be used is about 0.5 to 10 mol, preferably about 0.5 to 5 mol, per 1 mol of compound (8).

Examples of the base include alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal phosphates such as sodium phosphate, potassium phosphate and the like; alkali metal alkoxides having 1 to 6 carbon atoms such as sodium methoxide, sodium ethoxide, sodium tert-butoxide and the like; organic bases such as trimethylamine, triethylamine, N,N-diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithium diisopropylamide and the like, and the like.

The amount of the base to be used is about 1 to 20 mol, preferably about 1 to 5 mol, per 1 mol of compound (8).

Examples of the inert solvent include nitrile solvents, amide solvents, halogenated hydrocarbon solvents, hydrocarbon solvents, ether solvents and the like. They may be used in a mixture of two or more kinds thereof in an appropriate ratio. Among them, THF, DMF, toluene and the like are preferable.

This reaction is generally promoted by the use of a transition metal catalyst. Metal complexes containing various ligands can be used as a transition metal catalyst, and examples thereof include palladium compounds [e.g., palladium(II)acetate, tris(dibenzylideneacetone)dipalladium, tetrakis(triphenylphosphine)palladium(0), bis(triphenylphosphine)palladium(II) chloride, [1,1'-bis(diphenylphosphino)ferrocene]palladium(II) chloride, dichlorobis(triethylphosphine)palladium(II) and the like], nickel compounds [e.g., tetrakis(triphenylphosphine)nickel(0), bis(triethylphosphine)nickel(II) chloride, bis(triphenylphosphine)nickel(II) chloride and the like], rhodium compounds [e.g., tris(triphenylphosphine)rhodium(III) chloride and the like], cobalt compounds, copper compounds [e.g., copper oxide, copper(II) chloride and the like], platinum compounds and the like. Among them, palladium compounds, nickel compounds and copper compounds are preferable.

The amount of the transition metal catalyst to be used is about 0.000001 to 5 mol, preferably about 0.0001 to 1 mol, per 1 mol of compound (7). When a metal catalyst unstable for oxygen is used for the reaction, the reaction is preferably carried out in an inactive gas (e.g., argon gas or nitrogen gas) stream.

This reaction can be carried out in the presence of the above-mentioned transition metal catalyst and a ligand (e.g., phosphine etc.) separately to advantageously promote the reaction. Examples of the ligand include triphenylphosphine, 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, bis(2-diphenylphosphinophenyl)ether, 9,9-dimethyl-4,5-bis(diphenylphosphino)xanthene and the like.

The amount of the ligand to be used is generally 1 to 50 equivalents, preferably 1 to 10 equivalents, per 1 equivalent of the transition metal catalyst.

The reaction temperature is −10° C. to 250° C., preferably 0° C. to 150° C.

The reaction time is generally 1 min to 200 hr, preferably 5 min to 100 hr.

<Reaction Scheme 4>

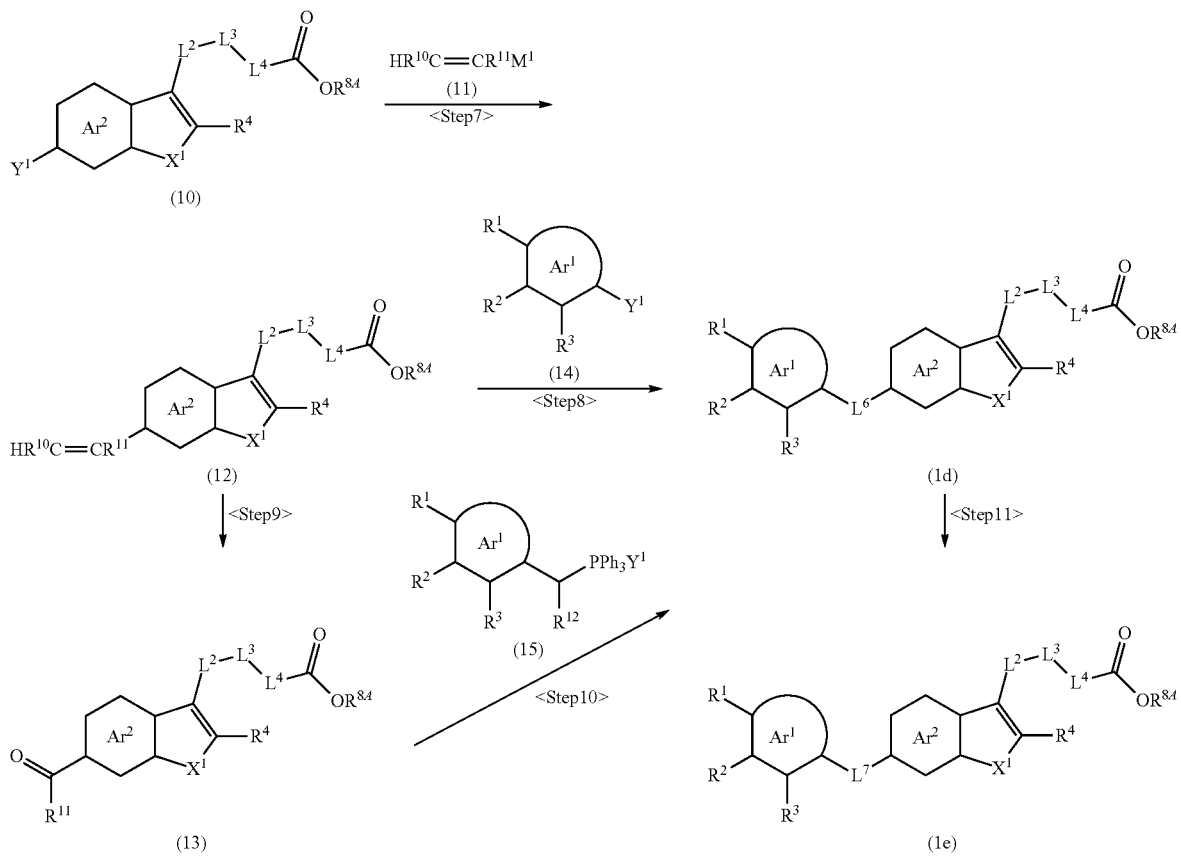

wherein $R^{10}$, $R^{11}$ and $R^{12}$ are each independently optionally substituted $C_{1-6}$ alkyl, $C_{1-6}$ alkoxy or the like, $M^1$ is a metal (e.g., boron, tin, silicon, potassium, sodium, lithium, aluminum, magnesium, copper, mercury, zinc, thallium and the like, which is optionally complexed or halogenated) or a hydrogen atom, $L^6$ is optionally substituted —CH=CH—, $L^7$ is optionally substituted —CH$_2$CH$_2$—, and the other symbols are as defined above.

<Step 7>

Compound (12) can be produced by reacting compound (10) with compound (11) according to the method exemplified in Step 6 or a method analogous thereto.

<Step 8>

Compound (1d) can be produced by reacting compound (12) with compound (14) according to the method exemplified in Step 6 or a method analogous thereto.

<Step 9>

Compound (13) can be produced by subjecting compound (12) to an oxidation reaction.

This reaction is carried out in the presence of an oxidant, in an inert solvent.

The oxidation reaction can be carried out according to a method known per se, for example, the method described in Heterocycles, pages 2263-2267, 1992 or the like or a method analogous thereto.

Examples of the oxidant include ozone, potassium permanganate, sodium periodate, osmium tetraoxide and the like.

The amount of the oxidant to be used is generally 1 to 5 equivalents, preferably 1 to 1.5 equivalents, relative to compound (12).

Examples of the inert solvent include alcohol solvents, nitrile solvents, amide solvents, halogenated hydrocarbon solvents, ether solvents, water and the like. They may be used in a mixture of two or more kinds thereof in an appropriate ratio. Among them, nitrile solvents, halogenated hydrocarbon solvents and the like are preferable.

The reaction temperature is generally −100° C. to 50° C., preferably −78° C. to 30° C.

The reaction time is generally 5 min to 48 hr, preferably 30 min to 24 hr.

<Step 10>

Compound (1d) can be produced by reacting compound (13) with compound (15) (Wittig reaction).

This reaction is carried out in the presence of a base, in an inert solvent. Examples of the base include those exemplified in Step 1, and the like.

The amount of the base to be used is generally 1 to 5 equivalents, preferably 1 to 1.5 equivalents, relative to compound (13).

The amount of compound (15) to be used is generally 0.5 to 5 equivalents, preferably 1 to 1.5 equivalents, relative to compound (13).

Examples of the inert solvent include alcohol solvents, nitrile solvents, amide solvents, halogenated hydrocarbon solvents, ether solvents and the like. They may be used in a mixture of two or more kinds thereof in an appropriate ratio. Among them, THF, DMF and the like are preferable.

The reaction temperature is generally −100° C. to 50° C., preferably −78° C. to 30° C.

The reaction time is generally 5 min to 48 hr, preferably 30 min to 24 hr.

<Step 11>

Compound (1e) can be produced by subjecting compound (1d) to a reduction reaction.

This reaction is carried out in the presence of a reducing agent, in an inert solvent.

Examples of the reducing agent include hydrogen. In this case, a catalyst (e.g., palladium carbon, palladium black, platinum dioxide, Raney-nickel, Raney-cobalt etc.) is used together with hydrogen.

The amount of the catalyst to be used is generally about 5 to about 1000 wt %, preferably about 10 to about 300 wt %, relative to compound (1d).

The hydrogenation reaction can also be carried out using various hydrogen sources instead of hydrogen gas.

Examples of the hydrogen source include formic acid, ammonium formate, triethylammonium formate, sodium phosphinate, hydrazine and the like.

The amount of the hydrogen source to be used is generally about 1 to about 10 mol, preferably about 1 to about 5 mol, per 1 mol of compound (1d).

Examples of the inert solvent include nitrile solvents, amide solvents, halogenated hydrocarbon solvents, hydrocarbon solvents, ether solvents, alcohol solvents, water and the like. They may be used in a mixture of two or more kinds thereof in an appropriate ratio. Among them, alcohol solvents are preferable.

The reaction temperature is −10° C. to 250° C., preferably 0° C.-60° C.

The reaction time is generally 1 min to 200 hr, preferably 5 min to 24 hr.

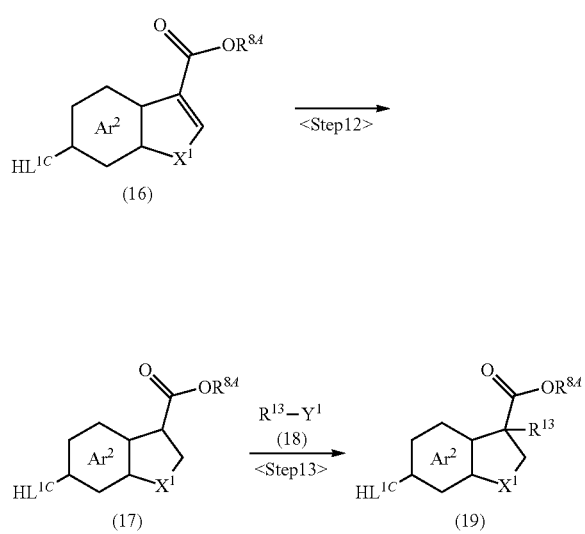

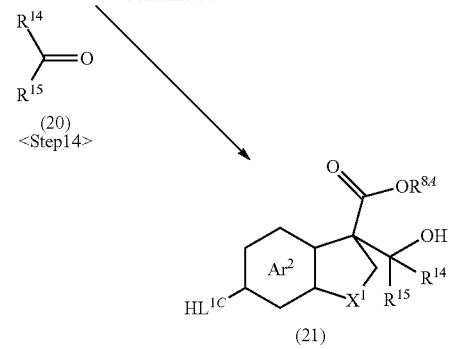

wherein $R^{13}$ is an optionally substituted $C_{1-6}$ alkyl group, $R^{14}$ and $R^{15}$ are each independently a hydrogen atom or an optionally substituted $C_{1-6}$ alkyl group, and the other symbols are as defined above.

<Step 12>

Compound (17) can be produced by reacting compound (16) according to the method exemplified in Step 11 or a method analogous thereto.

Compound (16) can be produced according to method exemplified in WO 2007/92751 or a method analogous thereto.

<Step 13>

Compound (19) can be produced by reacting compound (17) with compound (18).

This reaction is carried out in the presence of a base, in an inert solvent.

Examples of the base include those exemplified in Step 1. Examples of the inert solvent include nitrile solvents, amide solvents, halogenated hydrocarbon solvents, ether solvents, sulfoxide solvents and the like. Among them, THF, DMF and the like are preferable.

The amount of the base to be used is generally 1 to 5 equivalents, preferably 1 to 1.5 equivalents, relative to compound (17).

The amount of compound (18) to be used is generally 0.5 to 5 equivalents, preferably 1 to 1.5 equivalents, relative to compound (17).

The reaction temperature is generally −100° C. to 100° C., preferably −78° C. to 60° C.

The reaction time is generally 5 min to 48 hr, preferably 30 min to 24 hr.

<Step 14>

Compound (21) can be produced by reacting compound (17) with compound (20).

This reaction is carried out in the presence of a base, in an inert solvent.

Examples of the base include those exemplified in Step 1. Examples of the inert solvent include nitrile solvents, amide solvents, halogenated hydrocarbon solvents, ether solvents, sulfoxide solvents and the like. Among them, THF, DMF, DMSO and the like are preferable.

The amount of the base to be used is generally 1 to 5 equivalents, preferably 1 to 1.5 equivalents, relative to compound (17).

The amount of compound (20) to be used is generally 0.5 to 5 equivalents, preferably 1 to 1.5 equivalents, relative to compound (17).

The reaction temperature is generally −100° C. to 100° C., preferably −78° C. to 60° C.

The reaction time is generally 5 min to 48 hr, preferably 30 min to 24 hr.

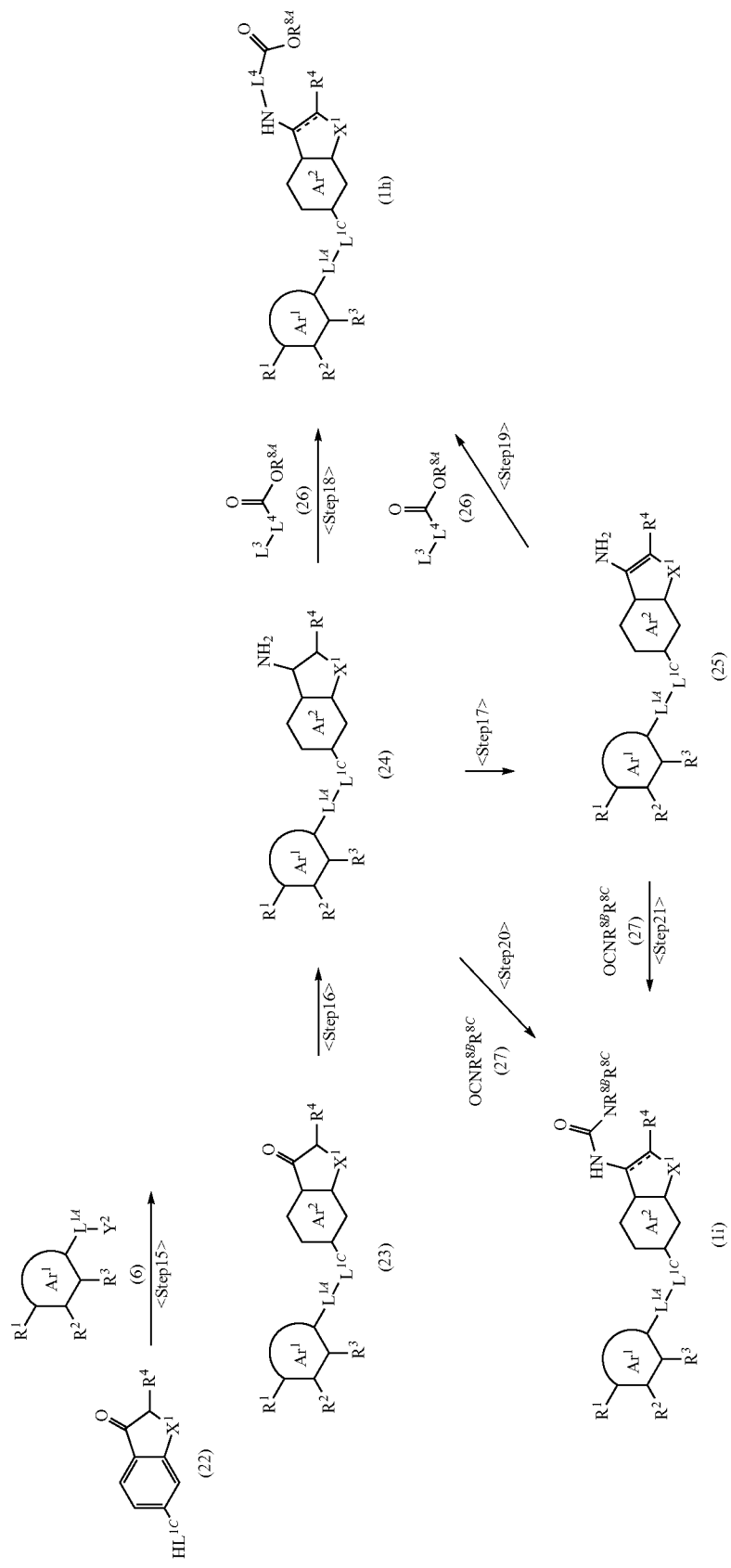

wherein Y³ is a leaving group, and the other symbols are as defined above.

Examples of the leaving group for Y³ include those similar to the leaving group for Y¹.

<Step 15>

Compound (23) can be produced by reacting compound (22) with compound (6) according to the method exemplified in Step 3 or a method analogous thereto.

<Step 16>

Compound (24) can be produced by subjecting compound (23) to a reduction amination reaction with an ammonia, O-methylhydroxylamine, ammonium chloride or O-methylhydroxylammonium chloride (e.g., the method described in 4th Edition Jikken Kagaku Kouza, vol. 20, pages 282-284 and 366-368 (The Chemical Society of Japan ed.); J. Am. Chem. Soc., vol. 93, pages 2897-2904, 1971; Synthesis, page 135, 1975 or the like).

To be specific, compound (24) can be produced by subjecting the imine compound (which is obtained by subjecting compound (23) to a dehydrating reaction with ammonia, O-methylhydroxylamine, ammonium chloride or O-methylhydroxylammonium chloride) to a reduction reaction in an inert solvent.

The dehydrating reaction can be promoted by adding a dehydrating agent (e.g., molecular sieves etc.) p-toluenesulfonic acid, zinc chloride, phosphoryl chloride, boron trifluoride, titanium tetrachloride, acetic acid, trifluoroacetic acid or the like to the reaction system, or by removing the water generated in the reaction system using Dean-Stark trap and the like, or by the combination thereof.

The amount of the ammonia, O-methylhydroxylamine, ammonium chloride or O-methylhydroxylammonium chloride to be used is generally 1 to 1000 mol, preferably 1 to 10 mol, per 1 mol of compound (23).

The reduction reaction is generally carried out using a reducing agent according to a conventional method.

Examples of the reducing agent include metal hydrides such as aluminum hydride, diisobutylaluminum hydride, tributyltin hydride and the like; metal hydride complex compounds such as sodium cyanoborohydride, sodium triacetoxyborohydride, sodium borohydride, lithium aluminum hydride and the like; borane complexes such as borane tetrahydrofuran complex, borane dimethylsulfide complex, picoline-borane complex and the like; alkylboranes such as hexylborane, disiamylborane and the like; diborane; metals such as zinc, aluminum, tin, iron and the like; alkali metal (e.g., sodium, lithium etc.)/liquid ammonia (Birch reduction), and the like.

The amount of the reducing agent to be used is generally about 0.25 to about 10 mol, preferably about 0.5 to about 5 mol, per 1 mol of compound (23).

Alternatively, the reduction reaction can also be carried out employing a hydrogenation reaction. In this case, a catalyst (e.g., palladium carbon, palladium black, platinum dioxide, Raney-nickel, Raney-cobalt etc.) can be used.

The amount of the catalyst to be used is generally about 5 to about 1000 wt %, preferably about 10 to about 300 wt %, relative to compound (23).

The hydrogenation reaction can also be carried out using various hydrogen sources instead of hydrogen gas.

Examples of the hydrogen source include formic acid, ammonium formate, triethylammonium formate, sodium phosphinate, hydrazine and the like.

The amount of the hydrogen source to be used is generally about 1 to about 10 mol, preferably about 1 to about 5 mol, per 1 mol of compound (23).

Examples of the inert solvent include halogenated hydrocarbon solvents, hydrocarbon solvents, ether solvents, water and the like. They may be used in a mixture of two or more kinds thereof in an appropriate ratio. Among them, THF, DMF and the like are preferable.

The reaction temperature is generally −100° C. to 150° C., preferably 0° C. to 100° C.

While the reaction time varied depending on the kind of the reagent and solvent to be used, it is generally 10 min to 100 hr, preferably 30 min to 50 hr.

<Step 17>

Compound (25) can be produced by subjecting compound (24) to an oxidation reaction.

This reaction is carried out in the presence of an oxidant, in an inert solvent.

Examples of the oxidant include 2,3-dichloro-5,6-dicyano-1,4-benzoquinone, manganese dioxide and the like.

The amount of the oxidant to be used is generally 1 to 100 equivalents, preferably 1 to 5 equivalents, relative to compound (25).

Examples of the inert solvent include halogenated hydrocarbon solvents, hydrocarbon solvents, ether solvents and the like. They may be used in a mixture of two or more kinds thereof in an appropriate ratio. Among them, halogenated hydrocarbon solvents, toluene and the like are preferable.

The reaction temperature is generally −100° C. to 150° C., preferably 0° C. to 100° C.

The reaction time is generally 5 min to 48 hr, preferably 30 min to 24 hr.

<Step 18>

Compound (1h) can be produced by reacting compound (24) with compound (26) according to the method exemplified in Step 1 or a method analogous thereto.

<Step 19>

Compound (1h) can be produced by reacting compound (25) with compound (26) according to the method exemplified in Step 1 or a method analogous thereto.

<Step 20>

Compound (1i) can be produced by reacting compound (24) with compound (27).

This reaction is carried out in the presence of a base, in an inert solvent.

Examples of the base include those exemplified in Step 1. Examples of the inert solvent include nitrile solvents, amide solvents, halogenated hydrocarbon solvents, ether solvents and the like. Among them, THF, DMF and the like are preferable.

The amount of the base to be used is generally about 0.25 to about 10 mol, preferably about 0.5 to about 5 mol, per 1 mol of compound (24).

The amount of compound (27) to be used is generally about 0.25 to about 10 mol, preferably about 0.5 to about 5 mol, per 1 mol of compound (24).

The reaction temperature is generally −100° C. to 100° C., preferably 0° C. to 60° C.

The reaction time is generally 5 min to 48 hr, preferably 30 min to 24 hr.

<Step 21>

Compound (ii) can be produced by reacting compound (25) with compound (27) according to the method exemplified in Step 20 or a method analogous thereto.

<Reaction Scheme 7>

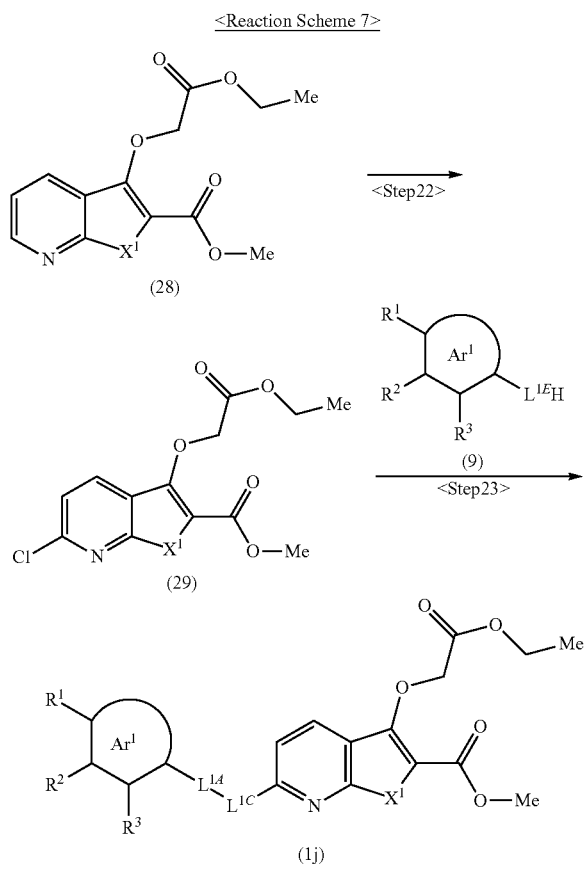

wherein each symbol is as defined above.

<Step 22>

Compound (29) can be produced by chlorinating compound (28).

This reaction is carried out by reacting compound (28) in the presence of an oxidant, in an inert solvent, and then reacting the resulting compound with a chlorinating agent.

Examples of the oxidant include those exemplified in Step 4. Examples of the inert solvent include nitrile solvents, amide solvents, halogenated hydrocarbon solvents, ether solvents and the like. Among them, acetonitrile and the like are preferable.

The amount of the oxidant to be used is generally 1 to 100 mol, preferably 1 to 10 mol, per 1 mol of compound (28).

Examples of the chlorinating agent include $POCl_3$, $(COCl)_2$, $SOCl_2$ and the like.

The amount of the chlorinating agent to be used is generally 1 to 1000 mol, preferably 1 to 100 mol, per 1 mol of compound (28).

The reaction time is generally 10 min to 100 hr, preferably 30 min to 50 hr.

The reaction temperature is generally −20 to 100° C., preferably 30 to 100° C.

Compound (28) can be produced according to the method exemplified in Bioorganic & Medicinal Chemistry 14 (2006), 2162 or a method analogous thereto.

<Step 23>

Compound (1j) can be produced by reacting compound (29) with compound (9). This reaction can be carried out according to the method shown in Step 3 or Step 6 or a method analogous thereto.

<Reaction Scheme 8>

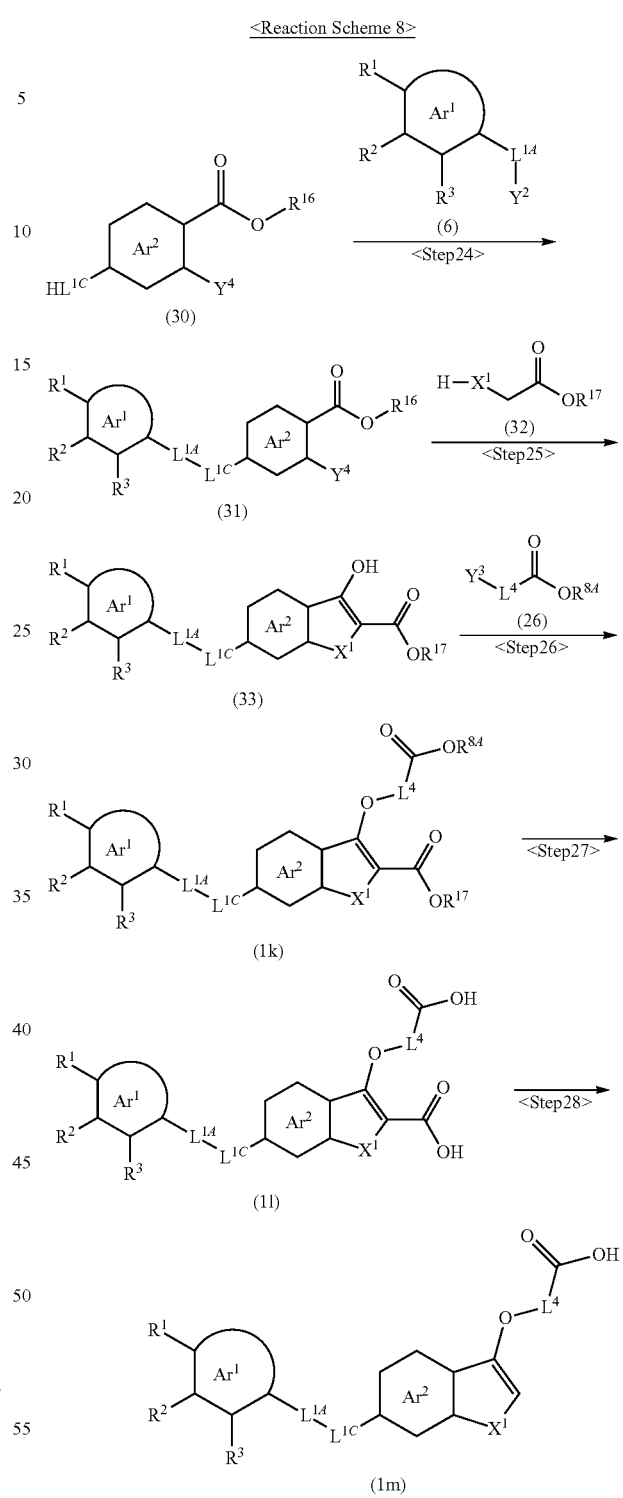

wherein $Y^4$ is a leaving group, $R^{16}$ and $R^{17}$ are each independently an optionally substituted $C_{1-6}$ alkyl group, and the other symbols are as defined above.

<Step 24>

Compound (31) can be produced by reacting compound (30) with compound (6) according to the method exemplified in Step 3 or a method analogous thereto.

<Step 25>

Compound (33) can be produced by reacting compound (31) with compound (32) according to the method exemplified in Step 1 or a method analogous thereto.

<Step 26>

Compound (1k) can be produced by reacting compound (33) with compound (26) according to the method exemplified in Step 1 or a method analogous thereto.

<Step 27>

Compound (11) can be produced by subjecting compound (1k) to hydrolysis.

This reaction is carried out in the presence of a base, in an inert solvent.

Examples of the base include inorganic bases such as lithium hydroxide, sodium hydroxide and the like, and the like.

The amount of the base to be used is generally 1 to 10 equivalents, preferably 1 to 1.5 equivalents, relative to compound (1k).

Examples of the inert solvent include alcohol solvents, nitrile solvents, aromatic solvents, aliphatic hydrocarbon solvents, ether solvents, amide solvents, halogenated hydrocarbon solvents and the like. They may be used in a mixture of two or more kinds thereof in an appropriate ratio, preferably in mixture with water in an appropriate ratio. Among them, alcohol solvents, THF are preferable.

The reaction temperature is generally −78° C. to 150° C., preferably −20° C. to 100° C.

The reaction time is generally 5 min to 100 hr, preferably 30 min to 24 hr.

<Step 28>

Compound (1m) can be produced by subjecting compound (11) to decarboxylation.

This reaction is carried out in the presence of a base, without solvent or in an inert solvent.

Examples of the base include organic bases such as quinoline, 1,8-diazabicyclo[5.4.0]-7-undecene and the like, and the like.

The amount of the base to be used is about 1 to 10000 mol, preferably about 1 to 100 mol, per 1 mol of compound (11).

This reaction can be promoted by using a metal catalyst.

Preferable examples of the metal catalyst include copper.

The amount of the metal catalyst to be used is about 0.01 to 5 mol, preferably about 0.01 to 1 mol, per 1 mol of compound (11).

Examples of the inert solvent include alcohol solvents, nitrile solvents, aromatic solvents, aliphatic hydrocarbon solvents, ether solvents, amide solvents, halogenated hydrocarbon solvents and the like. Among them, amide solvents are preferable.

The reaction temperature is generally −78° C. to 250° C., preferably 100° C. to 180° C.

The reaction time is generally 5 min to 100 hr, preferably 30 min to 24 hr.

<Reaction Scheme 9>

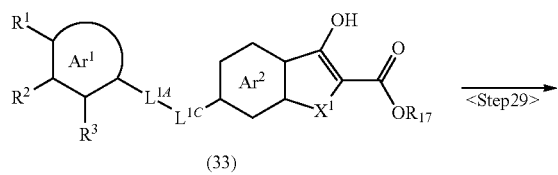

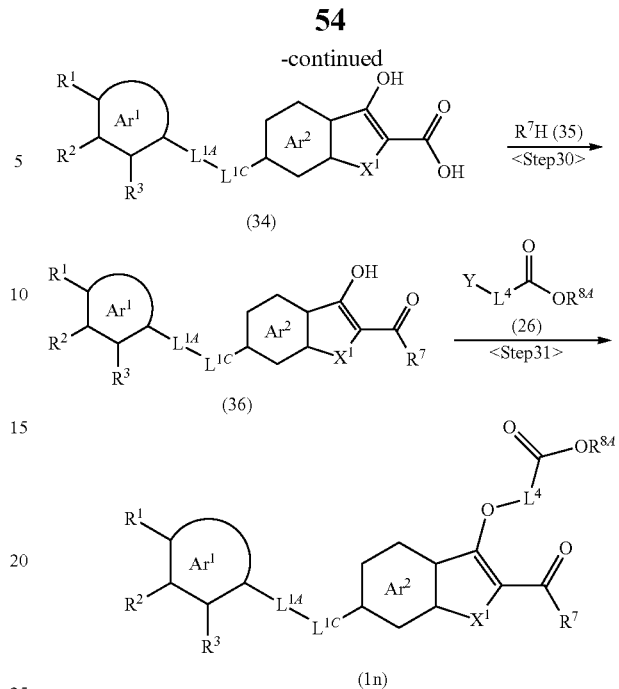

wherein each symbol is as defined above.

<Step 29>

Compound (34) can be produced by reacting compound (33) according to the method exemplified in Step 27 or a method analogous thereto.

<Step 30>

Compound (36) can be produced by subjecting compound (34) to an amidation or esterification reaction with compound (35). The above-mentioned reaction contains the method using the following dehydrating condensing agent, the method using the reactive derivative of the carboxylic acid, and the like.

i) Method Using a Dehydrating Condensing Agent

The method is performed by reacting compound (34) with compound (35) in the presence of a dehydrating condensing agent, in an inert solvent. Where necessary, the reaction can be carried out in the presence of 1-hydroxybenzotriazole (HOBt) in an amount of a catalytic amount to 5 equivalents, a base in an amount of a catalytic amount to 5 equivalents, or the like.

The amount of compound (35) to be used is generally 0.5 to 5 equivalents, preferably 1 to 1.5 equivalents, relative to compound (34).

Examples of the dehydrating condensing agent include dicyclohexylcarbodiimide (DCC), 1-ethyl-3-(3-dimethylaminopropyl)carbodiimide hydrochloride (EDCI), O-(7-azabenzotriazol-1-yl)-N,N,N',N'-tetramethyluronium hexafluorophosphate (HATU) and the like. Among them, EDCI is preferable.

The amount of the dehydrating condensing agent to be used is generally 1 to 10 equivalents, preferably 1 to 5 equivalents, relative to Compound (34).

Examples of the inert solvent include nitrile solvents, amide solvents, halogenated hydrocarbon solvents, ether solvents and the like. They may be used in a mixture of two or more kinds thereof in an appropriate ratio. Among them, amide solvents are preferable.

Examples of the base include aromatic amines, tertiary amines and the like. The reaction temperature is generally −70 to 150° C., preferably −20 to 100° C.

The reaction time is generally 0.1 to 100 hr, preferably 1 to 48 hr.

ii) Method Using the Reactive Derivative of the Carboxylic Acid

The method is performed by reacting the reactive derivative of compound (34) with compound (35) in an amount of 0.5 to 5 equivalents (preferably 0.8 to 3 equivalents) in an inert solvent. Where necessary, the reaction can be carried out in the presence of a base in an amount of 1 to 10 equivalents, preferably 1 to 3 equivalents.

Examples of the reactive derivative of compound (34) include acid halides (e.g., acid chlorides, acid bromides), mixed acid anhydrides (e.g., acid anhydrides with a $C_{1-6}$ alkyl-carboxylic acid, a $C_{6-10}$ aryl-carboxylic acid, a $C_{1-6}$ alkylcarbonic acid etc.), activated esters (e.g., esters with phenol optionally having substituent(s), HOBt, N-hydroxysuccinimide etc.) and the like. The reactive derivative is preferably an acid halide.

Examples of the inert solvent include ether solvents, halogenated hydrocarbon solvents, aromatic solvents, aliphatic hydrocarbon solvents, nitrile solvents, amide solvents, ketone solvents, sulfoxide solvents, water and the like. They may be used in a mixture of two or more kinds thereof in an appropriate ratio. Among them, acetonitrile, THF, dichloromethane, chloroform and the like are preferable.

Examples of the base include aromatic amines, tertiary amines and the like.

The reaction temperature is generally −20 to 100° C., preferably −20° C. to 50° C.

The reaction time is generally 5 min to 40 hr, preferably 30 min to 18 hr.

<Step 31>

Compound (1n) can be produced by reacting compound (36) with compound (26) according to the method exemplified in Step 1 or a method analogous thereto.

<Reaction Scheme 10>

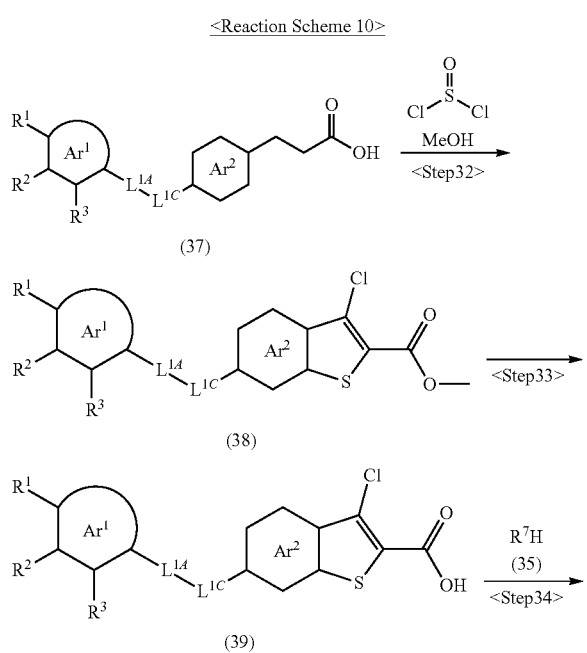

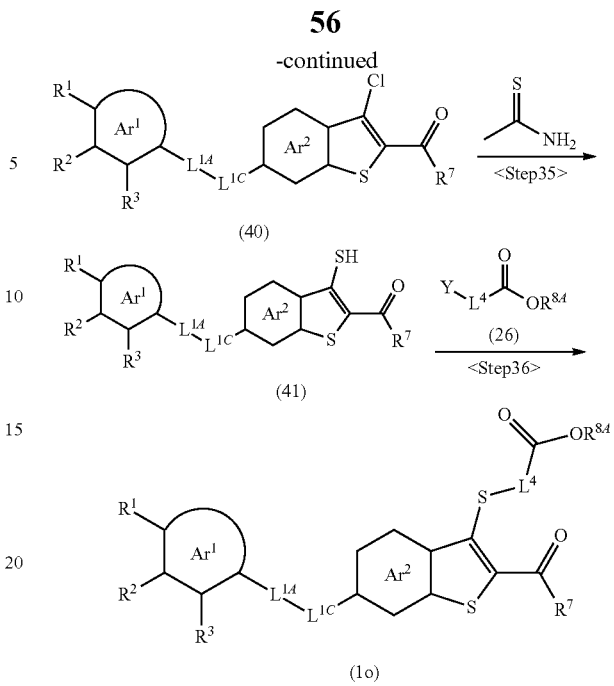

wherein each symbol is as defined above.

<Step 32>

Compound (38) can be produced by reacting compound (37) with thionyl chloride and then methanol.

This reaction is carried out in the presence of a base, in an inert solvent.

Examples of the base include those exemplified in Step 1. Among them, pyridine and the like are preferable.

The amount of the base to be used is generally 1 to 100 equivalents, preferably 1 to 1.5 equivalents, relative to compound (37).

The amount of the thionyl chloride to be used is generally 1 to 100 equivalents, preferably 1- to 1.5 equivalents, relative to compound (37).

The amount of the methanol to be used is generally 1 to 100 equivalents, preferably 1 to 1.5 equivalents, relative to compound (37).

Examples of the inert solvent include alcohol solvents, nitrile solvents, aromatic solvents, aliphatic hydrocarbon solvents, ether solvents, amide solvents, halogenated hydrocarbon solvents and the like. Among them, aromatic solvents are preferable.

The reaction temperature is generally 20 to 180° C., preferably 80° C. to 150° C.

The reaction time is generally 5 min to 40 hr, preferably 30 min to 18 hr.

<Step 33>

Compound (39) can be produced by reacting compound (38) according to the method exemplified in Step 27 or a method analogous thereto.

<Step 34>

Compound (40) can be produced by reacting compound (39) with compound (35) according to the method exemplified in Step 30 or a method analogous thereto.

<Step 35>

Compound (41) can be produced by reacting compound (40) with thioacetamide.

This reaction is carried out in the presence of a base, in an inert solvent.

Examples of the base include those exemplified in Step 1. Among them, 1,8-diazabicyclo[5.4.0]-7-undecene and the like are preferable.

The amount of the base to be used is generally 1 to 100 equivalents, preferably 1 to 1.5 equivalents, relative to compound (40).

The amount of the thioacetamide to be used is generally 1 to 100 equivalents, preferably 1 to 1.5 equivalents, relative to compound (40).

Examples of the inert solvent include halogenated hydrocarbon solvents, hydrocarbon solvents, ether solvents and the like. They may be used in a mixture of two or more kinds thereof in an appropriate ratio. Among them, DMF and the like are preferable.

The reaction temperature is generally 20 to 150° C., preferably 50° C. to 100° C.

The reaction time is generally 5 min to 40 hr, preferably min to 18 hr.
<Step 36>

Compound (1o) can be produced by reacting compound (41) with compound (26) according to the method exemplified in Step 1 or a method analogous thereto.

<Reaction Scheme 11>

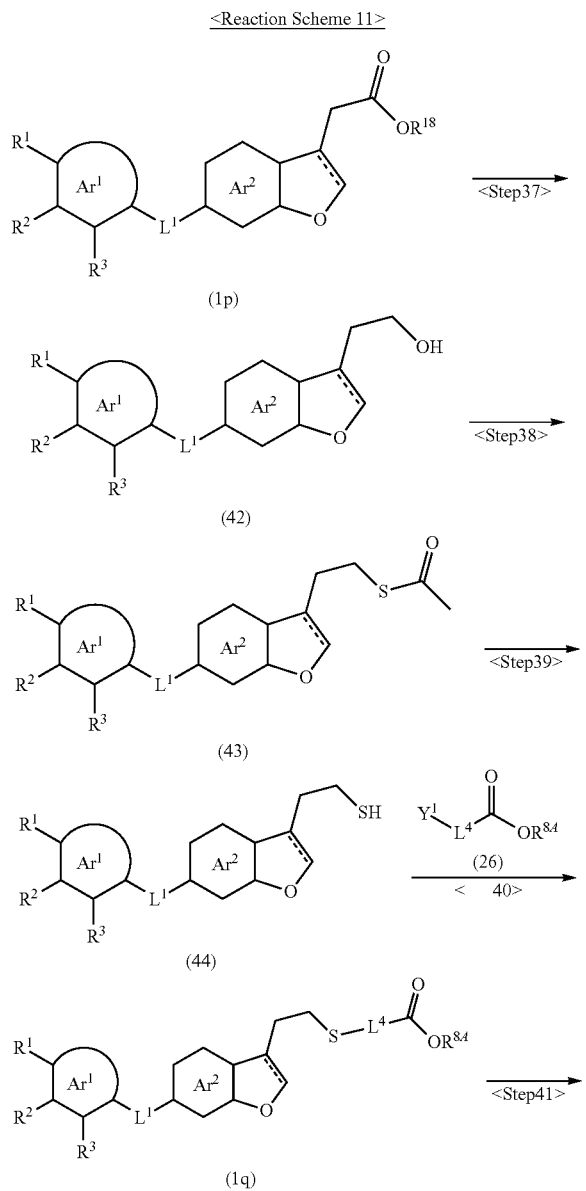

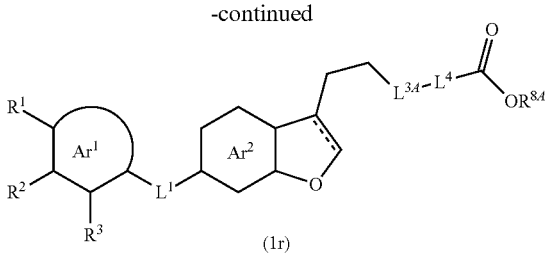

(1r)

wherein $L^{3A}$ is SO or $SO_2$, $R^{18}$ is an optionally substituted $C_{1-6}$ alkyl group, and the other symbols are as defined above.
<Step 37>

Compound (42) can be produced by subjecting compound (1p) to a reduction reaction.

This reaction is carried out in the presence of a reducing agent, in an inert solvent.

Examples of the reducing agent include metal hydrogen compounds (e.g., sodium aluminum bis(2-methoxyethoxy)hydride, diisobutylaluminum hydride), metal hydride complex compounds (e.g., sodium borohydride, lithium borohydride, lithium aluminum hydride, sodium aluminum hydride) and the like.

The amount of the reducing agent to be used is generally 0.1 to 20 equivalents, preferably 1 to 5 equivalents, relative to compound (1p).

Examples of the inert solvent include alcohol solvents, aromatic solvents, aliphatic hydrocarbon solvents, ether solvents, ester solvents, amide solvents and the like. Among them, THF and the like are preferable. They may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 40 hr.

Compound (1p) can be produced according to the method exemplified in WO 2008/001931 or a method analogous thereto.
<Step 38>

Compound (43) can be produced by reacting compound (42) with a halogenating agent or a sulfonylating agent, and then reacting the resulting compound with potassium thioacetate.

Examples of the halogenating agent include thionyl chloride and the like.

Examples of the sulfonylating agent include methanesulfonyl chloride, p-toluenesulfonyl chloride and the like.

This reaction is carried out in the presence of a base, in an inert solvent.

Examples of the base include those exemplified in Step 1. Among them, triethylamine and the like are preferable.

The amount of the base to be used is generally 0.1 to 20 equivalents, preferably 1 to 5 equivalents, relative to compound (42).

The amount of the halogenating agent or sulfonylating agent to be used is generally 0.1 to 20 equivalents, preferably 1 to 5 equivalents, relative to compound (42).

The amount of the potassium thioacetate to be used is generally 0.1 to 20 equivalents, preferably 1 to 5 equivalents, relative to compound (42).

Examples of the inert solvent include aromatic solvents, aliphatic hydrocarbon solvents, ether solvents, ester solvents, amide solvents and the like. They may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 40 hr.

<Step 39>

Compound (44) can be produced by reacting compound (43) according to the method exemplified in Step 27 or a method analogous thereto.

<Step 40>

Compound (1q) can be produced by reacting compound (44) with compound (26) according to the method exemplified in Step 1 or a method analogous thereto.

<Step 41>

Compound (1r) can be produced by reacting compound (1q) according to the method exemplified in Step 4 or a method analogous thereto.

The amount of the sodium azide to be used is generally 0.1 to 20 equivalents, preferably 1 to 5 equivalents, relative to compound (42).

Examples of the reducing agent include those exemplified in Step 7. Among them, platinum and the like are preferable.

The amount of the reducing agent to be used is generally 0.1 to 20 equivalents, preferably 1 to 5 equivalents, relative to compound (42).

Examples of the inert solvent include aromatic solvents, aliphatic hydrocarbon solvents, ether solvents, ester solvents, alcohol solvents, amide solvents and the like. They may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 40 hr.

<Step 43>

Compound (1s) can be produced by reacting compound (45) with compound (46) according to the method exemplified in Step 30 or a method analogous thereto.

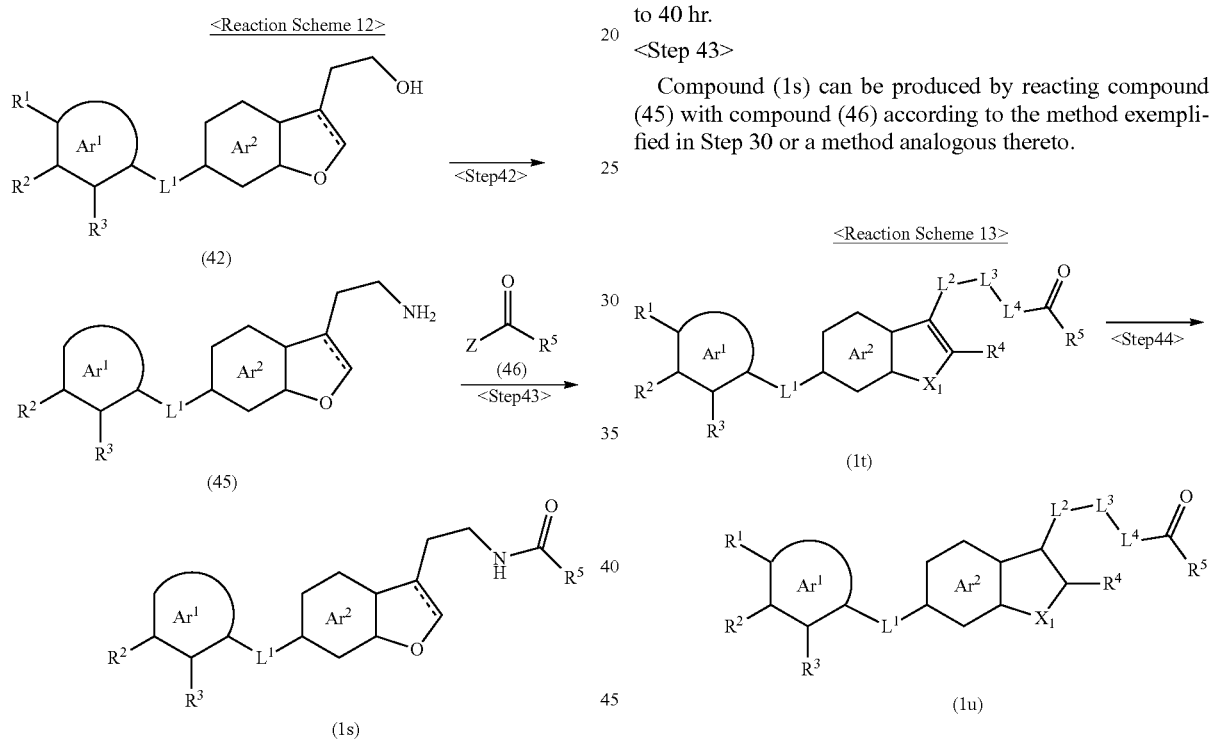

wherein Z is a chlorine atom, a hydroxyl group or OCOR$^5$, and the other symbols are as defined above.

<Step 42>

Compound (45) can be produced by reacting compound (42) with a halogenating agent or a sulfonylating agent in the presence of a base, in an inert solvent reaction, reacting the resulting compound with sodium azide in an inert solvent, and reacting the resulting compound with a reducing agent in an inert solvent.

Examples of the halogenating agent or sulfonylating agent include those exemplified in Step 38.

The amount of the halogenating agent or sulfonylating agent to be used is generally 0.1 to 20 equivalents, preferably 1 to 5 equivalents, relative to compound (42).

Examples of the base include those exemplified in Step 1. Among them, triethylamine and the like are preferable.

The amount of the base to be used is generally 0.1 to 20 equivalents, preferably 1 to 5 equivalents, relative to compound (42).

wherein each symbol is as defined above.

<Step 44>

Compound (1u) can be produced by subjecting compound (1t) to a reduction reaction according to the method exemplified in Step 11 or a method analogous thereto.

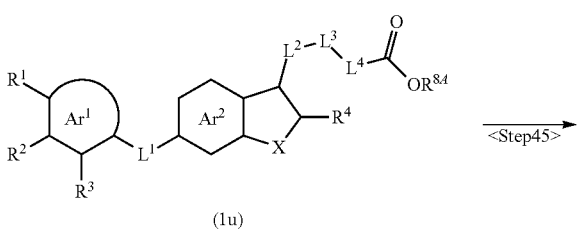

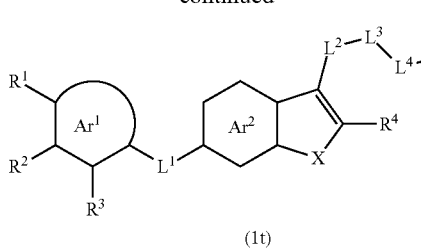

(1t)

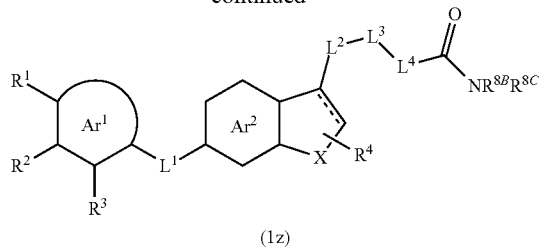

(1z)

wherein each symbol is as defined above.

<Step 45>

Compound (1t) can be produced by reacting compound (1u) according to the method exemplified in Step 17 or a method analogous thereto.

<Reaction Scheme 15>

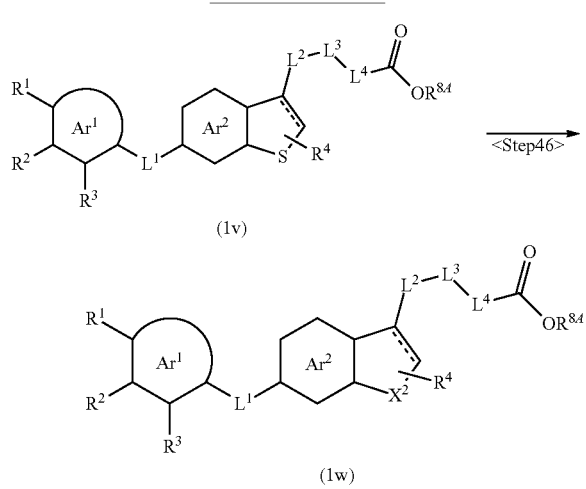

wherein $X^2$ is SO or $SO_2$, and the other symbols are as defined above.

<Step 46>

Compound (1w) can be produced by reacting compound (1v) according to the method exemplified in Step 4 or a method analogous thereto.

<Reaction Scheme 16>

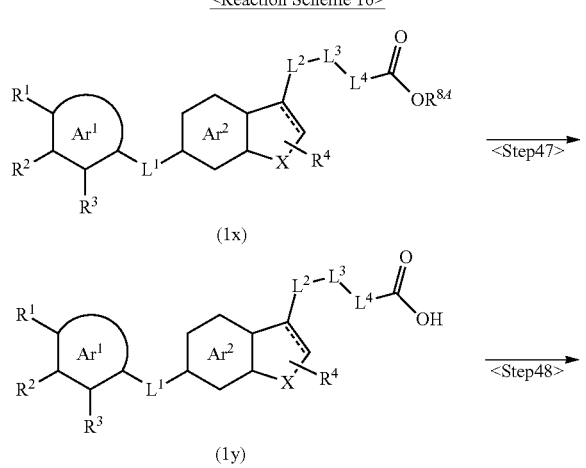

wherein each symbol is as defined above.

<Step 47>

Compound (1y) can be produced by subjecting compound (1x) wherein $R^{8A}$ is an optionally substituted $C_{1-6}$ alkyl group to hydrolysis. This reaction can be carried out according to the method exemplified in Step 27 or a method analogous thereto.

<Step 48>

Compound (1z) can be produced by reacting compound (1y) according to the method exemplified in Step 30 or a method analogous thereto.

In compound (I) thus obtained, a functional group within a molecule can also be converted to a desired functional group by a combination of chemical reactions known per se. Examples of the chemical reaction here include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production methods can be isolated and purified by a known means, for example, solvent extraction, liquid conversion, phase transfer, crystallization, recrystallization, chromatography and the like.

When compound (I) contains an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced by a method known per se.

Compound (I) may be a crystal.

Crystals of compound (I) (hereinafter sometimes to be abbreviated as the crystals of the present invention) can be produced by crystallization according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Examples, the following abbreviations are used.
mp: melting point, DMF: N,N-dimethylformamide, DMA: N,N-dimethylacetamide, THF: tetrahydrofuran, DMSO: dimethyl sulfoxide, DME:1,2-dimethoxyethane, $Et_2O$: diethyl ether, PE: petroleum ether, EtOAc: ethyl acetate, MeOH: methanol, EtOH: ethanol, t-BuOH: 2-methyl-2-propanol, IPE: diisopropyl ether, IPA: 2-propanol, DCM: dichloromethane, ADDP: 1,1'-(azodicarbonyl)dipiperidine, TsOH: p-toluenesulfonic acid, MsOH: methanesulfonic acid, DMAP: (4-dimethylamino)pyridine, TFA: trifluoroacetic acid, TFAA: trifluoroacetic anhydride, $Tf_2O$: trifluoromethanesulfonic anhydride, TEA: triethylamine, TBAF: tetrabutylammonium fluoride, DIPEA: N,N-diisopropylethylamine, mCPBA: m-chloroperbenzoic acid, EDCI: 1-(3-dimethylaminopropyl)-3-ethylcarbpdiimide hydrochloride, HOBt: 1-hydroxybenzotriazole, HATU: O-(7-azabenzotriazol-1-yl)-N,N,N',N'-tetramethyluronium hexafluorophosphate, DBU: 1,8-diazabicyclo[5.4.0]undec-7-ene, NMO: 4-methylmorpholine N-oxide, DPPA: diphenyl phosphoryl azide, DDQ: 2,3-dichloro-5,6-dicyano-p-benzoquinone, $Pd(OAc)_2$: palladium(II)acetate, $Pd(Ph_3P)_4$: tetrakis(triphenylphosphine)palladium(0), $PdCl_2(dppf)$: [1,1'-bis(diphenylphosphino)ferrocene]dichloro palladium(II), $Pd_2(dba)_3$: tris(dibenzylideneacetone)dipalladium (0), $AcONH_4$: ammonium acetate $^1H$ NMR (proton nuclear magnetic resonance spectrum) was measured by Fourier-transform type NMR. For the analysis, ACD/SpecManager (trade name) and the like were used. Protons with very broad peaks such as hydroxyl group, amino group and the like are not described.

Other abbreviations used in the specification mean the following.
s: singlet
d: doublet
t: triplet
q: quartet
m: multiplet
brs: broad singlet
J: coupling constant
Hz: hertz
$CDCl_3$: deuterated chloroform
DMSO-$d_6$: $d_6$-dimethyl sulfoxide
MeOD: deuterated methanol
$^1$H-NMR: proton nuclear magnetic resonance MS (mass spectrum) was measured by LC/MS (liquid chromatography mass spectrometer). As the ionization method, ESI (ElectroSpray Ionization) method, or APCI (Atmospheric Pressure Chemical Ionization) method was used. As an ionization mode, both or either of positive mode (ESI+) and negative mode (ESI−) was described. The data indicates those found. Generally, a molecular ion peak is observed. In the case of a compound having a tert-butoxycarbonyl group (—Boc), a peak after elimination of a tert-butoxycarbonyl group or tert-butyl group may be observed as a fragment ion. Depending on the compound, a molecular ion peak after addition of sodium ion (+Na) may be observed as a fragment ion. In the case of a compound having a hydroxyl group (—OH), a peak after elimination of $H_2O$ may be observed as a fragment ion. In the case of a salt, a molecular ion peak or fragment ion peak of free form is generally observed.

Example 1

Ethyl(6-((2,4-dichlorobenzyl)oxy)-1-benzothiophen-3-yl)acetate

To a mixture of ethyl(6-hydroxy-1-benzothiophen-3-yl) acetate (11.0 g) and DMF (200 mL) were added 2,4-dichlorobenzyl chloride (10.9 g) and $K_2CO_3$ (9.60 g). The mixture was stirred at 20° for 16 h. The mixture was diluted with EtOAc, and washed successively with water and brine. The organic layer was dried over anhydrous $Na_2SO_4$ and concentrated in vacuo. The residue was purified by silica gel column chromatography (EtOAc/PE) to give the title compound (15.5 g).
$^1$H NMR (400 MHz, $CDCl_3$) 51.19 (3H, t, J=7.2 Hz), 3.74 (2H, s), 4.10 (2H, q, J=7.2 Hz), 5.11 (2H, s), 7.03 (1H, dd, J=8.8, 2.4 Hz), 7.13 (1H, s), 7.18-7.22 (1H, m), 7.31 (1H, d, J=2.4 Hz), 7.37 (1H, d, J=2.0 Hz), 7.45 (1H, d, J=8.4 Hz), 7.60 (1H, d, J=8.8 Hz).

Example 2

(6-((2,4-Dichlorobenzyl)oxy)-1-benzothiophen-3-yl) acetic acid

To a mixture of ethyl(6-((2,4-dichlorobenzyl)oxy)-1-benzothiophen-3-yl)acetate (200 mg), MeOH (2.0 mL), THF (dry) (3.0 mL) and water (1.0 mL) was added lithium hydroxide hydrate (63.7 mg). The mixture was stirred at room temperature for 1 h. After the mixture was concentrated, the residue was neutralized with 1M HCl, and the mixture was extracted with EtOAc. The organic layer was washed with brine, dried over $MgSO_4$, filtered, and concentrated in vacuo. The residual solid was crystallized from EtOAc-hexane to give the title compound (177.7 mg).
$^1$H NMR (300 MHz, DMSO-$d_6$) δ3.79 (2H, s), 5.22 (2H, s), 7.12 (1H, dd, J=8.9, 2.5 Hz), 7.39 (1H, s), 7.49 (1H, dd, J=8.3, 2.3 Hz), 7.63-7.72 (4H, m), 12.40 (1H, brs).

Example 3

Ethyl(6-((2,6-dimethylpyridin-3-yl)methoxy)-1-benzothiophen-3-yl)acetate

To a mixture of tri-n-butylphosphine (7.10 mL), (2,6-dimethylpyridin-3-yl)methanol (3.00 g), ethyl(6-hydroxy-1-benzothiophen-3-yl)acetate (5.43 g) and THF (150 mL) was added ADDP (7.17 g) at room temperature. The mixture was stirred at room temperature under nitrogen atmosphere overnight. The mixture was concentrated. To the residue was added IPE and the precipitate was filtered off. The filtrate was concentrated in vacuo. The residue was purified by silica gel column chromatography (EtOAc/hexane) to give the title compound (7.74 g)
$^1$H NMR (300 MHz, $CDCl_3$) δ1.19-1.32 (3H, m), 2.54 (3H, s), 2.58 (3H, s), 3.81 (2H, d, J=0.8 Hz), 4.17 (2H, q, J=7.2 Hz), 5.08 (2H, s), 7.02 (1H, d, J=7.9 Hz), 7.08 (1H, dd, J=8.7, 2.3 Hz), 7.19 (1H, t, J=0.9 Hz), 7.39 (1H, d, J=2.3 Hz), 7.61 (1H, d, J=7.6 Hz), 7.67 (1H, d, J=8.7 Hz).

Example 4

(6-((2,6-Dimethylpyridin-3-yl)methoxy)-1-benzothiophen-3-yl)acetic acid

To a mixture of ethyl(6-((2,6-dimethylpyridin-3-yl)methoxy)-1-benzothiophen-3-yl)acetate (7.73 g), EtOH (75 mL) and THF (dry) (75 mL) was added 1N NaOH (45 mL). The mixture was stirred at room temperature for 2 h. To the mixture were added EtOH (50 mL) and MeOH (75 mL). The mixture was neutralized with 1N HCl (45 mL), and then water (500 mL) was added dropwise to the mixture. The precipitate was collected by filtration and washed with water. The solid was recrystallized from acetone-hexane to give the title compound (4.85 g).

$^1$H NMR (300 MHz, DMSO-$d_6$) δ 2.42 (3H, s), 2.48 (3H, brs), 3.79 (2H, s), 5.16 (2H, s), 7.06-7.14 (2H, m), 7.38 (1H, s), 7.63-7.72 (3H, m), 12.44 (1H, brs).

Example 5

Methyl(6-((2,4-dichlorobenzyl)oxy)-4-methyl-1-benzothiophen-3-yl)acetate

To a mixture of methyl(6-hydroxy-4-methyl-1-benzothiophen-3-yl)acetate (174 mg) and DMF (dry) (2 mL) were added $K_2CO_3$ (112 mg) and 2,4-dichlorobenzyl chloride (0.113 mL) at room temperature. After stirring at room temperature for 5 h, the mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (233 mg).

$^1$H NMR (300 MHz, CDCl$_3$) δ 2.66 (3H, s), 3.72 (3H, s), 4.01 (2H, s), 5.15 (2H, s), 6.79-6.87 (1H, m), 7.09 (1H, s), 7.20 (1H, d, J=2.6 Hz), 7.27-7.32 (1H, m), 7.40-7.46 (1H, m), 7.51 (1H, d, J=8.3 Hz).

Example 6

(6-((2,4-Dichlorobenzyl)oxy)-4-methyl-1-benzothiophen-3-yl)acetic acid

To a mixture of methyl(6-((2,4-dichlorobenzyl)oxy)-4-methyl-1-benzothiophen-3-yl)acetate (200 mg) and EtOH (2 mL) was added 1N NaOH (1 mL) at room temperature, and the mixture was refluxed for 15 min. The solution was cooled and concentrated under reduced pressure. The residue was neutralized with 1N HCl at 0° C. and extracted with EtOAc. The organic layer was separated, washed successively with 1N HCl and brine, dried over MgSO$_4$, and the mixture was concentrated in vacuo. The residue was crystallized from EtOAc to give the title compound (164 mg).

$^1$H NMR (300 MHz, DMSO-$d_6$) δ 2.60 (3H, s), 3.96 (2H, s), 5.18 (2H, s), 6.82-6.89 (1H, m), 7.31 (1H, s), 7.44-7.53 (2H, m), 7.63 (1H, d, J=8.3 Hz), 7.69 (1H, d, J=2.3 Hz), 12.46 (1H, brs).

Example 7

Methyl(6-((1,3-dimethyl-1H-pyrazol-5-yl)methoxy)-4-methyl-1-benzothiophen-3-yl)acetate To a mixture of methyl(6-hydroxy-4-methyl-1-benzothiophen-3-yl)acetate (150 mg) and DMF (2 mL) were added 5-(chloromethyl)-1,3-dimethyl-1H-pyrazole (101 mg) and $K_2CO_3$ (175 mg) at room temperature. The mixture was stirred at room temperature for 3 h. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane). The product was crystallized from Et$_2$O-hexane to give the title compound (155 mg).

$^1$H NMR (300 MHz, CDCl$_3$) δ 2.26 (3H, s), 2.64 (3H, s), 3.70-3.75 (3H, m), 3.84 (3H, s), 4.01 (2H, s), 5.01 (2H, s), 6.10 (1H, s), 6.76-6.81 (1H, m), 7.10 (1H, s), 7.23 (1H, d, J=2.3 Hz).

Example 8

(6-((1,3-Dimethyl-1H-pyrazol-5-yl)methoxy)-4-methyl-1-benzothiophen-3-yl)acetic acid To a mixture of methyl(6-((1,3-dimethyl-1H-pyrazol-5-yl)methoxy)-4-methyl-1-benzothiophen-3-yl)acetate (143 mg) and EtOH (2 mL) was added 1N NaOH (0.42 mL) at room temperature, and the mixture was refluxed for 30 min. The mixture was neutralized with 1N HCl at room temperature and extracted with EtOAc. The organic layer was separated, washed with brine, dried over MgSO$_4$ and concentrated in vacuo. The residual solid was crystallized from EtOAc-hexane to give the title compound (109 mg).

$^1$H NMR (300 MHz, DMSO-$d_6$) δ2.11 (3H, s), 2.59 (3H, s), 3.74 (3H, s), 3.96 (2H, s), 5.13 (2H, s), 6.15 (1H, s), 6.81-6.86 (1H, m), 7.30 (1H, s), 7.49 (1H, d, J=2.3 Hz), 12.47 (1H, d, J=0.8 Hz).

Example 9

Methyl(4-methyl-6-((2-methyl-6-(trifluoromethyl)pyridin-3-yl)methoxy)-1-benzothiophen-3-yl)acetate To a mixture of methyl(6-hydroxy-4-methyl-1-benzothiophen-3-yl)acetate (150 mg) and THF (dry) (5 mL) were added (2-methyl-6-(trifluoromethyl)pyridin-3-yl)methanol (133 mg), tri-n-butylphosphine (0.204 mL) and ADDP (192 mg) at room temperature. The mixture was stirred at room temperature for 4 h. The insoluble material was removed by filtration, and the filtrate was concentrated in vacuo. The residue was purified by silica gel column chromatography (EtOAc/hexane) to give the title compound (238 mg).

$^1$H NMR (300 MHz, CDCl$_3$) δ 2.66 (6H, s), 3.73 (3H, s), 4.02 (2H, s), 5.13 (2H, s), 6.81-6.86 (1H, m), 7.12 (1H, s), 7.21 (1H, d, J=2.3 Hz), 7.55 (1H, d, J=7.9 Hz), 7.94 (1H, d, J=7.9 Hz).

Example 10

(4-Methyl-6-((2-methyl-6-(trifluoromethyl)pyridin-3-yl)methoxy)-1-benzothiophen-3-yl)acetic acid To a mixture of methyl(4-methyl-6-((2-methyl-6-(trifluoromethyl)pyridin-3-yl)methoxy)-1-benzothiophen-3-yl)acetate (222.5 mg) and EtOH (5 mL) was added 1N NaOH (1 mL) at room temperature, and the mixture was refluxed for 2 h. The mixture was neutralized with 1N HCl at room temperature and extracted with EtOAc. The organic layer was separated, washed with brine, dried over MgSO$_4$ and concentrated in vacuo. The residue was crystallized from EtOAc-hexane to give the title compound (165 mg).

¹H NMR (300 MHz, DMSO-d₅) δ 2.61 (6H, s), 3.96 (2H, s), 5.30 (2H, s), 6.87-6.95 (1H, m), 7.31 (1H, s), 7.54 (1H, d, J=2.6 Hz), 7.76 (1H, d, J=7.9 Hz), 8.06 (1H, d, J=7.9 Hz), 12.28-12.82 (1H, m).

Example 11

Methyl(4-methyl-6-((1-methyl-3-(trifluoromethyl)-1H-pyrazol-5-yl)methoxy)-1-benzothiophen-3-yl) acetate To a mixture of tri-n-butylphosphine (0.162 mL), (1-methyl-3-(trifluoromethyl)-1H-pyrazol-5-yl)methanol (90 mg), methyl(6-hydroxy-4-methyl-1-benzothiophen-3-yl)acetate (118 mg) and THF (5.0 mL) was added ADDP (164 mg) at room temperature. The mixture was stirred at room temperature under nitrogen atmosphere overnight. The mixture was concentrated. To the residue was added IPE, the precipitate was filtered off, and the filtrate was concentrated in vacuo. The residue was purified by silica gel column chromatography (NH, EtOAc/hexane) and then silica gel column chromatography (EtOAc/hexane) to give the title compound (148.4 mg).

¹H NMR (300 MHz, CDCl₃) δ 2.66 (3H, s), 3.73 (3H, s), 3.98 (3H, s), 4.02 (2H, s), 5.07 (2H, s), 6.60 (1H, s), 6.79 (1H, s), 7.13 (1H, s), 7.23 (1H, d, J=2.6 Hz).

Example 12

(4-Methyl-6-((1-methyl-3-(trifluoromethyl)-1H-pyrazol-5-yl)methoxy)-1-benzothiophen-3-yl)acetic acid To a mixture of methyl(4-methyl-6-((1-methyl-3-(trifluoromethyl)-1H-pyrazol-5-yl)methoxy)-1-benzothiophen-3-yl)acetate (132.1 mg), MeOH (2.0 mL) and THF (dry) (2.0 mL) was added 1N NaOH (0.663 mL). The mixture was stirred at room temperature for 2 h. The mixture was concentrated. The mixture was neutralized with 1N HCl and extracted with EtOAc. The organic layer was washed with brine, dried over MgSO₄, and concentrated in vacuo. The residue was crystallized from EtOAc-hexane to give the title compound (117 mg).

¹H NMR (300 MHz, DMSO-d₆) δ 2.60 (3H, s), 3.94 (3H, s), 3.97 (2H, s), 5.27 (2H, s), 6.87 (1H, dd, J=2.6, 0.8 Hz), 6.89 (1H, s), 7.32 (1H, s), 7.54 (1H, d, J=2.3 Hz), 12.48 (1H, brs).

Example 13

Methyl(4-chloro-6-((2,6-dimethylpyridin-3-yl)methoxy)-1-benzothiophen-3-yl)acetate A) Methyl 4-((3-chloro-5-methoxyphenyl)sulfanyl)-3-oxobutanoate To a mixture of 3-chloro-5-methoxybenzenethiol (2.1 g) and DMF (dry) (30 mL) were added methyl 4-chloroacetoacetate (1.407 mL) and K₂CO₃ (1.994 g) at 0° C., and the mixture was stirred at room temperature for 5 h. The mixture was poured into water at room temperature and extracted with EtOAc. The organic layer was separated, washed successively with water and brine, dried over MgSO₄ and concentrated in vacuo. The residue was purified by silica gel column chromatography (EtOAc/hexane) to give the title compound (1.440 g).

B) Methyl(4-chloro-6-hydroxy-1-benzothiophen-3-yl)acetate

To MsOH (5 mL) was added methyl 4-((3-chloro-5-methoxyphenyl)sulfanyl)-3-oxobutanoate (1.41 g) at 0° C. The mixture was stirred at the same temperature for 15 min. The mixture was poured into ice water and extracted with EtOAc. The organic layer was separated, washed successively with 0.1N NaOH and brine, dried over MgSO₄ and concentrated in vacuo. The residue was subjected to silica gel column chromatography (EtOAc/hexane) to give methyl (4-chloro-6-methoxy-1-benzothiophen-3-yl)acetate as a crude product (1.280 g). The product was used to the next step without further purification. To a mixture of aluminum chloride (0.894 g) and toluene (30 mL) was added 1-dodecanethiol (5.32 mL) at 0° C., and the mixture was stirred at the same temperature for 30 min. A solution of methyl (4-chloro-6-methoxy-1-benzothiophen-3-yl)acetate obtained above (1.21 g) in toluene (15 mL) were added to the mixture at 0° C., and the mixture was stirred at room temperature for 40 h. The mixture was poured into water at 0° C. and extracted with EtOAc. The organic layer was separated, washed successively with water and brine, dried over MgSO₄ and concentrated in vacuo. The residue was diluted with MeOH (50 mL), and the mixture was treated with conc. H₂SO₄ (100 μL). The mixture was refluxed for 2 h. The mixture was concentrated under reduced pressure. To the residue was added brine at room temperature, and the mixture was extracted with EtOAc. The organic layer was separated, washed with brine, dried over MgSO₄ and concentrated in vacuo. The residue was purified by silica gel column chromatography (EtOAc/hexane) to give the title compound (0.558 g).

MS (ESI-): [M-H]⁻ 255.1.

C) Methyl(4-chloro-6-((2,6-dimethylpyridin-3-yl)methoxy)-1-benzothiophen-3-yl)acetate To a mixture of methyl(4-chloro-6-hydroxy-1-benzothiophen-3-yl)acetate (110 mg) and THF (dry) (5 mL) were added (2,6-dimethylpyridin-3-yl)methanol (58.8 mg), tri-n-butylphosphine (0.159 mL) and ADDP (130 mg) at room temperature. The mixture was stirred at room temperature for 12 h. The insoluble material was removed by filtration and the filtrate was concentrated in vacuo. The residue was purified by silica gel column chromatography (EtOAc/hexane) to give the title compound (139 mg).

¹H NMR (300 MHz, CDCl₃) δ 2.54 (3H, s), 2.57 (3H, s), 3.73 (3H, s), 4.11 (2H, s), 5.05 (2H, s), 7.02 (1H, d, J=7.9 Hz), 7.06-7.09 (1H, m), 7.13 (1H, s), 7.29 (1H, s), 7.58 (1H, d, J=7.9 Hz).

Example 14

(4-Chloro-6-((2,6-dimethylpyridin-3-yl)methoxy)-1-benzothiophen-3-yl)acetic acid To a mixture of methyl(4-chloro-6-((2,6-dimethylpyridin-3-yl)methoxy)-1-benzothiophen-3-yl)acetate (140 mg) and THF (1 mL) was added 1N NaOH (1 mL) at room temperature. The mixture was stirred at room temperature for 12 h. The mixture was neutralized with 1N HCl at room temperature and extracted with EtOAc. The organic layer was separated, washed with brine, dried over MgSO₄ and concentrated in vacuo. The residual solid was crystallized from EtOAc to give the title compound (95 mg).

$^1$H NMR (300 MHz, DMSO-$d_6$) δ 2.42 (3H, s), 2.48 (3H, s), 3.95-4.05 (2H, m), 5.17 (2H, s), 7.09 (1H, d, J=7.9 Hz), 7.18 (1H, d, J=2.3 Hz), 7.47 (1H, s), 7.65-7.71 (1H, m), 7.72 (1H, d, J=2.3 Hz), 12.36 (1H, brs).

Example 15

Methyl(4-chloro-6-((2-methyl-6-(trifluoromethyl)pyridin-3-yl)methoxy)-1-benzothiophen-3-yl)acetate To a mixture of methyl(4-chloro-6-hydroxy-1-benzothiophen-3-yl)acetate (110 mg) and THF (dry) (5 mL) were added (2-methyl-6-(trifluoromethyl)pyridin-3-yl)methanol (82 mg), tri-n-butylphosphine (0.159 mL), and ADDP (130 mg) at room temperature. The mixture was stirred at room temperature for 12 h. The insoluble material was removed by filtration, and the filtrate was concentrated in vacuo. The residue was purified by silica gel column chromatography (EtOAc/hexane) to give the title compound (164 mg). The compound was crystallized from IPE-hexane.

mp 102-104° C.

Example 16

(4-Chloro-6-((2-methyl-6-(trifluoromethyl)pyridin-3-yl)methoxy)-1-benzothiophen-3-yl)acetic acid To a mixture of methyl(4-chloro-6-((2-methyl-6-(trifluoromethyl)pyridin-3-yl)methoxy)-1-benzothiophen-3-yl)acetate (160 mg) and THF (2 mL) was added 1N NaOH (1 mL) at room temperature. The mixture was refluxed for 1 h. The mixture was neutralized with 1N HCl at room temperature and extracted with EtOAc. The organic layer was separated, washed with brine, dried over MgSO$_4$ and concentrated in vacuo. The residue was crystallized from EtOAc-hexane to give the title compound (143 mg).

$^1$H NMR (300 MHz, DMSO-$d_6$) δ 2.61 (3H, s), 4.01 (2H, s), 5.35 (2H, s), 7.22-7.29 (1H, m), 7.49 (1H, s), 7.74-7.81 (2H, m), 8.08 (1H, d, J=7.9 Hz), 12.37 (1H, brs).

Example 17

Ethyl(6-((1-methyl-3-(trifluoromethyl)-1H-pyrazol-5-yl)methoxy)-1-benzothiophen-3-yl)acetate To a mixture of tri-n-butylphosphine (0.165 mL), (1-methyl-3-(trifluoromethyl)-1H-pyrazol-5-yl)methanol (110 mg), ethyl(6-hydroxy-1-benzothiophen-3-yl)acetate (120 mg), and THF (5.0 mL) was added ADDP (167 mg) at room temperature. The mixture was stirred at room temperature under nitrogen atmosphere overnight. The mixture was concentrated. To the residue was added IPE and the precipitate was filtered off. The filtrate was concentrated in vacuo. The residue was purified by silica gel column chromatography (NH, EtOAc/hexane) and then silica gel column chromatography (EtOAc/hexane) to give the title compound (173 mg). The solid was crystallized from EtOH-hexane to give the title compound.

$^1$H NMR (300 MHz, CDCl$_3$) δ 1.26 (3H, t, J=7.2 Hz), 3.82 (2H, s), 3.99 (3H, s), 4.18 (2H, q, J=6.8 Hz), 5.11 (2H, s), 6.61 (1H, s), 7.06 (1H, s), 7.23 (1H, brs), 7.40 (1H, d, J=1.9 Hz), 7.69 (1H, d, J=8.7 Hz).

Example 18

(6-((1-Methyl-3-(trifluoromethyl)-1H-pyrazol-5-yl)methoxy)-1-benzothiophen-3-yl)acetic acid To a mixture of ethyl(6-((1-methyl-3-(trifluoromethyl)-1H-pyrazol-5-yl)methoxy)-1-benzothiophen-3-yl)acetate (129.8 mg), THF (2.0 mL) and EtOH (2.0 mL) was added 1N NaOH (0.98 mL) at room temperature. The mixture was stirred at room temperature for 3 h under nitrogen atmosphere. The mixture was concentrated. The residue was neutralized with 1N HCl and extracted with EtOAc. The organic layer was washed with brine, dried over MgSO$_4$, filtered and concentrated in vacuo. The solid was crystallized from EtOAc-hexane to give the title compound (106 mg).

$^1$H NMR (300 MHz, DMSO-$d_6$) δ 3.80 (2H, d, J=0.8 Hz), 3.95 (3H, s), 5.30 (2H, s), 6.90 (1H, s), 7.14 (1H, dd, J=8.9, 2.5 Hz), 7.40 (1H, s), 7.69 (1H, d, J=8.7 Hz), 7.72 (1H, d, J=2.3 Hz), 12.44 (1H, brs).

Example 19

Methyl(6-((2,6-dimethylpyridin-3-yl)methoxy)-4-vinyl-1-benzothiophen-3-yl)acetate A) Methyl 4-((3,5-dihydroxyphenyl)sulfanyl)-3-oxobutanoate To a mixture of 5-sulfanylbenzene-1,3-diol (12.2 g) and DMF (dry) (100 mL) was added methyl 4-chloroacetoacetate (10.0 mL) at room temperature, and the mixture was stirred at 70° C. for 4 h. The mixture was poured into water at room temperature and extracted with EtOAc. The organic layer was separated, washed successively with 1N HCl and brine, dried over MgSO$_4$ and concentrated in vacuo. The residue was purified by silica gel column chromatography (EtOAc/hexane) to give the title compound (15.1 g).

$^1$H NMR (300 MHz, CDCl$_3$) δ 3.65-3.68 (2H, m), 3.73 (3H, s), 3.78 (2H, s), 5.28 (2H, s), 6.20 (1H, t, J=2.3 Hz), 6.34-6.39 (2H, m).

B) Methyl(4,6-dihydroxy-1-benzothiophen-3-yl)acetate

To MsOH (50 mL) was added methyl 4-((3,5-dihydroxyphenyl)sulfanyl)-3-oxobutanoate (15.1 g) at room temperature. The mixture was stirred at room temperature for 30 min. The mixture was poured into ice-water at 0° C. and extracted with EtOAc. The organic layer was separated, washed successively with water and brine, dried over MgSO$_4$ and concentrated in vacuo. The residue was purified by silica gel column chromatography (EtOAc/hexane). The product was crystallized from EtOAc-IPE to give the title compound (7.20 g).

$^1$H NMR (300 MHz, DMSO-$d_6$) δ 3.59 (3H, s), 3.90 (2H, s), 6.23 (1H, d, J=2.3 Hz), 6.66 (1H, d, J=1.9 Hz), 6.95 (1H, s), 9.33 (1H, s), 9.80 (1H, s).

C) Methyl(4-hydroxy-6-((triisopropylsilyl)oxy)-1-benzothiophen-3-yl)acetate

To a mixture of methyl(4,6-dihydroxy-1-benzothiophen-3-yl)acetate (7.7 g) and DMF (dry) (150 mL) was added imidazole (4.40 g) at room temperature, and the mixture was added slowly triisopropylsilyl chloride (7.61 mL) over a period of 20 min, and the mixture was stirred at room temperature for 48 h. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (8.10 g).

$^1$H NMR (300 MHz, CDCl$_3$) δ 1.10 (8H, s), 1.12 (10H, s), 1.21-1.34 (3H, m), 3.77 (3H, s), 3.98 (2H, s), 6.50 (1H, d, J=2.3 Hz), 6.91 (1H, s), 6.94 (1H, s), 7.89 (1H, s).

D) Methyl(4-(((trifluoromethyl)sulfonyl)oxy)-6-((triisopropylsilyl)oxy)-1-benzothiophen-3-yl)acetate To a mixture of methyl(4-hydroxy-6-((triisopropylsilyl)oxy)-1-benzothiophen-3-yl)acetate (6.7 g) and THF (dry) (50 mL) were added 1,1,1-trifluoro-N-phenyl-N-((trifluoromethyl)sulfonyl)methanesulfonamide (6.07 g), TEA (4.73 mL) and DMAP (0.207 g) at 0° C., and the mixture was stirred at room temperature for 12 h. The mixture was poured into brine at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (8.27 g).

$^1$H NMR (300 MHz, CDCl$_3$) δ 1.11 (18H, d, J=6.8 Hz), 1.21-1.33 (3H, m), 3.73 (3H, s), 4.00 (2H, s), 6.95-6.98 (1H, m), 7.19 (1H, s), 7.30 (1H, d, J=2.3 Hz).

E) Methyl(6-hydroxy-4-vinyl-1-benzothiophen-3-yl)acetate

To a mixture of methyl(4-(((trifluoromethyl)sulfonyl)oxy)-6-((triisopropylsilyl)oxy)-1-benzothiophen-3-yl)acetate (900 mg) and EtOH (3 mL) were added potassium vinyl(trifluoro)borate (252 mg), [1,1'-bis(diphenylphosphino)ferrocene]dichloropalladium(II) (140 mg) and TEA (0.476 mL) at room temperature, and the mixture was stirred at 110° C. with microwave irradiation for 15 min. The mixture was poured into brine at room temperature and extracted with EtOAc. The organic layer was separated, washed with brine, and dried over MgSO$_4$ and concentrated in vacuo. The residue was purified by silica gel column chromatography (EtOAc/hexane) to give the title compound (379 mg).

$^1$H NMR (300 MHz, CDCl$_3$) δ 3.71 (3H, s), 3.97 (2H, s), 4.97 (1H, s), 5.32-5.43 (1H, m), 5.49-5.61 (1H, m), 6.86 (1H, d, J=2.3 Hz), 7.09 (1H, s), 7.16 (1H, d, J=2.7 Hz), 7.27-7.39 (1H, m).

F) Methyl(6-((2,6-dimethylpyridin-3-yl)methoxy)-4-vinyl-1-benzothiophen-3-yl)acetate To a mixture of methyl(6-hydroxy-4-vinyl-1-benzothiophen-3-yl)acetate (351 mg) and THF (dry) (3 mL) were added (2,6-dimethylpyridin-3-yl)methanol (233 mg), ADDP (535 mg) and tri-n-butylphosphine (0.523 mL) at room temperature. The precipitate was removed by filtration, and the filtrate was concentrated in vacuo. The residue was purified by silica gel column chromatography (EtOAc/hexane) to give the title compound (459 mg).

$^1$H NMR (300 MHz, CDCl$_3$) δ 2.54 (3H, s), 2.58 (3H, s), 3.68-3.72 (3H, m), 3.98 (2H, s), 5.07 (2H, s), 5.35-5.43 (1H, m), 5.51-5.61 (1H, m), 6.99-7.06 (2H, m), 7.12 (1H, s), 7.28-7.41 (2H, m), 7.61 (1H, d, J=7.9 Hz).

Example 20

Methyl(6-((2,6-dimethylpyridin-3-yl)methoxy)-4-formyl-1-benzothiophen-3-yl)acetate To a mixture of methyl(6-((2,6-dimethylpyridin-3-yl)methoxy)-4-vinyl-1-benzothiophen-3-yl)acetate (459 mg), CH$_3$CN (2 mL), water (2 mL) and acetone (2 mL) were added osmium(VIII) oxide (7% microcapsule, 907 mg) and NMO (439 mg) at room temperature. The mixture was stirred at room temperature for 20 h. The insoluble material was removed by filtration, and the filtrate was concentrated in vacuo. The residue was poured into aqueous solution of Na$_2$S$_2$O$_3$ at room temperature and extracted with EtOAc. The organic layer was separated, washed with brine, dried over MgSO$_4$ and concentrated in vacuo. To a mixture of the residue, THF (3 mL) and water (3 mL) was added sodium periodate (802 mg) at 0° C. The mixture was stirred at room temperature for 1 h. The mixture was quenched with aqueous solution of Na$_2$S$_2$O$_3$ at room temperature and extracted with EtOAc. The organic layer was separated, washed with brine twice, dried over MgSO$_4$ and concentrated in vacuo. The residue was purified by silica gel column chromatography (EtOAc/hexane) to give the title compound (293 mg).

Example 21

Methyl(4-chloro-6-((1-methyl-3-(trifluoromethyl)-1H-pyrazol-5-yl)methoxy)-1-benzothiophen-3-yl)acetate To a mixture of methyl(4-chloro-6-hydroxy-1-benzothiophen-3-yl)acetate (750 mg) and THF (dry) (10 mL) were added (1-methyl-3-(trifluoromethyl)-1H-pyrazol-5-yl)methanol (632 mg), ADDP (958 mg) and tri-n-butylphosphine (1.442 mL) at room temperature. The mixture was stirred at room temperature for 16 h. The insoluble material was removed by filtration, and the filtrate was concentrated in vacuo. The residue was purified by silica gel column chromatography (EtOAc/hexane). The product was crystallized from EtOAc-hexane to give the title compound (1132 mg).

$^1$H NMR (300 MHz, CDCl$_3$) δ 3.73 (3H, s), 3.98 (3H, s), 4.12 (2H, s), 5.08 (2H, s), 6.61 (1H, s), 7.05 (1H, d, J=2.7 Hz), 7.17 (1H, s), 7.30 (1H, d, J=2.3 Hz).

Example 22

(4-Chloro-6-((1-methyl-3-(trifluoromethyl)-1H-pyrazol-5-yl)methoxy)-1-benzothiophen-3-yl)acetic acid A mixture of methyl(4-chloro-6-((1-methyl-3-(trifluoromethyl)-1H-pyrazol-5-yl)methoxy)-1-benzothiophen-3-yl)acetate (1.9 g), 1N NaOH (10 mL), THF (10 mL) and MeOH (10 mL) was stirred at room temperature for 4 h. To the mixture were added 1N HCl (10 mL) and water, and the mixture was extracted with EtOAc. The organic layer was separated, washed with brine, dried over MgSO$_4$ and concentrated in vacuo. The residual solid was washed with hexane to give the crystals (1.75 g). The crystals were recrystallized from acetone-heptane to give the title compound.

mp 193-194° C.

Example 23

Methyl(4,7-dimethyl-6-((2-methyl-6-(trifluoromethyl)pyridin-3-yl)methoxy)-1-benzothiophen-3-yl)acetate A) 3-((4-Methoxybenzyl)sulfanyl)-2,5-dimethylphenyl acetate To a mixture of 3-hydroxy-2,5-dimethylphenyl acetate (1.04 g) and CH$_3$CN (57 mL) were added TEA (1.61 mL) and Tf$_2$O (1.17 mL) at 0° C. The mixture was stirred at 0° C. for 30 min under nitrogen atmosphere. The mixture was diluted with water at 0° C. and then concentrated in vacuo. The residue was extracted with EtOAc. The organic layer was washed with brine, dried over MgSO$_4$, and concentrated in vacuo. The residual crude material was dissolved in toluene (50 mL). To the solution were added DIPEA (1.79 mL), (9,9-dimethyl-9H-xanthene-4,5-diyl)bis(diphenylphosphine) (0.150 g), (4-methoxyphenyl)methanethiol (0.723 mL) and tris(dibenzylideneacetone)dipalladium (0) (Pd$_2$(dba)$_3$, 0.238 g) at room temperature. The mixture was refluxed for 4 h. After cooling, water was added to the mixture, and the mixture was extracted with EtOAc. The organic layer was separated, washed with brine, dried over MgSO$_4$ and concentrated in vacuo. The residue was purified by silica gel column chromatography (EtOAc/hexane) to give the title compound (1.27 g).

MS (ESI–): [M–H]$^-$ 315.1.

B) 2,5-Dimethyl-3-sulfanylphenol

To a mixture of 3-((4-methoxybenzyl)sulfanyl)-2,5-dimethylphenyl acetate (509.1 mg) and anisole (1.5 mL) was added TFA (5.0 mL) at 0° C. The mixture was stirred at 0° C. for 1 h and warmed to room temperature. Then the mixture was stirred at room temperature for 4 h. The mixture was concentrated. The residue was neutralized with 1N NaOH, and the mixture was extracted with EtOAc. The aqueous layer was acidified with 1N HCl and extracted with EtOAc. The organic layer was washed with brine, dried over MgSO$_4$, and concentrated in vacuo. The residue was purified by silica gel column chromatography (EtOAc/hexane) to give the title compound (128 mg).

$^1$H NMR (300 MHz, CDCl$_3$) δ 2.20 (6H, s), 3.28 (1H, s), 4.61 (1H, s), 6.41 (1H, d, J=1.5 Hz), 6.72 (1H, d, J=1.1 Hz).

C) Methyl 4-((3-hydroxy-2,5-dimethylphenyl)sulfanyl)-3-oxobutanoate

To a mixture of 2,5-dimethyl-3-sulfanylphenol (126 mg) and DMF (dry) (8.0 mL) were added K$_2$CO$_3$ (124 mg) and methyl 4-chloro-3-oxobutanoate (0.096 mL) at 0° C. The mixture was stirred at 0° C. for 3 h. The mixture was quenched with water at 0° C. and extracted with EtOAc. The organic layer was washed successively with water and brine, dried over MgSO$_4$, and concentrated in vacuo. The residue was purified by silica gel column chromatography (EtOAc/hexane) to give the title compound (179 mg).

MS (ESI–): [M–H]$^-$ 266.9.

D) Methyl(6-hydroxy-4,7-dimethyl-1-benzothiophen-3-yl)acetate

MsOH (1.0 mL) was added to methyl 4-((3-hydroxy-2,5-dimethylphenyl)sulfanyl)-3-oxobutanoate (175.1 mg) at 0°. The mixture was stirred at 0° C. for 15 min, and then poured into ice water. The mixture was extracted with EtOAc. The organic layer was separated, washed successively with saturated aqueous NaHCO$_3$ and brine, dried over MgSO$_4$ and concentrated in vacuo. The residue was purified by silica gel column chromatography (EtOAc/hexane) to give the title compound (130.3 mg).

$^1$H NMR (300 MHz, CDCl$_3$) δ 2.37 (3H, s), 2.60 (3H, s), 3.72 (3H, s), 4.00 (2H, s), 4.67 (1H, s), 6.64 (1H, s), 7.07 (1H, s).

E) Methyl(4,7-dimethyl-6-((2-methyl-6-(trifluoromethyl)pyridin-3-yl)methoxy)-1-benzothiophen-3-yl)acetate To a mixture of tri-n-butylphosphine (0.196 mL), (2-methyl-6-(trifluoromethyl)pyridin-3-yl)methanol (105 mg), methyl(6-hydroxy-4,7-dimethyl-1-benzothiophen-3-yl)acetate (130.9 mg) and THF (5.0 mL) was added ADDP (198 mg) at room temperature. The mixture was stirred at room temperature overnight under nitrogen atmosphere. The mixture was concentrated in vacuo. To the residue was added IPE, and the precipitate was filtered off. The filtrate was concentrated in vacuo. The residue was purified by silica gel column chromatography (EtOAc/hexane) to give the title compound (159 mg) as solid. The solid was crystallized from EtOAc-hexane.

$^1$H NMR (300 MHz, CDCl$_3$) δ 2.42 (3H, s), 2.67 (6H, s), 3.73 (3H, s), 4.03 (2H, s), 5.15 (2H, s), 6.79 (1H, s), 7.14 (1H, s), 7.57 (1H, d, J=7.9 Hz), 7.98 (1H, d, J=7.9 Hz).

Example 24

(4,7-Dimethyl-6-((2-methyl-6-(trifluoromethyl)pyridin-3-yl)methoxy)-1-benzothiophen-3-yl)acetic acid To a mixture of methyl(4,7-dimethyl-6-((2-methyl-6-(trifluoromethyl)pyridin-3-yl)methoxy)-1-benzothiophen-3-yl)acetate (124.6 mg), MeOH (2.0 mL) and THF (dry) (2.0 mL) was added 1N NaOH (0.883 mL). The mixture was stirred at room temperature for 2 h. The mixture was concentrated. The residue was neutralized with 1N HCl and extracted with EtOAc. The organic layer was washed with brine, dried over MgSO$_4$, and concentrated in vacuo. The solid was crystallized from EtOAc-hexane to give the title compound (108 mg).

$^1$H NMR (300 MHz, DMSO-d$_6$) δ 2.35 (3H, s), 2.63 (3H, s), 2.63 (3H, s), 3.97 (2H, s), 5.32 (2H, s), 7.08 (1H, s), 7.33 (1H, s), 7.78 (1H, d, J=7.9 Hz), 8.12 (1H, d, J=7.9 Hz), 12.47 (1H, brs).

Example 25

Methyl(4-chloro-6-((1,3-dimethyl-1H-pyrazol-5-yl)methoxy)-1-benzothiophen-3-yl)acetate To a mixture of methyl(4-chloro-6-hydroxy-1-benzothiophen-3-yl)acetate (125 mg) and DMF (dry) (2 mL) were added 5-(chloromethyl)-1,3-dimethyl-1H-pyrazole (84 mg) and K$_2$CO$_3$ (101 mg) at room temperature, and the mixture was stirred at 60° C. for 1 h. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (172 mg).

$^1$H NMR (300 MHz, CDCl$_3$) δ 2.26 (3H, s), 3.73 (3H, s), 3.85 (3H, s), 4.11 (2H, s), 5.02 (2H, s), 6.11 (1H, s), 7.05 (1H, d, J=2.3 Hz), 7.15 (1H, s), 7.29-7.32 (1H, m).

Example 26

(4-Chloro-6-((1,3-dimethyl-1H-pyrazol-5-yl)methoxy)-1-benzothiophen-3-yl)acetic acid To a mixture of methyl(4-chloro-6-((1,3-dimethyl-1H-pyrazol-5-yl)methoxy)-1-benzothiophen-3-yl)acetate (162 mg) and EtOH (3 mL) was added 1N NaOH (1 mL) at room temperature, and the mixture was refluxed for 1 h. The mixture was concentrated in vacuo, neutralized with 1N HCl at 0° C. and extracted with EtOAc. The organic layer was separated, washed successively with water and brine, dried over MgSO$_4$ and concentrated in vacuo. The residue was crystallized from EtOAc-hexane to give the title compound (141 mg).

$^1$H NMR (300 MHz, DMSO-d$_6$) δ 2.11 (3H, s), 3.75 (3H, s), 4.00 (2H, s), 5.19 (2H, s), 6.16 (1H, s), 7.16 (1H, s), 7.48 (1H, s), 7.72 (1H, d, J=2.3 Hz), 12.37 (1H, s).

Example 27

Methyl(4,7-dichloro-6-((1-methyl-3-(trifluoromethyl)-1H-m pyrazol-5-yl)methoxy)-1-benzothiophen-3-yl)acetate A) 2,5-Dichloro-1-methoxy-3-((4-methoxybenzyl)sulfanyl)benzene To a mixture of DIPEA (5.77 mL), 4,5-bis(diphenylphosphino)-9,9-dimethylxanthene (0.488 g), 1-bromo-2,5-dichloro-3-methoxybenzene (4.32 g) and (4-methoxyphenyl)methanethiol (2.47 mL) and toluene (100 mL) was added tris(dibenzylideneacetone)dipalladium (0) (Pd$_2$(dba)$_3$, 0.773 g) at room temperature. The mixture was refluxed for 5 h. After cooling, water was added to the mixture and the mixture was extracted with EtOAc. The organic layer was separated, washed with brine, dried over MgSO$_4$ and concentrated in vacuo. The residue was purified by silica gel column chromatography (EtOAc/hexane) to give the title compound (5.66 g).

$^1$H NMR (300 MHz, CDCl$_3$) δ 3.80 (3H, s), 3.88 (3H, s), 4.10 (2H, s), 6.73 (1H, d, J=1.9 Hz), 6.82-6.89 (3H, m), 7.28 (1H, s), 7.31 (1H, s).

B) 2,5-Dichloro-3-methoxybenzenethiol

The mixture of 2,5-dichloro-1-methoxy-3-((4-methoxybenzyl)sulfanyl)benzene (5.56 g) and anisole (9.18 mL) was added TFA (22.13 mL) at room temperature. The mixture was stirred at 80° C. for 20 min. After cooling, the mixture was diluted with water and extracted with EtOAc. The organic layer was extracted with 1N NaOH. The aqueous layer was acidified with 1N HCl, and extracted with EtOAc. The organic layer was washed with brine, dried over MgSO$_4$, filtered and concentrated in vacuo. The residue was purified by silica gel column chromatography (EtOAc/hexane) to give the title compound (2.38 g).

MS (ESI-): [M-H]$^-$ 207.1.

C) Methyl 4-((2,5-dichloro-3-methoxyphenyl)sulfanyl)-3-oxobutanoate

To a mixture of 2,5-dichloro-3-methoxybenzenethiol (2.36 g) and DMF (dry) (60 mL) were added K$_2$CO$_3$ (1.72 g) and methyl 4-chloro-3-oxobutanoate (1.46 mL) at 0° C. The mixture was stirred at room temperature for 2 h. The mixture was diluted with water and extracted with EtOAc. The organic layer was washed successively with water and brine, dried over MgSO$_4$, and concentrated in vacuo. The residue was purified by silica gel column chromatography (EtOAc/hexane) to give the title compound (3.37 g).

MS (ESI+): [M+H]$^+$ 323.2.

D) Methyl(4,7-dichloro-6-methoxy-1-benzothiophen-3-yl)acetate

MsOH (4.5 mL) was added to methyl 4-((2,5-dichloro-3-methoxyphenyl)sulfanyl)-3-oxobutanoate (1.03 g) at 0° C.

The mixture was stirred at 0° C. for 10 min and then at room temperature for 1.5 h. The mixture was poured into ice water and extracted with EtOAc. The organic layer was separated, washed successively with saturated aqueous NaHCO$_3$ and brine, dried over MgSO$_4$ and concentrated in vacuo. The residue was purified by silica gel column chromatography (EtOAc/hexane) to give a solid. The solid was washed with hexane to give the title compound (0.827 g).

$^1$H NMR (300 MHz, CDCl$_3$) δ 3.73 (3H, s), 3.96 (3H, s), 4.10 (2H, s), 7.06 (1H, s), 7.18 (1H, s).

E) Methyl(4,7-dichloro-6-hydroxy-1-benzothiophen-3-yl)acetate

A mixture of methyl(4,7-dichloro-6-methoxy-1-benzothiophen-3-yl)acetate (300.9 mg), DMF (dry) (9.0 mL) and sodium 2-methyl-2-propanethiolate (442 mg) was stirred at 160° C. for 20 min. The mixture was quenched with water and 1N HCl and extracted with EtOAc. The organic layer was washed successively with water and brine, dried over MgSO$_4$, and concentrated in vacuo to give (4,7-dichloro-6-hydroxy-1-benzothiophen-3-yl)acetic acid (327 mg) as a crude mixture. A crude mixture of (4,7-dichloro-6-hydroxy-1-benzothiophen-3-yl)acetic acid (369 mg) was dissolved in MeOH (10 mL). To the solution was added conc. H$_2$SO$_4$ (0.100 mL). The mixture was stirred at 80° C. for 40 min. The mixture was concentrated. The residue was neutralized with saturated aqueous NaHCO$_3$ and extracted with EtOAc. The organic layer was washed with brine, dried over MgSO$_4$, and concentrated in vacuo. The solid was washed with hexane to give the title compound (345 mg).

MS (ESI-): [M-H]$^-$ 289.1.

F) Methyl(4,7-dichloro-6-((1-methyl-3-(trifluoromethyl)-1H-pyrazol-5-yl)methoxy)-1-benzothiophen-3-yl)acetate To a mixture of tri-n-butylphosphine (0.193 mL), methyl (4,7-dichloro-6-hydroxy-1-benzothiophen-3-yl)acetate (150 mg), (1-methyl-3-(trifluoromethyl)-1H-pyrazol-5-yl)methanol (102 mg) and THF (5.0 mL) was added ADDP (195 mg) at room temperature. The mixture was stirred at room temperature under nitrogen atmosphere overnight. The mixture was concentrated in vacuo. To the residue was added IPE and the precipitate was filtered off. The filtrate was concentrated in vacuo. The residue was purified by silica gel column chromatography (NH, EtOAc/hexane) to give the title compound (205.9 mg). The solid was crystallized from EtOAc-hexane to give the title compound.

$^1$H NMR (300 MHz, DMSO-d$_6$) δ 3.64 (3H, s), 3.99 (3H, s), 4.13 (2H, s), 5.47 (2H, s), 6.89 (1H, s), 7.63 (1H, s), 7.66 (1H, s).

Example 28

(4,7-Dichloro-6-((1-methyl-3-(trifluoromethyl)-1H-pyrazol-5-yl)methoxy)-1-benzothiophen-3-yl)acetic acid To a mixture of methyl(4,7-dichloro-6-((1-methyl-3-(trifluoromethyl)-1H-pyrazol-5-yl)methoxy)-1-benzothiophen-3-yl)acetate (167.4 mg), THF (dry) (2.0 mL) and MeOH (2.0 mL) was added 1N NaOH (1.11 mL) at room temperature. The mixture was stirred at room temperature for 2 h. The mixture was neutralized with 1N HCl and concentrated in vacuo. The precipitate was collected by filtration, and crystallized from EtOAc-hexane to give the title compound (131 mg).

$^1$H NMR (300 MHz, DMSO-$d_6$) δ 3.99 (3H, s), 4.03 (2H, s), 5.47 (2H, s), 6.89 (1H, s), 7.62 (2H, s), 12.46 (1H, brs).

Example 29

Methyl(4,7-dichloro-6-((2-methyl-6-(trifluoromethyl)pyridin-3-yl)methoxy)-1-benzothiophen-3-yl)acetate To a mixture of tri-n-butylphosphine (0.336 mL), methyl (4,7-dichloro-6-hydroxy-1-benzothiophen-3-yl)acetate (130.7 mg), (2-methyl-6-(trifluoromethyl)pyridin-3-yl) methanol (94 mg) and THF (4.5 mL) was added ADDP (283 mg) at room temperature. The mixture was stirred at room temperature under nitrogen atmosphere overnight. The mixture was concentrated. To the residue was added IPE and the precipitate was filtered off. The filtrate was concentrated in vacuo. The residue was purified by silica gel column chromatography (NH, EtOAc/hexane) to give the title compound (153 mg).

$^1$H NMR (300 MHz, CDCl$_3$) δ 2.69 (3H, s), 3.74 (3H, s), 4.11 (2H, s), 5.21 (2H, s), 7.13 (1H, s), 7.25 (1H, s), 7.60 (1H, d, J=7.9 Hz), 8.05 (1H, d, J=7.9 Hz).

Example 30

(4,7-Dichloro-6-((2-methyl-6-(trifluoromethyl)pyridin-3-yl)methoxy)-1-benzothiophen-3-yl)acetic acid To a mixture of methyl(4,7-dichloro-6-((2-methyl-6-(trifluoromethyl)pyridin-3-yl)methoxy)-1-benzothiophen-3-yl) acetate (124.5 mg), THF (dry) (2.0 mL), and MeOH (2.0 mL) was added 1N NaOH (0.804 mL) at room temperature. The mixture was stirred at room temperature for 5 h. The mixture was neutralized with 1N HCl and concentrated in vacuo. The precipitate was collected by filtration to give a solid. The solid was crystallized from EtOH-hexane to give the title compound (96.6 mg).

$^1$H NMR (300 MHz, DMSO-$d_6$) δ 2.64 (3H, s), 4.02 (2H, s), 5.48 (2H, s), 7.61 (1H, s), 7.64 (1H, s), 7.82 (1H, d, J=7.9 Hz), 8.13 (1H, d, J=7.9 Hz).

Example 31

(6-((2,6-Dimethylpyridin-3-yl)methoxy)-4-(trifluoromethyl)-1-benzothiophen-3-yl)acetic acid A) Methyl 4-((3-methoxy-5-(trifluoromethyl)phenyl) sulfanyl)-3-oxobutanoate To a mixture of 3-methoxy-5-(trifluoromethyl)benzenethiol (1.36 g) and DMF (dry) (10 mL) were added methyl 4-chloroacetoacetate (1.146 mL) and K$_2$CO$_3$ (1.806 g) at room temperature. The mixture was stirred at room temperature for 1 h. The mixture was poured into water at room temperature and extracted with EtOAc. The organic layer was separated, washed successively with 1N HCl and brine, dried over MgSO$_4$ and concentrated in vacuo. The residue was purified by silica gel column chromatography (EtOAc/hexane) to give the title compound (1.120 g).

$^1$H NMR (300 MHz, CDCl$_3$) δ3.65 (2H, s), 3.73 (3H, s), 3.84 (3H, s), 3.86-3.88 (2H, m), 6.94-6.99 (1H, m), 7.02 (1H, dt, J=2.4, 0.9 Hz), 7.15 (1H, s).

B) Methyl(6-hydroxy-4-(trifluoromethyl)-1-benzothiophen-3-yl)acetate

Methyl 4-((3-methoxy-5-(trifluoromethyl)phenyl)sulfanyl)-3-oxobutanoate (810 mg) was added to Eaton's reagent (1994 μl) at room temperature for 2 h. The mixture was poured into water at room temperature and extracted with EtOAc. The organic layer was separated, washed successively with water and brine, dried over MgSO$_4$ and concentrated in vacuo. The residue was subjected to silica gel column chromatography (EtOAc/hexane) to give methyl(6-methoxy-4-(trifluoromethyl)-1-benzothiophen-3-yl)acetate as a crude product (604 mg). The product was used to the next step without further purification.

To a mixture of methyl(6-methoxy-4-(trifluoromethyl)-1-benzothiophen-3-yl)acetate obtained above (405 mg) and AcOH (1.5 mL) was added 48% hydrobromic acid (3 mL) at room temperature. The mixture was stirred at 130° C. for 40 min under microwave irradiation. The mixture was poured into brine at room temperature and extracted with EtOAc. The organic layer was separated, washed with brine, dried over MgSO$_4$ and concentrated in vacuo. A mixture of the residue, MeOH and conc. H$_2$SO$_4$ (0.071 mL) was refluxed for 1 h. The mixture was poured into brine at room temperature and extracted with EtOAc. The organic layer was separated, washed with brine twice, dried over MgSO$_4$ and concentrated in vacuo. The residue was purified by silica gel column chromatography (EtOAc/hexane) to give the title compound (232 mg).

$^1$H NMR (300 MHz, CDCl$_3$) δ 3.60 (3H, s), 3.96 (2H, s), 7.30 (1H, d, J=2.6 Hz), 7.61 (1H, s), 7.64 (1H, d, J=2.3 Hz), 10.24 (1H, brs).

C) (6-((2,6-Dimethylpyridin-3-yl)methoxy)-4-(trifluoromethyl)-1-benzothiophen-3-yl)acetic acid To a mixture of methyl(6-hydroxy-4-(trifluoromethyl)-1-benzothiophen-3-yl)acetate (60 mg) and THF (dry) (2 mL) were added (2,6-dimethylpyridin-3-yl)methanol (31.2 mg), ADDP (62.6 mg), and tri-n-butylphosphine (0.153 mL) at room temperature. After stirring at room temperature for 16 h, the insoluble material was removed by filtration. The filtrate was concentrated in vacuo. The residue was purified by silica gel column chromatography (EtOAc/hexane). To the mixture of crude material and THF (1 mL) was added 1N NaOH (1 mL) at room temperature, and the mixture was stirred at room temperature for 13 h. The mixture was neutralized with 1N HCl at 0° C. and extracted with EtOAc. The organic layer was separated, washed successively with water and brine, dried over MgSO$_4$ and concentrated in vacuo. The residual solid was crystallized from EtOAc-hexane to give the title compound (71.0 mg).

$^1$H NMR (300 MHz, DMSO-$d_6$) δ 2.43 (3H, s), 2.51 (3H, d, J=1.1 Hz), 3.90 (2H, s), 5.24 (2H, s), 7.10 (1H, d, J=7.6 Hz), 7.49 (1H, d, J=2.6 Hz), 7.67-7.75 (2H, m), 8.09-8.14 (1H, m), 12.34 (1H, brs).

Example 32

(6-((1-Methyl-3-(trifluoromethyl)-1H-pyrazol-5-yl) methoxy)-4-(trifluoromethyl)-1-benzothiophen-3-yl) acetic acid To a mixture of methyl(6-hydroxy-4-(trifluoromethyl)-1-benzothiophen-3-yl)acetate (60 mg) and THF (dry) (3 mL) were added (1-methyl-3-(trifluoromethyl)-1H-pyrazol-5-yl) methanol (37.2 mg), ADDP (62.6 mg) and tri-n-butylphosphine (0.071 mL) at room temperature. The mixture was stirred at room temperature for 12 h. The insoluble material was removed by filtration, and the filtrate was concentrated in vacuo. The residue was purified by silica gel column chromatography (EtOAc/hexane). To the mixture of the crude material and THF (1 mL) was added 1N NaOH (1 mL) at room temperature for 12 h. The mixture was neutralized with 1N HCl at 0° C. and extracted with EtOAc. The organic layer was separated, washed successively with water and brine, dried over $MgSO_4$ and concentrated in vacuo. The solid was crystallized from EtOAc-hexane to give the title compound (64.0 mg).

$^1$H NMR (300 MHz, DMSO-$d_6$) δ 3.90 (2H, s), 3.97 (3H, s), 5.39 (2H, s), 6.94 (1H, s), 7.52 (1H, d, J=2.6 Hz), 7.72 (1H, s), 8.15 (1H, d, J=2.6 Hz), 12.36 (1H, brs).

Example 33

Methyl(7-fluoro-4-methyl-6-((1-methyl-3-(trifluoromethyl)-1H-pyrazol-5-yl)methoxy)-1-benzothiophen-3-yl)acetate A) 2-Fluoro-1-methoxy-5-methyl-3-(methylsulfanyl)benzene To a mixture of 1-fluoro-2-methoxy-4-methylbenzene (1.0 g) and THF (dry) (60 mL) was added sec-butyllithium (1.04 mol/L cyclohexane solution, 13.72 mL) dropwise over a period of 20 min at −78° C. After stirring at −78° C. for 20 min, to the mixture was added dimethyl disulfide (1.41 mL) at the same temperature. The mixture was stirred at −78° C. under argon atmosphere for 1 h. The mixture was quenched with saturated aqueous $NH_4Cl$ at −78° C. and extracted with EtOAc. The combined organic layer was washed with brine, dried over $MgSO_4$, filtered and concentrated in vacuo. The residue was purified by silica gel column chromatography (EtOAc/hexane) to give the title compound (1.34 g).

$^1$H NMR (300 MHz, CDCl$_3$) S 2.30 (3H, s), 2.45 (3H, s), 3.86 (3H, s), 6.61 (1H, dd, J=7.6, 1.9 Hz), 6.63-6.67 (1H, m).

B) 2-Fluoro-1-methoxy-5-methyl-3-(methylsulfinyl)benzene

To a mixture of 2-fluoro-1-methoxy-5-methyl-3-(methylsulfanyl)benzene (557.4 mg), MeOH (20 mL) and water (4 mL) was added NaIO$_4$ (960 mg) at 0° C. The mixture was stirred at room temperature over weekend. The mixture was diluted with water. The precipitate was filtered off, and the filtrate was extracted with EtOAc. The organic layer was washed with brine, dried over $MgSO_4$, filtered and concentrated in vacuo. The residue was purified by silica gel column chromatography (EtOAc/hexane) to give the title compound (486 mg).

MS (ESI+): [M+H]$^+$ 203.0.

C) 2-Fluoro-3-methoxy-5-methylbenzenethiol

To a mixture of 2-fluoro-1-methoxy-5-methyl-3-(methylsulfinyl)benzene (486 mg) and CH$_3$CN (20 mL) was added TFAA (1.02 mL) at 0° C. The mixture was stirred at 0° C. for 1 h, and concentrated in vacuo. The residue was dissolved in a mixture of MeOH (3.5 mL) and TEA (3.5 mL) at 0° C. The solution was stirred at room temperature for 1 h, and concentrated in vacuo. The residue was diluted with saturated aqueous $NH_4Cl$, and the mixture was extracted with EtOAc. The organic layer was extracted with 1N NaOH. The aqueous layer was acidified with 1N HCl and extracted with EtOAc. The combined organic layer was washed with brine, dried over $MgSO_4$, and concentrated in vacuo to give the title compound (214 mg).

$^1$H NMR (300 MHz, CDCl$_3$) δ 2.23-2.29 (3H, m), 3.57 (1H, d, J=1.1 Hz), 3.85 (3H, s), 6.55 (1H, dd, J=7.6, 1.9 Hz), 6.65 (1H, s).

D) Methyl 4-((2-fluoro-3-methoxy-5-methylphenyl)sulfanyl)-3-oxobutanoate

To a mixture of 2-fluoro-3-methoxy-5-methylbenzenethiol (289.4 mg) and DMF (dry) (12 mL) were added K$_2$CO$_3$ (255 mg) and methyl 4-chloro-3-oxobutanoate (0.217 mL) at 0° C. The mixture was stirred at room temperature for 1.5 h. The mixture was diluted with water and extracted with EtOAc. The organic layer was washed successively with water and brine, dried over $MgSO_4$, and concentrated in vacuo. The residue was purified by silica gel column chromatography (EtOAc/hexane) to give the title compound (330 mg).

MS (ESI−): [M−H]$^−$ 285.1.

E) Methyl(7-fluoro-6-methoxy-4-methyl-1-benzothiophen-3-yl)acetate

MsOH (3.0 mL) was added to methyl 4-((2-fluoro-3-methoxy-5-methylphenyl)sulfanyl)-3-oxobutanoate (330 mg) at 0° C. After stirring at 0° C. for 10 min, the mixture was poured into ice water at 0° C. and extracted with EtOAc. The organic layer was separated, washed successively with saturated aqueous NaHCO$_3$ and brine, dried over $MgSO_4$ and concentrated in vacuo. The residue was purified by silica gel column chromatography (EtOAc/hexane) to give the title compound (299 mg).

MS (ESI+): [M+H]$^+$ 269.0.

F) (7-Fluoro-6-hydroxy-4-methyl-1-benzothiophen-3-yl)acetic acid

To a mixture of methyl(7-fluoro-6-methoxy-4-methyl-1-benzothiophen-3-yl)acetate (248.4 mg) and DMF (dry) (7.5 mL) was added sodium 2-methyl-2-propanethiolate (415 mg) at room temperature. The mixture was stirred at 160° C. for 20 min. After cooling, the mixture was diluted with water and 1N HCl and extracted with EtOAc. The organic layer was washed successively with water and brine, dried over $MgSO_4$, and concentrated in vacuo to give the title compound (273 mg).

MS (ESI−): [M−H]$^−$ 239.0.

G) Methyl(7-fluoro-6-hydroxy-4-methyl-1-benzothiophen-3-yl)acetate

To a mixture of (7-fluoro-6-hydroxy-4-methyl-1-benzothiophen-3-yl)acetic acid (267 mg) and MeOH (8.0 mL) was added conc. H$_2$SO$_4$ (0.100 mL). The mixture was stirred at 80° C. for 1 h. The mixture was concentrated. The mixture was neutralized with saturated aqueous NaHCO$_3$ and extracted with EtOAc. The organic layer was washed with brine, dried over $MgSO_4$, filtered and concentrated in vacuo. The residue was purified by silica gel column chromatography (EtOAc/hexane) to give the title compound (255.5 mg).

MS (ESI−): [M−H]$^−$ 253.1.

H) Methyl(7-fluoro-4-methyl-6-((1-methyl-3-(trifluoromethyl)-1H-pyrazol-5-yl)methoxy)-1-benzothiophen-3-yl)acetate To a mixture of tri-n-butylphosphine (0.338 mL), methyl (7-fluoro-6-hydroxy-4-methyl-1-benzothiophen-3-yl)acetate (131.3 mg), (1-methyl-3-(trifluoromethyl)-1H-pyrazol-5-yl)methanol (93 mg) and THF (4.0 mL) was added ADDP (284 mg) at room temperature. The mixture was stirred overnight at room temperature under nitrogen atmosphere. The mixture was concentrated. To the residue was added IPE and the precipitate was filtered off. The filtrate was concentrated in vacuo. The residue was purified by silica gel column chromatography (NH, EtOAc/hexane) to give the title compound (205.9 mg). The compound was crystallized from EtOAc-hexane.

$^1$H NMR (300 MHz, CDCl$_3$) δ 2.62 (3H, s), 3.73 (3H, s), 4.01 (2H, d, J=0.8 Hz), 4.04 (3H, s), 5.17 (2H, s), 6.56 (1H, s), 6.82-6.88 (1H, m), 7.21 (1H, s).

Example 34

(7-Fluoro-4-methyl-6-((1-methyl-3-(trifluoromethyl)-1H-pyrazol-5-yl)methoxy)-1-benzothiophen-3-yl)acetic acid To a mixture of methyl(7-fluoro-4-methyl-6-((1-methyl-3-(trifluoromethyl)-1H-pyrazol-5-yl)methoxy)-1-benzothiophen-3-yl)acetate (150.6 mg), THF (dry) (2.0 mL) and MeOH (2.0 mL) was added 1N NaOH (1.085 mL) at room temperature. The mixture was stirred at room temperature for 2 h. The mixture was neutralized with 1N HCl and concentrated. The precipitate was collected by filtration to give a solid. The solid was crystallized from EtOAc-hexane to give the title compound (123.5 mg).

$^1$H NMR (300 MHz, DMSO-d$_6$) δ 2.62 (3H, s), 3.98 (3H, s), 3.99 (2H, s), 5.37 (2H, s), 6.87 (1H, s), 7.23 (1H, d, J=7.6 Hz), 7.46 (1H, s), 12.56 (1H, brs).

Example 35

Methyl(7-fluoro-4-methyl-6-((2-methyl-6-(trifluoromethyl)pyridin-3-yl)methoxy)-1-benzothiophen-3-yl)acetate To a mixture of tri-n-butylphosphine (0.362 mL), methyl (7-fluoro-6-hydroxy-4-methyl-1-benzothiophen-3-yl)acetate (122.8 mg), (2-methyl-6-(trifluoromethyl)pyridin-3-yl)methanol (102 mg) and THF (4.5 mL) was added ADDP (305 mg) at room temperature. The mixture was stirred overnight at room temperature under nitrogen atmosphere. The mixture was concentrated. To the residue was added IPE and the precipitate was filtered off. The filtrate was concentrated in vacuo. The residue was purified by silica gel column chromatography (NH, EtOAc/hexane) to give the title compound (196 mg). The compound was crystallized from EtOAc-hexane.

$^1$H NMR (300 MHz, CDCl$_3$) δ 2.62 (3H, d, J=1.1 Hz), 2.68 (3H, s), 3.73 (3H, s), 4.01 (2H, d, J=0.8 Hz), 5.23 (2H, s), 6.86 (1H, dd, J=7.6, 0.8 Hz), 7.19 (1H, s), 7.57 (1H, d, J=7.9 Hz), 7.98 (1H, d, J=7.9 Hz).

Example 36

(7-Fluoro-4-methyl-6-((2-methyl-6-(trifluoromethyl) pyridin-3-yl)methoxy)-1-benzothiophen-3-yl)acetic acid To a mixture of methyl(7-fluoro-4-methyl-6-((2-methyl-6-(trifluoromethyl)pyridin-3-yl)methoxy)-1-benzothiophen-3-yl)acetate (159.8 mg), THF (dry) (2.0 mL) and MeOH (2.0 mL) was added 1N NaOH (1.122 mL) at room temperature. The mixture was stirred at room temperature for 2 h. The mixture was neutralized with 1N HCl and concentrated in vacuo. The precipitate was collected by filtration to give a solid. The solid was crystallized from EtOAc-hexane to give the title compound (134 mg).

$^1$H NMR (300 MHz, DMSO-d$_6$) δ 2.61 (3H, s), 2.63 (3H, s), 3.99 (2H, s), 5.40 (2H, s), 7.24 (1H, d, J=7.6 Hz), 7.45 (1H, s), 7.78 (1H, d, J=7.9 Hz), 8.09 (1H, d, J=7.9 Hz), 12.56 (1H, brs).

Example 37

Methyl(4-chloro-7-fluoro-6-((1-methyl-3-(trifluoromethyl)-1H-pyrazol-5-yl)methoxy)-1-benzothiophen-3-yl)acetate A) 4-Chloro-1-fluoro-2-methoxybenzene To a mixture of 5-chloro-2-fluorophenol (4.68 g) and DMF (dry) (50 mL) were added K$_2$CO$_3$ (8.83 g) and iodomethane (3.99 mL) at room temperature. The mixture was stirred at room temperature for 4.5 h. The mixture was diluted with water and extracted with EtOAc. The organic layer was washed successively with water and brine, dried over MgSO$_4$, and concentrated in vacuo. The residue was purified by silica gel column chromatography (EtOAc/hexane) to give the title compound (4.60 g).

$^1$H NMR (300 MHz, CDCl$_3$) δ 3.88 (3H, s), 6.83-6.90 (1H, m), 6.94 (1H, dd, J=7.4, 2.5 Hz), 7.00 (1H, dd, J=11.0, 8.7 Hz).

B) 5-Chloro-2-fluoro-1-methoxy-3-(methylsulfanyl) benzene

To a mixture of 4-chloro-1-fluoro-2-methoxybenzene (2.0 g) and THF (dry) (100 mL) was added sec-butyllithium (1.04 mol/L cyclohexane solution, 23.95 mL) dropwise over a period of 45 min at −78° C. After stirring at −78° C. for 30 min, to the mixture was added dimethyl disulfide (2.468 mL) at the same temperature. The mixture was stirred at −78° C. for 1.5 h under argon atmosphere. The mixture was quenched with saturated aqueous NH$_4$Cl at −78° C. and extracted with EtOAc. The organic layer was washed with brine, dried over MgSO$_4$, and concentrated in vacuo. The residue was purified by silica gel column chromatography (EtOAc/hexane) to give a solid. The solid was washed with hexane to give the title compound (1.77 g).

$^1$H NMR (300 MHz, CDCl$_3$) δ 2.46 (3H, s), 3.87 (3H, s), 6.75-6.81 (2H, m).

C) 5-Chloro-2-fluoro-1-methoxy-3-(methylsulfinyl) benzene

To a mixture of 5-chloro-2-fluoro-1-methoxy-3-(methylsulfanyl)benzene (576.1 mg), MeOH (20 mL) and water (4.0 mL) was added NaIO$_4$ (894 mg) at 0° C. The mixture was stirred at room temperature for 1 day. The mixture was concentrated. The residue was diluted with water. The precipitate was filtered off, and the filtrate was extracted with EtOAc. The organic layer was washed with brine, dried over MgSO$_4$, and concentrated in vacuo. The residue was purified by silica gel column chromatography (EtOAc/hexane) to give the title compound (501 mg).

MS (ESI+): [M+H]$^+$ 223.0.

D) 5-Chloro-2-fluoro-3-methoxybenzenethiol

To a mixture of 5-chloro-2-fluoro-1-methoxy-3-(methylsulfinyl)benzene (501 mg) and CH$_3$CN (20 mL) was added TFAA (0.953 mL) at 0° C. The mixture was stirred at 0° C. for 1 h and then at room temperature for 1 h. The mixture was concentrated. The residue was dissolved in a mixture of MeOH (3.5 mL) and TEA (3.5 mL) at 0° C. The solution was stirred at 0° C. for 10 min, and concentrated in vacuo. The mixture was diluted with saturated aqueous $NH_4Cl$ and extracted with EtOAc. The organic layer was extracted with 1N NaOH. The aqueous layer was acidified with 1N HCl and extracted with EtOAc. The organic layer was washed with brine, dried over $MgSO_4$, and concentrated in vacuo to give the title compound (303 mg).

MS (ESI−): [M−H]− 191.0.

E) Methyl 4-((5-chloro-2-fluoro-3-methoxyphenyl)sulfanyl)-3-oxobutanoate

To a mixture of 5-chloro-2-fluoro-3-methoxybenzenethiol (303 mg) and DMF (dry) (12 mL) were added $K_2CO_3$ (239 mg) and methyl 4-chloro-3-oxobutanoate (0.204 mL) at 0° C. The mixture was stirred at room temperature for 45 min. The mixture was diluted with water and extracted with EtOAc. The combined organic layer was washed successively with water and brine, dried over $MgSO_4$, and concentrated in vacuo. The residue was purified by silica gel column chromatography (EtOAc/hexane) to give the title compound (402 mg).

MS (ESI−): [M−H]− 305.0.

F) Methyl(4-chloro-7-fluoro-6-methoxy-1-benzothiophen-3-yl)acetate

MsOH (4.0 mL) was added to methyl 4-((5-chloro-2-fluoro-3-methoxyphenyl)sulfanyl)-3-oxobutanoate (400 mg) at 0° C. After stirring at 0° C. for 20 min, the mixture was warmed to room temperature and stirred for 2 h. The mixture was poured into ice water at 0° C. and extracted with EtOAc. The organic layer was separated, washed successively with saturated aqueous $NaHCO_3$ and brine, dried over $MgSO_4$ and concentrated in vacuo. The residue was purified by silica gel column chromatography (EtOAc/hexane) to give the title compound (338 mg).

$^1$H NMR (300 MHz, $CDCl_3$) δ 3.73 (3H, s), 3.95 (3H, s), 4.10 (2H, s), 7.08 (1H, d, J=6.8 Hz), 7.17 (1H, s).

G) Methyl(4-chloro-7-fluoro-6-hydroxy-1-benzothiophen-3-yl)acetate

To a mixture of methyl(4-chloro-7-fluoro-6-methoxy-1-benzothiophen-3-yl)acetate (284.8 mg) and DMF (dry) (8.0 mL) was added sodium 2-methyl-2-propanethiolate (443 mg). The mixture was stirred at 160° C. for 45 min. After cooling, the mixture was diluted with water and 1N HCl and extracted with EtOAc. The organic layer was washed successively with water and brine, dried over $MgSO_4$, filtered and concentrated in vacuo. The residue was dissolved in MeOH (6.0 mL). To the solution was added conc. $H_2SO_4$ (0.100 mL). The mixture was stirred at 70° C. for 1 h. The mixture was concentrated. The residue was neutralized with saturated aqueous $NaHCO_3$, and the mixture was extracted with EtOAc. The combined organic layer was washed with brine, dried over $MgSO_4$, filtered and concentrated in vacuo. The residual solid was washed with toluene and hexane to give the title compound (229.3 mg).

MS (ESI−): [M−H]− 272.9.

H) Methyl(4-chloro-7-fluoro-6-((1-methyl-3-(trifluoromethyl)-1H-pyrazol-5-yl)methoxy)-1-benzothiophen-3-yl)acetate To a mixture of tri-n-butylphosphine (0.249 mL), methyl (4-chloro-7-fluoro-6-hydroxy-1-benzothiophen-3-yl)acetate (109.7 mg), (1-methyl-3-(trifluoromethyl)-1H-pyrazol-5-yl)methanol (86 mg) and THF (4.0 mL) was added ADDP (202 mg) at room temperature. The mixture was stirred at room temperature under nitrogen atmosphere for 1 h. The mixture was concentrated. To the residue was added IPE and the precipitate was filtered off. The filtrate was concentrated in vacuo. The residue was purified by silica gel column chromatography (EtOAc/hexane) to give the title compound (155 mg).

$^1$H NMR (300 MHz, $CDCl_3$) δ 3.73 (3H, s), 4.04 (3H, s), 4.11 (2H, s), 5.17 (2H, s), 6.58 (1H, s), 7.12 (1H, d, J=6.8 Hz), 7.25 (1H, s).

Example 38

(4-Chloro-7-fluoro-6-((1-methyl-3-(trifluoromethyl)-1H-pyrazol-5-yl)methoxy)-1-benzothiophen-3-yl)acetic acid To a mixture of methyl(4-chloro-7-fluoro-6-((1-methyl-3-(trifluoromethyl)-1H-pyrazol-5-yl)methoxy)-1-benzothiophen-3-yl)acetate (133 mg), THF (dry) (2.0 mL) and MeOH (2.0 mL) was added 1N NaOH (0.913 mL) at room temperature. The mixture was stirred at room temperature for 2 h. The mixture was neutralized with 1N HCl. The resulting precipitate was collected by filtration to give a solid. The solid was crystallized from EtOAc-hexane to give the title compound (114 mg).

$^1$H NMR (300 MHz, DMSO-$d_6$) δ 3.98 (3H, s), 4.03 (2H, s), 5.43 (2H, s), 6.88 (1H, s), 7.57-7.65 (2H, m), 12.46 (1H, brs).

Example 39

Methyl(4-chloro-7-fluoro-6-((2-methyl-6-(trifluoromethyl)pyridin-3-yl)methoxy)-1-benzothiophen-3-yl)acetate To a mixture of tri-n-butylphosphine (0.264 mL), methyl (4-chloro-7-fluoro-6-hydroxy-1-benzothiophen-3-yl)acetate (116 mg), (2-methyl-6-(trifluoromethyl)pyridin-3-yl)methanol (89 mg) and THF (4.0 mL) was added ADDP (213 mg) at room temperature. The mixture was stirred at room temperature under nitrogen atmosphere for 1 h. The mixture was concentrated in vacuo. To the residue was added IPE and the precipitate was filtered off. The filtrate was concentrated in vacuo. The residue was purified by silica gel column chromatography (NH, EtOAc/hexane) to give the title compound (172 mg).

$^1$H NMR (300 MHz, $CDCl_3$) δ 2.68 (3H, s), 3.74 (3H, s), 4.11 (2H, s), 5.23 (2H, s), 7.14 (1H, d, J=6.8 Hz), 7.24 (1H, s), 7.58 (1H, d, J=7.9 Hz), 7.97 (1H, d, J=7.9 Hz).

Example 40

(4-Chloro-7-fluoro-6-((2-methyl-6-(trifluoromethyl)pyridin-3-yl)methoxy)-1-benzothiophen-3-yl)acetic acid To a mixture of methyl(4-chloro-7-fluoro-6-((2-methyl-6-(trifluoromethyl)pyridin-3-yl)methoxy)-1-benzothiophen-3- yl)acetate (150.2 mg), THF (dry) (1.5 mL) and MeOH (1.5 mL) was added 1N NaOH (1.01 mL). The mixture was stirred at room temperature for 2 h. The mixture was neutralized with 1N HCl. The resulting precipitate was collected by filtration to give a solid. The solid was crystallized from EtOAc-hexane to give the title compound (126.6 mg).

$^1$H NMR (300 MHz, DMSO-$d_6$) δ 2.63 (3H, s), 4.03 (2H, s), 5.46 (2H, s), 7.61-7.66 (2H, m), 7.79 (1H, d, J=7.9 Hz), 8.09 (1H, d, J=7.9 Hz), 12.47 (1H, brs).

Example 41

Methyl(7-chloro-6-((2,4-dichlorobenzyl)oxy)-1-benzofuran-3-yl)acetate

A) 8-Chloro-4-(chloromethyl)-7-hydroxy-2H-chromen-2-one

To ethyl 4-chloro-3-oxobutanoate (4.91 mL) was added sulfuric acid (12.91 mL) at 0° C., then was added 2-chlorobenzene-1,3-diol (5.0 g) in several portions at 0° C. The mixture was warmed to room temperature and stirred at the same temperature for 2 h. The reaction mixture was poured into water under stirring at 0° C. The precipitate was collected by m filtration and washed with hexane to give the title compound (2.78 g).

MS (ESI-): [M-H]$^-$ 243.1.

B) (7-Chloro-6-hydroxy-1-benzofuran-3-yl)acetic acid

A mixture of 1N NaOH (56.7 mL) and 8-chloro-4-(chloromethyl)-7-hydroxy-2H-chromen-2-one (2.78 g) was stirred at 100° C. for 1 h. After cooling, the reaction mixture was acidified with 6N HCl (10 mL). The precipitate was collected by filtration to give the title compound (1.65 g).

MS (ESI-): [M-H]$^-$ 225.1

C) Methyl(7-chloro-6-hydroxy-1-benzofuran-3-yl)acetate

To a mixture of (7-chloro-6-hydroxy-1-benzofuran-3-yl) acetic acid (1.65 g) and MeOH (40 mL) was added conc. $H_2SO_4$ (0.078 mL). The mixture was stirred at 60° C. for 3 h. The mixture was concentrated in vacuo. The residue was neutralized with saturated aqueous $NaHCO_3$ and extracted with EtOAc. The organic layer was washed with brine, dried over $MgSO_4$, and concentrated in vacuo. The residue was dissolved in toluene and hexane. The insoluble material was filtered and washed with toluene and hexane. The filtrate was purified by silica gel column chromatography (EtOAc/hexane) to give the title compound (1.49 g).

MS (ESI-): [M-H]$^-$ 239.0.

D) Methyl(7-chloro-6-((2,4-dichlorobenzyl)oxy)-1-benzofuran-3-yl)acetate

To a mixture of methyl(7-chloro-6-hydroxy-1-benzofuran-3-yl)acetate (200 mg) and DMF (dry) (8.0 mL) were added $K_2CO_3$ (172 mg) and 2,4-dichlorobenzyl chloride (0.138 mL). The mixture was stirred at 60° C. for 1.5 h. The mixture was quenched with water. The precipitate was collected by filtration and washed with water and hexane to give the title compound (272 mg) as a solid. The solid was crystallized from EtOAc-hexane to give the title compound.

$^1$H NMR (300 MHz, CDCl$_3$) δ 3.68 (2H, d, J=0.8 Hz), 3.73 (3H, s), 5.25 (2H, s), 6.98 (1H, d, J=8.7 Hz), 7.30 (1H, dd, J=8.3, 1.9 Hz), 7.37 (1H, d, J=8.7 Hz), 7.43 (1H, d, J=2.3 Hz), 7.64 (2H, t, J=4.2 Hz).

Example 42

(7-Chloro-6-((2,4-dichlorobenzyl)oxy)-1-benzofuran-3-yl)acetic acid

To a mixture of methyl(7-chloro-6-((2,4-dichlorobenzyl) oxy)-1-benzofuran-3-yl)acetate (218.9 mg), MeOH (2.0 mL) and THF (dry) (2.0 mL) was added 1N NaOH (1.643 mL) at room temperature. The mixture was stirred at room temperature for 2 h. The residue was concentrated. The residue was neutralized with 1N HCl, and the mixture was extracted with EtOAc. The combined organic layer was washed with brine, dried over $MgSO_4$, and concentrated in vacuo. The precipitate was collected by filtration, and crystallized from EtOH-hexane to give the title compound (184 mg).

$^1$H NMR (300 MHz, DMSO-$d_6$) δ 3.68 (2H, s), 5.30 (2H, s), 7.26 (1H, d, J=8.7 Hz), 7.49-7.55 (2H, m), 7.67 (1H, d, J=8.3 Hz), 7.71 (1H, d, J=2.3 Hz), 7.92 (1H, s).

Example 43

Methyl(6-((2,6-dimethylpyridin-3-yl)methoxy)-4,7-dimethyl-1-benzofuran-3-yl)acetate A) Methyl(6-hydroxy-4,7-dimethyl-1-benzofuran-3-yl)acetate To ethyl 4-chloro-3-oxobutanoate (3.08 mL) was added sulfuric acid (8.10 mL) at 0° C., then was added 2,5-dimethylbenzene-1,3-diol (3.0 g) in several portions at 0° C. The mixture was warmed to room temperature and stirred at room temperature for 2 h. The reaction mixture was poured into water under stirring at 0° C. The precipitate was collected by filtration and washed with hexane to give a solid. The solid was added to 1N NaOH (40 mL) at room temperature. The mixture was stirred at 100° C. for 1 h. After cooling, the reaction mixture was acidified with 6 N HCl (7.0 mL). The mixture was extracted with EtOAc. The organic layer was washed with brine, dried over $MgSO_4$, and concentrated in vacuo to give the crude product. To a mixture of the crude product and MeOH (50 mL) was added $H_2SO_4$ (0.057 mL). The mixture was stirred at 60° C. for 2 h. The mixture was concentrated. The residue was neutralized with saturated aqueous $NaHCO_3$ and extracted with EtOAc. The organic layer was washed with brine, dried over $MgSO_4$, and concentrated in vacuo. The residue was purified by silica gel column chromatography (EtOAc/hexane) to give the title compound (865 mg).

MS (ESI+): [M+H]$^+$ 235.0.

B) Methyl(6-((2,6-dimethylpyridin-3-yl)methoxy)-4,7-dimethyl-1-benzofuran-3-yl)acetate To a mixture of tri-n-butylphosphine (0.240 mL), (2,6-dimethylpyridin-3-yl)methanol (92 mg), methyl(6-hydroxy-4,7-dimethyl-1-benzofuran-3-yl)acetate (150 mg) and THF (6.0 mL) was added ADDP (242 mg) at room temperature. The mixture was stirred at room temperature overnight under nitrogen atmosphere. The mixture was concentrated. To the residue was added. IPE and the precipitate was filtered off and the filtrate was concentrated in vacuo. The residue was purified by silica gel column chromatography (EtOAc/hexane) to give the title compound (163.9 mg).

$^1$H NMR (300 MHz, CDCl$_3$) δ 2.33 (3H, s), 2.54 (3H, s), 2.55 (3H, s), 2.58 (3H, s), 3.73 (3H, s), 3.80 (2H, d, J=1.1 Hz), 5.04 (2H, s), 6.68 (1H, s), 7.02 (1H, d, J=7.6 Hz), 7.51 (1H, s), 7.63 (1H, d, J=7.9 Hz).

Example 44

(6-((2,6-Dimethylpyridin-3-yl)methoxy)-4,7-dimethyl-1-benzofuran-3-yl)acetic acid To a mixture of methyl(6-((2,6-dimethylpyridin-3-yl)methoxy)-4,7-dimethyl-1-benzofuran-3-yl)acetate (142.0 mg), MeOH (2.0 mL) and THF (dry) (2.0 mL) was added 1N NaOH (1.21 mL) at room temperature. The mixture was stirred at room temperature for 2 h. The mixture was neutralized with 1N HCl. The precipitate was collected by filtration. The solid was crystallized from IPA-EtOAc to give the title compound (100 mg).

$^1$H NMR (300 MHz, DMSO-d$_6$) δ 2.23 (3H, s), 2.43 (3H, s), 2.49 (6H, s), 3.74 (2H, s), 5.11 (2H, s), 6.88 (1H, s), 7.09 (1H, d, J=7.9 Hz), 7.68 (1H, d, J=7.9 Hz), 7.71 (1H, s), 12.47 (1H, brs).

Example 45

Methyl(6-((2,4-dichlorobenzyl)oxy)-4,7-dimethyl-1-benzofuran-3-yl)acetate

To a mixture of methyl(6-hydroxy-4,7-dimethyl-1-benzofuran-3-yl)acetate (150 mg) and DMF (dry) (6.4 mL) were added K$_2$CO$_3$ (133 mg) and 2,4-dichlorobenzyl chloride (0.107 mL). The mixture was stirred at room temperature overnight. The mixture was quenched with water. The precipitate was collected by filtration and washed with water and hexane to give the title compound (176.5 mg).

Example 46

(6-((2,4-Dichlorobenzyl)oxy)-4,7-dimethyl-1-benzofuran-3-yl)acetic acid

To a mixture of methyl(6-((2,4-dichlorobenzyl)oxy)-4,7-dimethyl-1-benzofuran-3-yl)acetate (147 mg), MeOH (2.0 mL) and THF (dry) (2.0 mL) was added 1N NaOH (1.12 mL) at room temperature. The mixture was stirred at room temperature for 2 h, and then concentrated in vacuo. The residue was neutralized with 1N HCl, and the mixture was extracted with EtOAc. The organic layer was washed with brine and, dried over MgSO$_4$, and concentrated in vacuo. The precipitate was collected by filtration, and crystallized from EtOAc-hexane to give the title compound (118 mg).

$^1$H NMR (300 MHz, DMSO-d$_6$) δ 2.26 (3H, s), 2.48 (3H, brs), 3.74 (2H, s), 5.17 (2H, s), 6.84 (1H, s), 7.49 (1H, dd, J=8.3, 2.3 Hz), 7.65 (1H, d, J=8.3 Hz), 7.69 (1H, d, J=2.3 Hz), 7.72 (1H, s), 12.48 (1H, brs).

Example 47

Ethyl(6-((2,4-dichlorobenzyl)oxy)-1,1-dioxido-1-benzothiophen-3-yl)acetate

To a mixture of ethyl(6-((2,4-dichlorobenzyl)oxy)-1-benzothiophen-3-yl)acetate (10.0 g) in anhydrous DCM (400 mL) was added mCPBA (85%, 15.7 g), and the resulting solution was stirred at 25° C. for 3 d. To the reaction mixture was added Na$_2$SO$_3$ (30.0 g), and the mixture was stirred at 25° C. for 0.5 h. The reaction mixture was washed successively with saturated aqueous NaHCO$_3$ and brine, dried over Na$_2$SO$_4$ and concentrated in vacuo. The residue was washed with EtOAc to give the title compound (8.50 g).

Example 48

(6-((2,4-Dichlorobenzyl)oxy)-1,1-dioxido-1-benzothiophen-3-yl)acetic acid

To a mixture of ethyl(6-((2,4-dichlorobenzyl)oxy)-1,1-dioxido-1-benzothiophen-3-yl)acetate (8.00 g), THF (64 mL), MeOH (64 mL) and H$_2$O (32 mL) was added lithium hydroxide hydrate (1.58 g) and the resulting mixture was stirred at 25° C. for 16 h. The solvent was removed under reduced pressure. The residue was suspended in water, and the mixture was acidified by 6N HCl. The resulting solid was collected by filtration, and dried under reduced pressure to give the title compound (4.00 g).

Example 49

Ethyl(6-((2,4-dichlorobenzyl)oxy)-2,3-dihydro-1-benzothiophen-3-yl)acetate

To a solution of ethyl(6-hydroxy-2,3-dihydro-1-benzothiophen-3-yl)acetate (17.2 g) in DMF (300 mL) were added 2,4-dichlorobenzyl chloride (17.0 g) and K$_2$CO$_3$ (15.0 g) and the resulting solution was stirred at 20° C. for 72 h. The mixture was diluted with EtOAc, washed successively with water and brine. The organic layer was dried over Na$_2$SO$_4$ and concentrated in vacuo. The residue was purified by silica gel column chromatography (PE/EtOAc) to give the title compound (19.6 g).

Example 50

(6-((2,4-Dichlorobenzyl)oxy)-2,3-dihydro-1-benzothiophen-3-yl)acetic acid

The title compound was obtained in a same manner as the procedure in Example 2 by using the corresponding ester.

Example 51

Ethyl(6-((2,4-dichlorobenzyl)oxy)-1,1-dioxido-2,3-dihydro-1-benzothiophen-3-yl)acetate The title compound was obtained in a same manner as the procedure in Example 47 by using ethyl(6-((2,4-dichlorobenzyl)oxy)-2,3-dihydro-1-benzothiophen-3-yl)acetate.

Example 52

(6-((2,4-Dichlorobenzyl)oxy)-1,1-dioxido-2,3-dihydro-1-benzothiophen-3-yl)acetic acid The title compound was obtained in a same manner as the procedure in Example 48 by using the corresponding ester.

Example 53

Ethyl N-((6-((2,4-dichlorobenzyl)oxy)-1-benzothiophen-3-yl)acetyl)glycinate

To a mixture of (6-((2,4-dichlorobenzyl)oxy)-1-benzothiophen-3-yl)acetic acid (150 mg) in DMF (dry) (3.0 mL)

were added ethyl 2-aminoacetate hydrochloride (57.0 mg), HOBt (71.7 mg), EDCI (102 mg) and triethylamine (0.171 mL). The mixture was stirred at room temperature for 17 h. The mixture was diluted with saturated aqueous NaHCO$_3$ and water. The mixture was extracted with EtOAc. The combined organic layer was washed successively with water and brine, dried over MgSO$_4$, filtered and concentrated in vacuo. The residue was washed with hexane to give the title compound (158 mg).

Example 54

Methyl N-((6-((2,4-dichlorobenzyl)oxy)-1-benzothiophen-3-yl)acetyl)serinate

The title compound was obtained in a same manner as the procedure in Example 53 by using (6-((2,4-dichlorobenzyl)oxy)-1-benzothiophen-3-yl)acetic acid and methyl 2-amino-3-hydroxypropanoate hydrochloride.

Example 55

N-((6-((2,4-Dichlorobenzyl)oxy)-1-benzothiophen-3-yl)acetyl)glycine

The title compound was obtained in a same manner as the procedure in Example 2 by using the corresponding ester.

Example 56

N-((6-((2,4-Dichlorobenzyl)oxy)-1-benzothiophen-3-yl)acetyl)serine

The title compound was obtained in a same manner as the procedure in Example 2 by using the corresponding ester.

Example 57

2-(6-((2,4-Dichlorobenzyl)oxy)-1-benzothiophen-3-yl)-N-methylacetamide

The title compound was obtained in a same manner as the procedure in Example 53 by using (6-((2,4-dichlorobenzyl)oxy)-1-benzothiophen-3-yl)acetic acid and methylamine hydrochloride Example 58

2-(6-((2,4-Dichlorobenzyl)oxy)-1-benzothiophen-3-yl)-1-(morpholin-4-yl)ethanone

The title compound was obtained in a same manner as the procedure in Example 53 by using (6-((2,4-dichlorobenzyl)oxy)-1-benzothiophen-3-yl)acetic acid and morpholine.

Example 59

Ethyl(6-((2,4-dimethyl-1,3-thiazol-5-yl)methoxy)-1-benzothiophen-3-yl)acetate

The title compound was obtained in a same manner as the procedure in Example 3 using ethyl(6-hydroxy-1-benzothiophen-3-yl)acetate and (2,4-dimethyl-1,3-thiazol-5-yl)methanol.

Example 60

(6-((2,4-Dimethyl-1,3-thiazol-5-yl)methoxy)-1-benzothiophen-3-yl)acetic acid

The title compound was obtained in a same manner as the procedure in Example 12 by using the corresponding ester.

Example 61

Ethyl(6-((2-Chloro-4-(trifluoromethyl)benzyl)oxy)-1-benzothiophen-3-yl)acetate

The title compound was obtained in a same manner as the procedure in Example 3 using ethyl(6-hydroxy-1-benzothiophen-3-yl)acetate and 2-chloro-4-(trifluoromethyl)benzyl alcohol.

Example 62

(6-((2-chloro-4-(trifluoromethyl)benzyl)oxy)-1-benzothiophen-3-yl)acetic acid

The title compound was obtained in a same manner as the procedure in Example 12 by using the corresponding ester.

Example 63

Ethyl 6-((2,4-dichlorobenzyl)oxy)-3-(2-ethoxy-2-oxoethoxy)-1-benzothiophene-2-carboxylate A) Ethyl 4-((2,4-dichlorobenzyl)oxy)-2-fluorobenzoate The title compound was obtained in a same manner as the procedure in Example 5 by using ethyl 2-fluoro-4-hydroxybenzoate and 2,4-dichlorobenzyl chloride.
MS (ESI−): [M−H]− 341.0.

B) Ethyl 6-((2,4-dichlorobenzyl)oxy)-3-hydroxy-1-benzothiophene-2-carboxylate

To a mixture of ethyl 4-((2,4-dichlorobenzyl)oxy)-2-fluorobenzoate (2.0 g) in DMF (dry) (40 mL) were added lithium hydroxide monohydrate (0.978 g) and ethyl 2-mercaptoacetate (1.92 mL) at room temperature. The mixture was stirred at room temperature for 2 d. The mixture was diluted with water and the precipitate was collected by filtration, and washed with IPE to give the title compound (2.30 g).
$^1$H NMR (300 MHz, DMSO-d$_6$) δ 1.23 (3H, t, J=7.2 Hz), 4.13 (2H, q, J=7.2 Hz), 5.19 (2H, s), 6.88 (1H, dd, J=8.5, 2.1 Hz), 7.26 (1H, d, J=2.3 Hz), 7.46-7.53 (1H, m), 7.60 (1H, d, J 8.7 Hz), 7.65 (1H, d, J=8.3 Hz), 7.71 (1H, d, J=2.3 Hz), 7.95 (1H, s).

C) Ethyl 6-((2,4-dichlorobenzyl)oxy)-3-(2-ethoxy-2-oxoethoxy)-1-benzothiophene-2-carboxylate To a mixture of ethyl 6-((2,4-dichlorobenzyl)oxy)-3-hydroxy-1-benzothiophene-2-carboxylate (200 mg) in DMF (dry) (5.0 mL) were added K$_2$CO$_3$ (104 mg) and ethyl 2-bromoacetate (0.084 mL). The mixture was stirred at room temperature for 16 h. The mixture was diluted with water and extracted with EtOAc. The combined organic layer was washed successively with water and brine, dried over MgSO$_4$,

Example 64

((6-((2,4-Dichlorobenzyl)oxy)-1-benzothiophen-3-yl)oxy)acetic acid

The mixture of 3-(carboxymethoxy)-6-((2,4-dichlorobenzyl)oxy)-1-benzothiophene-2-carboxylic acid (92.0 mg), copper (13.7 mg) and quinoline (1.5 mL) was heated at 190° C. for 10 min. The mixture was diluted with EtOAc. The mixture was washed successively with 1N HCl and brine, dried over $MgSO_4$, and concentrated in vacuo. The residue was purified by silica gel column chromatography (EtOAc/hexane), and washed with hexane to give the title compound (63.9 mg).

Example 65

Ethyl((2-carbamoyl-6-((2,4-dichlorobenzyl)oxy)-1-benzothiophen-3-yl)sulfanyl)acetate

A) Methyl 3-(4-((2,4-dichlorobenzyl)oxy)phenyl)propanoate

The title compound was obtained in a same manner as the procedure in Example 5 by using methyl 3-(4-hydroxyphenyl)propanoate and 2,4-dichlorobenzyl chloride.
$^1$H NMR (300 MHz, $CDCl_3$) δ 2.55-2.67 (2H, m), 2.83-2.96 (2H, m), 3.67 (3H, s), 5.09 (2H, s), 6.86-6.89 (1H, m), 6.89-6.92 (1H, m), 7.10-7.13 (1H, m), 7.13-7.16 (1H, m), 7.26 (1H, dd, J=8.3, 1.9 Hz), 7.41 (1H, d, J=1.9 Hz), 7.49 (1H, d, J=8.3 Hz).

B) 3-(4-((2,4-Dichlorobenzyl)oxy)phenyl)propanoic acid

The title compound was obtained in a same manner as the procedure in Example 2 by using methyl 3-(4-((2,4-dichlorobenzyl)oxy)phenyl)propanoate.
MS (ESI−): [M−H]$^-$ 323.0.

C) Methyl 3-chloro-6-((2,4-dichlorobenzyl)oxy)-1-benzothiophene-2-carboxylate To a mixture of 3-(4-((2,4-dichlorobenzyl)oxy)phenyl)propanoic acid (1.5 g) in chlorobenzene (10 mL) were added pyridine (0.037 mL) and thionyl chloride (0.421 mL) at 150° C. To the mixture was added dropwise thionyl chloride (1.094 mL), and the mixture was stirred at 150° C. for 3.5 h. After cooling, the residue was diluted with MeOH (10 mL). The mixture was stirred at 80° C. for 2.5 h. After cooling, the mixture was diluted with MeOH and the precipitate was collected by filtration to give the title compound (0.620 g).
MS (ESI+): [M+H]$^+$ 401.1.

D) 3-Chloro-6-((2,4-dichlorobenzyl)oxy)-1-benzothiophene-2-carboxylic acid

The title compound was obtained in a same manner as the procedure in Example 2 using methyl 3-chloro-6-((2,4-dichlorobenzyl)oxy)-1-benzothiophene-2-carboxylate.
$^1$H NMR (300 MHz, DMSO-$d_6$) δ 5.27 (2H, s), 7.29 (1H, dd, J=8.7, 2.3 Hz), 7.51 (1H, dd, J=8.3, 1.9 Hz), 7.68 (1H, d, J=8.3 Hz), 7.73 (1H, d, J=2.3 Hz), 7.83-7.88 (2H, m).

E) 3-Chloro-6-((2,4-dichlorobenzyl)oxy)-1-benzothiophene-2-carboxamide

To a solution of 3-chloro-6-((2,4-dichlorobenzyl)oxy)-1-benzothiophene-2-carboxylic acid (190.4 mg) in DMF (dry) (4.9 mL) were added HOBt ammonia complex (112 mg), EDCI (141 mg) and triethylamine (0.205 mL). The mixture was stirred at room temperature overnight. The mixture was diluted with saturated aqueous $NaHCO_3$ and water. The precipitate was collected by filtration, and washed with water and hexane to give the title compound (195 mg).
$^1$H NMR (300 MHz, $CDCl_3$) δ 5.08-5.19 (1H, m), 5.21 (2H, s), 6.93-7.05 (1H, m), 7.19 (1H, dd, J=8.7, 2.3 Hz), 7.28-7.32 (1H, m), 7.34 (1H, d, J=2.3 Hz), 7.46 (1H, d, J=2.3 Hz), 7.51 (1H, d, J=8.3 Hz), 7.80 (1H, d, J=8.7 Hz).

F) 6-((2,4-Dichlorobenzyl)oxy)-3-sulfanyl-1-benzothiophene-2-carboxamide

To a mixture of 3-chloro-6-((2,4-dichlorobenzyl)oxy)-1-benzothiophene-2-carboxamide (193.6 mg) in DMF (dry) (2.5 mL) were added DBU (0.225 mL) and thioacetamide (113 mg). The mixture was stirred at 80° C. for 5.5 h. After cooling, the mixture was diluted with 1N HCl and extracted with EtOAc. The combined organic layer was washed successively with water and brine, dried over $MgSO_4$, and concentrated in vacuo. The precipitate was washed with hexane and THF to give the title compound (41.6 mg).
MS (ESI−): [M−H]$^-$ 382.1.

G) Ethyl((2-carbamoyl-6-((2,4-dichlorobenzyl)oxy)-1-benzothiophen-3-yl)sulfanyl)acetate To a mixture of 6-((2,4-dichlorobenzyl)oxy)-3-sulfanyl-1-benzothiophene-2-carboxamide (40 mg) in THF (dry) (4.0 mL) were added sodium hydrogen carbonate (13.1 mg) and ethyl 2-bromoacetate (0.017 mL). The mixture was stirred overnight at room temperature. To the mixture was added DMF (1.0 mL) and stirred at room temperature over weekend. The mixture was quenched with water and extracted with EtOAc. The combined organic layer was washed successively with water and brine, dried over $MgSO_4$, and concentrated in vacuo. The residue was purified by silica gel column chromatography (EtOAc/hexane) to give the title compound (25.2 mg).

Example 66

((2-Carbamoyl-6-((2,4-dichlorobenzyl)oxy)-1-benzothiophen-3-yl)sulfanyl)acetic acid The title compound was obtained in a same manner as the procedure in Example 2 by using ethyl((2-carbamoyl-6-((2,4-dichlorobenzyl)oxy)-1-benzothiophen-3-yl)sulfanyl)acetate.

Example 67

Ethyl 3-(2-tert-butoxy-2-oxoethoxy)-6-((2,4-dichlorobenzyl)oxy)-1-benzothiophene-2-carboxylate A mixture of t-butyl bromoacetate (0.736 mL), $K_2CO_3$ (0.626 g), ethyl 6-((2,4-dichlorobenzyl)oxy)-3-hydroxy-1-benzothiophene-2-carboxylate (1.8 g) and DMF (20 mL) was stirred at room temperature for 20 h. Water was added to the mixture and the mixture was extracted with EtOAc. The EtOAc extract was washed successively with water and brine, dried over MgSO$_4$, and concentrated in vacuo. The residue was purified by silica gel column chromatography (EtOAc/hexane) to give the title compound (1.330 g). The obtained crystals were recrystallized from acetone-hexane.

Example 68

Ethyl(6-((4-methoxy-2-methylpyrimidin-5-yl)methoxy)-1-benzothiophen-3-yl)acetate The title compound was obtained in a same manner as the procedure in Example 3 using ethyl(6-hydroxy-1-benzothiophen-3-yl)acetate and (4-methoxy-2-methylpyrimidin-5-yl)methanol.

Example 69

(6-((4-Methoxy-2-methylpyrimidin-5-yl)methoxy)-1-benzothiophen-3-yl)acetic acid

The title compound was obtained in a same manner as the procedure in Example 2 by using the corresponding ester.

Example 70

3-(Carboxymethoxy)-6-((2,4-dichlorobenzyl)oxy)-1-benzothiophene-2-carboxylic acid A mixture of ethyl 3-(2-tert-butoxy-2-oxoethoxy)-6-((2,4-dichlorobenzyl)oxy)-1-benzothiophene-2-carboxylate (1.1 g), 1N NaOH (5 mL), EtOH (5 mL) and THF (10 mL) was stirred at 50° C. for 24 h. Water and 1N HCl (5 mL) were added to the mixture and the mixture was extracted with THF-EtOAc. The organic layer was washed with brine, dried over MgSO$_4$ and concentrated in vacuo. The residue was washed with hexane to give the title compound (0.850 g). The obtained crystals were recrystallized from acetone-water.

Example 71

Ethyl(6-((4-chloro-2-methylpyrimidin-5-yl)methoxy)-1-benzothiophen-3-yl)acetate

The title compound was obtained in a same manner as the procedure in Example 3 using ethyl(6-hydroxy-1-benzothiophen-3-yl)acetate and (4-chloro-2-methylpyrimidin-5-yl)methanol.

Examples 72 and 73

(6-((4-Chloro-2-methylpyrimidin-5-yl)methoxy)-1-benzothiophen-3-yl)acetic acid (Example 72) and (6-((4-ethoxy-2-methylpyrimidin-5-yl)methoxy)-1-benzothiophen-3-yl)acetic acid

Example 73

To a mixture of ethyl(6-((4-chloro-2-methylpyrimidin-5-yl)methoxy)-1-benzothiophen-3-yl)acetate (70 mg) in THF (3 mL) and EtOH (2 mL) was added 4N LiOH (0.186 mL) at room temperature. The mixture was stirred at room temperature for 5 h. The mixture was neutralized with 1N HCl at room temperature and concentrated in vacuo. Water and saturated aqueous NH$_4$Cl were poured into the residue and extracted with EtOAc. The organic layer was separated, dried over Na$_2$SO$_4$ and concentrated in vacuo. The residue was purified by preparative HPLC (C18, water/CH$_3$CN (including 0.1% TFA)). The fraction including Example 72 was neutralized with saturated aqueous NaHCO$_3$ and extracted with EtOAc. The organic layer was washed with brine, dried over Na$_2$SO$_4$ and concentrated in vacuo. The residual solid was recrystallized from EtOAc-hexane to give (6-((4-chloro-2-methylpyrimidin-5-yl)methoxy)-1-benzothiophen-3-yl)acetic acid (Example 72, 18 mg). The fraction including Example 73 was neutralized with saturated aqueous NaHCO$_3$ and extracted with EtOAc. The organic layer was washed with brine, dried over Na$_2$SO$_4$ and concentrated in vacuo. The residual solid was recrystallized from EtOAc-hexane to give (6-((4-ethoxy-2-methylpyrimidin-5-yl)methoxy)-1-benzothiophen-3-yl)acetic acid (Example 73, 12.8 mg).

Example 74

2-(6-((2,4-Dichlorobenzyl)oxy)-1-benzothiophen-3-yl)acetamide

To a mixture of (6-(2,4-dichlorobenzyl)oxy)-1-benzothiophen-3-yl)acetic acid (300 mg) in DMF (dry) (4.1 mL) were added HOBt ammonia complex (186 mg), EDCI (235 mg) and triethylamine (0.342 mL). The mixture was stirred at room temperature over weekend. The mixture was diluted with saturated aqueous NaHCO$_3$ and water. The precipitate was collected by filtration, and washed with water and hexane to give the title compound (280.5 mg).

Example 75

Ethyl(6-((2,4-dimethyl-1,3-oxazol-5-yl)methoxy)-1-benzothiophen-3-yl)acetate

The title compound was obtained in a same manner as the procedure in Example 3 using ethyl(6-hydroxy-1-benzothiophen-3-yl)acetate and (2,4-dimethyl-1,3-oxazol-5-yl)methanol.

Example 76

(6-((2,4-Dimethyl-1,3-oxazol-5-yl)methoxy)-1-benzothiophen-3-yl)acetic acid

The title compound was obtained in a same manner as the procedure in Example 12 by using the corresponding ester.

Example 77

Ethyl(6-((2,5-dimethyl-1,3-oxazol-4-yl)methoxy)-1-benzothiophen-3-yl)acetate

The title compound was obtained in a same manner as the procedure in Example 3 using ethyl(6-hydroxy-1-benzothiophen-3-yl)acetate and (2,5-dimethyl-1,3-oxazol-4-yl)methanol.

Example 78

(6-((2,5-Dimethyl-1,3-oxazol-4-yl)methoxy)-1-benzothiophen-3-yl)acetic acid

The title compound was obtained in a same manner as the procedure in Example 12 by using the corresponding ester.

Example 79

Ethyl(6-((2,4-dichlorobenzyl)sulfanyl)-1-benzothiophen-3-yl)acetate

A) Ethyl(6-(((trifluoromethyl)sulfonyl)oxy)-1-benzothiophen-3-yl)acetate

To a solution of ethyl(6-hydroxy-1-benzothiophen-3-yl)acetate (500 mg) and triethylamine (0.592 mL) in $CH_3CN$ (20 mL) was added $Tf_2O$ (0.417 mL). The mixture was stirred at 0° C. for 10 min. The mixture was poured into water at room temperature and extracted with EtOAc. The organic layer was separated, washed successively with 1N HCl and brine, dried over $Na_2SO_4$ and concentrated in vacuo. The residue was purified by silica gel column chromatography (EtOAc/hexane) to give the title compound (745 mg).

MS (ESI−): [M−H]⁻ 367.1.

B) Ethyl(6-((2,4-dichlorobenzyl)sulfanyl)-1-benzothiophen-3-yl)acetate

To a solution of 4,5-bis(diphenylphosphino)-9,9-dimethylxanthene (15.71 mg), DIPEA (0.187 ml), 2,4-dichlorobenzyl mercaptan (0.085 mL) and ethyl(6-(((trifluoromethyl)sulfonyl)oxy)-1-benzothiophen-3-yl)acetate (200 mg) in toluene (6 mL) was added tris(dibenzylideneacetone)dipalladium(0) (24.86 mg) at room temperature. The mixture was refluxed 1.5 h. After cooling, water was poured into mixture, and the mixture was extracted with EtOAc. The organic layer was washed with brine, dried over $Na_2SO_4$ and concentrated in vacuo. The residue was purified by silica gel column chromatography (EtOAc/hexane) to give the title compound (238 mg).

Example 80

(6-((2,4-Dichlorobenzyl)sulfanyl)-1-benzothiophen-3-yl)acetic acid

The title compound was obtained in a same manner as the procedure in Example 12 by using the corresponding ester.

Example 81

Ethyl(6-((2,4-dichlorobenzyl)sulfonyl)-1-benzothiophen-3-yl)acetate

To a mixture of ethyl(6-((2,4-dichlorobenzyl)sulfanyl)-1-benzothiophen-3-yl)acetate (300 mg), MeOH (3 mL), water (3.00 mL) and $CH_3CN$ (2.00 mL) was added OXONE® ($2KHSO_5$—$KHSO_4$—$K_2SO_4$) (1793 mg) at room temperature. The mixture was stirred at room temperature overnight. To the mixture was added saturated aqueous $Na_2S_2O_3$ at room temperature, and the mixture was extracted with EtOAc. The organic layer was washed with brine, dried over $Na_2SO_4$ and concentrated in vacuo. The residue was purified by silica gel column chromatography (EtOAc/hexane) to give the title compound (226 mg). The residue was recrystallized from EtOAc-hexane to give the title compound.

Example 82

Ethyl(6-((2,4-dichlorobenzyl)sulfinyl)-1-benzothiophen-3-yl)acetate

To a mixture of ethyl(6-((2,4-dichlorobenzyl)sulfanyl)-1-benzothiophen-3-yl)acetate (315 mg), water (3.00 mL) and $CH_3CN$ (3.00 mL) was added $NaIO_4$ (164 mg) at room temperature. The mixture was stirred at room temperature for 1 day. To the mixture was added $NaIO_4$ (164 mg), and the mixture was stirred for further 1 day. To the mixture was added saturated aqueous $Na_2S_2O_3$ at room temperature, and the mixture was extracted with EtOAc. The organic layer was washed with brine, dried over $Na_2SO_4$ and concentrated in vacuo. The residue was purified by silica gel column chromatography (EtOAc/hexane) to give the title compound (204 mg). The residue was recrystallized from EtOAc-hexane to give the title compound.

Example 83

(6-((2,4-Dichlorobenzyl)sulfonyl)-1-benzothiophen-3-yl)acetic acid

The title compound was obtained in a same manner as the procedure in Example 12 by using the corresponding ester.

Example 84

(6-((2,4-Dichlorobenzyl)sulfinyl)-1-benzothiophen-3-yl)acetic acid

The title compound was obtained in a same manner as the procedure in Example 12 by using the corresponding ester.

Example 85

Ethyl((6-((2,4-dichlorobenzyl)oxy)-2-((2-methoxyethyl)carbamoyl)-1-benzothiophen-3-yl)oxy)acetate

A) Ethyl 6-((2,4-dichlorobenzyl)oxy)-3-(methoxymethoxy)-1-benzothiophene-2-carboxylate The title compound was obtained in a same manner as the procedure in Example 67 by using chloromethyl methyl ether instead of t-butyl bromoacetate.

MS (ESI−): [M−H]⁻ 439.1.

B) 6-((2,4-Dichlorobenzyl)oxy)-3-(methoxymethoxy)-1-benzothiophene-2-carboxylic acid The title compound was obtained in a same manner as the procedure in Example 12 by using the corresponding ester.

MS (ESI−): [M−H]⁻ 411.1.

C) 6-((2,4-Dichlorobenzyl)oxy)-N-(2-methoxyethyl)-3-(methoxymethoxy)-1-benzothiophene-2-carboxamide A mixture of 2-methoxyethylamine (0.082 mL), EDCI (181 mg), HOBt (128 mg), 6-((2,4-dichlorobenzyl)oxy)-3-(methoxymethoxy)-1-benzothiophene-2-carboxylic acid (260 mg) and DMF (5 mL) was stirred at room temperature for 18 h. Water was added to the mixture, and the mixture was extracted with EtOAc. The EtOAc extract was washed successively with 1N HCl, saturated aqueous $NaHCO_3$ and brine, dried over $MgSO_4$, and concentrated in vacuo. The residue was purified by silica gel column chromatography (EtOAc/hexane) to give the title compound (205 mg). The obtained crystals were recrystallized from EtOAc-hexane.

MS (ESI+): [M+H]⁺ 469.9.

D) 6-((2,4-Dichlorobenzyl)oxy)-3-hydroxy-N-(2-methoxyethyl)-1-benzothiophene-2-carboxamide A mixture of 6M HCl (3 mL), 6-((2,4-dichlorobenzyl)oxy)-N-(2-methoxyethyl)-3-(methoxymethoxy)-1-benzothiophene-2-carboxamide (170 mg) and THF (10 mL) was stirred at room temperature for 4 h. To the mixture was added saturated aqueous NaHCO$_3$, and the mixture was extracted with EtOAc. The organic layer was separated, washed with brine, dried over MgSO$_4$ and concentrated in vacuo. The residue was collected by filtration and washed with hexane to give the title compound (150 mg). The obtained crystals were recrystallized from acetone-hexane.

MS (ESI+): [M+H]$^±$425.8.

E) Ethyl((6-((2,4-dichlorobenzyl)oxy)-2-((2-methoxyethyl)carbamoyl)-1-benzothiophen-3-yl)oxy)acetate The title compound was obtained in a same manner as the procedure in Example 67 by using ethyl bromoacetate and 6-((2,4-dichlorobenzyl)oxy)-3-hydroxy-N-(2-methoxyethyl)-1-benzothiophene-2-carboxamide.

Example 86

((6-((2,4-Dichlorobenzyl)oxy)-2-((2-methoxyethyl)carbamoyl)-1-benzothiophen-3-yl)oxy)acetic acid The title compound was obtained in a same manner as the procedure in Example 12 by using the corresponding ester.

Example 87

((2-Carbamoyl-6-((2,4-dichlorobenzyl)oxy)-1-benzothiophen-3-yl)oxy)acetic acid

A) 6-((2,4-Dichlorobenzyl)oxy)-3-(methoxymethoxy)-1-benzothiophene-2-carboxamide A mixture of HOBt ammonia complex (387 mg), EDCI (487 mg), 6-((2,4-dichlorobenzyl)oxy)-3-(methoxymethoxy)-1-benzothiophene-2-carboxylic acid (700 mg) and DMF (5 mL) was stirred at room temperature for 15 h. Water was added to the mixture and the mixture was extracted with THF-AcOEt. The organic layer was washed successively with water and brine, dried over MgSO$_4$, and concentrated in vacuo. The residue was washed with IPE and hexane to give the title compound (510 mg).

MS (ESI+): [M+H]$^+$ 412.3.

B) 6-((2,4-Dichlorobenzyl)oxy)-3-hydroxy-1-benzothiophene-2-carboxamide

The title compound was obtained in a same manner as the procedure in step D of Example 85. The crude solid was used to the next step without further purification.

C) Ethyl((2-carbamoyl-6-((2,4-dichlorobenzyl)oxy)-1-benzothiophen-3-yl)oxy)acetate The title compound was obtained in a same manner as the procedure in Example 67 by using the crude solid of 6-((2,4-dichlorobenzyl)oxy)-3-hydroxy-1-benzothiophene-2-carboxamide.

$^1$H NMR (300 MHz, CDCl$_3$) δ1.33 (3H, t, J=7.19 Hz), 4.32 (2H, q, J=6.94 Hz), 4.95 (2H, s), 5.18 (2H, brs.), 5.67 (1H, brs.), 7.04-7.15 (1H, m), 7.24-7.34 (2H, m), 7.42-7.54 (2H, m), 7.64-7.73 (1H, m), 8.23 (1H, brs.).

D) ((2-Carbamoyl-6-((2,4-dichlorobenzyl)oxy)-1-benzothiophen-3-yl)oxy)acetic acid The title compound was obtained as a crude product in a same manner as the procedure in Example 12. The obtained product was purified using a preparative HPLC (C18, water/CH$_3$CN (including 10 mM NH$_4$HCO$_3$)). The obtained solution was concentrated in vacuo to remove organic solvent. To the mixture was added dil. HCl and the mixture was extracted with THF-EtOAc. The organic layer was washed with brine, dried over MgSO$_4$, and concentrated in vacuo to give crystals which were washed with IPE. The crystals were recrystallized from THF-hexane to give the title compound.

Example 88

Ethyl(6-((2-chloro-4-iodobenzyl)oxy)-1-benzothiophen-3-yl)acetate

The title compound was obtained in a same manner as the procedure in Example 3 by using (2-chloro-4-iodophenyl)methanol and ethyl(6-hydroxy-1-benzothiophen-3-yl)acetate.

Example 89

(6-((2-Chloro-4-iodobenzyl)oxy)-1-benzothiophen-3-yl)acetic acid

The title compound was obtained in a same manner as the procedure in Example 12 by using the corresponding ester.

Example 90

Ethyl(6-((2,4-dimethylbenzyl)oxy)-1-benzothiophen-3-yl)acetate

The title compound was obtained in a same manner as the procedure in Example 3 using ethyl(6-hydroxy-1-benzothiophen-3-yl)acetate and 2,4-dimethylbenzyl alcohol.

Example 91

(6-((2,4-Dimethylbenzyl)oxy)-1-benzothiophen-3-yl)acetic acid

The title compound was obtained in a same manner as the procedure in Example 12 by using the corresponding ester.

Example 92

Ethyl(6-((2-ethyl-6-methylpyridin-3-yl)methoxy)-1-benzothiophen-3-yl)acetate

A) Methyl 2-ethyl-6-methylnicotinate

To a mixture of methyl propionylacetate (1.93 mL), 4-trimethylsilyl-3-butyn-2-one (2.65 mL) in MeOH (100 mL) was added ammonium acetate (3.55 g) at room temperature. The mixture was stirred at 60° C. overnight. After cooling, the mixture was concentrated. The residue was diluted with water, and the mixture was extracted with EtOAc. The organic layer was washed with brine, dried over MgSO$_4$ and concentrated in vacuo. The residue was dissolved in EtOAc and the insoluble material was removed by filtration. The filtrate was concentrated and the residue was purified by silica gel column chromatography (NH, EtOAc/hexane) to give the title compound (1.56 g).

MS (ESI+): [M+H]$^+$ 180.2.

B) (2-Ethyl-6-methylpyridin-3-yl)methanol

To a mixture of lithium aluminum hydride (220 mg) and THF (dry) (15 mL) was added a solution of methyl 2-ethyl- 6-methylnicotinate (519 mg) in THF (dry) (5 mL) at 0° C. The mixture was stirred at 0° C. under nitrogen atmosphere for 20 min. To the mixture was added sodium sulfate decahydrate (1.8 g) and the mixture was stirred overnight. After filtrating, the filtrate was concentrated in vacuo, and the residue was purified by silica gel column chromatography (EtOAc/hexane) to give the title compound (365 mg).
MS (ESI+): [M+H]$^+$ 152.2.

C) Ethyl(6-((2-ethyl-6-methylpyridin-3-yl)methoxy)-1-benzothiophen-3-yl)acetate

The title compound was obtained in a same manner as the procedure in Example 3 by using ethyl(6-hydroxy-1-benzothiophen-3-yl)acetate and (2-ethyl-6-methylpyridin-3-yl)methanol.

Example 93

(6-((2-Ethyl-6-methylpyridin-3-yl)methoxy)-1-benzothiophen-3-yl)acetic acid

The title compound was obtained in a same manner as the procedure in Example 12 by using the corresponding ester.

Example 94

Ethyl(6-((4-amino-2-methylpyrimidin-5-yl)methoxy)-1-benzothiophen-3-yl)acetate

A mixture of ethyl(6-((4-chloro-2-methylpyrimidin-5-yl)methoxy)-1-benzothiophen-3-yl)acetate (100 mg) and 2M ammonia in EtOH (10 mL) was stirred at 100° C. for 5 h under microwave irradiation. The mixture was concentrated in vacuo. The residual solid was recrystallized from EtOAc-IPE to give the title compound (92 mg).

Example 95

(6-((4-Amino-2-methylpyrimidin-5-yl)methoxy)-1-benzothiophen-3-yl)acetic acid

The title compound was obtained in a same manner as the procedure in Example 12 by using the corresponding ester.

Example 96

Ethyl(6-((2,4-dimethylpyrimidin-5-yl)methoxy)-1-benzothiophen-3-yl)acetate

The title compound was obtained in a same manner as the procedure in Example 3 using ethyl(6-hydroxy-1-benzothiophen-3-yl)acetate and (2,4-dimethylpyrimidin-5-yl)methanol.

Example 97

(6-((2,4-Dimethylpyrimidin-5-yl)methoxy)-1-benzothiophen-3-yl)acetic acid

The title compound was obtained in a same manner as the procedure in Example 12 by using the corresponding ester.

Example 98

Ethyl(6-((1,3-dimethyl-1H-pyrazol-5-yl)methoxy)-1-benzothiophen-3-yl)acetate

The title compound was obtained in a same manner as the procedure in Example 5 by using 5-(chloromethyl)-1,3-dimethyl-1H-pyrazole and ethyl(6-hydroxy-1-benzothiophen-3-yl)acetate.
The obtained crystals were recrystallized from EtOAc-hexane.

Example 99

(6-((1,3-Dimethyl-1H-pyrazol-5-yl)methoxy)-1-benzothiophen-3-yl)acetic acid

The title compound was obtained in a same manner as the procedure in Example 12 by using the corresponding ester. The obtained crystals were recrystallized from EtOAc-hexane.

Example 100

Ethyl(6-((2-isopropyl-4-methyl-1,3-thiazol-5-yl)methoxy)-1-benzothiophen-3-yl)acetate A) Ethyl 2-isopropyl-4-methyl-1,3-thiazole-5-carboxylate To a solution of 2-methylpropanethioamide (1.51 g) in EtOH (40 mL) was added ethyl 2-chloroacetoacetate (2.409 g) at room temperature. The mixture was refluxed for 2 h. After cooling, the mixture was concentrated in vacuo. The residue was purified by silica gel column chromatography (NH, EtOAc/hexane) to give the title compound (2.42 g).
MS (ESI+): [M+H]$^+$ 214.1

B) (2-Isopropyl-4-methyl-1,3-thiazol-5-yl)methanol

To a solution of ethyl 2-isopropyl-4-methyl-1,3-thiazole-5-carboxylate (2.42 g) in THF (50 mL) was added lithium aluminum hydride (0.431 g) at 0° C. The mixture was stirred at 0° C. under argon atmosphere for 1 h. To the mixture was added sodium sulfate decahydrate and the mixture was stirred for 10 min. The precipitate was filtered off through celite and the filtrate was concentrated in vacuo to give the title compound (1.9 g).
MS (ESI+): [M+H]$^+$ 172.1

C) Ethyl(6-((2-isopropyl-4-methyl-1,3-thiazol-5-yl)methoxy)-1-benzothiophen-3-yl)acetate The title compound was obtained in a same manner as the procedure in Example 3 using ethyl(6-hydroxy-1-benzothiophen-3-yl)acetate and (2-isopropyl-4-methyl-1,3-thiazol-5-yl)methanol.

Example 101

(6-((2-Isopropyl-4-methyl-1,3-thiazol-5-yl)methoxy)-1-benzothiophen-3-yl)acetic acid The title compound was obtained in a same manner as the procedure in Example 12 by using the corresponding ester.

Example 102

Ethyl(6-((6-methyl-2-(trifluoromethyl)pyridin-3-yl)methoxy)-1-benzothiophen-3-yl)acetate A) (6-Methyl-2-(trifluoromethyl)pyridin-3-yl)methanol The title compound was obtained in a same manner as the procedure in step B of Example 92 by using ethyl 6-methyl-2-(trifluoromethyl)nicotinate.
MS (ESI+): [M+H]$^+$ 192.1.

B) Ethyl(6-((6-methyl-2-(trifluoromethyl)pyridin-3-yl)methoxy)-1-benzothiophen-3-yl)acetate The title compound was obtained in a same manner as the procedure in Example 3 using ethyl(6-hydroxy-1-benzothiophen-3-yl)acetate and (6-methyl-2-(trifluoromethyl)pyridin-3-yl)methanol.

Example 103

(6-((6-Methyl-2-(trifluoromethyl)pyridin-3-yl)methoxy)-1-benzothiophen-3-yl)acetic acid The title compound was obtained in a same manner as the procedure in Example 12 by using the corresponding ester.

Example 104

Ethyl(6-((6-ethyl-2-methylpyridin-3-yl)methoxy)-1-benzothiophen-3-yl)acetate

A) (6-Ethyl-2-methylpyridin-3-yl)methanol

The title compound was obtained in a same manner as the procedure in step B of Example 92 by using ethyl 6-ethyl-2-methylnicotinate.
MS (ESI+): [M+H]$^+$ 152.2.

B) Ethyl(6-((6-ethyl-2-methylpyridin-3-yl)methoxy)-1-benzothiophen-3-yl)acetate

The title compound was obtained in a same manner as the procedure in Example 3 using ethyl(6-hydroxy-1-benzothiophen-3-yl)acetate and (6-ethyl-2-methylpyridin-3-yl)methanol.

Example 105

(6-((6-Ethyl-2-methylpyridin-3-yl)methoxy)-1-benzothiophen-3-yl)acetic acid

The title compound was obtained in a same manner as the procedure in Example 12 by using the corresponding ester.

Example 106

Ethyl(6-((6-methoxy-2-methylpyridin-3-yl)methoxy)-1-benzothiophen-3-yl)acetate

The title compound was obtained in a same manner as the procedure in Example 3 using ethyl(6-hydroxy-1-benzothiophen-3-yl)acetate and (6-methoxy-2-methylpyridin-3-yl)methanol.

Example 107

(6-((6-Methoxy-2-methylpyridin-3-yl)methoxy)-1-benzothiophen-3-yl)acetic acid

The title compound was obtained in a same manner as the procedure in Example 12 by using the corresponding ester.

Example 108

Ethyl(6-((2-ethyl-4-methyl-1,3-thiazol-5-yl)methoxy)-1-benzothiophen-3-yl)acetate The title compound was obtained in a same manner as the procedure in Example 3 using ethyl(6-hydroxy-1-benzothiophen-3-yl)acetate and (2-ethyl-4-methyl-1,3-thiazol-5-yl)methanol.

Example 109

(6-((2-Ethyl-4-methyl-1,3-thiazol-5-yl)methoxy)-1-benzothiophen-3-yl)acetic acid The title compound was obtained in a same manner as the procedure in Example 12 by using the corresponding ester.

Example 110

Ethyl(6-((4-ethyl-2-methyl-1,3-thiazol-5-yl)methoxy)-1-benzothiophen-3-yl)acetate A) (4-Ethyl-2-methyl-1,3-thiazol-5-yl)methanol To a borane tetrahydrofuran complex solution (1.2 M in THF, 5 mL) was added 4-ethyl-2-methylthiazole-5-carboxylic acid (400 mg) at 0° C. The mixture was stirred at 0° C. to room temperature under argon atmosphere overnight. To the mixture was added 1N HCl at room temperature, and the mixture was extracted with EtOAc. The organic layer was separated, washed successively with brine and water, dried over Na$_2$SO$_4$ and concentrated in vacuo. The residue was purified by silica gel column chromatography (EtOAc/hexane) to give the title compound (125 mg).
MS (ESI+): [M+H]$^+$ 158.2.

B) Ethyl(6-((4-ethyl-2-methyl-1,3-thiazol-5-yl)methoxy)-1-benzothiophen-3-yl)acetate The title compound was obtained in a same manner as the procedure in Example 3 using ethyl(6-hydroxy-1-benzothiophen-3-yl)acetate and (4-ethyl-2-methyl-1,3-thiazol-5-yl)methanol.

Example 111

(6-((4-Ethyl-2-methyl-1,3-thiazol-5-yl)methoxy)-1-benzothiophen-3-yl)acetic acid The title compound was obtained in a same manner as the procedure in Example 12 by using the corresponding ester.

Example 112

Methyl(6-((2,4-dichlorobenzyl)oxy)-7-methyl-1-benzothiophen-3-yl)acetate

A) Methyl 4-((3-methoxy-2-methylphenyl)sulfanyl)-3-oxobutanoate

To a mixture of 3-methoxy-2-methylbenzenethiol (2.52 g) and DMF (dry) (10 mL) were added methyl 4-chloroacetoacetate (2.114 mL) and $K_2CO_3$ (2.60 g) at room temperature. The mixture was stirred at room temperature for 2 h. The mixture was poured into water at room temperature and extracted with EtOAc. The organic layer was separated, washed successively with water and brine, dried over $MgSO_4$ and concentrated in vacuo. The residue was purified by silica gel column chromatography (EtOAc/hexane) to give the title compound (3.65 g).

$^1$H NMR (300 MHz, $CDCl_3$) δ 2.31 (3H, s), 3.62 (2H, s), 3.71 (3H, s), 3.76 (2H, s), 3.81 (3H, s), 6.75 (1H, d, J=8.0 Hz), 6.89 (1H, d, J=8.0 Hz), 7.06-7.16 (1H, m).

B) Methyl(6-methoxy-7-methyl-1-benzothiophen-3-yl)acetate

Methyl 4-((3-methoxy-2-methylphenyl)sulfanyl)-3-oxobutanoate (3.51 g) was added to MsOH (20 mL) at room temperature. The mixture was stirred at room temperature for 15 min. The mixture was poured into ice-water at 0° C. and extracted with EtOAc. The organic layer was separated, washed successively with 1N NaOH and brine, dried over $MgSO_4$ and concentrated in vacuo. The residue was purified by silica gel column chromatography (EtOAc/hexane) to give the title compound (3.10 g).

$^1$H NMR (300 MHz, $CDCl_3$) δ2.42 (3H, s), 3.66-3.74 (3H, m), 3.82 (2H, s), 3.90 (3H, s), 7.05 (1H, d, J=8.7 Hz), 7.18 (1H, s), 7.55 (1H, d, J=8.7 Hz).

C) Methyl(6-hydroxy-7-methyl-1-benzothiophen-3-yl)acetate

To a mixture of aluminum chloride (3.30 g) and toluene (30 mL) was added 1-dodecanethiol (17.80 mL) at room temperature, and the mixture was stirred at room temperature for 30 min. To the mixture was added methyl(6-methoxy-7-methyl-1-benzothiophen-3-yl)acetate (3.1 g) at room temperature. The mixture was stirred at room temperature for 13 h. The mixture was quenched with ice water at 0° C. and extracted with EtOAc. The organic layer was separated, washed successively with 1N HCl and brine, dried over $MgSO_4$ and concentrated in vacuo. The residue was purified by silica gel column chromatography (EtOAc/hexane) to give the title compound (1.580 g).

$^1$H NMR (300 MHz, $CDCl_3$) δ 2.43 (3H, s), 3.70 (3H, s), 3.81 (2H, s), 4.85 (1H, s), 6.90 (1H, d, J=8.7 Hz), 7.17 (1H, s), 7.46 (1H, d, J=8.3 Hz).

D) Methyl(6-((2,4-dichlorobenzyl)oxy)-7-methyl-1-benzothiophen-3-yl)acetate

The title compound was obtained in a same manner as the procedure in Example 5 using methyl(6-hydroxy-7-methyl-1-benzothiophen-3-yl)acetate and 2,4-dichlorobenzyl chloride.

Example 113

(6-((2,4-Dichlorobenzyl)oxy)-7-methyl-1-benzothiophen-3-yl)acetic acid

The title compound was obtained in a same manner as the procedure in Example 6 by using the corresponding ester.

Example 114

Methyl(6-((2,6-dimethylpyridin-3-yl)methoxy)-7-methyl-1-benzothiophen-3-yl)acetate The title compound was obtained in a same manner as the procedure in Example 3 using methyl(6-hydroxy-7-methyl-1-benzothiophen-3-yl)acetate and (2,6-dimethylpyridin-3-yl)methanol.

Example 115

(6-((2,6-Dimethylpyridin-3-yl)methoxy)-7-methyl-1-benzothiophen-3-yl)acetic acid The title compound was obtained in a same manner as the procedure in Example 6 by using the corresponding ester.

Example 116

Methyl(6-((2,6-dimethylpyridin-3-yl)methoxy)-4-methyl-1-benzothiophen-3-yl)acetate The title compound was obtained in a same manner as the procedure in Example 3 using methyl(6-hydroxy-4-methyl-1-benzothiophen-3-yl)acetate and (2,6-dimethylpyridin-3-yl)methanol.

Example 117

(6-((2,6-Dimethylpyridin-3-yl)methoxy)-4-methyl-1-benzothiophen-3-yl)acetic acid The title compound was obtained in a same manner as the procedure in Example 6 by using the corresponding ester.

Example 118

Ethyl(6-((2-methyl-4-(trifluoromethyl)-1,3-thiazol-5-yl)methoxy)-1-benzothiophen-3-yl)acetate A) (2-Methyl-4-(trifluoromethyl)-1,3-thiazol-5-yl)methanol The title compound was obtained in a same manner as the procedure in step B of Example 92 by using (2-methyl-4-(trifluoromethyl)-1,3-thiazol-5-yl)carboxylic acid.

$^1$H NMR (300 MHz, $CDCl_3$) δ 2.19 (1H, t, J=6.06 Hz), 2.70 (3H, s), 4.98 (2H, d, J=4.54 Hz).

B) Ethyl(6-((2-methyl-4-(trifluoromethyl)-1,3-thiazol-5-yl)methoxy)-1-benzothiophen-3-yl)acetate The title compound was obtained in a same manner as the procedure in Example 3 using ethyl(6-hydroxy-1-benzothiophen-3-yl)acetate and (2-methyl-4-(trifluoromethyl)-1,3-thiazol-5-yl)methanol.

Example 119

(6-((2-Methyl-4-(trifluoromethyl)-1,3-thiazol-5-yl)methoxy)-1-benzothiophen-3-yl)acetic acid The title compound was obtained in a same manner as the procedure in Example 12 by using the corresponding ester. The obtained compound was purified by preparative HPLC (C18, $H_2O/CH_2CN$ (including 0.1% TFA)). The pure fraction was combined and neutralized with saturated aqueous $NaHCO_3$, extracted with EtOAc, dried over $Na_2SO_4$ and concentrated in vacuo to give the title compound.

Example 120

Ethyl(6-((4-methyl-2-(trifluoromethyl)-1,3-thiazol-5-yl)methoxy)-1-benzothiophen-3-yl)acetate

A) Ethyl 4-methyl-2-(trifluoromethyl)-1,3-thiazole-5-carboxylate

To a mixture of 2,2,2-trifluoroethanethioamide (200 mg) and t-BuOH (10 mL) was added ethyl 2-chloro-3-oxobutanoate (0.217 mL) at room temperature. The mixture was refluxed for 2 days. After cooling, EtOAc was poured into the mixture, and the mixture was washed successively with water and brine, dried over $Na_2SO_4$ and concentrated in vacuo. The residue was purified by silica gel column chromatography (NH, EtOAc/hexane) to give the title compound (133 mg).

$^1$H NMR (300 MHz, $CDCl_3$) δ 1.39 (3H, t, J=7.16 Hz), 2.79 (3H, s), 4.38 (2H, q, J=6.91 Hz)

B) (4-Methyl-2-(trifluoromethyl)-1,3-thiazol-5-yl)methanol

The title compound was obtained in a same manner as the procedure in step B of Example 92 by using ethyl(4-methyl-2-(trifluoromethyl)-1,3-thiazol-5-yl)carboxylate.

$^1$H NMR (300 MHz, $CDCl_3$) δ 2.06 (1H, t, J=5.67 Hz), 2.46 (3H, s), 4.87 (2H, d, J=5.29 Hz)

C) Ethyl(6-((4-methyl-2-(trifluoromethyl)-1,3-thiazol-5-yl)methoxy)-1-benzothiophen-3-yl)acetate The title compound was obtained in a same manner as the procedure in Example 3 using ethyl(6-hydroxy-1-benzothiophen-3-yl)acetate and (4-methyl-2-(trifluoromethyl)-1,3-thiazol-5-yl)methanol.

Example 121

(6-((4-Methyl-2-(trifluoromethyl)-1,3-thiazol-5-yl)methoxy)-1-benzothiophen-3-yl)acetic acid The title compound was obtained in a same manner as the procedure in Example 12 by using the corresponding ester.

Example 122

Ethyl(6-((2-methoxy-6-methylpyridin-3-yl)methoxy)-1-benzothiophen-3-yl)acetate

The title compound was obtained in a same manner as the procedure in Example 3 using ethyl(6-hydroxy-1-benzothiophen-3-yl)acetate and (2-methoxy-6-methylpyridin-3-yl)methanol.

Example 123

(6-((2-Methoxy-6-methylpyridin-3-yl)methoxy)-1-benzothiophen-3-yl)acetic acid

The title compound was obtained in a same manner as the procedure in Example 12 by using the corresponding ester.

Example 124

Ethyl(6-((3,5-dimethylpyrazin-2-yl)methoxy)-1-benzothiophen-3-yl)acetate

A) 3,5-Dimethyl-2-vinylpyrazine

To a mixture of 2-chloro-3,5-dimethylpyrazine (2 g) and EtOH (20 mL) were added potassium vinyltrifluoroborate (2.067 g) and TEA (2.93 mL) at room temperature, and the mixture was stirred under nitrogen atmosphere. To the mixture was added $PdCl_2(dppf)$ (1.026 g), and the mixture was refluxed for 2 h.

The mixture was concentrated, and the residue was poured into water at room temperature, and the mixture was extracted with EtOAc. The organic layer was separated, washed successively with water and brine, dried over $MgSO_4$ and concentrated in vacuo. The residue was purified by silica gel column chromatography (EtOAc/hexane) to give the title compound (1.650 g)

$^1$H NMR (300 MHz, $CDCl_3$) δ 2.51 (3H, s), 2.54-2.62 (3H, m), 5.47-5.62 (1H, m), 6.22-6.47 (1H, m), 6.86-7.03 (1H, m), 8.25 (1H, s).

B) (3,5-Dimethylpyrazin-2-yl)methanol

Ozone was bubbled through a solution of 3,5-dimethyl-2-vinylpyrazine (1.60 g) in MeOH (5 mL) over 15 min at −78° C. After the starting material was consumed (monitored by TLC), the mixture was bubbled with nitrogen for 5 min. The mixture was added $NaBH_4$ (2.256 g) at −78° C., and the mixture was gradually allowed to warm to room temperature. The mixture was quenched with 1N NaOH at 0° C. and extracted with EtOAc. The organic layer was separated, washed successively with 1N NaOH and brine, dried over $MgSO_4$ and concentrated in vacuo. The residue was purified by silica gel column chromatography (EtOAc/hexane) to give the title compound (1.240 g).

$^1$H NMR (300 MHz, $CDCl_3$) δ 2.45 (3H, s), 2.54 (3H, s), 4.07 (1H, t, J=4.7 Hz), 4.65-4.81 (2H, m), 8.24 (1H, s).

C) Ethyl(6-((3,5-dimethylpyrazin-2-yl)methoxy)-1-benzothiophen-3-yl)acetate

The title compound was obtained in a same manner as the procedure in Example 3 using methyl(6-hydroxy-1-benzothiophen-3-yl)acetate and (3,5-dimethylpyrazin-2-yl)methanol.

Example 125

(6-((3,5-Dimethylpyrazin-2-yl)methoxy)-1-benzothiophen-3-yl)acetic acid

The title compound was obtained in a same manner as the procedure in Example 6 by using the corresponding ester.

Example 126

Methyl(6-((3,5-dimethylpyrazin-2-yl)methoxy)-7-methyl-1-benzothiophen-3-yl)acetate The title compound was obtained in a same manner as the procedure in Example 3 using ethyl(6-hydroxy-7-methyl-1-benzothiophen-3-yl)acetate and (3,5-dimethylpyrazin-2-yl)methanol.

Example 127

(6-((3,5-Dimethylpyrazin-2-yl)methoxy)-7-methyl-1-benzothiophen-3-yl)acetic acid The title compound was obtained in a same manner as the procedure in Example 6 by using the corresponding ester.

Example 128

2-(6-((2,6-Dimethylpyridin-3-yl)methoxy)-1-benzothiophen-3-yl)acetamide

To a mixture of 2-(6-((2,6-dimethylpyridin-3-yl)methoxy)-1-benzothiophen-3-yl)acetic acid (98 mg) and THF (dry) (5 mL) was added oxalyl chloride (0.026 mL). The mixture was stirred at room temperature for 1 h. The mixture was concentrated in vacuo. To a mixture of the residue and THF (dry) (5 mL) were added 28% aqueous $NH_3$ (18.25 mg) and TEA (0.042 mL). The mixture was stirred at room temperature for 3 h. The mixture was poured into water and extracted with EtOAc. The organic layer was separated, washed successively with water and brine, dried over $MgSO_4$ and concentrated in vacuo. The residue was purified by silica gel column chromatography (MeOH/EtOAc) to give the title compound (25.00 mg), which was crystallized from EtOAc-hexane.

Example 129

2-(6-((2,4-Dichlorobenzyl)oxy)-1-benzothiophen-3-yl)-N-(methylsulfonyl)acetamide To a mixture of 2-(6-((2,4-dichlorobenzyl)oxy)-1-benzothiophen-3-yl)acetamide (73.3 mg) and THF (dry) (10 mL) was added sodium bis(trimethylsilyl)amide (0.158 ml, 1.9 M in toluene) at −78° C. The mixture was stirred at −40° C. under argon atmosphere for 30 min. And then methanesulfonyl chloride (34.4 mg) was added thereto. The resulting mixture was stirred at room temperature under argon atmosphere overnight. The mixture was poured into water and extracted with EtOAc. The organic layer was separated, washed successively with water and brine, dried over $MgSO_4$ and concentrated in vacuo. The residue was purified by silica gel column chromatography (EtOAc/hexane) to give the title compound (11.00 mg).

Example 130

Methyl(6-((2,4-dichlorobenzyl)oxy)-4-methoxy-1-benzothiophen-3-yl)acetate

A) Methyl 4-((3,5-dimethoxyphenyl)sulfanyl)-3-oxobutanoate

The title compound was obtained in a same manner as the procedure in step A of Example 112 using 3,5-dimethoxybenzenethiol and methyl 4-chloroacetoacetate.

$^1$H NMR (300 MHz, $CDCl_3$) δ 3.65 (2H, s), 3.72 (3H, s), 3.75-3.79 (6H, m), 3.81 (2H, s), 6.27-6.33 (1H, m), 6.47 (2H, d, J=2.3 Hz).

B) Methyl(4,6-dimethoxy-1-benzothiophen-3-yl)acetate

The title compound was obtained in a same manner as the procedure in step B of Example 112.

$^1$H NMR (300 MHz, $CDCl_3$) δ 3.68-3.71 (3H, m), 3.81-3.83 (3H, m), 3.84 (3H, s), 3.95 (2H, s), 6.37 (1H, d, J=2.3 Hz), 6.87 (1H, d, J=2.3 Hz), 6.90 (1H, s).

C) Methyl(6-hydroxy-4-methoxy-1-benzothiophen-3-yl)acetate

The title compound was obtained in a same manner as the procedure in step C of Example 112.

$^1$H NMR (300 MHz, $CDCl_3$) δ 3.72 (3H, s), 3.80 (3H, s), 3.94 (2H, s), 5.22 (1H, s), 6.20-6.28 (1H, m), 6.70 (1H, d, J=2.3 Hz), 6.87 (1H, s).

D) Methyl(6-((2,4-dichlorobenzyl)oxy)-4-methoxy-1-benzothiophen-3-yl)acetate

The title compound was obtained in a same manner as the procedure in Example 5 using methyl(6-hydroxy-4-methoxy-1-benzothiophen-3-yl)acetate and 2,4-dichlorobenzyl chloride.

$^1$H NMR (300 MHz, $CDCl_3$) δ 3.66-3.73 (3H, m), 3.80-3.87 (3H, m), 3.95 (2H, s), 5.15 (2H, s), 6.46 (1H, d, J=2.3 Hz), 6.88-6.94 (2H, m), 7.21-7.31 (1H, m), 7.44 (1H, d, J=2.3 Hz), 7.51 (1H, d, J=8.3 Hz).

Example 131

(6-((2,4-Dichlorobenzyl)oxy)-4-methoxy-1-benzothiophen-3-yl)acetic acid

The title compound was obtained in a same manner as the procedure in Example 6.

Example 132

Ethyl(6-((4-chloro-2-methylbenzyl)oxy)-1-benzothiophen-3-yl)acetate

The title compound was obtained in a same manner as the procedure in Example 3 using ethyl(6-hydroxy-1-benzothiophen-3-yl)acetate and 4-chloro-2-methylbenzyl alcohol.

Example 133

(6-((4-Chloro-2-methylbenzyl)oxy)-1-benzothiophen-3-yl)acetic acid

The title compound was obtained in a same manner as the procedure in Example 12 by using the corresponding ester.

Example 134

Ethyl(6-((2-methyl-6-(trifluoromethyl)pyridin-3-yl)methoxy)-1-benzothiophen-3-yl)acetate The title compound was obtained in a same manner as the procedure in Example 3 using ethyl(6-hydroxy-1-benzothiophen-3-yl)acetate and (2-methyl-6-(trifluoromethyl)pyridin-3-yl)methanol.

Example 135

(6-((2-Methyl-6-(trifluoromethyl)pyridin-3-yl)methoxy)-1-benzothiophen-3-yl)acetic acid The title compound was obtained in a same manner as the procedure in Example 12 by using the corresponding ester.

Example 136

Ethyl(6-((4-methyl-2-(trifluoromethyl)pyrimidin-5-yl)methoxy)-1-benzothiophen-3-yl)acetate A) (4-Methyl-2-(trifluoromethyl)pyrimidin-5-yl)methanol To a mixture of ethyl 4-methyl-2-(trifluoromethyl)pyrimidine-5-carboxylate (122.4 mg) in toluene (5.1 mL) was added diisobutylaluminum hydride (1.0 mol/L in hexane, 1.150 mL) at 0° C. The mixture was stirred at 0° C. under nitrogen atmosphere for 2.5 h, and then at room temperature for 2 h. To the mixture was added diisobutylaluminum hydride (1.0 mol/L in hexane, 0.58 mL) again at 0° C. and the mixture was stirred at 0° C. for 2 h. To the mixture was added sodium sulfate decahydrate (556 mg), and the mixture was stirred at room temperature overnight. The mixture was filtered through on the pad of Celite®. The filtrate was concentrated in vacuo to give the title compound (97.6 mg).

$^1$HNMR (300 MHz, CDCl$_3$) δ 2.00 (1H, brs), 2.63 (3H, s), 4.85 (2H, brs), 8.83 (1H, s).

B) Ethyl(6-((4-methyl-2-(trifluoromethyl)pyrimidin-5-yl)methoxy)-1-benzothiophen-3-yl)acetate The title compound was obtained in a same manner as the procedure in Example 3 using ethyl(6-hydroxy-1-benzothiophen-3-yl)acetate and (4-methyl-2-(trifluoromethyl)pyrimidin-5-yl)methanol.

Example 137

(6-((4-Methyl-2-(trifluoromethyl)pyrimidin-5-yl)methoxy)-1-benzothiophen-3-yl)acetic acid The title compound was obtained in a same manner as the procedure in Example 12 by using the corresponding ester. The obtained compound was purified by a preparative HPLC (C18, H$_2$O/CH$_3$CN (including 5 mM AcONH$_4$)). The fraction was concentrated. The residue was extracted with EtOAc. The combined organic layer was washed with brine, dried over MgSO$_4$, and concentrated in vacuo. The solid was crystallized from EtOAc-hexane to give the title compound (21.4 mg).

Example 138

2-(6-((2,4-Dichlorobenzyl)oxy)-1-benzothiophen-3-yl)-N-(ethylsulfonyl)acetamide

The title compound was obtained in a same manner as the procedure in Example 129 using 2-(6-((2,4-dichlorobenzyl)oxy)-1-benzothiophen-3-yl)acetamide and ethanesulfonyl chloride.

Example 139

Methyl(4-methyl-6-((4-methyl-2-(trifluoromethyl)pyrimidin-5-yl)methoxy)-1-benzothiophen-3-yl)acetate The title compound was obtained in a same manner as the procedure in Example 3 using methyl(6-hydroxy-4-methyl-1-benzothiophen-3-yl)acetate and (4-methyl-2-(trifluoromethyl)pyrimidin-5-yl)methanol.

Example 140

(4-Methyl-6-((4-methyl-2-(trifluoromethyl)pyrimidin-5-yl)methoxy)-1-benzothiophen-3-yl)acetic acid The title compound was obtained in a same manner as the procedure in Example 12 by using the corresponding ester.

Example 141

Ethyl 2-(6-((2,6-dimethylpyridin-3-yl)methoxy)-1-benzothiophen-3-yl)propanoate

To a mixture of ethyl(6-((2,6-dimethylpyridin-3-yl)methoxy)-1-benzothiophen-3-yl)acetate (710 mg) and iodomethane (0.373 ml) and THF (10 mL) was added sodium hydride (60% in oil, 160 mg) at 0° C. The mixture was stirred 0° C. to room temperature under argon atmosphere overnight. To the mixture was added 1N HCl at room temperature, and the mixture was adjusted to pH 6-7 with saturated aqueous NaHCO$_3$ and extracted with EtOAc. The organic layer was washed successively with brine and water, dried over Na$_2$SO$_4$ and concentrated in vacuo. The residue was purified by silica gel column chromatography (EtOAc/hexane) to give the title compound (230 mg).

Example 142

2-(6-((2,6-Dimethylpyridin-3-yl)methoxy)-1-benzothiophen-3-yl)propanoic acid

The title compound was obtained in a same manner as the procedure in Example 12 by using the corresponding ester.

Example 143

Ethyl(6-((2-methyl-4-(trifluoromethyl)benzyl)oxy)-1-benzothiophen-3-yl)acetate

The title compound was obtained in a same manner as the procedure in Example 3 using ethyl(6-hydroxy-1-benzothiophen-3-yl)acetate and (2-methyl-4-(trifluoromethyl)benzyl alcohol.

Example 144

(6-((2-Methyl-4-(trifluoromethyl)benzyl)oxy)-1-benzothiophen-3-yl)acetic acid

The title compound was obtained in a same manner as the procedure in Example 12 by using the corresponding ester.

Example 145

Methyl(6-((2,6-dimethylpyridin-3-yl)methoxy)-4-methoxy-1-benzothiophen-3-yl)acetate The title compound was obtained in a same manner as the procedure in Example 3 using methyl(6-hydroxy-4-methoxy-1-benzothiophen-3-yl)acetate and (2,6-dimethylpyridin-3-yl)methanol.

Example 146

(6-((2,6-Dimethylpyridin-3-yl)methoxy)-4-methoxy-1-benzothiophen-3-yl)acetic acid The title compound was obtained in a same manner as the procedure in Example 6 by using the corresponding ester.

Example 147

Methyl(6-((2,4-dichlorobenzyl)oxy)-4-vinyl-1-benzothiophen-3-yl)acetate

The title compound was obtained in a same manner as the procedure in Example 5 using methyl(6-hydroxy-4-vinyl-1-benzothiophen-3-yl)acetate and 2,4-dichlorobenzyl chloride.

Example 148

(6-((2,4-Dichlorobenzyl)oxy)-4-vinyl-1-benzothiophen-3-yl)acetic acid

The title compound was obtained in a same manner as the procedure in Example 6 by using the corresponding ester.

Example 149

Methyl(4-cyclopropyl-6-((2,6-dimethylpyridin-3-yl)methoxy)-1-benzothiophen-3-yl)acetate A) Methyl(4-cyclopropyl-6-((triisopropylsilyl)oxy)-1-benzothiophen-3-yl)acetate To a mixture of methyl(4-(((trifluoromethyl)sulfonyl)oxy)-6-((triisopropylsilyl)oxy)-1-benzothiophen-3-yl)acetate (512 mg) and DMF (10 mL) were added cyclopropylboronic acid (167 mg), potassium phosphate (1238 mg), Pd(OAc)$_2$ (21.83 mg) and tricyclohexylphosphine (82 mg) at room temperature, and the mixture was refluxed for 16 h. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (372 mg).

$^1$H NMR (300 MHz, CDCl$_3$) δ 0.75-0.84 (2H, m), 0.93-1.01 (2H, m), 1.07-1.14 (18H, m), 1.20-1.33 (3H, m), 2.23-2.35 (1H, m), 3.71 (3H, s), 4.24 (2H, s), 6.70 (1H, d, J=2.7 Hz), 7.09 (1H, s), 7.14 (1H, d, J=2.3 Hz).

B) Methyl(4-cyclopropyl-6-hydroxy-1-benzothiophen-3-yl)acetate

To a mixture of methyl(4-cyclopropyl-6-((triisopropylsilyl)oxy)-1-benzothiophen-3-yl)acetate (372 mg) and THF (2 mL) was added TBAF (1M in THF, 1.333 mL) at room temperature. The mixture was stirred at room temperature for 1 h. The mixture was poured into water at room temperature and extracted with EtOAc. The organic layer was separated, washed with brine, dried over MgSO$_4$ and concentrated in vacuo. The residue was purified by silica gel column chromatography (EtOAc/hexane) to give the title compound (201 mg).

$^1$H NMR (300 MHz, CDCl$_3$) δ 0.78-0.86 (2H, m), 0.93-1.02 (2H, m), 2.21-2.36 (1H, m), 3.72 (3H, s), 4.24 (2H, s), 4.93 (1H, s), 6.66 (1H, d, J=2.6 Hz), 7.04-7.10 (2H, m).

C) Methyl(4-cyclopropyl-6-((2,6-dimethylpyridin-3-yl)methoxy)-1-benzothiophen-3-yl)acetate The title compound was obtained in a same manner as the procedure in Example 3 using methyl(4-cyclopropyl-6-hydroxy-1-benzothiophen-3-yl)acetate and (2,6-dimethylpyridin-3-yl)methanol.

Example 150

(4-Cyclopropyl-6-((2,6-dimethylpyridin-3-yl)methoxy)-1-benzothiophen-3-yl)acetic acid The title compound was obtained in a same manner as the procedure in Example 6 by using the corresponding ester.

Example 151

Methyl(4-cyclopropyl-6-((2,4-dichlorobenzyl)oxy)-1-benzothiophen-3-yl)acetate

The title compound was obtained in a same manner as the procedure in Example 5 using methyl(4-cyclopropyl-6-hydroxy-1-benzothiophen-3-yl)acetate and 2,4-dichlorobenzyl chloride.

Example 152

(4-Cyclopropyl-6-((2,4-dichlorobenzyl)oxy)-1-benzothiophen-3-yl)acetic acid

The title compound was obtained in a same manner as the procedure in Example 6 by using the corresponding ester.

Example 153

Methyl(6-((2,6-dimethylpyridin-3-yl)methoxy)-4-ethyl-1-benzothiophen-3-yl)acetate A) Methyl(6-hydroxy-4-ethyl-1-benzothiophen-3-yl)acetate A mixture of methyl(6-hydroxy-4-vinyl-1-benzothiophen-3-yl)acetate (230 mg), 10% Pd—C (50% wet, 99 mg) and EtOAc (5 mL) was hydrogenated under balloon pressure at room temperature overnight. The catalyst was removed by filtration and the filtrate was concentrated in vacuo. The residue was purified by silica gel column chromatography (EtOAc/hexane) to give the title compound (89 mg).

$^1$H NMR (300 MHz, CDCl$_3$) δ 1.28 (3H, t, J=7.3 Hz), 2.97 (2H, q, J=7.5 Hz), 3.72 (3H, s), 3.99 (2H, s), 4.86 (1H, d, J=2.3 Hz), 6.72 (1H, d, J=2.6 Hz), 7.07 (1H, s), 7.09 (1H, d, J=2.6 Hz).

B) Methyl(6-((2,6-dimethylpyridin-3-yl)methoxy)-4-ethyl-1-benzothiophen-3-yl)acetate The title compound was obtained in a same manner as the procedure in Example 3 using methyl(4-ethyl-6-hydroxy-1-benzothiophen-3-yl)acetate and (2,6-dimethylpyridin-3-yl)methanol.

Example 154

(6-((2,6-Dimethylpyridin-3-yl)methoxy)-4-ethyl-1-benzothiophen-3-yl)acetic acid

The title compound was obtained in a same manner as the procedure in Example 6 by using the corresponding ester.

Example 155

Methyl(6-((2,6-dimethylpyridin-3-yl)methoxy)-4,7-dimethyl-1-benzothiophen-3-yl)acetate The title compound was obtained in a same manner as the procedure in Example 3 using methyl(4,7-dimethyl-6-hydroxy-1-benzothiophen-3-yl)acetate and (2,6-dimethylpyridin-3-yl)methanol.

Example 156

(6-((2,6-Dimethylpyridin-3-yl)methoxy)-4,7-dimethyl-1-benzothiophen-3-yl)acetic acid The title compound was obtained in a same manner as the procedure in Example 12 by using the corresponding ester.

Example 157

Methyl(6-((2,4-dichlorobenzyl)oxy)-4,7-dimethyl-1-benzothiophen-3-yl)acetate

The title compound was obtained in a same manner as the procedure in Example 5 using methyl(4,7-dimethyl-6-hydroxy-1-benzothiophen-3-yl)acetate and 2,4-dichlorobenzyl chloride.

Example 158

(6-((2,4-Dichlorobenzyl)oxy)-4,7-dimethyl-1-benzothiophen-3-yl)acetic acid

The title compound was obtained in a same manner as the procedure in Example 12 by using the corresponding ester.

Example 159

Methyl(6-((2,4-dimethylpyrimidin-5-yl)methoxy)-4-methyl-1-benzothiophen-3-yl)acetate The title compound was obtained in a same manner as the procedure in Example 3 using methyl(6-hydroxy-4-methyl-1-benzothiophen-3-yl)acetate and (2,4-dimethylpyrimidin-5-yl)methanol.

Example 160

(6-((2,4-Dimethylpyrimidin-5-yl)methoxy)-4-methyl-1-benzothiophen-3-yl)acetic acid The title compound was obtained in a same manner as the procedure in Example 6 by using the corresponding ester.

Example 161

Methyl(6-((2,6-dimethylpyridin-3-yl)methoxy)-4-(hydroxymethyl)-1-benzothiophen-3-yl)acetate To a solution of methyl 2-(6-((2,6-dimethylpyridin-3-yl)methoxy)-4-formyl-1-benzothiophen-3-yl)acetate (140 mg, 0.38 mmol) in MeOH (3 mL) was added $NaBH_4$ (21.51 mg) at 0° C. After stirring at 0° C. for 1 h, the mixture was quenched with saturated aqueous $NH_4Cl$ at room temperature and extracted with EtOAc. The organic layer was separated, washed successively with saturated aqueous $NH_4Cl$ and brine, dried over $MgSO_4$ and concentrated in vacuo. The residue was purified by silica gel column chromatography (EtOAc/hexane) to give the title compound (17.2 mg).

Example 162

(6-((2,6-Dimethylpyridin-3-yl)methoxy)-4-(hydroxymethyl)-1-benzothiophen-3-yl)acetic acid The title compound was obtained in a same manner as the procedure in Example 12 by using the corresponding ester.

Example 163

Ethyl(6-((4-chloro-2,6-dimethylpyridin-3-yl)methoxy)-1-benzothiophen-3-yl)acetate A) Ethyl 4-chloro-2,6-dimethylnicotinate Ethyl 3-amino-2-butenoate (18.8 g) was added gradually to phosphorus(V) oxychloride (27.1 mL) at 100° C. The mixture was stirred at 100° C. for 30 min, and then cooled to room temperature. The mixture was concentrated in vacuo. The residue was poured into ice-water. The mixture was basified (pH=8) with $Na_2CO_3$ and extracted with EtOAc. The organic layer was separated, washed with brine, dried over $MgSO_4$ and concentrated in vacuo. The residue was purified by silica gel column chromatography (NH, EtOAc/hexane) to give the title compound (9.50 g).
MS (ESI+): [M+H]$^+$ 214.1.

B) (4-Chloro-2,6-dimethylpyridin-3-yl)methanol

To a mixture of ethyl 4-chloro-2,6-dimethylnicotinate (1.5 g) and THF (50 mL) was added diisobutylaluminum hydride (1M in toluene, 42.0 mL) at 0° C. After stirring at room temperature for 1 h, sodium sulfate decahydrate (13.5 g) and THF were added to the mixture and the mixture was stirred at room temperature for 3 h. The mixture was passed through Celite®. The filtrate was concentrated in vacuo. The residue was purified by silica gel column chromatography (EtOAc/hexane) to give the title compound (0.920 g). The obtained crystals were recrystallized from EtOAc-hexane.
MS (ESI+): [M+H]$^+$ 172.1.

C) Ethyl(6-((4-chloro-2,6-dimethylpyridin-3-yl)methoxy)-1-benzothiophen-3-yl)acetate The title compound was obtained in a same manner as the procedure in Example 3 using ethyl(6-hydroxy-1-benzothiophen-3-yl)acetate and (4-chloro-2,6-dimethylpyridin-3-yl)methanol.

Example 164

(6-((4-Chloro-2,6-dimethylpyridin-3-yl)methoxy)-1-benzothiophen-3-yl)acetic acid The title compound was obtained in a same manner as the procedure in Example 12 by using the corresponding ester. The obtained crystals were recrystallized from acetone-hexane.

Example 165

Methyl(6-((4-chloro-2,6-dimethylpyridin-3-yl)methoxy)-4-methyl-1-benzothiophen-3-yl)acetate The title compound was obtained in a same manner as the procedure in Example 3 using methyl(6-hydroxy-4-methyl-1-benzothiophen-3-yl)acetate and (4-chloro-2,6-dimethylpyridin-3-yl)methanol.

Example 166

(6-((4-Chloro-2,6-dimethylpyridin-3-yl)methoxy)-1-benzothiophen-3-yl)acetic acid The title compound was obtained in a same manner as the procedure in Example 12 by using the corresponding ester. The obtained crystals were recrystallized from acetone-hexane.

Example 167

Methyl(6-((4,6-dimethylpyridin-3-yl)methoxy)-4-methyl-1-benzothiophen-3-yl)acetate The title compound was obtained in a same manner as the procedure in Example 3 using methyl(6-hydroxy-4-methyl-1-benzothiophen-3-yl)acetate and (4,6-dimethylpyridin-3-yl)methanol.

Example 168

(6-((4,6-Dimethylpyridin-3-yl)methoxy)-4-methyl-1-benzothiophen-3-yl)acetic acid The title compound was obtained in a same manner as the procedure in Example 12 by using the corresponding ester.

Example 169

Methyl(4-(dimethylcarbamoyl)-6-((2-methyl-6-(trifluoromethyl)pyridin-3-yl)methoxy)-1-benzothiophen-3-yl)acetate

A) 3-(2-Methoxy-2-oxoethyl)-4-vinyl-1-benzothiophen-6-yl pivalate

To a mixture of methyl 2-(6-hydroxy-4-vinyl-1-benzothiophen-3-yl)acetate (551 mg) and THF (dry) (5 mL) were added trimethylacetic anhydride (0.495 mL), TEA (0.619 mL), and DMAP (271 mg) at room temperature. The mixture was stirred at room temperature for 12 h. The mixture was poured into water at room temperature and extracted with EtOAc. The organic layer was separated, washed successively with 1N HCl and brine, dried over $MgSO_4$ and concentrated in vacuo. The residue was purified by silica gel column chromatography (EtOAc/hexane) to give the title compound (480 mg).

$^1$H NMR (300 MHz, $CDCl_3$) δ 1.38 (9H, s), 3.70 (3H, s), 4.00 (2H, s), 5.38-5.45 (1H, m), 5.53-5.62 (1H, m), 7.03 (1H, d, J=2.3 Hz), 7.26 (1H, s), 7.30-7.41 (1H, m), 7.48-7.51 (1H, m).

B) 4-Formyl-3-(2-methoxy-2-oxoethyl)-1-benzothiophen-6-yl pivalate

To a mixture of 3-(2-methoxy-2-oxoethyl)-4-vinyl-1-benzothiophen-6-yl pivalate (480 mg), acetone (500 μL), water (500 μL) and $CH_3CN$ (500 μL) were added $OsO_4$ (7% microcapsule, 524 mg) and NMO (507 mg) at room temperature. The mixture was stirred at room temperature for 20 h. The insoluble material was removed by filtration, and the filtrate was concentrated in vacuo. The mixture was poured into water at room temperature and extracted with EtOAc. The organic layer was separated, washed successively with water and brine, dried over MgSO4 and concentrated in vacuo. To a mixture of the residue, THF (3 mL) and water (3 mL) was added $NaIO_4$ (403 mg, 1.88 mmol) at room temperature. After stirring at room temperature for 1 h, the m mixture was poured into water at room temperature and extracted with EtOAc. The organic layer was separated, washed successively with water and brine, dried over $MgSO_4$ and concentrated in vacuo. The residue was purified by silica gel column chromatography (EtOAc/hexane) to give the title compound (152 mg).

$^1$H NMR (300 MHz, $CDCl_3$) δ 1.38-1.43 (9H, m), 3.71 (3H, s), 4.22 (2H, s), 7.47 (1H, s), 7.63 (1H, d, J=2.6 Hz), 7.84 (1H, d, J=2.3 Hz), 10.29 (1H, s).

C) 6-((2,2-Dimethylpropanoyl)oxy)-3-(2-methoxy-2-oxoethyl)-1-benzothiophene-4-carboxylic acid To a mixture of 4-formyl-3-(2-methoxy-2-oxoethyl)-1-benzothiophen-6-yl pivalate (150 mg), acetone (1 mL) and water (1 mL) was added $KMnO_4$ (85 mg, 0.54 mmol) at room temperature. The mixture was stirred at room temperature for 1 h. The mixture was poured into water at room temperature and extracted with EtOAc. The organic layer was separated, washed successively with water and brine, dried over $MgSO_4$ and concentrated in vacuo. The residue was purified by silica gel column chromatography (EtOAc/hexane) to give the title compound (145 mg).

$^1$H NMR (300 MHz, $CDCl_3$) δ 1.37-1.41 (9H, m), 3.67 (3H, s), 4.14 (2H, s), 7.41 (1H, s), 7.69 (1H, d, J=2.3 Hz), 7.80 (1H, d, J=2.3 Hz).

D) 4-(Dimethylcarbamoyl)-3-(2-methoxy-2-oxoethyl)-1-benzothiophen-6-yl pivalate To a mixture of 6-((2,2-dimethylpropanoyl)oxy)-3-(2-methoxy-2-oxoethyl)-1-benzothiophene-4-carboxylic acid (145 mg) and DMF (dry) (5 mL) were added dimethylamine hydrochloride (50.6 mg), TEA (0.115 mL) and HATU (236 mg) at room temperature. The mixture was stirred at room temperature for 4 h. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (133 mg).

$^1$H NMR (300 MHz, CDCl$_3$) δ 1.37 (9H, s), 2.86 (3H, s), 3.13 (3H, s), 3.70 (3H, s), 3.81 (1H, m), 3.96-4.08 (1H, m), 6.97 (1H, d, J=2.3 Hz), 7.35 (1H, s), 7.61 (1H, d, J=2.3 Hz).

E) Methyl(4-(dimethylcarbamoyl)-6-hydroxy-1-benzothiophen-3-yl)acetate

To a mixture of 4-(dimethylcarbamoyl)-3-(2-methoxy-2-oxoethyl)-1-benzothiophen-6-yl pivalate (128 mg) and MeOH (3 mL) was added K$_2$CO$_3$ (46.9 mg) at room temperature. The mixture was stirred at room temperature for 12 h. The mixture was poured into water at room temperature and extracted with EtOAc. The organic layer was separated, washed with brine, dried over MgSO$_4$ and concentrated in vacuo. The residue was purified by silica gel column chromatography (EtOAc/hexane) to give the title compound (75 mg).

$^1$H NMR (300 MHz, DMSO-d$_6$) δ 2.66-2.73 (3H, m), 2.97 (3H, d, J=1.9 Hz), 3.60 (3H, s), 3.74-3.80 (2H, m), 6.61-6.73 (1H, m), 7.24-7.39 (2H, m), 9.85 (1H, brs).

F) Methyl(4-(dimethylcarbamoyl)-6-((2-methyl-6-(trifluoromethyl)pyridin-3-yl)methoxy)-1-benzothiophen-3-yl)acetate The title compound was obtained in a same manner as the procedure in Example 3 using methyl(4-(dimethylcarbamoyl)-6-hydroxy-1-benzothiophen-3-yl)acetate and (2-methyl-6-(trifluoromethyl)pyridin-3-yl)methanol.

Example 170

(4-(Dimethylcarbamoyl)-6-((2-methyl-6-(trifluoromethyl)pyridin-3-yl)methoxy)-1-benzothiophen-3-yl)acetic acid The title compound was obtained in a same manner as the procedure in Example 12 by using the corresponding ester.

Example 171

Methyl(4-(dimethylcarbamoyl)-6-((2,6-dimethylpyridin-3-yl)methoxy)-1-benzothiophen-3-yl)acetate The title compound was obtained in a same manner as the procedure in Example 3 using methyl(4-(dimethylcarbamoyl)-6-hydroxy-1-benzothiophen-3-yl)acetate and (2,6-dimethylpyridin-3-yl)methanol.

Example 172

(4-(Dimethylcarbamoyl)-6-((2,6-dimethylpyridin-3-yl)methoxy)-1-benzothiophen-3-yl)acetic acid The title compound was obtained in a same manner as the procedure in Example 12 by using the corresponding ester.

Example 173

Ethyl(6-((2-chloro-6-(trifluoromethyl)pyridin-3-yl)methoxy)-1-benzothiophen-3-yl)acetate The title compound was obtained in a same manner as the procedure in Example 3 using ethyl(6-hydroxy-1-benzothiophen-3-yl)acetate and (2-chloro-6-(trifluoromethyl)pyridin-3-yl)methanol.

Example 174

(6-((2-Chloro-6-(trifluoromethyl)pyridin-3-yl)methoxy)-1-benzothiophen-3-yl)acetic acid The title compound was obtained in a same manner as the procedure in Example 2 by using the corresponding ester.

Example 175

Ethyl(6-((2-(pyrrolidin-1-yl)-6-(trifluoromethyl)pyridin-3-yl)methoxy)-1-benzothiophen-3-yl)acetate To a mixture of ethyl(6-((2-chloro-6-(trifluoromethyl)pyridin-3-yl)methoxy)-1-benzothiophen-3-yl)acetate (90 mg), pyrrolidine (59.6 mg) and DMF (dry) (10 mL) was added K$_2$CO$_3$ (57.9 mg). The mixture was stirred at 80° C. under argon atmosphere overnight. The mixture was poured into water and extracted with EtOAc. The organic layer was separated, washed successively with water and brine, dried over MgSO$_4$ and concentrated in vacuo. The residue was purified by silica gel column chromatography (EtOAc/hexane) to give title compound (46.0 mg).

Example 176

(6-((2-(Pyrrolidin-1-yl)-6-(trifluoromethyl)pyridin-3-yl)methoxy)-1-benzothiophen-3-yl)acetic acid The title compound was obtained in a same manner as the procedure in Example 12 by using the corresponding ester.

Example 177

(4-Chloro-6-((4-methyl-2-(trifluoromethyl)pyrimidin-5-yl)methoxy)-1-benzothiophen-3-yl)acetic acid A) Methyl(4-chloro-6-((4-methyl-2-(trifluoromethyl)pyrimidin-5-yl)methoxy)-1-benzothiophen-3-yl)acetate The title compound was obtained in a same manner as the procedure in Example 3 as a crude product using methyl(4-chloro-6-hydroxy-1-benzothiophen-3-yl)acetate and (4-methyl-2-(trifluoromethyl)pyrimidin-5-yl)methanol. The crude product was subject to next step without further purification.

MS (ESI−): [M−H]⁻ 428.9.

B) (4-Chloro-6-((4-methyl-2-(trifluoromethyl)pyrimidin-5-yl)methoxy)-1-benzothiophen-3-yl)acetic acid The title compound was obtained in a same manner as the procedure in Example 12 by using the crude product of methyl (4-chloro-6-((4-methyl-2-(trifluoromethyl)pyrimidin-5-yl)methoxy)-1-benzothiophen-3-yl)acetate. The obtained compound was purified by a preparative HPLC (C18, H$_2$O/CH$_3$CN (including 5 mM AcONH$_4$)). The fraction was concentrated. The residue was extracted with EtOAc. The combined organic layer was washed with brine, dried over MgSO$_4$, and concentrated in vacuo. The solid was crystallized from EtOAc-hexane to give the title compound.

Example 178

2-(4-Chloro-6-((1-methyl-3-(trifluoromethyl)-1H-pyrazol-5-yl)methoxy)-1-benzothiophen-3-yl)acetamide To a mixture of (4-chloro-6-((1-methyl-3-(trifluoromethyl)-1H-pyrazol-5-yl)methoxy)-1-benzothiophen-3-yl) acetic acid (365 mg) and THF (dry) (5 mL) were added oxalyl chloride (0.095 mL) and DMF (6.98 µl) at room temperature. The mixture was stirred at room temperature for 20 min. The mixture was concentrated under reduced pressure. The residue was dissolved in THF (5 mL), and the solution was poured into stirred 28% aqueous ammonium hydroxide (5 mL) at room temperature. After stirring at room temperature for 15 min, the mixture was poured into water at room temperature and extracted with EtOAc. The organic layer was separated, washed with brine, dried over $MgSO_4$ and concentrated in vacuo. The solid was crystallized from MeOH to give the title compound (320 mg).

Examples 179 and 180

Ethyl(6-((E)-2-(2,6-dimethylpyridin-3-yl)vinyl)-1-benzothiophen-3-yl)acetate (example 179) and ethyl (6-((Z)-2-(2,6-dimethylpyridin-3-yl)vinyl)-1-benzothiophen-3-yl)acetate

Example 180

A) Ethyl(6-vinyl-1-benzothiophen-3-yl)acetate

To a mixture of ethyl(6-(((trifluoromethyl)sulfonyl)oxy)-1-benzothiophen-3-yl)acetate (600 mg) and EtOH (10 mL) were added potassium vinyl(trifluoro) borate (240 mg), $PdCl_2$ (dppf) (119 mg) and TEA (0.454 mL) at room temperature, and the mixture was heated to 110° C. with microwave irradiation for 15 min. The mixture was poured into brine at room temperature and extracted with EtOAc. The organic layer was separated, washed with brine, and dried over $MgSO_4$ and concentrated in vacuo. The residue was purified by silica gel column chromatography (EtOAc/hexane) to give the title compound (320 mg).

$^1$H NMR (300 MHz, $CDCl_3$) δ 1.25 (3H, t, J=6.99 Hz), 3.83 (2H, d, J=0.76 Hz), 4.17 (2H, q, J=7.18 Hz), 5.29 (1H, d, J=10.95 Hz), 5.75-5.90 (1H, m), 6.82 (1H, dd, J=17.37, 10.95 Hz), 7.33 (1H, s), 7.49 (1H, dd, J=8.31, 1.51 Hz), 7.71 (1H, d, J=8.31 Hz), 7.84 (1H, d, J=1.51 Hz).

B) Ethyl(6-(1,2-dihydroxyethyl)-1-benzothiophen-3-yl)acetate

To a mixture of 4-methylmorpholine 4-oxide hydrate (527 mg), ethyl(6-vinyl-1-benzothiophen-3-yl)acetate (320 mg), acetone (0.5 mL), $CH_3CN$ (0.500 mL) and water (0.500 mL) was added osmium(VIII) oxide (7% microcapsule, 472 mg) at room temperature. The mixture was stirred at room temperature for 4 d. The insoluble material was removed by filtration through Celite®, and the filtrate was concentrated in vacuo. Water was added to the mixture and the mixture was extracted with EtOAc. The organic layer was separated, washed successively with water and brine, dried over $MgSO_4$ and concentrated in vacuo. The residue was purified by silica gel column chromatography (EtOAc/hexane) to give the title compound (200 mg).

$^1$H NMR (300 MHz, $CDCl_3$) δ 1.25 (3H, t, J=7.18 Hz), 2.10 to 2.35 (1H, m), 2.72 (1H, brs.), 3.63-3.87 (4H, m), 4.17 (2H, q, J=7.18 Hz), 4.85-5.01 (1H, m), 7.32-7.44 (2H, m), 7.74 (1H, d, J=8.31 Hz), 7.89 (1H, s).

C) Ethyl(6-formyl-1-benzothiophen-3-yl)acetate

To a mixture of ethyl(6-(1,2-dihydroxyethyl)-1-benzothiophen-3-yl)acetate (200 mg), THF (2 mL) and water (2.0 mL) was added $NaIO_4$ (458 mg) at room temperature. The mixture was stirred at room temperature for 30 min. The mixture was quenched with saturated aqueous $Na_2S_2O_3$ at room temperature and extracted with EtOAc. The organic layer was separated, washed successively with brine twice, dried over $MgSO_4$ and concentrated in vacuo. The residue was purified by silica gel column chromatography (EtOAc/hexane) to give the title compound (160 mg).

$^1$H NMR (300 MHz, $CDCl_3$) δ 1.26 (3H, t, J=7.18 Hz), 3.90 (2H, d, J=0.76 Hz), 4.19 (2H, q, J=7.18 Hz), 7.65 (1H, t, J=0.94 Hz), 7.81-7.98 (2H, m), 8.37 (1H, d, J=0.76 Hz), 10.11 (1H, s).

D) ((2,6-Dimethylpyridin-3-yl)methyl)(triphenyl) phosphonium chloride

A mixture of triphenylphosphine (885 mg), 3-(chloromethyl)-2,6-dimethylpyridine (500 mg) and $CH_3CN$ (20 mL) was refluxed for 24 h. The mixture was concentrated in vacuo. The residual solid was washed with IPE to give the title compound (1060 mg).

$^1$H NMR (300 MHz, $CDCl_3$) δ 1.71-1.81 (3H, m), 2.41-2.47 (3H, m), 5.60 (2H, d, J=14.39 Hz), 6.82 (1H, d, J=7.95 Hz), 7.51-7.84 (16H, m).

E) Ethyl(6-((E)-2-(2,6-dimethylpyridin-3-yl)vinyl)-1-benzothiophen-3-yl)acetate (example 179) and ethyl(6-((Z)-2-(2,6-dimethylpyridin-3-yl)vinyl)-1-benzothiophen-3-yl)acetate

Example 180

A mixture of $K_2CO_3$ (134 mg), ethyl(6-formyl-1-benzothiophen-3-yl)acetate (160 mg), ((2,6-dimethylpyridin-3-yl)methyl) (triphenyl)phosphonium chloride (323 mg) and DMF (5 mL) was stirred at room temperature for 3 d. The mixture was quenched with water and extracted with EtOAc. The organic layer was separated, washed with brine, dried over $MgSO_4$ and concentrated in vacuo. The residue was purified by silica gel column chromatography (EtOAc/hexane) to give ethyl(6-((E)-2-(2,6-dimethylpyridin-3-yl)vinyl)-1-benzothiophen-3-yl)acetate (example 179, 60 mg) and ethyl(6-((Z)-2-(2,6-dimethylpyridin-3-yl)vinyl)-1-benzothiophen-3-yl)acetate (example 180, 110 mg).

Example 181

Ethyl(6-(2-(2,6-dimethylpyridin-3-yl)ethyl)-1-benzothiophen-3-yl)acetate

A mixture of ethyl(6-((Z)-2-(2,6-dimethylpyridin-3-yl)vinyl)-1-benzothiophen-3-yl)acetate (110 mg), 10% Pd—C (50% wet, 50 mg) and THF (5 mL) was hydrogenated under atmospheric pressure for 30 min. The catalyst was removed by filtration. The filtrate was concentrated in vacuo. The residue was purified by silica gel column chromatography (EtOAc/hexane) to give the title compound (90 mg).

Example 182

(6-(2-(2,6-Dimethylpyridin-3-yl)ethyl)-1-benzothiophen-3-yl)acetic acid

The title compound was obtained in a same manner as the procedure in Example 12 by using the corresponding ester. The obtained crystals were recrystallized from acetone-hexane.

Example 183

(6-((E)-2-(2,6-dimethylpyridin-3-yl)vinyl)-1-benzothiophen-3-yl)acetic acid

The title compound was obtained in a same manner as the procedure in Example 12 by using the corresponding ester. The obtained crystals were recrystallized from acetone-hexane.

Example 184

(4-(Difluoromethyl)-6-((2,6-dimethylpyridin-3-yl)methoxy)-1-benzothiophen-3-yl)acetic acid A) 4-(Difluoromethyl)-3-(2-methoxy-2-oxoethyl)-1-benzothiophen-6-yl pivalate To a mixture of 4-formyl-3-(2-methoxy-2-oxoethyl)-1-benzothiophen-6-yl pivalate (460 mg) and toluene (5 mL) was added [bis(2-methoxyethyl)amino]sulfur trifluoride (0.76 mL) at room temperature. The mixture was stirred at 70° C. for 5 h. The mixture was quenched with saturated aqueous NaHCO$_3$ at 0° C. and extracted with EtOAc. The organic layer was separated, washed successively with water and brine, dried over MgSO$_4$ and concentrated in vacuo. The residue was purified by silica gel column chromatography (EtOAc/hexane) to give the title compound (374 mg).
$^1$H NMR (300 MHz, CDCl$_3$) δ 1.36-1.42 (9H, m), 3.72 (3H, s), 4.02 (2H, s), 7.39 (1H, d, J=2.7 Hz), 7.45 (1H, s), 7.57 (1H, d, J=2.3 Hz), 7.71-7.74 (1H, m).

B) Methyl(4-(difluoromethyl)-6-hydroxy-1-benzothiophen-3-yl)acetate

The title compound was obtained in a same manner as the procedure in step E of Example 169.
$^1$H NMR (300 MHz, DMSO-d$_6$) δ 3.62 (3H, s), 4.01 (2H, s), 7.14-7.20 (1H, m), 7.36 (1H, s), 7.44-7.56 (2H, m), 10.00 (1H, brs).

C) (4-(Difluoromethyl)-6-((2,6-dimethylpyridin-3-yl)methoxy)-1-benzothiophen-3-yl)acetic acid To a mixture of methyl(4-(difluoromethyl)-6-hydroxy-1-benzothiophen-3-yl)acetate (78 mg) and THF (dry) (2 mL) were added (2,6-dimethylpyridin-3-yl)methanol (43.2 mg), tri-n-butylphosphine (0.212 mL) and ADDP (94 mg) at room temperature. The mixture was stirred at room temperature for 2 h. To the mixture were added ADDP (94 mg) and tri-n-butylphosphine (0.212 mL), and the mixture was stirred at room temperature for 30 min. The insoluble material was removed by filtration, and the filtrate was concentrated in vacuo. The residue was purified by short pad of silica gel (EtOAc/hexane). To a mixture of the residue and THF (2 mL) was added 1N NaOH (1 mL) at room temperature. The mixture was stirred at room temperature for 16 h. The mixture was neutralized with 1N HCl at room temperature and extracted with EtOAc. The organic layer was separated, washed successively with water and brine, dried over MgSO$_4$ and concentrated in vacuo. The crude product was purified by preparative HPLC (C18, H$_2$O/CH$_3$CN (including 10 mM NH$_4$HCO$_3$)). The fraction was extracted with EtOAc. The organic layer was separated, washed successively with water and brine, dried over MgSO$_4$ and concentrated in vacuo. The residue was crystallized from EtOAc-hexane to give the title compound (29.1 mg).

Example 185

(4-(Difluoromethyl)-6-((1-methyl-3-(trifluoromethyl)-1H-pyrazol-5-yl)methoxy)-1-benzothiophen-3-yl)acetic acid The title compound was obtained in a same manner as the procedure in step C of Example 184 using methyl(4-(difluoromethyl)-6-hydroxy-1-benzothiophen-3-yl)acetate and (1-methyl-3-(trifluoromethyl)-1H-pyrazol-5-yl)methanol.

Example 186

Methyl(4-chloro-6-((2-methyl-5-(trifluoromethyl)-3-furyl)methoxy)-1-benzothiophen-3-yl)acetate A) Ethyl 2-acetyl-5,5,5-trifluoro-4-oxopentanoate To a mixture of ethyl acetoacetate (3.98 mL) in THF (dry) (50 mL) was added NaH (1.571 g) at 0° C., and the mixture was stirred for 30 min at the same temperature. To the mixture was added 3-bromo-1,1,1-trifluoroacetone (5 g) 0° C., and the mixture was stirred for 3 h. The mixture was poured into brine at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (1.570 g).
$^1$H NMR (300 MHz, CDCl$_3$) δ 1.27-1.37 (3H, m), 2.23-2.30 (3H, m), 4.23-4.40 (3H, m), 4.47-4.52 (1H, m), 4.66 (1H, d, J=11.3 Hz).

B) Ethyl 2-methyl-5-(trifluoromethyl)furan-3-carboxylate

To a mixture of ethyl 2-acetyl-5,5,5-trifluoro-4-oxopentanoate (1.37 g) and toluene (5 mL) was added TsOH monohydrate (0.109 g) at room temperature, and the mixture was refluxed with azeotropic removal of water by Dean-Stark apparatus for 14 h. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (0.730 g).
$^1$H NMR (300 MHz, CDCl$_3$) δ 1.32-1.38 (3H, m), 2.60 (3H, s), 4.28-4.36 (2H, m), 7.61 (1H, q, J=1.1 Hz).

C) (2-Methyl-5-(trifluoromethyl)-3-furyl)methanol

To a mixture of ethyl 2-methyl-5-(trifluoromethyl)furan-3-carboxylate (720 mg) and THF (dry) (10 mL) was added lithium aluminum hydride (123 mg) at 0° C., and the mixture was stirred for 3 h. The mixture was quenched with EtOAc at 0° C. and 1N HCl was added to the mixture at same temperature. The organic layer was separated, washed successively with 1N HCl and brine, dried over MgSO$_4$ and concentrated in vacuo to give title compound.

$^1$H NMR (300 MHz, CDCl$_3$) δ 2.34 (3H, s), 4.55 (2H, s), 7.58-7.62 (1H, m).

D) Methyl(4-chloro-6-((2-methyl-5-(trifluoromethyl)-3-furyl)methoxy)-1-benzothiophen-3-yl)acetate The title compound was obtained in a same manner as the procedure in Example 3 using methyl(4-chloro-6-hydroxy-1-benzothiophen-3-yl)acetate and (2-methyl-5-(trifluoromethyl)-3-furyl)methanol.

Example 187

(4-Chloro-6-((2-methyl-5-(trifluoromethyl)-3-furyl)methoxy)-1-benzothiophen-3-yl)acetic acid The title compound was obtained in a same manner as the procedure in Example 6 by using the corresponding ester.

Example 188

Methyl(4-chloro-6-((1,3-dimethyl-1H-pyrazol-4-yl)methoxy)-1-benzothiophen-3-yl)acetate The title compound was obtained in a same manner as the procedure in Example 3 using methyl(4-chloro-6-hydroxy-1-benzothiophen-3-yl)acetate and (1,3-dimethyl-1H-pyrazol-4-yl)methanol.

Example 189

(4-Chloro-6-((1,3-dimethyl-1H-pyrazol-4-yl)methoxy)-1-benzothiophen-3-yl)acetic acid The title compound was obtained in a same manner as the procedure in Example 12 by using the corresponding ester.

Example 190

1-((4-Chloro-6-((1-methyl-3-(trifluoromethyl)-1H-pyrazol-5-yl)methoxy)-1-benzothiophen-3-yl)methyl)urea To a mixture of 2-(4-chloro-6-((1-methyl-3-(trifluoromethyl)-1H-pyrazol-5-yl)methoxy)-1-benzothiophen-3-yl)acetic acid (120 mg) and toluene (2 mL) were added DPPA (0.076 mL) and TEA (0.050 mL) at room temperature, and the mixture was refluxed for 1 h. To the mixture was added 28% aqueous ammonium hydroxide (0.035 mL) at room temperature, and the mixture was stirred for 30 min. The mixture was poured into brine at room temperature and extracted with EtOAc. The organic layer was separated, washed with brine, dried over MgSO$_4$ and concentrated in vacuo. The solid was crystallized from EtOAc to give title compound (24.00 mg).

Example 191

Methyl 6-((2,4-dichlorobenzyl)oxy)-1-benzofuran-3-carboxylate

The title compound was obtained in a same manner as the procedure in Example 5 using methyl(6-hydroxy-1-benzofuran-3-yl)acetate and 2,4-dichlorobenzyl chloride.

Example 192

6-((2,4-Dichlorobenzyl)oxy)-1-benzofuran-3-carboxylic acid

The title compound was obtained in a same manner as the procedure in Example 12 by using the corresponding ester.

Example 193

Methyl((3S)-6-((2,4-dichlorobenzyl)oxy)-2,3-dihydro-1-benzofuran-3-yl)acetate The title compound was obtained in a same manner as the procedure in Example 5 using methyl((3S)-6-hydroxy-2,3-dihydro-1-benzofuran-3-yl)acetate and 2,4-dichlorobenzyl chloride.

Example 194

Methyl(6-((2,4-dichlorobenzyl)oxy)-1-benzofuran-3-yl)acetate

To a mixture of methyl((3S)-6-((2,4-dichlorobenzyl)oxy)-2,3-dihydro-1-benzofuran-3-yl)acetate (367 mg) in toluene (5.0 mL) was added DDQ (272 mg). The mixture was stirred at 80° C. for 17 h. After cooling, the insoluble material was removed by filtration and the filtrate was concentrated in vacuo. The residue was purified by silica gel column chromatography (EtOAc/hexane) to give the title compound (263.6 mg).

Example 195

(6-((2,4-Dichlorobenzyl)oxy)-1-benzofuran-3-yl)acetic acid

The title compound was obtained in a same manner as the procedure in Example 2 by using the corresponding ester.

Example 196

N-(2-(6-(2,4-Dichlorobenzyloxy)-1-benzofuran-3-yl)ethyl)acetamide

The title compound was obtained in a same manner as the procedure in Example 194 by using N-(2-((3S)-6-((2,4-dichlorobenzyl)oxy)-2,3-dihydro-1-benzofuran-3-yl)ethyl)acetamide.

Example 197

N-(2-((3S)-6-((2,4-Dichlorobenzyl)oxy)-2,3-dihydro-1-benzofuran-3-yl)ethyl)acetamide

A) 2-((3S)-6-((2,4-Dichlorobenzyl)oxy)-2,3-dihydro-1-benzofuran-3-yl)ethanamine To a mixture of 2-((3S)-6-((2,4-dichlorobenzyl)oxy)-2,3-dihydro-1-benzofuran-3-yl)ethanol (678 mg) and THF (dry) (20 mL) were added methanesulfonyl chloride (0.310 mL) and TEA (0.836 mL) at room temperature. The mixture was stirred at room temperature for 30 min. The mixture was concentrated in vacuo.

To the residue were added DMF (dry) (20.00 mL) and sodium azide (260 mg). The mixture was stirred at 70° C. for 3 h. The mixture was poured into saturated aqueous NaHCO$_3$ and extracted with EtOAc. The organic layer was separated, washed successively with water and brine, dried over MgSO$_4$ and concentrated in vacuo. The residue was purified by silica gel column chromatography (EtOAc/hexane) to give a compound (ca. 600 mg) as a white solid. A mixture of the compound and PtO$_2$ (50 mg), MeOH (20.00 mL) and THF (dry) (20.00 mL) was hydrogenated under balloon pressure at room temperature for 3 h. The catalyst was removed by filtration and the filtrate was concentrated in vacuo to give the title compound (490 mg).

MS (ESI+): [M+H]$^+$ 338.0.

B) N-(2-((3S)-6-((2,4-Dichlorobenzyl)oxy)-2,3-dihydro-1-benzofuran-3-yl)ethyl)acetamide To a mixture of 2-((3S)-6-((2,4-dichlorobenzyl)oxy)-2,3-dihydro-1-benzofuran-3-yl)ethanamine (320 mg) and DMA (10 mL) was added acetyl chloride (74.3 mg). The mixture was stirred for 2 h. The mixture was poured into saturated aqueous NaHCO$_3$ and extracted with EtOAc. The organic layer was separated, washed successively with water and brine, dried over MgSO$_4$ and concentrated in vacuo. The residue was purified by silica gel column chromatography (EtOAc/hexane) to give the title compound (170 mg).

MS (ESI+): [M+H]$^-$ 380.0.

Example 198

N-(2-((3S)-6-((2,4-Dichlorobenzyl)oxy)-2,3-dihydro-1-benzofuran-3-yl)ethyl)propanamide The title compound was obtained in a same manner as the procedure in step B of Example 197 using 2-((3S)-6-((2,4-dichlorobenzyl)oxy)-2,3-dihydro-1-benzofuran-3-yl)ethanamine and propanoyl chloride.

Example 199

N-(2-((3S)-6-((2,4-Dichlorobenzyl)oxy)-2,3-dihydro-1-benzofuran-3-yl)ethyl)-2-hydroxy-3-methylbutanamide To a mixture of 2-((3S)-6-((2,4-dichlorobenzyl)oxy)-2,3-dihydro-1-benzofuran-3-yl)ethanamine (33.8 mg) and DMF (dry) (5 mL) were added 2-hydroxy-3-methylbutanoic acid (17.72 mg), EDCI (31.0 mg) and HOBt (27.0 mg). The mixture was stirred at room temperature overnight. The mixture was poured into saturated aqueous NaHCO$_3$ and extracted with EtOAc. The organic layer was separated, washed successively with water and brine, dried over MgSO$_4$ and concentrated in vacuo. The residue was purified by silica gel column chromatography (EtOAc/hexane) to give the title compound (26.0 mg).

Example 200

N-(2-((3S)-6-((2,4-Dichlorobenzyl)oxy)-2,3-dihydro-1-benzofuran-3-yl)ethyl)-2,2,2-trifluoroacetamide To a mixture of 2-((3S)-6-((2,4-dichlorobenzyl)oxy)-2,3-dihydro-1-benzofuran-3-yl)ethanamine (33.8 mg) in THF (dry) (5 mL) were added TFAA (21.00 mg) and TEA (0.014 mL). The mixture was stirred at room temperature for 30 min. The mixture was poured into water and extracted with EtOAc. The organic layer was separated, washed successively with water and brine, dried over MgSO$_4$ and concentrated in vacuo. The residue was purified by silica gel column chromatography (EtOAc/hexane) to give the title compound (20.00 mg).

Example 201

Ethyl((2-((3S)-6-((2,4-dichlorobenzyl)oxy)-2,3-dihydro-1-benzofuran-3-yl)ethyl)sulfanyl)acetate A) 2-((3S)-6-((2,4-Dichlorobenzyl)oxy)-2,3-dihydro-1-benzofuran-3-yl)ethanol The title compound was obtained in a same manner as the procedure in step B of Example 92 by using methyl((3S)-6-((2,4-dichlorobenzyl)oxy)-2,3-dihydro-1-benzofuran-3-yl) acetate.

$^1$H NMR (300 MHz, DMSO-d$_6$) δ 1.51-1.71 (1H, m), 1.79-1.92 (1H, m), 3.35-3.55 (3H, m), 4.20 (1H, dd, J=9.0, 6.8 Hz), 4.55 (1H, t, J=5.1 Hz), 4.62 (1H, t, J=9.0 Hz), 5.08 (2H, s), 6.43-6.52 (2H, m), 7.10 (1H, d, J=7.9 Hz), 7.43-7.51 (1H, m), 7.56-7.62 (1H, m), 7.68 (1H, d, J=2.3 Hz).

B) S-(2-((3S)-6-((2,4-Dichlorobenzyl)oxy)-2,3-dihydro-1-benzofuran-3-yl)ethyl) ethanethioate To a mixture of 2-((3S)-6-((2,4-dichlorobenzyl)oxy)-2,3-dihydro-1-benzofuran-3-yl)ethanol (678 mg) and THF (dry) (20 mL) were added methanesulfonyl chloride (0.310 mL) and Et$_3$N (0.279 mL). The mixture was stirred at room temperature for 30 min. And then DMF (dry) (20.00 mL) and potassium ethanethioate (228 mg) were added to the mixture. The volatiles (THF) were removed by evaporation. The resulting mixture was stirred at 70° C. for 2 h. The mixture was poured into water and extracted with EtOAc. The organic layer was separated, washed successively with water and brine, dried over MgSO$_4$ and concentrated in vacuo. The residue was purified by silica gel column chromatography (EtOAc/hexane) to give the title compound (570 mg).

MS (ESI+): [M+H]$^+$ 398.2.

C) 2-((3S)-6-((2,4-Dichlorobenzyl)oxy)-2,3-dihydro-1-benzofuran-3-yl)ethanethiol To a mixture of S-(2-((3S)-6-((2,4-dichlorobenzyl)oxy)-2,3-dihydro-1-benzofuran-3-yl)ethyl) ethanethioate (160 mg), THF (dry) (2 mL) and MeOH (2 mL) was added 1N NaOH (1.208 mL).

The mixture was stirred at room temperature for 1 h. The mixture was neutralized with 1N HCl and extracted with EtOAc. The organic layer was separated, washed successively with water and brine, dried over MgSO$_4$ and concentrated in vacuo to give title compound (120 mg).

MS (ESI-): [M-H]$^-$ 353.0.

D) Ethyl((2-((3S)-6-((2,4-dichlorobenzyl)oxy)-2,3-dihydro-1-benzofuran-3-yl)ethyl)sulfanyl)acetate To a mixture of 2-((3S)-6-((2,4-dichlorobenzyl)oxy)-2,3-dihydro-1-benzofuran-3-yl)ethanethiol (30 mg), DIPEA (0.029 mL) and DMF (dry) (15 mL) was added ethyl 2-bromoacetate (21.15 mg). The mixture was stirred at room temperature under argon atmosphere overnight. The mixture was poured into water and extracted with EtOAc. The organic layer was separated, washed successively with water and brine, dried over MgSO$_4$ and concentrated in vacuo. The

Example 202

((2-((3S)-6-((2,4-Dichlorobenzyl)oxy)-2,3-dihydro-1-benzofuran-3-yl)ethyl)sulfanyl)acetic acid The title compound was obtained in a same manner as the procedure in Example 12 by using the corresponding ester.

Example 203

Ethyl((2-(6-((2,4-dichlorobenzyl)oxy)-1-benzofuran-3-yl)ethyl)sulfanyl)acetate

The title compound was obtained in a same manner as the procedure in Example 194 followed by the procedures in steps C and D of Example 201 using S-(2-((3S)-6-((2,4-dichlorobenzyl)oxy)-2,3-dihydro-1-benzofuran-3-yl)ethyl) ethanethioate.

Example 204

2-(2-(6-(2,4-Dichlorobenzyloxy)-1-benzofuran-3-yl)ethylsulfanyl)acetic acid

The title compound was obtained in a same manner as the procedure in Example 12 by using the corresponding ester.

Example 205

Ethyl 2-(2-(6-(2,4-dichlorobenzyloxy)-1-benzofuran-3-yl)ethylsulfonyl)acetate

To a mixture of ethyl 2-(2-(6-(2,4-dichlorobenzyloxy)-1-benzofuran-3-yl)ethylsulfanyl)acetate (40 mg) in acetone (5 mL) was added OXONE® (2KHSO$_5$—KHSO$_4$.K$_2$SO$_4$) (224 mg) in water (5.00 mL). The mixture was stirred at room temperature overnight. The mixture was poured into water and extracted with EtOAc. The organic layer was separated, washed successively with water and brine, dried over MgSO$_4$ and concentrated in vacuo. The residue was purified by silica gel column chromatography (EtOAc/hexane) to give the title compound (33.0 mg).

Example 206

2-(2-(6-(2,4-Dichlorobenzyloxy)-1-benzofuran-3-yl)ethylsulfonyl)acetic acid

The title compound was obtained in a same manner as the procedure in Example 12 by using the corresponding ester.

Example 207

Methyl N-((6-((2,4-dichlorobenzyl)oxy)-1-benzofuran-3-yl)acetyl)serinate

The title compound was obtained in a same manner as the procedure in Example 53 using (6-((2,4-dichlorobenzyl)oxy)-1-benzofuran-3-yl)acetic acid and methyl serinate hydrochloride.

Example 208

N-((6-((2,4-Dichlorobenzyl)oxy)-1-benzofuran-3-yl)acetyl)serine

The title compound was obtained in a same manner as the procedure in Example 12 by using the corresponding ester.

Example 209

Methyl((3S)-5-chloro-6-((2,4-dichlorobenzyl)oxy)-2,3-dihydro-1-benzofuran-3-yl)acetate A) Methyl((3S)-5-chloro-6-hydroxy-2,3-dihydro-1-benzofuran-3-yl)acetate To a mixture of methyl((3S)-6-hydroxy-2,3-dihydro-1-benzofuran-3-yl)acetate (10.4 g) and THF (20 mL) was added N-chlorosuccinimide (6.67 g). The mixture was stirred at room temperature overnight. The mixture was poured into water and extracted with EtOAc. The organic layer was separated, washed successively with water and brine, dried over MgSO$_4$ and concentrated in vacuo. The residue was purified by silica gel column chromatography (EtOAc/hexane) to give the title compound (8.8 g).
$^1$H NMR (300 MHz, DMSO-d6) δ 2.53-2.66 (1H, m), 2.82 (1H, dd, J=16.6, 5.7 Hz), 3.62 (3H, s), 3.65-3.76 (1H, m), 4.19 (1H, dd, J=9.1, 6.8 Hz), 4.67 (1H, t, J=9.1 Hz), 6.38 (1H, s), 7.16 (1H, d, J=0.8 Hz), 10.02 (1H, s).

B) Methyl((3S)-5-chloro-6-((2,4-dichlorobenzyl)oxy)-2,3-dihydro-1-benzofuran-3-yl)acetate The title compound was obtained in a same manner as the procedure in Example 5 using methyl((3S)-5-chloro-6-hydroxy-2,3-dihydro-1-benzofuran-3-yl)acetate and 2,4-dichlorobenzyl chloride.

Example 210

((3S)-5-Chloro-6-((2,4-dichlorobenzyl)oxy)-2,3-dihydro-1-benzofuran-3-yl)acetic acid The title compound was obtained in a same manner as the procedure in Example 12 by using the corresponding ester.

Example 211

Methyl(5-chloro-6-((2,4-dichlorobenzyl)oxy)-1-benzofuran-3-yl)acetate

The title compound was obtained in a same manner as the procedure in Example 194 by using methyl((3S)-5-chloro-6-((2,4-dichlorobenzyl)oxy)-2,3-dihydro-1-benzofuran-3-yl)acetate.

Example 212

(5-Chloro-6-((2,4-dichlorobenzyl)oxy)-1-benzofuran-3-yl)acetic acid

The title compound was obtained in a same manner as the procedure in Example 12 by using the corresponding ester.

Example 213

Methyl((3S)-5-bromo-6-((2,4-dichlorobenzyl)oxy)-
2,3-dihydro-1-benzofuran-3-yl)acetate

A) Methyl((3S)-5-bromo-6-hydroxy-2,3-dihydro-1-benzofuran-3-yl)acetate

To a mixture of methyl((3S)-6-hydroxy-2,3-dihydro-1-benzofuran-3-yl)acetate (10 g) in THF (dry) (192 mL) was added N-bromosuccinimide (8.55 g) at 0° C. The mixture was gradually warmed to room temperature and stirred at room temperature for 1.5 day. The mixture was quenched with saturated aqueous NaHCO$_3$ and extracted with EtOAc. The combined organic layer was washed with brine, dried over MgSO$_4$, and concentrated in vacuo. The residue was purified by silica gel column chromatography (EtOAc/hexane) to give the title compound (13.78 g).
MS (ESI-): [M-H]$^-$ 284.8.

B) Methyl((3S)-5-bromo-6-((2,4-dichlorobenzyl)oxy)-2,3-dihydro-1-benzofuran-3-yl)acetate The title compound was obtained in a same manner as the procedure in Example 5 using methyl((3S)-5-bromo-6-hydroxy-2,3-dihydro-1-benzofuran-3-yl)acetate and 2,4-dichlorobenzyl chloride.

Example 214

Methyl(5-bromo-6-((2,4-dichlorobenzyl)oxy)-1-benzofuran-3-yl)acetate

The title compound was obtained in a same manner as the procedure in Example 194 by using methyl((3S)-5-bromo-6-((2,4-dichlorobenzyl)oxy)-2,3-dihydro-1-benzofuran-3-yl) acetate.
$^1$H NMR (300 MHz, CDCl$_3$) δ3.66 (2H, s), 3.75 (3H, s), 5.21 (2H, s), 7.09 (1H, s), 7.29-7.35 (1H, m), 7.43 (1H, d, J=2.3 Hz), 7.56 (1H, s), 7.69 (1H, d, J=8.3 Hz), 7.76 (1H, s).

Example 215

Methyl(6-((2,4-dichlorobenzyl)oxy)-5-methyl-1-benzofuran-3-yl)acetate

To the mixture of methyl(5-bromo-6-((2,4-dichlorobenzyl)oxy)-1-benzofuran-3-yl)acetate (166 mg), aqueous 2M Na$_2$CO$_3$ (0.561 mL) and methylboronic acid (44.7 mg) in DME (3.7 mL) was added Pd(Ph$_3$P)$_4$ (43.2 mg). The mixture was stirred at 80° C. for 7 h. To the mixture was added methylboronic acid (44.8 mg) again. The mixture was stirred at 80° C. under nitrogen atmosphere over weekend. The mixture was diluted with water and extracted with EtOAc. The organic layer was washed with brine, dried over MgSO$_4$, and concentrated in vacuo. The residue was purified by silica gel column chromatography (EtOAc/hexane) to give the title compound (45.0 mg).

Example 216

(6-((2,4-Dichlorobenzyl)oxy)-5-methyl-1-benzofuran-3-yl)acetic acid

The title compound was obtained in a same manner as the procedure in Example 12 by using the corresponding ester.

Example 217

Methyl(5-cyclopropyl-6-((2,4-dichlorobenzyl)oxy)-1-benzofuran-3-yl)acetate

The title compound was obtained in a same manner as the procedure in Example 215 by using methyl(5-bromo-6-((2,4-dichlorobenzyl)oxy)-1-benzofuran-3-yl)acetate and cyclopropylboronic acid.

Example 218

(5-Cyclopropyl-6-((2,4-dichlorobenzyl)oxy)-1-benzofuran-3-yl)acetic acid

The title compound was obtained in a same manner as the procedure in Example 12 by using the corresponding ester.

Example 219

Methyl(5-(4-chlorophenyl)-6-((2,4-dichlorobenzyl)oxy)-1-benzofuran-3-yl)acetate

The title compound was obtained in a same manner as the procedure in Example 215 using methyl(5-bromo-6-((2,4-dichlorobenzyl)oxy)-1-benzofuran-3-yl)acetate and 4-chlorophenylboronic acid.

Example 220

Methyl(6-((2,4-dichlorobenzyl)oxy)-5-(1-methyl-1H-pyrazol-4-yl)-1-benzofuran-3-yl)acetate The title compound was obtained in a same manner as the procedure in Example 215 by using methyl(5-bromo-6-((2,4-dichlorobenzyl)oxy)-1-benzofuran-3-yl)acetate and 1-methyl-4-(4,4,5,5-tetramethyl-1,3,2-dioxaborolan-2-yl)-1H-pyrazole.

Example 221

(6-((2,4-Dichlorobenzyl)oxy)-5-(1-methyl-1H-pyrazol-4-yl)-1-benzofuran-3-yl)acetic acid The title compound was obtained in a same manner as the procedure in Example 12 by using the corresponding ester.

Example 222

(5-(4-Chlorophenyl)-6-((2,4-dichlorobenzyl)oxy)-1-benzofuran-3-yl)acetic acid

The title compound was obtained in a same manner as the procedure in Example 12 by using the corresponding ester.

Example 223

Methyl(6-((2,4-dichlorobenzyl)oxy)-5-(1,3,5-trimethyl-1H-pyrazol-4-yl)-1-benzofuran-3-yl)acetate The title compound was obtained in a same manner as the procedure in Example 215 by using methyl(5-bromo-6-((2,4-dichlorobenzyl)oxy)-1-benzofuran-3-yl)acetate and 1,3,5-trimethyl-4-(4,4,5,5-tetramethyl-1,3,2-dioxaborolan-2-yl)-1H-pyrazole.

Example 224

(6-((2,4-Dichlorobenzyl)oxy)-5-(1,3,5-trimethyl-1H-pyrazol-4-yl)-1-benzofuran-3-yl)acetic acid The title compound was obtained in a same manner as the procedure in Example 12 by using the corresponding ester.

Example 225

Methyl((3S)-7-bromo-5-chloro-6-((2,4-dichlorobenzyl)oxy)-2,3-dihydro-1-benzofuran-3-yl)acetate

A) Methyl((3S)-5-chloro-6-hydroxy-2,3-dihydro-1-benzofuran-3-yl)acetate

To a mixture of methyl((3S)-6-hydroxy-2,3-dihydro-1-benzofuran-3-yl)acetate (10 g) in THF (dry) (192 mL) was added N-chlorosuccinimide (6.41 g) portionwise at 0° C. The mixture was stirred at room temperature over weekend. The mixture was quenched with water and extracted with EtOAc. The combined organic layer was washed with brine, dried over $MgSO_4$, and concentrated in vacuo. The residue was purified by silica gel column chromatography (EtOAc/hexane) to give the title compound (10.12 g).
MS (ESI−): [M−H]⁻ 241.3.

B) Methyl((3S)-7-bromo-5-chloro-6-hydroxy-2,3-dihydro-1-benzofuran-3-yl)acetate The title compound was obtained in a same manner as the procedure in the step A of Example 213 by using methyl((3S)-5-chloro-6-hydroxy-2,3-dihydro-1-benzofuran-3-yl)acetate.
MS (ESI−): [M−H]⁻ 319.0.

C) Methyl((3S)-7-bromo-5-chloro-6-((2,4-dichlorobenzyl)oxy)-2,3-dihydro-1-benzofuran-3-yl)acetate The title compound was obtained in a same manner as the procedure in Example 5 using methyl((3S)-7-bromo-5-chloro-6-hydroxy-2,3-dihydro-1-benzofuran-3-yl)acetate and 2,4-dichlorobenzyl chloride.

Example 226

((3S)-7-Bromo-5-chloro-6-((2,4-dichlorobenzyl)oxy)-2,3-dihydro-1-benzofuran-3-yl)acetic acid The title compound was obtained in a same manner as the procedure in Example 12 by using the corresponding ester.

Example 227

Methyl(7-bromo-5-chloro-6-((2,4-dichlorobenzyl)oxy)-1-benzofuran-3-yl)acetate

The title compound was obtained in a same manner as the procedure in Example 194 by using methyl((3S)-7-bromo-5-chloro-6-((2,4-dichlorobenzyl)oxy)-2,3-dihydro-1-benzofuran-3-yl)acetate.

Example 228

(7-Bromo-5-chloro-6-((2,4-dichlorobenzyl)oxy)-1-benzofuran-3-yl)acetic acid

The title compound was obtained in a same manner as the procedure in Example 12 by using the corresponding ester.

Example 229

Methyl((3S)-6-(1-(2,4-dichlorophenyl)ethoxy)-2,3-dihydro-1-benzofuran-3-yl)acetate The title compound was obtained in a same manner as the procedure in Example 3 using methyl((3S)-6-hydroxy-2,3-dihydro-1-benzofuran-3-yl)acetate and 1-(2,4-dichlorophenyl)ethanol.

Example 230

((3S)-6-(1-(2,4-Dichlorophenyl)ethoxy)-2,3-dihydro-1-benzofuran-3-yl)acetic acid The title compound was obtained in a same manner as the procedure in Example 12 by using the corresponding ester.

Example 231

Methyl(6-(1-(2,4-dichlorophenyl)ethoxy)-1-benzofuran-3-yl)acetate

The title compound was obtained in a same manner as the procedure in Example 194 by using methyl((3S)-6-(1-(2,4-dichlorophenyl)ethoxy)-2,3-dihydro-1-benzofuran-3-yl)acetate.

Example 232

(6-(1-(2,4-Dichlorophenyl)ethoxy)-1-benzofuran-3-yl)acetic acid

The title compound was obtained in a same manner as the procedure in Example 12.

Example 233

Methyl(6-((2,4-dichlorobenzyl)oxy)-7-methyl-1-benzofuran-3-yl)acetate

A) 4-(Chloromethyl)-7-hydroxy-8-methyl-2H-chromen-2-one

To ethyl 4-chloro-3-oxobutanoate (5.77 mL) was added conc.$H_2SO_4$ (15.03 mL) at 0° C. Then to the mixture was added 2-methylbenzene-1,3-diol (5.0 g) in several portions at 0° C. The mixture was stirred at 0° C. for 30 min. The mixture was warmed to room temperature for 1.5 h. The reaction mixture was poured into water under stirring at 0° C. The precipitate was collected by filtration and washed with water to give the title compound (8.58 g).
MS (ESI−): [M−H]⁻ 223.1.

B) (6-Hydroxy-7-methyl-1-benzofuran-3-yl)acetic acid

A mixture of 1M NaOH (89 mL) and 4-(chloromethyl)-7-hydroxy-8-methyl-2H-chromen-2-one (4.0 g) was stirred at 100° C. for 1 h. After cooling, the reaction mixture was acidified with 6N HCl. The precipitate was collected by filtration, and washed with water and hexane to give the title compound (2.62 g). The filtrate was extracted with EtOAc. The organic layer was washed with brine, dried over $MgSO_4$, filtered and concentrated in vacuo. The solid was washed with hexane to give the title compound (831.4 mg). Total yield: 3.45 g.

MS (ESI+): $[M+H]^+$ 207.0.

C) Methyl(6-hydroxy-7-methyl-1-benzofuran-3-yl)acetate

To a mixture of (6-hydroxy-7-methyl-1-benzofuran-3-yl)acetic acid (2.61 g) in MeOH (80 mL) was added conc. $H_2SO_4$ (0.135 mL). The mixture was stirred at 60° C. for 1 h. The mixture was concentrated. The mixture was neutralized with saturated aqueous $NaHCO_3$ and extracted with EtOAc. The combined organic layer was washed with brine, dried over $MgSO_4$, and concentrated in vacuo. The residue was purified by silica gel column chromatography (EtOAc/hexane) to give the title compound (2.52 g).

MS (ESI+): $[M+H]^+$ 220.9.

D) Methyl(6-((2,4-dichlorobenzyl)oxy)-7-methyl-1-benzofuran-3-yl)acetate

The title compound was obtained in a same manner as the procedure in Example 5 using methyl(6-hydroxy-7-methyl-1-benzofuran-3-yl)acetate and 2,4-dichlorobenzyl chloride.

Example 234

(6-((2,4-Dichlorobenzyl)oxy)-7-methyl-1-benzofuran-3-yl)acetic acid

The title compound was obtained in a same manner as the procedure in Example 12 by using the corresponding ester.

Example 235

Methyl(6-((2,6-dimethylpyridin-3-yl)methoxy)-7-methyl-1-benzofuran-3-yl)acetate

The title compound was obtained in a same manner as the procedure in Example 3 using methyl(6-hydroxy-7-methyl-1-benzofuran-3-yl)acetate and (2,6-dimethylpyridin-3-yl)methanol.

Example 236

(6-((2,6-Dimethylpyridin-3-yl)methoxy)-7-methyl-1-benzofuran-3-yl)acetic acid

The title compound was obtained in a same manner as the procedure in Example 12 by using the corresponding ester.

Example 237

Methyl(6-((2,6-dimethylpyridin-3-yl)methoxy)-1-benzofuran-3-yl)acetate

The title compound was obtained in a same manner as the procedure in Example 3 using methyl(6-hydroxy-1-benzofuran-3-yl)acetate and (2,6-dimethylpyridin-3-yl)methanol.

Example 238

(6-((2,6-Dimethylpyridin-3-yl)methoxy)-1-benzofuran-3-yl)acetic acid

A mixture of methyl(6-((2,6-dimethylpyridin-3-yl)methoxy)-1-benzofuran-3-yl)acetate (430 mg), 1N NaOH (5 mL), THF (5 mL) and MeOH (5 mL) was stirred at room temperature for 1 h. The mixture was washed with $Et_2O$. Water and 1N HCl (5 mL) were added to the water layer to be pH=4. The precipitate was collected by filtration and washed with water and $Et_2O$ respectively to give crystals. The crystals were recrystallized from acetone-hexane to give the title compound.

Example 239

Methyl(6-((2,6-dimethylpyridin-3-yl)methoxy)-7-propyl-1-benzofuran-3-yl)acetate

A) 4-(Chloromethyl)-7-hydroxy-8-propyl-2H-chromen-2-one

The title compound was obtained in a same manner as the procedure in step A of Example 233 by using 2-propylbenzene-1,3-diol.

MS (ESI−): $[M-H]^-$ 251.0.

B) (6-Hydroxy-7-propyl-1-benzofuran-3-yl)acetic acid

The title compound was obtained in a same manner as the procedure in step B of Example 233 by using 4-(chloromethyl)-7-hydroxy-8-propyl-2H-chromen-2-one.

MS (ESI+): $[M+H]^+$ 235.0.

C) Methyl(6-hydroxy-7-propyl-1-benzofuran-3-yl)acetate

The title compound was obtained in a same manner as the procedure in step C of Example 233 by using (6-hydroxy-7-propyl-1-benzofuran-3-yl)acetic acid.

MS (ESI+): $[M+H]^+$ 248.0.

D) Methyl(6-((2,6-dimethylpyridin-3-yl)methoxy)-7-propyl-1-benzofuran-3-yl)acetate The title compound was obtained in a same manner as the procedure in Example 3 using methyl(6-hydroxy-7-propyl-1-benzofuran-3-yl)acetate and (2,6-dimethylpyridin-3-yl)methanol.

Example 240

(6-((2,6-Dimethylpyridin-3-yl)methoxy)-7-propyl-1-benzofuran-3-yl)acetic acid

The title compound was obtained in a same manner as the procedure in Example 12 by using the corresponding ester.

Example 241

Methyl(6-((2,4-dichlorobenzyl)oxy)-7-propyl-1-benzofuran-3-yl)acetate

The title compound was obtained in a same manner as the procedure in Example 5 using methyl(6-hydroxy-7-propyl-1-benzofuran-3-yl)acetate and 2,4-dichlorobenzyl chloride.

Example 242

(6-((2,4-Dichlorobenzyl)oxy)-7-propyl-1-benzofuran-3-yl)acetic acid

The title compound was obtained in a same manner as the procedure in Example 12 by using the corresponding ester.

Example 243

Methyl(6-((1,3-dimethyl-1H-pyrazol-5-yl)methoxy)-7-methyl-1-benzofuran-3-yl)acetate The title compound was obtained in a same manner as the procedure in Example 5 by using 5-(chloromethyl)-1,3-dimethyl-1H-pyrazole and methyl(6-hydroxy-7-methyl-1-benzofuran-3-yl)acetate. The obtained crystals were recrystallized from EtOAc-hexane.

Example 244

(6-((1,3-Dimethyl-1H-pyrazol-5-yl)methoxy)-7-methyl-1-benzofuran-3-yl)acetic acid The title compound was obtained in a same manner as the procedure in Example 12 by using the corresponding ester. The obtained crystals were recrystallized from acetone-hexane.

Example 245

Methyl(6-((2,4-dichlorobenzyl)oxy)-7-methoxy-1-benzofuran-3-yl)acetate

A) Methyl(6-hydroxy-7-methoxy-1-benzofuran-3-yl)acetate

The title compound was obtained in a same manner as the procedure in steps A, B, and C of Example 233 by using 2-methoxybenzene-1,3-diol.
MS (ESI+): [M+H]$^+$ 237.1.

B) Methyl(6-((2,4-dichlorobenzyl)oxy)-7-methoxy-1-benzofuran-3-yl)acetate

The title compound was obtained in a same manner as the procedure in Example 5 using methyl(6-hydroxy-7-methoxy-1-benzofuran-3-yl)acetate and 2,4-dichlorobenzyl chloride.

Example 246

(6-((2,4-Dichlorobenzyl)oxy)-7-methoxy-1-benzofuran-3-yl)acetic acid

The title compound was obtained in a same manner as the procedure in Example 12 by using the corresponding ester.

Example 247

Methyl(6-((2,6-dimethylpyridin-3-yl)methoxy)-7-methoxy-1-benzofuran-3-yl)acetate The title compound was obtained in a same manner as the procedure in Example 3 using methyl(6-hydroxy-7-methoxy-1-benzofuran-3-yl)acetate and (2,6-dimethylpyridin-3-yl)methanol.

Example 248

(6-((2,6-Dimethylpyridin-3-yl)methoxy)-7-methoxy-1-benzofuran-3-yl)acetic acid

The title compound was obtained in a same manner as the procedure in Example 12 by using the corresponding ester.

Example 249

Methyl(6-((3,5-dimethylpyrazin-2-yl)methoxy)-1-benzofuran-3-yl)acetate

The title compound was obtained in a same manner as the procedure in Example 3 using methyl(6-hydroxy-1-benzofuran-3-yl)acetate and (3,5-dimethylpyrazin-2-yl)methanol.

Example 250

(6-((3,5-Dimethylpyrazin-2-yl)methoxy)-1-benzofuran-3-yl)acetic acid

The title compound was obtained in a same manner as the procedure in Example 12 by using the corresponding ester.

Example 251

Methyl(7-acetyl-6-((2,4-dichlorobenzyl)oxy)-1-benzofuran-3-yl)acetate

A) 8-Acetyl-4-(chloromethyl)-7-hydroxy-2H-chromen-2-one

The title compound was obtained in a same manner as the procedure in the step A of Example 233 by using 1-(2,6-dihydroxyphenyl)ethanone.
MS (ESI−): [M−H]$^-$ 251.0.

B) Methyl(7-acetyl-6-hydroxy-1-benzofuran-3-yl)acetate

The title compound was obtained in a same manner as the procedure in steps B and C of Example 233 by using 8-Acetyl-4-(chloromethyl)-7-hydroxy-2H-chromen-2-one.
MS (ESI+): [M+H]$^+$ 249.0.

C) Methyl(7-acetyl-6-((2,4-dichlorobenzyl)oxy)-1-benzofuran-3-yl)acetate

The title compound was obtained in a same manner as the procedure in Example 5 using methyl(7-acetyl-6-hydroxy-1-benzofuran-3-yl)acetate and 2,4-dichlorobenzyl chloride.

Example 252

(7-Acetyl-6-((2,4-dichlorobenzyl)oxy)-1-benzofuran-3-yl)acetic acid

The title compound was obtained in a same manner as the procedure in Example 12 by using the corresponding ester.

Example 253

Methyl(6-((2,4-dichlorobenzyl)oxy)-7-(1-hydroxyethyl)-1-benzofuran-3-yl)acetate

To a mixture of methyl(7-acetyl-6-((2,4-dichlorobenzyl)oxy)-1-benzofuran-3-yl)acetate (100 mg) in MeOH (2.5 mL)

was added NaBH₄ (10.2 mg). The mixture was stirred at room temperature for 20 min. The mixture was quenched with water. The resulting solid was collected by filtration to give the title compound (89 mg).
MS (ESI−): [M−H]⁻ 407.0.

Example 254

(6-((2,4-Dichlorobenzyl)oxy)-7-(1-hydroxyethyl)-1-benzofuran-3-yl)acetic acid

The title compound was obtained in a same manner as the procedure in Example 12 by using the corresponding ester.

Example 255

Methyl(7-acetyl-6-((2,6-dimethylpyridin-3-yl)methoxy)-1-benzofuran-3-yl)acetate

The title compound was obtained in a same manner as the procedure in Example 3 using methyl(7-acetyl-6-hydroxy-1-benzofuran-3-yl)acetate and (2,6-dimethylpyridin-3-yl)methanol.

Example 256

(7-Acetyl-6-((2,6-dimethylpyridin-3-yl)methoxy)-1-benzofuran-3-yl)acetic acid

The title compound was obtained in a same manner as the procedure in Example 12 by using the corresponding ester.

Example 257

Methyl(6-((2,6-dimethylpyridin-3-yl)methoxy)-7-(1-hydroxyethyl)-1-benzofuran-3-yl)acetate The title compound was obtained in a same manner as the procedure in Example 253 by using methyl(7-acetyl-6-((2,6-dimethylpyridin-3-yl)methoxy)-1-benzofuran-3-yl)acetate.

Example 258

(6-((2,6-Dimethylpyridin-3-yl)methoxy)-7-(1-hydroxyethyl)-1-benzofuran-3-yl)acetic acid The title compound was obtained in a same manner as the procedure in Example 12 by using the corresponding ester.

Example 259

Methyl(7-chloro-6-((2,6-dimethylpyridin-3-yl)methoxy)-1-benzofuran-3-yl)acetate

A) 8-Chloro-4-(chloromethyl)-7-hydroxy-2H-chromen-2-one

The title compound was obtained in a same manner as the procedure in the step A of Example 233 by using 2-chlorobenzene-1,3-diol.
MS (ESI−): [M−H]⁻ 243.1.

B) (7-Chloro-6-hydroxy-1-benzofuran-3-yl)acetic acid

The title compound was obtained in a same manner as the procedure in the step B of Example 233 by using 8-chloro-4-(chloromethyl)-7-hydroxy-2H-chromen-2-one.
MS (ESI−): [M−H]⁻ 225.1.

C) Methyl(7-chloro-6-hydroxy-1-benzofuran-3-yl)acetate

The title compound was obtained in a same manner as the procedure in the step C of Example 233 by using (7-chloro-6-hydroxy-1-benzofuran-3-yl)acetic acid.
MS (ESI−): [M−H]⁻ 239.0.

D) Methyl(7-chloro-6-((2,6-dimethylpyridin-3-yl)methoxy)-1-benzofuran-3-yl)acetate The title compound was obtained in a same manner as the procedure in Example 3 using methyl(7-chloro-6-hydroxy-1-benzofuran-3-yl)acetate and (2,6-dimethylpyridin-3-yl)methanol.

Example 260

(7-Chloro-6-((2,6-dimethylpyridin-3-yl)methoxy)-1-benzofuran-3-yl)acetic acid

The title compound was obtained in a same manner as the procedure in Example 12 by using the corresponding ester.

Example 261

(6-((2,4-Dichlorobenzyl)oxy)-2,3-dihydro-1-benzofuran-3-yl)acetic acid

The title compound was obtained in a same manner as the procedures in Example 5 and 12 by using methyl(6-hydroxy-2,3-dihydro-1-benzofuran-3-yl)acetate.

Example 262

((3S)-6-((2,4-Dichlorobenzyl)oxy)-2,3-dihydro-1-benzofuran-3-yl)acetic acid

The title compound was obtained in a same manner as the procedure in Example 12 by using the corresponding ester.

Example 263

((3R)-6-((2,4-Dichlorobenzyl)oxy)-2,3-dihydro-1-benzofuran-3-yl)acetic acid

The title compound was obtained in a same manner as the procedures in Example 5 and 12 by using methyl((3R)-6-hydroxy-2,3-dihydro-1-benzofuran-3-yl)acetate.

Example 264

Methyl 6-((2,4-dichlorobenzyl)oxy)-2,3-dihydro-1-benzofuran-3-carboxylate

A) Methyl 6-(benzyloxy)-1-benzofuran-3-carboxylate

To a mixture of 6-(benzyloxy)-1-benzofuran-3(2H)-one (66.67 g), DIPEA (43.17 g) and anhydrous DCM (1.5 L) was added dropwise Tf₂O (94.23 g) at −78° C. After stirred at −78° C. for 3 h, the reaction mixture was poured into water (1 L). The organic layer was separated and aqueous layer was extracted with DCM (500 mL). The combined extracts were washed successively with saturated aqueous NaHCO₃ (300 mL) and brine (300 mL), dried over Na$_2$SO$_4$ and concentrated under reduced pressure to give crude product (48.22 g). A mixture of the crude compound (48.22 g), TEA (32.89 g), palladium(II)acetate (2.92 g), 1,3-bis(diphenylphosphino)propane (5.36 g) in anhydrous DMF (400 mL) and absolute MeOH (800 mL) was stirred at 80° C. under carbon monooxide atmosphere (50 psi) for 22 h. After cooled to 25° C., the reaction mixture was concentrated under reduced pressure and the residue was purified by silica gel column chromatography (PE/EtOAc) to give the title compound (31.56 g).

MS (ESI+): [M+H]$^+$ 282.9.

B) Methyl 6-hydroxy-2,3-dihydro-1-benzofuran-3-carboxylate

To a mixture of methyl 6-(benzyloxy)-1-benzofuran-3-carboxylate (10 g) and MeOH (200 mL) was added 10% Pd—C (2 g). The mixture was stirred under hydrogen atmosphere overnight. The catalyst was removed by filtration. The filtrate was concentrated in vacuo to give the title compound (7.08 g).

$^1$H NMR (300 MHz, DMSO-d$_6$) δ 3.67 (3H, s), 4.30 (1H, dd, J=9.4, 6.0 Hz), 4.61 (1H, t, J=9.3 Hz), 4.68-4.77 (1H, m), 6.20 (1H, d, J=1.9 Hz), 6.28 (1H, dd, J=8.1, 2.1 Hz), 7.05 (1H, dd, J=8.1, 0.9 Hz), 9.47 (1H, brs).

C) Methyl 6-((2,4-dichlorobenzyl)oxy)-2,3-dihydro-1-benzofuran-3-carboxylate

The title compound was obtained in a same manner as the procedure in Example 5 using methyl 6-hydroxy-2,3-dihydro-1-benzofuran-3-carboxylate and 2,4-dichlorobenzyl chloride.

Example 265

6-((2,4-Dichlorobenzyl)oxy)-2,3-dihydro-1-benzofuran-3-carboxylic acid

The title compound was obtained in a same manner as the procedure in Example 12 by using the corresponding ester.

Example 266

(6-((2,4-Dichlorobenzyl)oxy)-2,3-dihydro-1-benzofuran-3-yl)(pyrrolidin-1-yl)methanone The title compound was obtained in a same manner as the procedure in Example 53 using (6-((2,4-dichlorobenzyl)oxy)-2,3-dihydro-1-benzofuran-3-yl)acetic acid and pyrrolidine.

Example 267

6-((2,4-Dichlorobenzyl)oxy)-2,3-dihydro-1-benzofuran-3-carboxamide

The title compound was obtained in a same manner as the procedure in Example 74 using (6-((2,4-dichlorobenzyl)oxy)-2,3-dihydro-1-benzofuran-3-yl)acetic acid and HOBt ammonia complex.

Example 268

(6-((2,4-Dichlorobenzyl)oxy)-2,3-dihydro-1-benzofuran-3-yl)(morpholin-4-yl)methanone The title compound was obtained in a same manner as the procedure in Example 53 using (6-((2,4-dichlorobenzyl)oxy)-2,3-dihydro-1-benzofuran-3-yl)acetic acid and morpholine.

Example 269

6-((2,4-Dichlorobenzyl)oxy)-N-methyl-2,3-dihydro-1-benzofuran-3-carboxamide

The title compound was obtained in a same manner as the procedure in Example 53 using (6-((2,4-dichlorobenzyl)oxy)-2,3-dihydro-1-benzofuran-3-yl)acetic acid and methylamine hydrochloride.

Example 270

Methyl 6-((2,4-dichlorobenzyl)oxy)-3-hydroxy-2,3-dihydro-1-benzofuran-3-carboxylate To a mixture of methyl 6-((2,4-dichlorobenzyl)oxy)-2,3-dihydro-1-benzofuran-3-carboxylate (120 mg) in DMF (dry) (3.4 mL) was added sodium hydride (15.0 mg) at 0° C. After stirring for 30 min, to the mixture was added paraformaldehyde (20.4 mg) at 0° C. The mixture was stirred at room temperature under nitrogen atmosphere for 2 h. The mixture was quenched with saturated aqueous NH$_4$Cl at 0° C. and extracted with EtOAc. The organic layer was separated, washed successively with water and brine, dried over MgSO$_4$ and concentrated in vacuo. The residue was purified by silica gel column chromatography (EtOAc/hexane) to give the title compound (12.4 mg).

Example 271

6-((2,4-Dichlorobenzyl)oxy)-N-(methylsulfonyl)-2,3-dihydro-1-benzofuran-3-carboxamide To a mixture of 6-((2,4-dichlorobenzyl)oxy)-2,3-dihydro-1-benzofuran-3-carboxylic acid (120 mg) in DMF (dry) (3.5 mL) were added methanesulfonamide (101 mg), EDCI (203 mg) and DMAP (130 mg). The mixture was stirred at room temperature overnight.

The mixture was quenched with 1N HCl at 0° C. and the solid was collected by filtration. The solid was washed with EtOAc and hexane to give the title compound (111.3 mg).

Example 272

2-((3S)-6-((2,4-Dichlorobenzyl)oxy)-2,3-dihydro-1-benzofuran-3-yl)-N-methylacetamide The title compound was obtained in a same manner as the procedure in Example 53 using ((3S)-6-((2,4-dichlorobenzyl)oxy)-2,3-dihydro-1-benzofuran-3-yl)acetic acid and methylamine hydrochloride.

Example 273

2-((3S)-6-((2,4-Dichlorobenzyl)oxy)-2,3-dihydro-1-benzofuran-3-yl)-1-(pyrrolidin-1-yl)ethanone The title compound was obtained in a same manner as the procedure in Example 53 using ((3S)-6-((2,4-dichlorobenzyl)oxy)-2,3-dihydro-1-benzofuran-3-yl)acetic acid and pyrrolidine.

Example 274

2-((3S)-6-((2,4-Dichlorobenzyl)oxy)-2,3-dihydro-1-benzofuran-3-yl)acetamide

The title compound was obtained in a same manner as the procedure in Example 74 using ((3S)-6-((2,4-dichlorobenzyl)oxy)-2,3-dihydro-1-benzofuran-3-yl)acetic acid and HOBt ammonia complex.

Example 275

Methyl 6-((2,4-dichlorobenzyl)oxy)-3-methyl-2,3-dihydro-1-benzofuran-3-carboxylate To a mixture of methyl 6-((2,4-dichlorobenzyl)oxy)-2,3-dihydro-1-benzofuran-3-carboxylate (150 mg) in DMF (dry) (3.0 mL) was added sodium hydride (18.7 mg) at 0° C. After 30 min, to the mixture was added iodomethane (0.034 mL) at 0° C. The mixture was allowed to room temperature and stirred at room temperature overnight. The mixture was quenched with water at 0° C. and extracted with EtOAc. The combined organic layer was washed successively with water and brine, dried over MgSO$_4$, filtered and concentrated in vacuo. The residue was purified by silica gel column chromatography (EtOAc/hexane) to give the title compound (103.8 mg).

MS (ESI−): [M−H]$^-$ 364.9.

Example 276

6-((2,4-Dichlorobenzyl)oxy)-3-methyl-2,3-dihydro-1-benzofuran-3-carboxylic acid

The title compound was obtained in a same manner as the procedure in Example 2 by using the corresponding ester.

Example 277

1-(6-((2,4-Dichlorobenzyl)oxy)-2,3-dihydro-1-benzofuran-3-yl)-3-ethylurea

A) 6-((2,4-Dichlorobenzyl)oxy)-N-methoxy-1-benzofuran-3(2H)-imine

To a mixture of 6-(2,4-dichlorobenzyloxy)benzofuran-3(2H)-one (2.0 g) in MeOH (20 mL) were added sodium acetate (0.531 g) and O-methylhydroxylamine hydrochloride (0.540 g). The mixture was refluxed overnight. After cooling, the mixture was concentrated. The residue was washed with water and EtOAc to give the title compound (1.24 g).

MS (ESI+): [M+H]$^+$ 338.0.

B) 6-((2,4-Dichlorobenzyl)oxy)-2,3-dihydro-1-benzofuran-3-amine

The mixture of 6-((2,4-Dichlorobenzyl)oxy)-N-methoxy-1-benzofuran-3(2H)-imine (1.23 g) and THF (dry) (36 mL) was added dropwise to a solution of borane tetrahydrofuran complex solution (1.0 mol/L, 7.27 mL) at 0° C. The mixture was stirred at 60° C. overnight. After cooling, the mixture was quenched with water and 1N NaOH (15 mL). The mixture was stirred at 60° C. for 5 h. After cooling, the mixture was extracted with EtOAc. The combined organic layer was washed with brine, dried over MgSO$_4$, and concentrated in vacuo. The solid was dissolved in EtOAc and to the solution was added 4M HCl in EtOAc dropwise. The precipitate (850 mg) was collected by filtration. The solid was dissolved in 28% aqueous ammonia and extracted with EtOAc. The combined organic layer was washed with brine, dried over MgSO$_4$, and concentrated in vacuo to give the title compound (721.3 mg).

$^1$H NMR (300 MHz, DMSO-d$_6$) δ 2.16 (1H, brs), 4.02-4.07 (1H, m), 4.43-4.51 (1H, m), 4.52-4.63 (1H, m), 5.09 (2H, s), 6.46 (1H, d, J=1.9 Hz), 6.51 (1H, dd, J=7.9, 2.3 Hz), 7.21 (1H, d, J 8.3 Hz), 7.47 (1H, dd, J=8.3, 1.9 Hz), 7.59 (1H, d, J=8.3 Hz), 7.68 (1H, d, J=1.9 Hz).

C) 1-(6-((2,4-Dichlorobenzyl)oxy)-2,3-dihydro-1-benzofuran-3-yl)-3-ethylurea

To a mixture of 6-((2,4-dichlorobenzyl)oxy)-2,3-dihydro-1-benzofuran-3-amine (146 mg) and THF (dry) (4.0 mL) was added ethyl isocyanate (0.048 mL) at 0° C. The mixture was stirred at 0° C. for 1 h. The mixture was poured into saturated aqueous NH$_4$Cl at 0° C. and extracted with EtOAc. The organic layer was m washed with brine, dried over MgSO$_4$, and concentrated in vacuo. The solid was washed with EtOH to give the title compound (74.0 mg).

Example 278

Methyl 6-((2,4-dichlorobenzyl)oxy)-3-(hydroxymethyl)-2,3-dihydro-1-benzofuran-3-carboxylate To a mixture of methyl 6-((2,4-dichlorobenzyl)oxy)-2,3-dihydro-1-benzofuran-3-carboxylate (400 mg) and DMSO (11 mL) were added paraformaldehyde (37.4 mg) and sodium methoxide (6.8 mg). The mixture was stirred at room temperature for 2 h. The mixture was quenched with water and 1N HCl at 0° C. and extracted with EtOAc. The organic layer was separated, washed successively with water and brine, dried over MgSO$_4$ and concentrated in vacuo. The residue was purified by silica gel column chromatography (EtOAc/hexane) to give the title compound (332.6 mg).

Example 279

6-((2,4-Dichlorobenzyl)oxy)-3-(hydroxymethyl)-2,3-dihydro-1-benzofuran-3-carboxylic acid The title compound was obtained in a same manner as the procedure in Example 2 by using the corresponding ester.

Example 280

Methyl 6-((2,4-dichlorobenzyl)oxy)-3-(methoxymethyl)-2,3-dihydro-1-benzofuran-3-carboxylate To a mixture of methyl 6-((2,4-dichlorobenzyl)oxy)-3-(hydroxymethyl)-2,3-dihydro-1-benzofuran-3-carboxylate (89 mg) in toluene (2.0 mL) were added silver(I)oxide (135 mg) and iodomethane (0.217 mL). The mixture was stirred at 70° C. for 2 d. After cooling, the residue was purified by silica gel column chromatography (EtOAc/hexane) to give the title compound (65.8 mg).

Example 281

6-((2,4-Dichlorobenzyl)oxy)-3-(methoxymethyl)-2,3-dihydro-1-benzofuran-3-carboxylic acid The title compound was obtained in a same manner as the procedure in Example 2 by using the corresponding ester.

Example 282

Ethyl N-((6-((2,4-dichlorobenzyl)oxy)-2,3-dihydro-1-benzofuran-3-yl)carbonyl)glycinate The title compound was obtained in a same manner as the procedure in Example 53 using (6-((2,4-dichlorobenzyl)oxy)-2,3-dihydro-1-benzofuran-3-yl)acetic acid and ethyl glycinate hydrochloride.

Example 283

N-((6-((2,4-Dichlorobenzyl)oxy)-2,3-dihydro-1-benzofuran-3-yl)carbonyl)glycine

The title compound was obtained in a same manner as the procedure in Example 2 by using the corresponding ester.

Example 284

Methyl 2-(6-((2,4-dichlorobenzyl)oxy)-2,3-dihydro-1-benzofuran-3-yl)-3-hydroxypropanoate A) Methyl 3-hydroxy-2-(6-((4-methoxybenzyl)oxy)-1-benzofuran-3-yl)propanoate The title compound was obtained in a same manner as the procedure in Example 278 by using methyl(6-((4-methoxybenzyl)oxy)-1-benzofuran-3-yl)acetate.
MS (ESI+): [M+H]$^+$ 357.3.

B) Methyl 3-hydroxy-2-(6-hydroxy-2,3-dihydro-1-benzofuran-3-yl)propanoate

To a mixture of methyl 3-hydroxy-2-(6-((4-methoxybenzyl)oxy)-1-benzofuran-3-yl)propanoate (86.9 mg) and MeOH (2.4 mL) was added 10% palladium on carbon (15 mg). The mixture was hydrogenated under balloon pressure for 21 h. The catalyst was removed by filtration and concentrated to give the title compound (56.0 mg).
MS (ESI+): [M+H]$^+$ 238.7.

C) Methyl 2-(6-((2,4-dichlorobenzyl)oxy)-2,3-dihydro-1-benzofuran-3-yl)-3-hydroxypropanoate The title compound was obtained in a same manner as the procedure in Example 5 using methyl 3-hydroxy-2-(6-hydroxy-2,3-dihydro-1-benzofuran-3-yl)propanoate and 2,4-dichlorobenzyl chloride.

Example 285

2-(6-((2,4-Dichlorobenzyl)oxy)-2,3-dihydro-1-benzofuran-3-yl)-3-hydroxypropanoic acid The title compound was obtained in a same manner as the procedure in Example 2 by using the corresponding ester.

Example 286

Ethyl N-(6-((2,4-dichlorobenzyl)oxy)-2,3-dihydro-1-benzofuran-3-yl)glycinate

The mixture of 6-((2,4-dichlorobenzyl)oxy)-2,3-dihydro-1-benzofuran-3-amine (127.3 mg) and THF (4.0 mL) were added TEA (0.172 mL) and ethyl 2-bromoacetate (0.055 mL) at 0° C. The mixture was stirred at room temperature for 4 h. The mixture was quenched with water and extracted with EtOAc. The combined organic layer was washed with brine, dried over MgSO$_4$, and concentrated in vacuo. The residue was purified by silica gel column chromatography (EtOAc/hexane) to give the title compound (32.0 mg).

Example 287

N-(6-((2,4-Dichlorobenzyl)oxy)-2,3-dihydro-1-benzofuran-3-yl)glycine

The title compound was obtained in a same manner as the procedure in Example 2 by using the corresponding ester.

Example 288

Methyl(6-((2,6-dimethylpyridin-3-yl)methoxy)-4,7-dimethyl-2,3-dihydro-1-benzofuran-3-yl)acetate A) Methyl(6-hydroxy-4,7-dimethyl-2,3-dihydro-1-benzofuran-3-yl)acetate The title compound was obtained in a same manner as the procedure in the step B of Example 284 by using methyl(6-hydroxy-4,7-dimethyl-1-benzofuran-3-yl)acetate.
MS (ESI+): [M+H]$^+$ 237.1.

B) Methyl(6-((2,6-dimethylpyridin-3-yl)methoxy)-4,7-dimethyl-2,3-dihydro-1-benzofuran-3-yl)acetate The title compound was obtained in a same manner as the procedure in Example 3 using methyl(6-hydroxy-4,7-dimethyl-2,3-dihydro-1-benzofuran-3-yl)acetate and (2,6-dimethylpyridin-3-yl)methanol.

Example 289

(6-((2,6-Dimethylpyridin-3-yl)methoxy)-4,7-dimethyl-2,3-dihydro-1-benzofuran-3-yl)acetic acid The title compound was obtained in a same manner as the procedure in Example 12 by using the corresponding ester.

Example 290

Methyl(6-((2,4-dichlorobenzyl)oxy)-4,7-dimethyl-2,3-dihydro-1-benzofuran-3-yl)acetate The title compound was obtained in a same manner as the procedure in Example 5 using methyl(6-hydroxy-4,7-dimethyl-2,3-dihydro-1-benzofuran-3-yl)acetate and 2,4-dichlorobenzyl chloride.

Example 291

(6-((2,4-Dichlorobenzyl)oxy)-4,7-dimethyl-2,3-dihydro-1-benzofuran-3-yl)acetic acid The title compound was obtained in a same manner as the procedure in Example 12 by using the corresponding ester.

Example 292

Methyl 6-((2,4-dichlorobenzyl)sulfanyl)-3-(2-ethoxy-2-oxoethoxy)thieno[2,3-b]pyridine-2-carboxylate A) Methyl 3-(2-ethoxy-2-oxoethoxy)thieno[2,3-b]pyridine-2-carboxylate 7-oxide To a mixture of methyl 3-(2-ethoxy-2-oxoethoxy)thieno[2,3-b]pyridine-2-carboxylate (500 mg), urea hydrogen peroxide (239 mg) and CH$_3$CN (8 mL) was added TFAA (0.353 mL) at room temperature. The mixture was stirred at room temperature for 4 h and at 70° C. overnight. To the mixture were added urea hydrogen peroxide (80 mg) and TFAA (0.118 mL). The mixture was stirred at 70° C. for 2 h. After cooling, to the mixture was added saturated aqueous NaHCO$_3$. The resulting precipitate was collected by filtration to give the title compound (246 mg). The filtrate was concentrated. The residue was extracted with EtOAc. The combined organic layer was washed with brine, dried over MgSO$_4$ and concentrated in vacuo to give the title compound (85.1 mg). Total yield: 331 mg.
MS (ESI+): [M+H]$^+$ 312.2.

B) Methyl 6-chloro-3-(2-ethoxy-2-oxoethoxy)thieno[2,3-b]pyridine-2-carboxylate

To a mixture of methyl 3-(2-ethoxy-2-oxoethoxy)thieno[2,3-b]pyridine-2-carboxylate 7-oxide (245.4 mg) and toluene (7.9 mL) was added phosphoryl chloride (0.367 mL). The mixture was stirred at 80° C. for 3 h. After cooling, the mixture was concentrated. The residue was neutralized with saturated aqueous NaHCO$_3$ and extracted with EtOAc. The organic layer was washed with brine, dried over MgSO$_4$, and concentrated in vacuo. The residue was purified by silica gel column chromatography (EtOAc/hexane) to give the title compound (147 mg).
MS (ESI+): [M+H]$^+$ 329.9.

C) Methyl 6-((2,4-dichlorobenzyl)sulfanyl)-3-(2-ethoxy-2-oxoethoxy)thieno[2,3-b]pyridine-2-carboxylate To a mixture of methyl 6-chloro-3-(2-ethoxy-2-oxoethoxy)thieno[2,3-b]pyridine-2-carboxylate (126.4 mg) and DMSO (3.8 mL) were added K$_2$CO$_3$ (63.6 mg) and 2,4-dichlorobenzyl mercaptan (0.065 mL). The mixture was stirred at 80° C. for 3 h. The mixture was quenched with saturated aqueous NaHCO$_3$ and extracted with EtOAc. The combined organic layer was washed successively with water and brine, dried over MgSO$_4$, and concentrated in vacuo. The residue was purified by silica gel column chromatography (EtOAc/hexane) to give the title compound (73.9 mg).

Example 293

3-(Carboxymethoxy)-6-((2,4-dichlorobenzyl)sulfanyl)thieno[2,3-b]pyridine-2-carboxylic acid The title compound was obtained in a same manner as the procedure in Example 12 by using methyl 6-((2,4-dichlorobenzyl)sulfanyl)-3-(2-ethoxy-2-oxoethoxy)thieno[2,3-b]pyridine-2-carboxylate.

Example 294

((6-((2,4-Dichlorobenzyl)sulfanyl)thieno[2,3-b]pyridin-3-yl)oxy)acetic acid

The title compound was obtained in a same manner as the procedure in Example 64 by using 3-(carboxymethoxy)-6-((2,4-dichlorobenzyl)sulfanyl)thieno[2,3-b]pyridine-2-carboxylic acid.

Example 295

Methyl 6-((2,4-dichlorobenzyl)oxy)-3-(2-ethoxy-2-oxoethoxy)thieno[2,3-b]pyridine-2-carboxylate A) Methyl 3-(2-ethoxy-2-oxoethoxy)-6-hydroxythieno[2,3-b]pyridine-2-carboxylate To a mixture of methyl 3-(2-ethoxy-2-oxoethoxy)thieno[2,3-b]pyridine-2-carboxylate 7-oxide (500 mg) and DMF (8 mL) was added TFAA (2.233 mL) at 0° C. The mixture was stirred at room temperature for 4 h. After evaporation of TFAA, the residue was added to water at 0° C., and the resulting precipitate was collected by filtration, washed with hexane to give the title compound (418.5 mg).
MS (ESI+): [M+H]$^+$ 312.1.

B) Methyl 6-((2,4-dichlorobenzyl)oxy)-3-(2-ethoxy-2-oxoethoxy)thieno[2,3-b]pyridine-2-carboxylate The title compound was obtained in a same manner as the procedure in Example 5 using methyl 3-(2-ethoxy-2-oxoethoxy)-6-hydroxythieno[2,3-b]pyridine-2-carboxylate and 2,4-dichlorobenzyl chloride.

Example 296

3-(Carboxymethoxy)-6-((2,4-dichlorobenzyl)oxy)thieno[2,3-b]pyridine-2-carboxylic acid The title compound was obtained in a same manner as the procedure in Example 12 by using methyl 6-((2,4-dichlorobenzyl)oxy)-3-(2-ethoxy-2-oxoethoxy)thieno[2,3-b]pyridine-2-carboxylate.

Example 297

((6-((2,4-Dichlorobenzyl)oxy)thieno[2,3-b]pyridin-3-yl)oxy)acetic acid

The title compound was obtained in a same manner as the procedure in Example 64 by using 3-(carboxymethoxy)-6-((2,4-dichlorobenzyl)oxy)thieno[2,3-b]pyridine-2-carboxylic acid.

Example 298

Methyl(4-cyano-6-((2,4-dichlorobenzyl)oxy)-1-benzothiophen-3-yl)acetate

A) Methyl(4-cyano-6-((triisopropylsilyl)oxy)-1-benzothiophen-3-yl)acetate

To a mixture of methyl(4-(((trifluoromethyl)sulfonyl)oxy)-6-((triisopropylsilyl)oxy)-1-benzothiophen-3-yl)acetate (5.8 g) and DMF (dry) (80 mL) were added zinc cyanide (2.095 mL) and Pd(Ph$_3$P)$_4$ (1.273 g) at room temperature, and the mixture was stirred at 100° C. for 20 h. The mixture was cooled to room temperature. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (1.920 g).

$^1$H NMR (300 MHz, CDCl$_3$) δ1.09-1.13 (18H, m), 1.23-1.32 (3H, m), 3.77 (3H, s), 4.16 (2H, s), 7.29 (1H, d, J=2.3 Hz), 7.32 (1H, s), 7.53 (1H, d, J=2.3 Hz).

B) Methyl(4-cyano-6-hydroxy-1-benzothiophen-3-yl)acetate

To a mixture of methyl(4-cyano-6-((triisopropylsilyl)oxy)-1-benzothiophen-3-yl)acetate (1.92 g) and EtOH (30 mL) was added potassium fluoride dihydrate (0.448 g) at room temperature, and the mixture was refluxed for 30 min. The mixture was concentrated under reduced pressure. The residue was poured into water at room temperature and extracted with EtOAc. The organic layer was separated, washed successively with 0.1N HCl and brine, dried over MgSO$_4$ and concentrated in vacuo. The residue was crystallized from EtOAc-hexane to give the title compound (0.935 g).

MS (ESI–): [M–H]$^-$ 245.9.

C) Methyl(4-cyano-6-((2,4-dichlorobenzyl)oxy)-1-benzothiophen-3-yl)acetate

The title compound was obtained in a same manner as the procedure in Example 5 using methyl(4-cyano-6-hydroxy-1-benzothiophen-3-yl)acetate and 2,4-dichlorobenzyl chloride.

Example 299

(4-Cyano-6-((2,4-dichlorobenzyl)oxy)-1-benzothiophen-3-yl)acetic acid

The title compound was obtained in a same manner as the procedure in Example 12 by using the corresponding ester.

Example 300

Methyl(6-((2-chloro-4-fluorobenzyl)oxy)-4-cyano-1-benzothiophen-3-yl)acetate

The title compound was obtained in a same manner as the procedure in Example 5 using methyl(4-cyano-6-hydroxy-1-benzothiophen-3-yl)acetate and 2-chloro-4-fluorobenzyl chloride.

$^1$H NMR (300 MHz, DMSO-d$_6$) δ 3.65 (3H, s), 4.04-4.20 (2H, m), 5.27 (2H, s), 7.30 (1H, td, J=8.5, 2.6 Hz), 7.55 (1H, dd, J=8.9, 2.6 Hz), 7.66-7.76 (3H, m), 8.16 (1H, d, J=2.5 Hz).

Example 301

(6-((2-Chloro-4-fluorobenzyl)oxy)-4-cyano-1-benzothiophen-3-yl)acetic acid

The title compound was obtained in a same manner as the procedure in Example 12 by using the corresponding ester.

Example 302

Methyl(4-fluoro-6-((1-methyl-3-(trifluoromethyl)-1H-pyrazol-5-yl)methoxy)-1-benzothiophen-3-yl)acetate A) 1-Fluoro-3-methoxy-5-((4-methoxybenzyl)sulfanyl)benzene To a mixture of 1-bromo-3-fluoro-5-methoxybenzene (5 g), (4-methoxyphenyl)methanethiol (3.76 g), and toluene (100 mL) were added Pd$_2$(dba)$_3$ (0.447 g), 4,5-bis(diphenylphosphino)-9,9-dimethylxanthene (0.564 g) and DIPEA (8.52 mL). The mixture was stirred at room temperature overnight. The mixture was poured into water and extracted with EtOAc. The organic layer was separated, washed successively with water and brine, dried over MgSO$_4$ and concentrated in vacuo. The residue was purified by silica gel column chromatography (EtOAc/hexane) to give the title compound (6.20 g).

MS (ESI–): [M–H]$^-$ 277.1.

B) 3-Fluoro-5-methoxybenzenethiol

A mixture of anisole (12.04 g), 1-fluoro-3-methoxy-5-((4-methoxybenzyl)sulfanyl)benzene (6.2 g) and TFA (20 mL) was refluxed for 1 h, then concentrated in vacuo. Water was added to the residue and the mixture was extracted with EtOAc. The organic layer was washed with saturated aqueous NaHCO$_3$ and extracted with 2N NaOH (100 mL×3). The water layer was acidified with 6N HCl and extracted with EtOAc. The EtOAc extract was washed successively with water and brine, dried over MgSO$_4$, and concentrated in vacuo to give the title compound (2.30 g).

$^1$H NMR (300 MHz, CDCl$_3$) δ 3.51 (1H, s), 3.76 (3H, s), 6.41 (1H, dt, J=10.58, 2.27 Hz), 6.54-6.62 (2H, m).

C) Methyl 4-((3-fluoro-5-methoxyphenyl)sulfanyl)-3-oxobutanoate

A mixture of methyl 4-chloroacetoacetate (1.871 mL), K$_2$OC$_3$ (2.210 g), 3-fluoro-5-methoxybenzenethiol (2.3 g) and DMF (30 mL) was stirred at room temperature for 1 h. The mixture was poured into water and extracted with EtOAc. The organic layer was separated, washed successively with water and brine, dried over MgSO$_4$ and concentrated in vacuo. The residue was purified by silica gel column chromatography (EtOAc/hexane) to give the title compound (2.87 g).

MS (ESI–): [M–H]$^-$ 271.1.

D) Methyl(4-fluoro-6-methoxy-1-benzothiophen-3-yl)acetate

MsOH (13.68 mL) was added dropwise to methyl 4-((3-fluoro-5-methoxyphenyl)sulfanyl)-3-oxobutanoate (2.87 g) at 0° C. The mixture was stirred at 0° C. for 30 min. The mixture was poured into iced water and extracted with EtOAc. The organic layer was separated, washed successively with water, saturated aqueous NaHCO$_3$ and brine, dried over MgSO$_4$ and concentrated in vacuo. The residue was purified by silica gel column chromatography (EtOAc/hexane) to give the title compound (900 mg).

$^1$H NMR (300 MHz, DMSO-d$_6$) δ 3.63 (3H, s), 3.82 (3H, s), 3.95 (2H, s), 6.84 (1H, dd, J=13.25, 2.27 Hz), 7.38 (1H, s), 7.42 (1H, d, J=1.89 Hz).

E) Methyl(4-fluoro-6-hydroxy-1-benzothiophen-3-yl)acetate

To a suspension of aluminum chloride (713 mg) in toluene (10 mL) was added dodecane-1-thiol (4.00 mL) at 0° C. After stirring at 0° C. for 30 min, a solution of methyl(4-fluoro-6-methoxy-1-benzothiophen-3-yl)acetate (850 mg) in toluene (10 mL) was added dropwise to the mixture. The mixture was stirred at room temperature for 45 h. To the mixture was added aluminum chloride (713 mg) again, and the mixture was stirred at room temperature for 4 h. The mixture was poured into ice water. To the mixture was added 6N HCl, and the mixture was extracted with EtOAc. The EtOAc extract was washed successively with 1N HCl and brine, dried over $MgSO_4$, and concentrated in vacuo. A mixture of the residue, conc. $H_2SO_4$ (0.5 mL) and MeOH (50 mL) was stirred at 75° C. for 4 h then concentrated in vacuo. To the residue was added saturated aqueous $NaHCO_3$ and the mixture was extracted with EtOAc. The EtOAc extract was washed with brine, dried over $MgSO_4$, and concentrated in vacuo. The residual crystals were washed with toluene and IPE to give the title compound (330 mg). The mother liquid was concentrated in vacuo. The residue was purified by silica gel column chromatography (EtOAc/hexane) to give the title compound (180 mg). Total yield, 510 mg. The crystals were recrystallized from acetone-hexane.

MS (ESI−): [M−H]− 239.0.

F) Methyl(4-fluoro-6-((1-methyl-3-(trifluoromethyl)-1H-pyrazol-5-yl)methoxy)-1-benzothiophen-3-yl)acetate To a mixture of tri-n-butylphosphine (0.793 mL), (1-methyl-3-(trifluoromethyl)-1H-pyrazol-5-yl)methanol (187 mg), methyl(4-fluoro-6-hydroxy-1-benzothiophen-3-yl)acetate (250 mg) and THF (dry) (15 mL) was added ADDP (801 mg) at room temperature. The mixture was stirred at room temperature for 2 h and then concentrated in vacuo. To the residue was added IPE and the insoluble materials were removed by filtration. The filtrate was concentrated in vacuo. The residue was purified by silica gel column chromatography (NH, EtOAc/hexane) and silica gel column chrothatography (EtOAc/hexane) to give the title compound (310 mg). The crystals were recrystallized from acetone-hexane.

$^1$H NMR (300 MHz, $CDCl_3$) δ 3.73 (3H, s), 3.96 (2H, s), 3.98 (3H, s), 5.08 (2H, s), 6.61 (1H, s), 6.72 (1H, dd, J=12.42, 2.12 Hz), 7.12 (1H, s), 7.17 (1H, d, J=2.08 Hz).

Example 303

(4-Fluoro-6-((1-methyl-3-(trifluoromethyl)-1H-pyrazol-5-yl)methoxy)-1-benzothiophen-3-yl)acetic acid A mixture of methyl(4-fluoro-6-((1-methyl-3-(trifluoromethyl)-1H-pyrazol-5-yl)methoxy)-1-benzothiophen-3-yl)acetate (220 mg), 1N NaOH (2 mL), THF (2 mL) and MeOH (2 mL) was stirred at room temperature for 1.5 h. To the mixture were added 1N HCl (2 mL) and water. The mixture was extracted with EtOAc. The organic layer was separated, washed with brine, dried over $MgSO_4$ and concentrated in vacuo. The residual solid was washed with hexane to give the title compound (180 mg). The crystals were crystallized from acetone-hexane.

$^1$H NMR (300 MHz, DMSO-$d_6$) δ 3.86 (2H, s), 3.95 (3H, s), 5.31 (2H, s), 6.90 (1H, s), 6.98 (1H, dd, J=12.98, 2.03 Hz), 7.39 (1H, s), 7.58 (1H, d, J=2.08 Hz), 12.36 (1H, s).

Example 304

Methyl(4-fluoro-6-((2-methyl-6-(trifluoromethyl)pyridin-3-yl)methoxy)-1-benzothiophen-3-yl)acetate To a mixture of tri-n-butylphosphine (0.655 mL), (2-methyl-6-(trifluoromethyl)pyridin-3-yl)methanol (167 mg), methyl(4-fluoro-6-hydroxy-1-benzothiophen-3-yl)acetate (210 mg) and THF (dry) (15 mL) was added ADDP (662 mg, 2.62 mmol) at room temperature. The mixture was stirred at room temperature for 2 h and then concentrated in vacuo. To the residue was added IPE and the insoluble materials were removed by filtration. The filtrate was concentrated in vacuo. The residue was purified by silica gel column chromatography (NH, EtOAc/hexane) and silica gel column chromatography (EtOAc/hexane) to give the title compound (310 mg). The crystals were recrystallized from acetone-hexane.

$^1$H NMR (300 MHz, DMSO-$d_6$) δ 2.61 (3H, s), 3.63 (3H, s), 3.97 (2H, s), 5.34 (2H, s), 7.03 (1H, dd, J=13.03, 2.08 Hz), 7.42 (1H, s), 7.61 (1H, d, J=2.08 Hz), 7.77 (1H, d, J=7.93 Hz), 8.08 (1H, d, J=7.93 Hz).

Example 305

(4-Fluoro-6-((2-methyl-6-(trifluoromethyl)pyridin-3-yl)methoxy)-1-benzothiophen-3-yl)acetic acid A mixture of methyl(4-fluoro-6-((2-methyl-6-(trifluoromethyl)pyridin-3-yl)methoxy)-1-benzothiophen-3-yl)acetate (240 mg), 1N NaOH (2 mL), THF (2 mL) and MeOH (2 mL) was stirred at room temperature for 1.5 h. To the mixture were added 1N HCl (2 mL) and water. The mixture was extracted with EtOAc. The organic layer was separated, washed with brine, dried over $MgSO_4$ and concentrated in vacuo. The residual solid was washed with hexane to give the title compound (210 mg). The crystals were crystallized from acetone-hexane.

$^1$H NMR (300 MHz, DMSO-$d_6$) δ 2.61 (3H, s), 3.86 (2H, s), 5.34 (2H, s), 7.02 (1H, dd, J=13.03, 2.08 Hz), 7.38 (1H, s), 7.60 (1H, d, J=2.08 Hz), 7.77 (1H, d, J=7.93 Hz), 8.08 (1H, d, J=7.93 Hz), 12.38 (1H, brs).

Example 306

Methyl(4-chloro-2-methyl-6-((1-methyl-3-(trifluoromethyl)-1H-pyrazol-5-yl)methoxy)-1-benzothiophen-3-yl)acetate

A) Methyl 4-((3-chloro-5-methoxyphenyl)sulfanyl)-3-oxopentanoate

A mixture of 3-chloro-5-methoxybenzenethiol (1.90 g), methyl 4-bromo-3-oxopentanoate (2.50 g) and $K_2CO_3$ (1.80 g) in DMF (dry) (36.3 mL) was stirred at room temperature overnight. The reaction was quenched with $H_2O$ and diluted with EtOAc. The organic layer was separated, washed successively with water and brine, dried over $MgSO_4$, and concentrated in vacuo. The residue was purified by silica gel column chromatography (EtOAc/hexane) to give the title compound (2.09 g).

$^1$H NMR (300 MHz, $CDCl_3$) δ 1.45 (3H, d, J=7.0 Hz), 3.71 (2H, d, J=1.1 Hz), 3.73 (3H, s), 3.79 (3H, s), 3.92 (1H, q, J=7.1 Hz), 6.80-6.84 (2H, m), 6.97 (1H, t, J=1.7 Hz).

B) Methyl(4-chloro-6-methoxy-2-methyl-1-benzothiophen-3-yl)acetate

To methyl 4-((3-chloro-5-methoxyphenyl)sulfanyl)-3-oxopentanoate (1.86 g) was added methanesulfonic acid (5.98 mL) at 0° C. The mixture was stirred at 0° C. under nitrogen atmosphere for 15 min. The mixture was poured into water and extracted with EtOAc. The organic layer was washed with brine, dried over MgSO$_4$, and concentrated in vacuo. The residue was purified by silica gel column chromatography (EtOAc/hexane) to give the title compound (1.01 g).

MS (ESI+): [M+H]$^+$ 285.0.

C) Methyl(4-chloro-6-hydroxy-2-methyl-1-benzothiophen-3-yl)acetate

To a solution of 1-dodecanethiol (3.38 mL) in toluene (5.0 mL) was added aluminum chloride (627 mg) at 0° C. After being stirred at 0° C. for 50 min, to the solution was added a mixture of methyl(4-chloro-6-methoxy-2-methyl-1-benzothiophen-3-yl)acetate (670 mg) in toluene (10 mL) at 0° C. The mixture was stirred at 80° C. for 14 h. To the suspension was added aluminum chloride (627 mg) again. The mixture was stirred at 80° C. for 5 h. The mixture was quenched with water and 1N HCl, and extracted with EtOAc. The organic layer was washed with brine, dried over MgSO$_4$, and concentrated in vacuo. The residue was dissolved in MeOH (2.0 mL), and to the solution was added conc.H$_2$SO$_4$ (0.025 mL). The mixture was stirred at 80° C. for 2 h. The mixture was concentrated and the residue was neutralized with saturated aqueous NaHCO$_3$ and extracted with EtOAc. The combined organic layer was washed with brine, dried over MgSO$_4$, and concentrated in vacuo. The solid was washed with hexane to give the title compound (557.8 mg).

MS (ESI+): [M+H]$^+$ 271.0.

D) Methyl(4-chloro-2-methyl-6-((1-methyl-3-(trifluoromethyl)-1H-pyrazol-5-yl)methoxy)-1-benzothiophen-3-yl)acetate To a mixture of tri-n-butylphosphine (0.415 mL), methyl (4-chloro-6-hydroxy-2-methyl-1-benzothiophen-3-yl)acetate (150 mg) and (1-methyl-3-(trifluoromethyl)-1H-pyrazol-5-yl)methanol (105 mg) in THF (4.0 mL) was added ADDP (419 mg) at room temperature. The mixture was stirred at room temperature under nitrogen atmosphere for 1 h. The mixture was concentrated. To the residue was added IPE and the precipitate was filtered off and the filtrate was concentrated in vacuo. The residue was purified by silica gel column chromatography (NH, EtOAc/hexane) and silica gel column chromatography (EtOAc/hexane) to give the title compound (218 mg) as a colorless solid. The solid was crystallized from EtOAc-hexane.

$^1$H NMR (300 MHz, CDCl$_3$) δ 2.46 (3H, s), 3.72 (3H, s), 3.98 (3H, d, J=0.4 Hz), 4.08 (2H, s), 5.06 (2H, s), 6.59 (1H, s), 7.00 (1H, d, J=2.3 Hz), 7.21 (1H, d, J=2.3 Hz).

Example 307

(4-Chloro-2-methyl-6-((1-methyl-3-(trifluoromethyl)-1H-pyrazol-5-yl)methoxy)-1-benzothiophen-3-yl)acetic acid To a mixture of methyl(4-chloro-2-methyl-6-((1-methyl-3-(trifluoromethyl)-1H-pyrazol-5-yl)methoxy)-1-benzothiophen-3-yl)acetate (184.5 mg), THF (dry) (2.0 mL) and MeOH (2.0 mL) was added 1N NaOH (1.28 mL). The mixture was stirred at room temperature for 2 h and at 50° C. for 1 h. The mixture was neutralized with 1N HCl. The generated precipitate was collected by filtration to give a colorless solid. The solid was crystallized from EtOAc-hexane to give the title compound (161 mg).

$^1$H NMR (300 MHz, DMSO-d$_6$) δ 2.41 (3H, s), 3.94 (3H, s), 3.96 (2H, s), 5.30 (2H, s), 6.89 (1H, s), 7.15 (1H, d, J=2.3 Hz), 7.67 (1H, d, J=2.3 Hz).

Example 308

Methyl(4-chloro-2-methyl-6-((2-methyl-6-(trifluoromethyl)pyridin-3-yl)methoxy)-1-benzothiophen-3-yl)acetate To a mixture of tri-n-butylphosphine (0.418 mL), methyl (4-chloro-6-hydroxy-2-methyl-1-benzothiophen-3-yl)acetate (151.2 mg) and (2-methyl-6-(trifluoromethyl)pyridin-3-yl)methanol (112 mg) and THF (5.0 mL) was added ADDP (423 mg) at room temperature. The mixture was stirred at room temperature under nitrogen atmosphere for 1 h. The mixture was concentrated. To the residue was added IPE and the precipitate was filtered off and the filtrate was concentrated in vacuo. The residue was purified by silica gel column chromatography (EtOAc/hexane) to give the title compound (165 mg). The solid was crystallized from EtOAc-hexane.

$^1$H NMR (300 MHz, CDCl$_3$) δ 2.45 (3H, s), 2.66 (3H, s), 3.72 (3H, s), 4.08 (2H, s), 5.12 (2H, s), 7.04 (1H, d, J=2.3 Hz), 7.21 (1H, d, J=2.5 Hz), 7.56 (1H, d, J=7.9 Hz), 7.92 (1H, d, J=7.6 Hz).

Example 309

(4-Chloro-2-methyl-6-((2-methyl-6-(trifluoromethyl)pyridin-3-yl)methoxy)-1-benzothiophen-3-yl)acetic acid To a mixture of methyl(4-chloro-2-methyl-6-((2-methyl-6-(trifluoromethyl)pyridin-3-yl)methoxy)-1-benzothiophen-3-yl)acetate (132.1 mg), THF (dry) (1.5 mL) and MeOH (1.5 mL) was added 1N NaOH (0.893 mL) at room temperature. The mixture was stirred at 50° C. for 2 h. The mixture was neutralized with 1N HCl. The resulting precipitate was collected by filtration to give a colorless solid. The solid was crystallized from acetone-hexane to give the title compound (87 mg).

$^1$H NMR (300 MHz, DMSO-d$_6$) δ 2.41 (3H, s), 2.61 (3H, s), 3.97 (2H, s), 5.33 (2H, s), 7.20 (1H, d, J=2.3 Hz), 7.68 (1H, d, J=2.5 Hz), 7.76 (1H, d, J=7.9 Hz), 8.08 (1H, d, J=7.7 Hz).

Example 310

(6-((2-Chloro-4-(3-methoxypropoxy)benzyl)oxy)-2,3-dihydro-1-benzofuran-3-yl)acetic acid A) (2-Chloro-4-((triisopropylsilyl)oxy)phenyl)methanol To a mixture of methyl 2-chloro-4-hydroxybenzoate (4.43 g) and 2,6-lutidine (6.64 mL) in DCM (50 mL) cooled with an ice bath was added triisopropylsilyl trifluoromethanesulfonate (7.66 mL). After being stirred at 0° C. for 1 h, saturated aqueous NaHCO$_3$ was added thereto. The mixture was diluted with Et$_2$O and layers were separated. The aqueous layer was extracted with Et$_2$O. The combined organic layer was washed with brine, dried over MgSO$_4$ and concentrated. The residue was purified by silica gel column chromatography (EtOAc/hexane). The product was dissolved in diethyl ether (175 mL). To the solution cooled with an ice bath was added lithium aluminum hydride (1.08 g). After being stirred at 0° C. for 30 min, sodium sulfate decahydrate was added thereto. The mixture was filtered through a pad of celite. The filtrate was concentrated. The residue was purified by silica gel column chromatography (EtOAc/hexane) to give the title compound (6.87 g).

$^1$H NMR (300 MHz, CDCl$_3$) δ 1.06-1.13 (18H, m), 1.18-1.32 (3H, m), 1.85 (1H, t, J=6.2 Hz), 4.70 (2H, d, J=6.4 Hz), 6.78 (1H, dd, J=8.3, 2.7 Hz), 6.91 (1H, d, J=2.3 Hz), 7.28 (1H, d, J=8.3 Hz).

B) Methyl 2-(6-((2-chloro-4-((triisopropylsilyl)oxy)benzyl)oxy)-2,3-dihydro-1-benzofuran-3-yl)acetate The title compound was obtained in a same manner as the procedure in Example 3 using methyl(6-hydroxy-2,3-dihydro-1-benzofuran-3-yl)acetate and (2-chloro-4-((triisopropylsilyl)oxy)phenyl)methanol.

$^1$H NMR (300 MHz, CDCl$_3$) δ 1.05-1.14 (18H, m), 1.18-1.33 (3H, m), 2.56 (1H, dd, J=16.7, 9.5 Hz), 2.76 (1H, dd, J=16.7, 5.7 Hz), 3.72 (3H, s), 3.75-3.87 (1H, m), 4.27 (1H, dd, J=9.1, 6.1 Hz), 4.76 (1H, t, J=8.9 Hz), 5.02 (2H, s), 6.45-6.52 (2H, m), 6.78 (1H, dd, J=8.3, 2.7 Hz), 6.93 (1H, d, J=2.7 Hz), 7.03 (1H, d, J=8.0 Hz), 7.34 (1H, d, J=8.3 Hz).

C) Methyl 2-(6-((2-chloro-4-hydroxybenzyl)oxy)-2,3-dihydro-1-benzofuran-3-yl)acetate To a mixture of methyl 2-(6-((2-chloro-4-((triisopropylsilyl)oxy)benzyl)oxy)-2,3-dihydro-1-benzofuran-3-yl)acetate (5.70 g) and THF (50 mL) cooled with an ice bath was added tetrabutylammonium fluoride (1.0 M THF solution, 14.1 mL). After being stirred for 20 min, the mixture was diluted with brine and EtOAc. The layers were separated, and the aqueous layer was extracted with EtOAc. The combined organic layer was washed with brine, dried over MgSO$_4$ and concentrated. The residue was purified by silica gel column chromatography (EtOAc/hexane) to give the title compound (2.68 g).

$^1$H NMR (300 MHz, CDCl$_3$) δ 2.56 (1H, dd, J=16.4, 9.2 Hz), 2.76 (1H, dd, J=16.6, 5.7 Hz), 3.72 (3H, s), 3.75-3.87 (1H, m), 4.27 (1H, dd, J=9.2, 6.0 Hz), 4.76 (1H, t, J=9.0 Hz), 4.94 (1H, s), 5.03 (2H, s), 6.44-6.52 (2H, m), 6.74 (1H, dd, J=8.4, 2.5 Hz), 6.91 (1H, d, J=2.4 Hz), 7.03 (1H, d, J=8.1 Hz), 7.37 (1H, d, J=8.3 Hz).

D) (6-((2-Chloro-4-(3-methoxypropoxy)benzyl)oxy)-2,3-dihydro-1-benzofuran-3-yl)acetic acid To the solution of methyl(6-((2-chloro-4-hydroxybenzyl)oxy)-2,3-dihydro-1-benzofuran-3-yl)acetate (34.9 mg) in toluene (0.25 mL) and THF (0.25 mL) were added a solution of 3-methoxy-1-propanol (13.5 mg) in toluene (0.5 mL) and a solution of tributylphosphine (40.5 mg) in toluene (0.5 mL). To the mixture was added ADDP (50.5 mg) and the mixture was stirred at room temperature overnight. To the mixture was added water (1.0 mL), and the mixture was extracted with EtOAc (2.0 mL). The organic layer was separated and concentrated. The residue was purified by preparative HPLC (C18, eluent: water/CH$_3$CN (including 0.1% TFA)). After solvent evaporated, the residue was added 1.0 N NaOH (0.5 mL) and the mixture was stirred at 50° C. overnight. The mixture was added EtOAc (3.0 mL), and the organic layer was separated. The aqueous layer was acidified with 10% aqueous citric acid solution (0.5 mL), and extracted with EtOAc (3.0 mL). The organic layer was separated and concentrated. The residue was purified by preparative HPLC (C18, eluent: water/CH$_3$CN (including 0.1% TFA)). The solvent was evaporated to give the title compound (13.1 mg).

Example 311

(6-((4-(Benzyloxy)-2-chlorobenzyl)oxy)-2,3-dihydro-1-benzofuran-3-yl)acetic acid The title compound was obtained in a same manner as the procedure in step D of Example 310 using methyl(6-((2-chloro-4-hydroxybenzyl)oxy)-2,3-dihydro-1-benzofuran-3-yl)acetate and benzyl alcohol.

Example 312

(6-((2-Chloro-4-(pyridin-3-ylmethoxy)benzyl)oxy)-2,3-dihydro-1-benzofuran-3-yl)acetic acid The title compound was obtained in a same manner as the procedure in step D of Example 310 using methyl(6-((2-chloro-4-hydroxybenzyl)oxy)-2,3-dihydro-1-benzofuran-3-yl)acetate and pyridin-3-ylmethanol.

Example 313

(6-((2-Chloro-4-(2-phenylethoxy)benzyl)oxy)-2,3-dihydro-1-benzofuran-3-yl)acetic acid The title compound was obtained in a same manner as the procedure in step D of Example 310 using methyl(6-((2-chloro-4-hydroxybenzyl)oxy)-2,3-dihydro-1-benzofuran-3-yl)acetate and 2-phenylethanol.

Example 314

(6-((2-Chloro-4-((2,5-dimethylhexan-3-yl)oxy)benzyl)oxy)-2,3-dihydro-1-benzofuran-3-yl)acetic acid The title compound was obtained in a same manner as the procedure in step D of Example 310 using methyl(6-((2-chloro-4-hydroxybenzyl)oxy)-2,3-dihydro-1-benzofuran-3-yl)acetate and 2,5-dimethyl-3-hexanol.

Example 315

(6-((2-Chloro-4-(cyclopropyl(phenyl)methoxy)benzyl)oxy)-2,3-dihydro-1-benzofuran-3-yl)acetic acid The title compound was obtained in a same manner as the procedure in step D of Example 310 using methyl(6-((2-chloro-4-hydroxybenzyl)oxy)-2,3-dihydro-1-benzofuran-3-yl)acetate and cyclopropyl(phenyl)methanol.

Example 316

(6-((4-Butoxy-2-chlorobenzyl)oxy)-2,3-dihydro-1-benzofuran-3-yl)acetic acid The title compound was obtained in a same manner as the procedure in step D of Example 310 using methyl(6-((2-chloro-4-hydroxybenzyl)oxy)-2,3-dihydro-1-benzofuran-3-yl)acetate and butanol.

Example 317

((3S)-6-[(2,4-Difluorobenzyl)oxy]-2,3-dihydro-1-benzofuran-3-yl)acetic acid To a stirred mixture of methyl(3S)-(2,3-dihydro-6-hydroxy-1-benzofuran-3-yl)acetate (20.8 mg) and K$_2$CO$_3$ (20.7 mg) in DMF (0.5 mL) was added 2,4-difluorobenzyl chloride (24.4 mg) at room temperature. After stirring at 55° C. for 15 h, water (2.0 mL) and EtOAc (3.0 mL) were added to the mixture with stirring. The organic layer was separated by phase separation filter kit, and the filtrate was evaporated by blowing away with the air at 60° C. The resulting residue was dissolved in MeOH (0.5 mL) and 1N LiOH (0.3 mL), and the mixture was stirred at room temperature for 1 h. To the mixture was added 1N HCl (0.2 mL) and the solution was evaporated by blowing away with the air at 60° C. The resulting residue was dissolved in DMSO (1.0 mL) and the solution was purified by preparative HPLC (C18, eluent: water/CH$_3$CN (including 5 mM AcONH$_4$)). The eluted fraction was evaporated by air blowing at 60° C. to give the title compound (11.0 mg, 34.4%).

Example 318

((3S)-6-[(2,4-Dichloro-5-fluorobenzyl)oxy]-2,3-dihydro-1-benzofuran-3-yl)acetic acid The title compound was obtained in a same manner as the procedure in Example 317 using methyl(3S)-(2,3-dihydro-6-hydroxy-1-benzofuran-3-yl)acetate and 2,4-dichloro-5-fluorobenzyl chloride.

Example 319

Methyl(4-cyano-6-((2,6-dimethylpyridin-3-yl)methoxy)-1-benzothiophen-3-yl)acetate To a mixture of methyl(6-((2,6-dimethylpyridin-3-yl)methoxy)-4-formyl-1-benzothiophen-3-yl)acetate (100 mg), THF (5 mL) and water (5 mL) was added hydroxylamine-O-sulfonic acid (45.9 mg) at room temperature, and the mixture was refluxed for 48 h. The suspension was diluted with EtOAc, and TEA (1 mL) was added to the mixture. The mixture was refluxed for 1 h. The mixture was poured into water at room temperature and extracted with EtOAc. The organic layer was separated, washed successively with water and brine, dried over MgSO$_4$ and concentrated in vacuo. The residue was purified by silica gel column chromatography (EtOAc/hexane) to give the title compound (96 mg).

Example 320

(4-Cyano-6-((2,6-dimethylpyridin-3-yl)methoxy)-1-benzothiophen-3-yl)acetic acid

To a mixture of methyl(4-cyano-6-((2,6-dimethylpyridin-3-yl)methoxy)-1-benzothiophen-3-yl)acetate (96 mg), THF (3 mL) and MeOH (3 mL) was added 1N NaOH (1.179 mL) at room temperature. The mixture was stirred at room temperature for 12 h. The mixture was neutralized with 1N HCl at room temperature and extracted with EtOAc. The organic layer was separated, washed with brine, dried over MgSO$_4$ and concentrated in vacuo. The crystals were crystallized from EtOAc to give the title compound (80 mg).

Example 321

(6-((2,6-Dimethylpyridin-3-yl)methoxy)-4-fluoro-1-benzothiophen-3-yl)acetic acid The title compound was obtained in a same manner as the procedures in Examples 3 and 12 using methyl(4-fluoro-6-hydroxy-1-benzothiophen-3-yl)acetate and (2,6-dimethylpyridin-3-yl)methanol.

The structures and $^1$H NMR data and/or MS data of the compounds of Examples 1 to 321 are shown in the following Tables 1 to 33.

TABLE 1

| Ex. No. | Name | Structure | MS (ESI+): [M + H]+ | MS (ESI−): [M − H]− | $^1$H NMR |
|---|---|---|---|---|---|
| 1 | Ethyl (6-((2,4-diehlorobenzyl)oxy)-1-benzothiophen-3-yl)acetate | 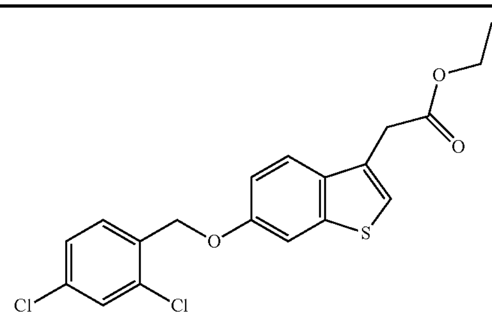 | 394.8 | | |
| 2 | (6-((2,4-Dichlorobenzyl)oxy)-1-benzothiophen-3-yl)acetic acid | 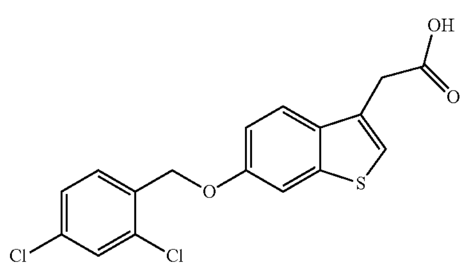 [SMILES: O=C(O)Cc1csc2cc(OCc3ccc(Cl)cc3Cl)ccc12] | | 365.2 | |

TABLE 1-continued

| Ex. No. | Name | Structure | MS (ESI+): [M + H]+ | MS (ESI−): [M − H]− | ¹H NMR |
|---|---|---|---|---|---|
| 3 | Ethyl (6-((2,6-dimethylpyridin-3-yl)methoxy)-1-benzothiophen-3-yl)acetate | 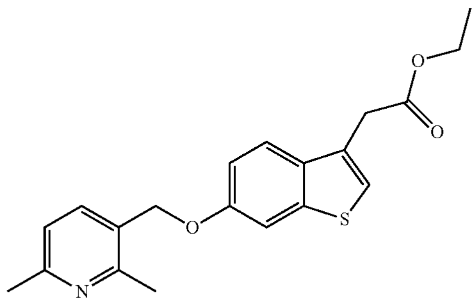 [SMILES: CCOC(=O)Cc1csc2cc(OCc3ccc(C)nc3C)ccc12] | 356.2 | | |
| 4 | (6-((2,6-Dimethylpyridin-3-yl)methoxy)-1-benzothiophen-3-yl)acetic acid | 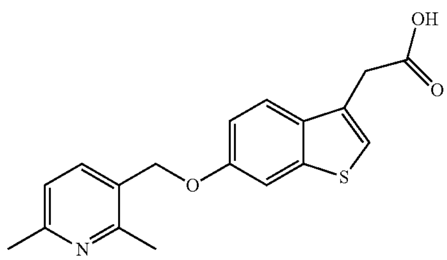 [SMILES: Cc1ccc(COc2ccc3c(CC(=O)O)csc3c2)c(C)n1] | 328.1 | | |
| 5 | Methyl (6-((2,4-dichlorobenzyl)oxy)-4-methyl-1-benzothiophen-3-yl)acetate | 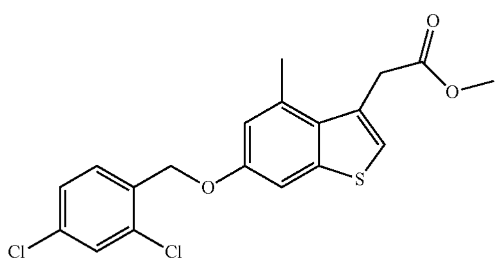 [SMILES: COC(=O)Cc1csc2cc(OCc3ccc(Cl)cc3Cl)cc(C)c12] | 392.9 | | |
| 6 | (6-((2,4-Dichlorobenzyl)oxy)-4-methyl-1-benzothiophen-3-yl)acetic acid | 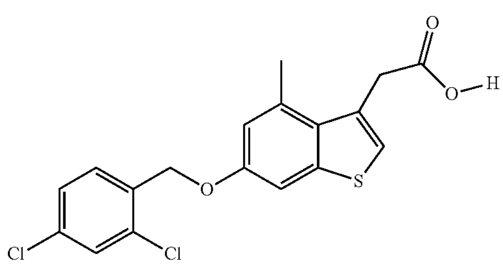 [SMILES: Cc1cc(OCc2ccc(Cl)cc2Cl)cc2scc(CC(=O)O)c12] | | 379.0 | |
| 7 | Methyl (6-((1,3-dimethyl-1H-pyrazol-5-yl)methoxy)-4-methyl-1-benzothiophen-3-yl)acetate | 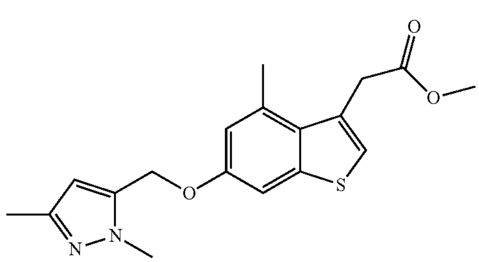 | 345.1 | | |

TABLE 1-continued

| Ex. No. | Name | Structure | MS (ESI+): [M + H]+ | MS (ESI−): [M − H]− | ¹H NMR |
|---|---|---|---|---|---|
| 8 | (6-((1,3-Dimethyl-1H-pyrazol-5-yl)methoxy)-4-methyl-1-benzothiophen-3-yl)acetic acid | 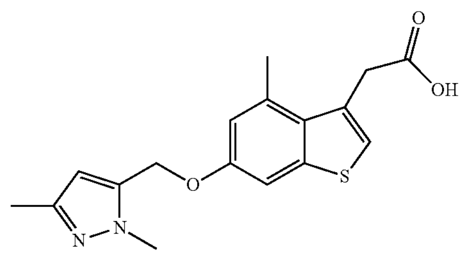 [SMILES: Cc1cc(COc2cc(C)c3c(CC(=O)O)csc3c2)n(C)n1] | 331.1 | | |
| 9 | Methyl (4-methyl-6-((2-methyl-6-(trifluoromethyl)pyridin-3-yl)methoxy)-1-benzothiophen-3-yl)acetate | 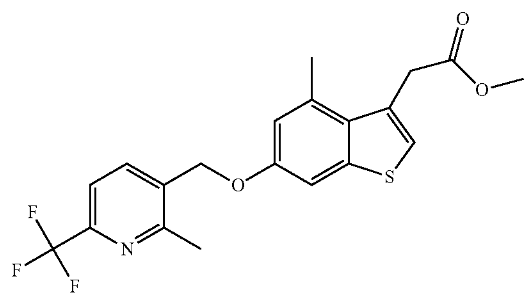 | 410.0 | | |
| 10 | (4-Methyl-6-((2-methyl-6-(trifluoromethyl)pyridin-3-yl)methoxy)-1-benzothiophen-3-yl)acetic acid | 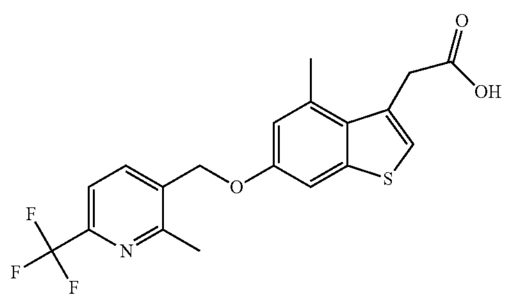 | 396.1 | | |

TABLE 2

| Ex. No. | Name | Structure | MS (ESI+): [M + H]+ | MS (ESI−): [M − H]− | ¹H NMR |
|---|---|---|---|---|---|
| 11 | Methyl (4-methyl-6-((1-methyl-3-(trifluoromethyl)-1H-pyrazol-5-yl)methoxy)-1-benzothiophen-3-yl)acetate | 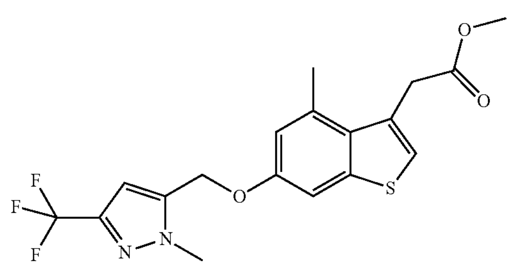 [SMILES: COC(=O)Cc1csc2cc(OCc3cc(C(F)(F)F)nn3C)cc(C)c12] | 397.0 | | |

TABLE 2-continued

| Ex. No. | Name | Structure | MS (ESI+): [M + H]+ | MS (ESI−): [M − H]− | ¹H NMR |
|---|---|---|---|---|---|
| 12 | (4-Methyl-6-((1-methyl-3-(trifluoromethyl)-1H-pyrazol-5-yl)methoxy)-1-benzothiophen-3-yl)acetic acid | 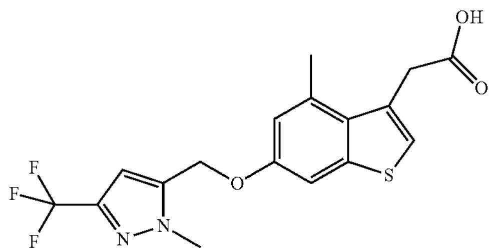 [SMILES: Cc1cc(OCc2cc(C(F)(F)F)nn2C)cc2scc(CC(=O)O)c12] | | 383.0 | |
| 13 | Methyl (4-chloro-6-((2,6-dimethylpyridin-3-yl)methoxy)-1-benzothiophen-3-yl)acetate | 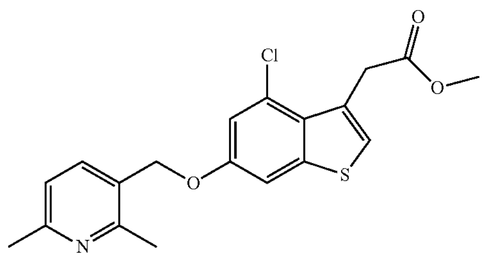 | 376.1 | | |
| 14 | (4-Chloro-6-((2,6-dimethylpyridin-3-yl)methoxy)-1-benzothiophen-3-yl)acetic acid | 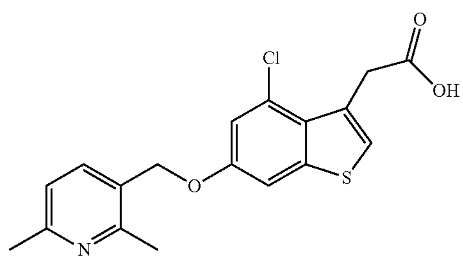 [SMILES: Cc1ccc(COc2cc(Cl)c3c(CC(=O)O)csc3c2)c(C)n1] | | 362.0 | |
| 15 | Methyl (4-chloro-6-((2-methyl-6-(trifluoromethyl)pyridin-3-yl)methoxy)-1-benzothiophen-3-yl)acetate | 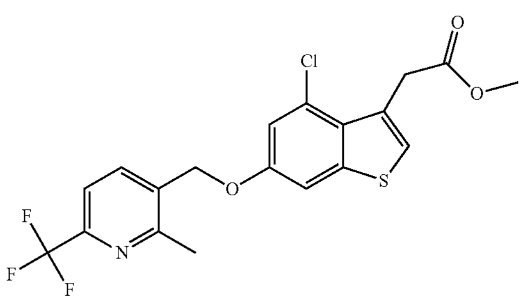 [SMILES: COC(=O)Cc1csc2cc(OCc3ccc(C(F)(F)F)nc3C)cc(Cl)c12] | | | ¹H NMR (300 MHz, CDCl₃) δ 2.66 (3H, s), 3.73 (3H, s), 4.12 (2H, s), 5.14 (2H, s), 7.09 (1H, d, J = 2.3 Hz), 7.16 (1H, s), 7.30 (1H, s), 7.57 (1H, d, J = 7.9 Hz), 7.92 (1H, d, J = 7.9 Hz). |
| 16 | (4-Chloro-6-((2-methyl-6-(trifluoromethyl)pyridin-3-yl)methoxy)-1-benzothiophen-3-yl)acetic acid | 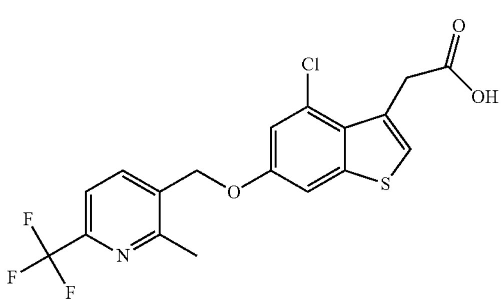 [SMILES: Cc1nc(C(F)(F)F)ccc1COc1cc(Cl)c2c(CC(=O)O)csc2c1] | | 414.1 | |

TABLE 2-continued

| Ex. No. | Name | Structure | MS (ESI+): [M + H]+ | MS (ESI−): [M − H]− | ¹H NMR |
|---|---|---|---|---|---|
| 17 | Ethyl (6-((l-methyl-3-(trifluoromethyl)-1H-pyrazol-5-yl)methoxy)-1-benzothiophen-3-yl)acetate | 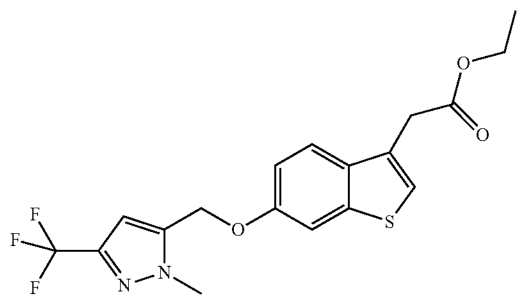 [SMILES: CCOC(=O)Cc1csc2cc(OCc3cc(C(F)(F)F)nn3C)ccc12] | 397.1 | | |
| 18 | (6-((1-Methyl-3-(trifluoromethyl)-1H-pyrazol-5-yl)methoxy)-1-benzothiophen-3-yl)acetic acid | 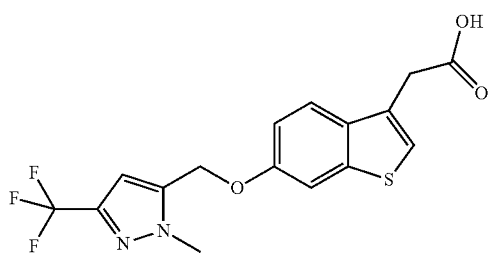 [SMILES: Cn1nc(C(F)(F)F)cc1COc1ccc2c(CC(=O)O)csc2c1] | 369.1 | | |
| 19 | Methyl (6-((2,6-dimethylpyridin-3-yl)methoxy)-4-vinyl-1-benzothiophen-3-yl)acetate | 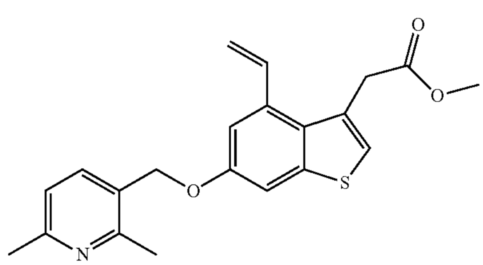 | 368.2 | | |
| 20 | Methyl (6-((2,6-dimethylpyridin-3-yl)methoxy)-4-formyl-1-benzothiophen-3-yl)acetate | 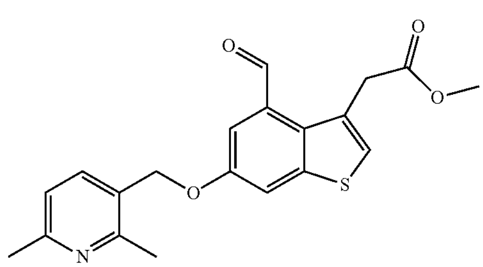 | | | ¹H NMR (300 MHz, CDCl₃) δ 2.55 (3H, s), 2.57-2.61 (3H, m), 3.66-3.73 (3H, m), 4.18 (2H, s), 5.13 (2H, s), 7.03 (1H, d, J = 7.6 Hz), 7.31 (1H, s), 7.56-7.64 (3H, m), 10.26 (1H, s). |

TABLE 3

| Ex. No. | Name | Structure | MS (ESI+): [M + H]+ | MS (ESI−): [M − H]− | ¹H NMR |
|---|---|---|---|---|---|
| 21 | Methyl (4-chloro-6-((1-methyl-3-(trifluoromethyl)-1H-pyrazol-5-yl)methoxy)-1-benzothiophen-3-yl)acetate | 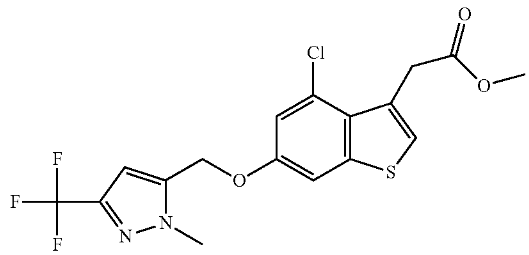 [SMILES: COC(=O)Cc1csc2cc(OCc3cc(C(F)(F)F)nn3C)cc(Cl)c12] | | 416.9 | |
| 22 | (4-Chloro-6-((1-methyl-3-(trifluoromethyl)-1H-pyrazol-5-yl)methoxy)-1-benzothiophen-3-yl)acetic acid | 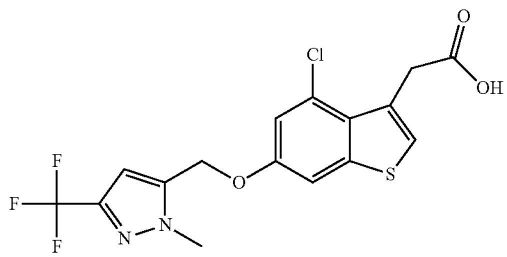 [SMILES: Cn1nc(C(F)(F)F)cc1COc1cc(Cl)c2c(CC(=O)O)csc2c1] | | | ¹H NMR (300 MHz, DMSO-d$_6$) δ 3.95 (3H, s), 4.01 (2H, s), 5.32 (2H, s), 6.90 (1H, s), 7.21 (1H, d, J = 2.27 Hz), 7.50 (1H, s), 7.76 (1H, d, J = 2.27 Hz), 12.37 (1H, brs). |
| 23 | Methyl (4,7-dimethyl-6-((2-methyl-6-(trifluoromethyl)pyridin-3-yl)methoxy)-1-benzothiophen-3-yl)acetate | 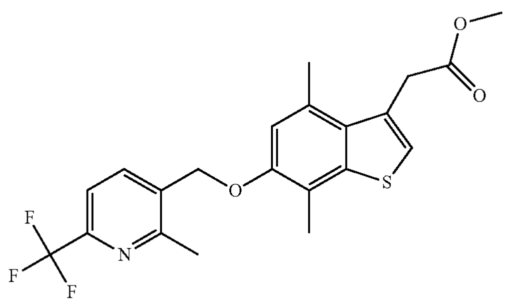 [SMILES: COC(=O)Cc1csc2c(C)c(OCc3ccc(C(F)(F)F)nc3C)cc(C)c12] | 424.1 | | |
| 24 | (4,7-Dimethyl-6-((2-methyl-6-(trifluoromethyl)pyridin-3-yl)methoxy)-1-benzothiophen-3-yl)acetic acid | 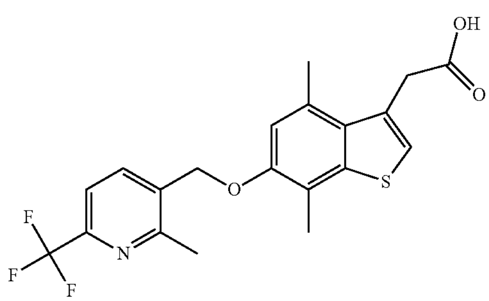 [SMILES: Cc1nc(C(F)(F)F)ccc1COc1cc(C)c2c(CC(=O)O)csc2c1C] | | 410.0 | |
| 25 | Methyl (4-chloro-6-((1,3-dimethyl-1H-pyrazol-5-yl)methoxy)-1-benzothiophen-3-yl)acetate | 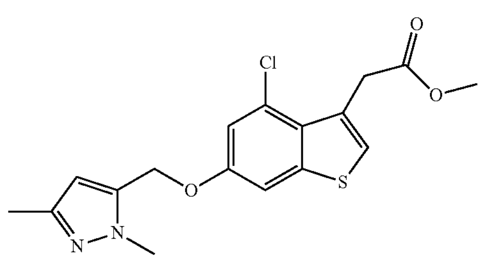 | 365.2 | | |

TABLE 3-continued

| Ex. No. | Name | Structure | MS (ESI+): [M + H]+ | MS (ESI−): [M − H]− | ¹H NMR |
|---|---|---|---|---|---|
| 26 | 4-Chloro-6-((1,3-dimethyl-1H-pyrazol-5-yl)methoxy)-1-benzothiophen-3-yl)acetic acid | 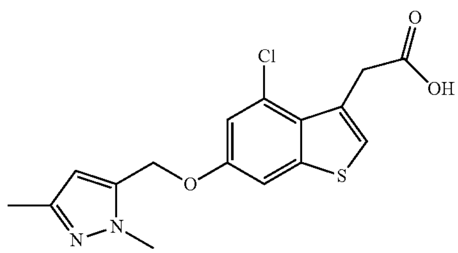 [SMILES: Cc1cc(COc2cc(Cl)c3c(CC(=O)O)csc3c2)n(C)n1] | 351.1 | | |
| 27 | Methyl (4,7-dichloro-6-((1-methyl-3-(trifluoromethyl)-1H-pyrazol-5-yl)methoxy)-1-benzothiophen-3-yl)acetate | 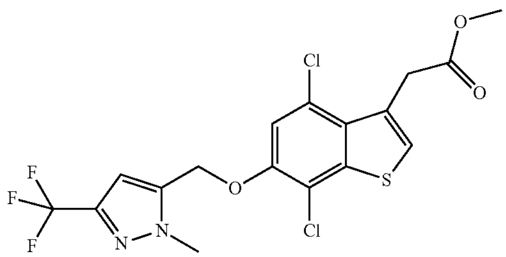 [SMILES: COC(=O)Cc1csc2c(Cl)c(OCc3cc(C(F)(F)F)nn3C)cc(Cl)c12] | 453.0 | | |
| 28 | (4,7-Dichloro-6-((1-methyl-3-(trifluoromethyl)-1H-pyrazol-5-yl)methoxy)-1-benzothiophen-3-yl)acetic acid | 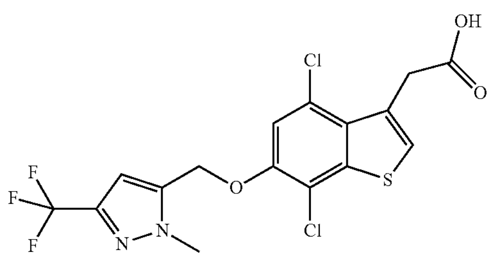 [SMILES: Cn1nc(C(F)(F)F)cc1COc1cc(Cl)c2c(CC(=O)O)csc2c1Cl] | 436.9 | | |
| 29 | Methyl (4,7-dichloro-6-((2-methyl-6-(trifluoromethyl)pyridin-3-yl)methoxy)-1-benzothiophen-3-yl)acetate | 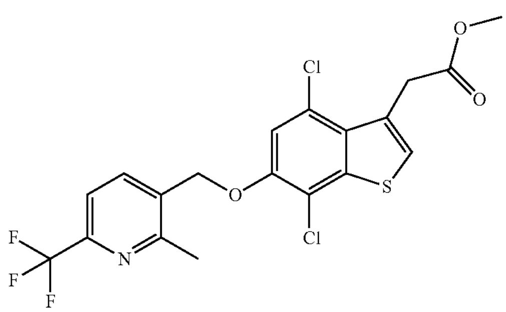 [SMILES: COC(=O)Cc1csc2c(Cl)c(OCc3ccc(C(F)(F)F)nc3C)cc(Cl)c12] | 461.9 | | |
| 30 | (4,7-Dichloro-6-((2-methyl-6-(trifluoromethyl)pyridin-3-yl)methoxy)-1-benzothiophen-3-yl)acetic acid | 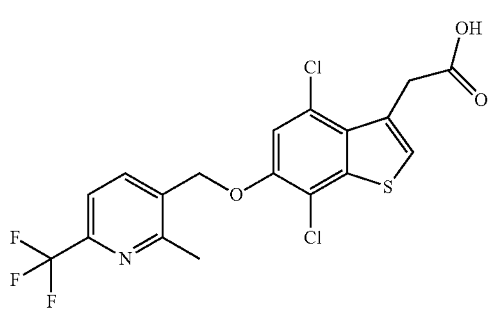 [SMILES: Cc1nc(C(F)(F)F)ccc1COc1cc(Cl)c2c(CC(=O)O)csc2c1Cl] | 449.9 | | |

TABLE 4

| Ex. No. | Name | Structure | MS (ESI+): [M + H]+ | MS (ESI−): [M − H]− | 1H NMR |
|---|---|---|---|---|---|
| 31 | (6-((2,6-Dimethylpyridin-3-yl))methoxy)-4-(trifluoromethyl)-1-benzothiophen-3-yl)acetic acid | 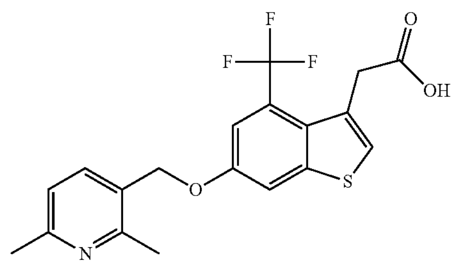 [SMILES: Cc1ccc(COc2cc(C(F)(F)F)c3c(CC(=O)O)csc3c2)c(C)n1] | 396.1 | | |
| 32 | (6-((1-Methyl-3-(trifluoromethyl)-1H-pyrazol-5-yl)methoxy)-4-(trifluoromethyl)-1-benzothiophen-3-yl)acetic acid | 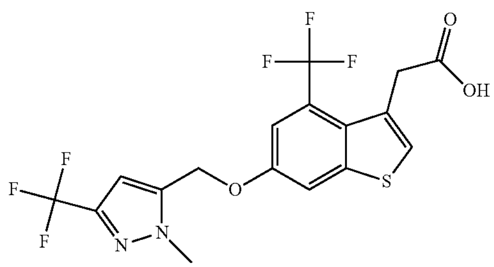 [SMILES: Cn1nc(C(F)(F)F)cc1COc1cc(C(F)(F)F)c2c(CC(=O)O)csc2c1] | 437.0 | | |
| 33 | Methyl (7-fluoro-4-methyl-6-((1-methyl-3-(trifluoromethyl)-1H-pyrazol-5-yl)methoxy)-1-benzothiophen-3-yl)acetate | 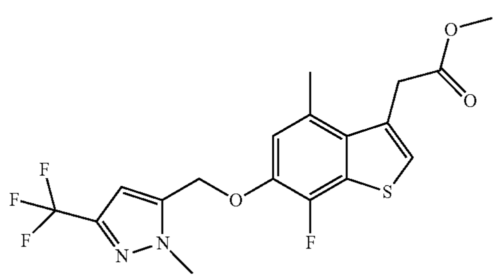 [SMILES: COC(=O)Cc1csc2c(F)c(OCc3cc(C(F)(F)F)nn3C)cc(C)c12] | 417.0 | | |
| 34 | (7-Fluoro-4-methyl-6-((1-methyl-3-(trifluoromethyl)-1H-pyrazol-5-yl)methoxy)-1-benzothiophen-3-yl)acetic acid | 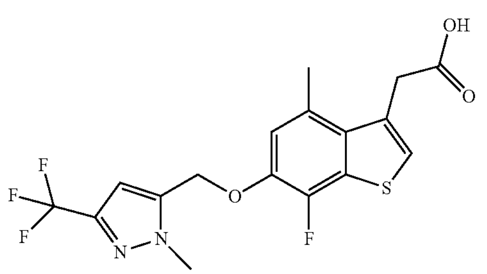 [SMILES: Cc1cc(OCc2cc(C(F)(F)F)nn2C)c(F)c2scc(CC(=O)O)c12] | 401.0 | | |
| 35 | Methyl (7-fluoro-4-methyl-6-((2-methyl-6-(trifluoromethyl)pyridin-3-yl)methoxy)-1-benzothiophen-3-yl)acetate | 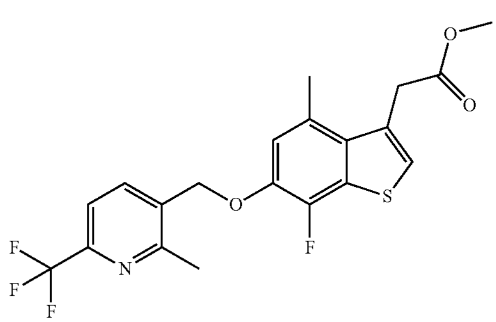 [SMILES: COC(=O)Cc1csc2c(F)c(OCc3ccc(C(F)(F)F)nc3C)cc(C)c12] | 428.0 | | |

TABLE 4-continued

| Ex. No. | Name | Structure | MS (ESI+): [M + H]+ | MS (ESI−): [M − H]− | 1H NMR |
|---|---|---|---|---|---|
| 36 | (7-Fluoro-4-methyl-6-((2-methyl-6-(trifluoromethyl)pyridin-3-yl)methoxy)-1-benzothiophen-3-yl)acetic acid | 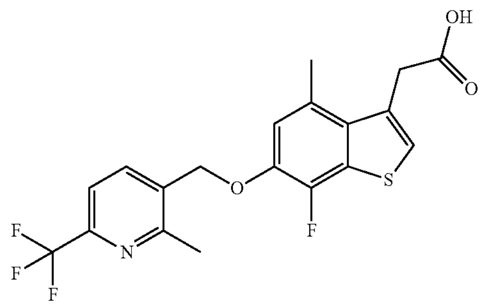 [SMILES: Cc1nc(C(F)(F)F)ccc1COc1cc(C)c2c(CC(=O)O)csc2c1F] | 413.9 | | |
| 37 | Methyl (4-chloro-7-fluoro-6-((1-methyl-3-(trifluoromethyl)-1H-pyrazol-5-yl)methoxy)-1-benzothiophen-3-yl)acetate | 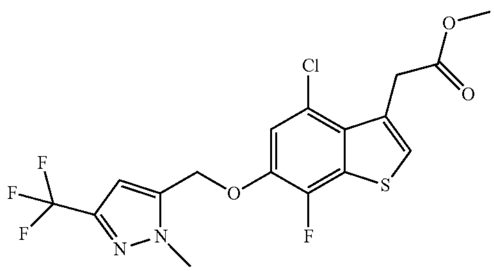 | 437.1 | | |
| 38 | (4-Chloro-7-fluoro-6-((1-methyl-3-(trifluoromethyl)-1H-pyrazol-5-yl)methoxy)-1-benzothiophen-3-yl)acetic acid | 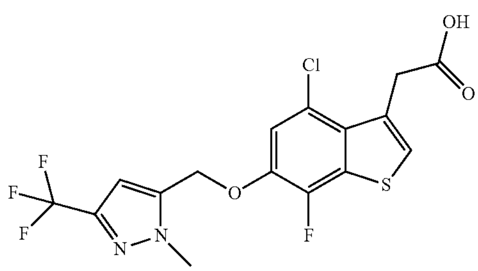 [SMILES: Cn1nc(C(F)(F)F)cc1COc1cc(Cl)c2c(CC(=O)O)csc2c1F] | 421.0 | | |
| 39 | Methyl (4-chloro-7-fluoro-6-((2-methyl-6-(trifluoromethyl)pyridin-3-yl)methoxy)-1-benzothiophen-3-yl)acetate | 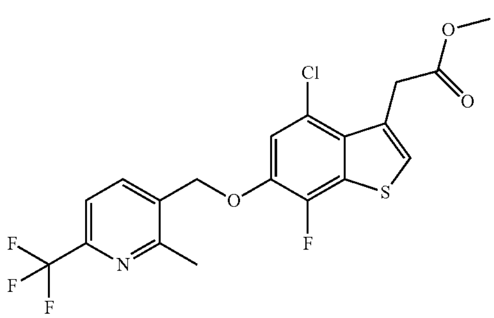 | 448.0 | | |
| 40 | (4-Chloro-7-fluoro-6-((2-methyl-6-(tirifluoromethyl)pyridin-3-yl)methoxy)-1-benzothiophen-3-yl)acetic acid | 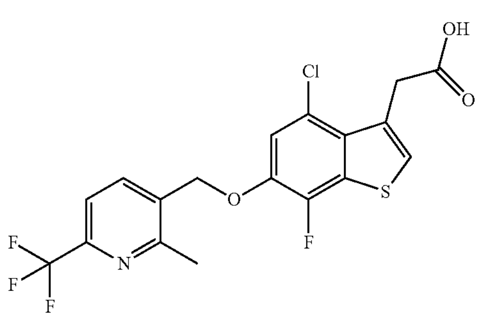 [SMILES: Cc1nc(C(F)(F)F)ccc1COc1cc(Cl)c2c(CC(=O)O)csc2c1F] | 434.0 | | |

TABLE 5

| Ex. No. | Name | Structure | MS (ESI+): [M + H]+ | MS (ESI−): [M − H]− | ¹H NMR |
|---|---|---|---|---|---|
| 41 | Methyl (7-chloro-6-((2,4-dichlorobenzyl)oxy)-1-benzofuran-3-yl)acetate | 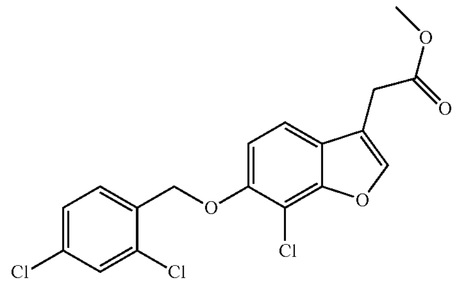 [SMILES: COC(=O)Cc1coc2c(Cl)c(OCc3ccc(Cl)cc3Cl)ccc12] | | 396.8 | |
| 42 | (7-Chloro-6-((2,4-dichlorobenzyl)oxy)-1-benzofuran-3-yl)acetic acid | 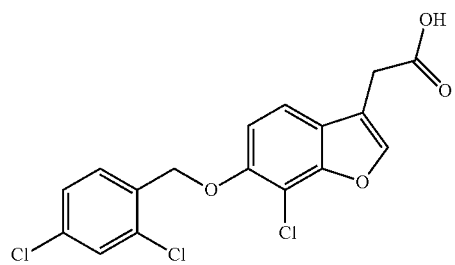 | | 383.0 | |
| 43 | Methyl (6-((2,6-dimethylpyridin-3-yl)methoxy)-4,7-dimethyl-1-benzofuran-3-yl)acetate | 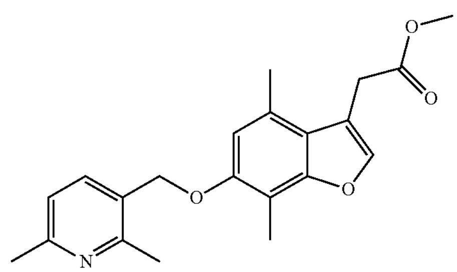 | 354.2 | | |
| 44 | (6-((2,6-Dimethylpyridin-3-yl)methoxy)-4,7-dimethyl-1-benzofuran-3-yl)acetic acid | 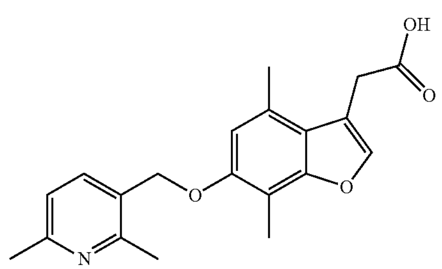 [SMILES: Cc1ccc(COc2cc(C)c3c(CC(=O)O)coc3c2C)c(C)n1] | | 340.1 | |
| 45 | Methyl (6-((2,4-dichlorobenzyl)oxy)-4,7-dimethyl-1-benzofuran-3-yl)acetate | 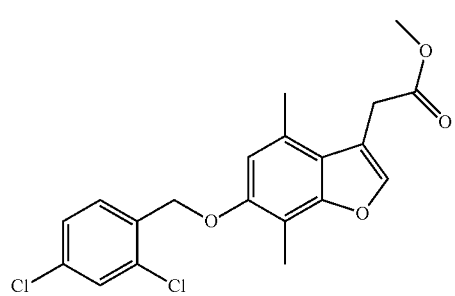 | | | ¹H NMR (300 MHz, CDCl₃) δ 2.38 (3H, s), 2.52 (3H, s), 3.73 (3H, s), 3.79 (2H, d, J = 1.1 Hz), 5.14 (2H, s), 6.64 (1H, s), 7.26-7.31 (1H, m), 7.43 (1H, d, J = 2.3 Hz), 7.50-7.53 (1H, m), 7.55 (1H, d, J = 8.3 Hz). |

TABLE 5-continued

| Ex. No. | Name | Structure | MS (ESI+): [M + H]+ | MS (ESI−): [M − H]− | ¹H NMR |
|---|---|---|---|---|---|
| 46 | (6-((2,4-Dichloro-benzyl)oxy)-4,7-dimethyl-1-benzofuran-3-yl)acetic acid | 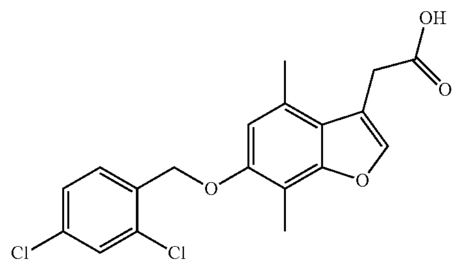 | 376.9 | | |
| 47 | Ethyl (6-((2,4-dichlorobenzyl)oxy)-1,1-dioxido-1-benzothiophen-3-yl)acetate | 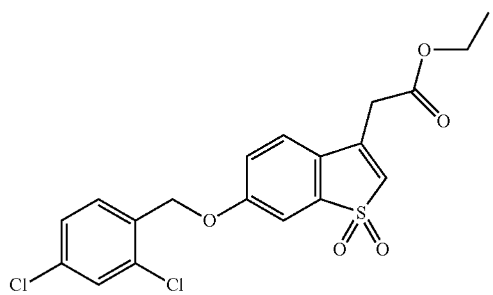 [SMILES: CCOC(=O)CC1=CS(=O)(=O)c2cc(OCc3ccc(Cl)cc3Cl)ccc21] | | | ¹H NMR (400 MHz, DMSO-d₆) δ 1.26 (3H, t, J = 7.2 Hz), 4.19 (2H, q, J = 7.2 Hz), 4.74 (2H, d, J = 1.8 Hz), 5.33 (2H, s), 6.83 (1H, s), 7.35-7.56 (2H, m), 7.56-7.79 (3H, m), 8.22 (1H, d, J = 9.0 Hz). |
| 48 | (6-((2,4-Dichloro-benzyl)oxy)-1,1-dioxido-1-benzo-thiophen-3-yl)acetic acid | 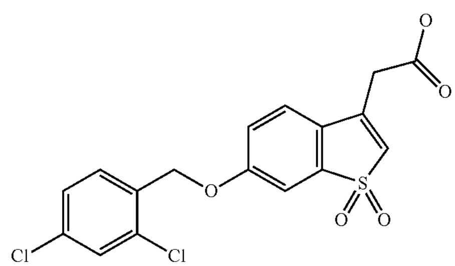 [SMILES: O=C(O)CC1=CS(=O)(=O)c2cc(OCc3ccc(Cl)cc3Cl)ccc21] | | | ¹H NMR (300 MHz, DMSO-d₆) δ 4.64 (2H, d, J = 1.8 Hz), 5.27 (2H, s), 6.51 (1H, s), 7.33 (1H, dd, J = 8.7, 2.4 Hz), 7.42-7.55 (2H, m), 7.60-7.75 (2H, m), 7.90 (1H, d, J = 8.7 Hz). |
| 49 | Ethyl (6-((2,4-di-chlorobenzyl)oxy)-2,3-dihydro-1-benzothiophen-3-yl)acetate | 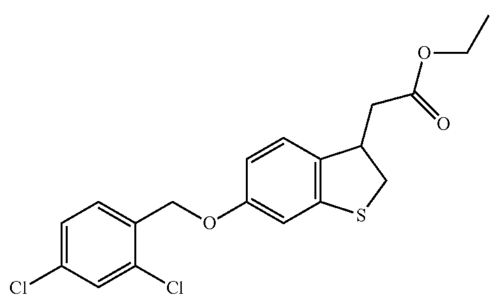 [SMILES: CCOC(=O)CC1CSc2cc(OCc3ccc(Cl)cc3Cl)ccc21] | | | ¹H NMR (400 MHz, CDCl₃) δ 1.27 (3H, t, J = 7.2 Hz), 2.58-2.72 (2H, m), 3.05-3.18 (1H, m), 3.58-3.68 (1H, m), 3.77-3.88 (1H, m), 4.18 (2H, q, J = 7.2 Hz), 5.07 (2H, s), 6.62 (1H, dd, J = 8.4, 2.4 Hz), 6.83 (1H, d, J = 2.4 Hz), 7.03 (1H, d, J = 8.4 Hz), 7.20-7.30 (1H, m), 7.41 (1H, d, J = 2.0 Hz), 7.46 (1H, d, J = 8.4 Hz). |
| 50 | (6-((2,4-Dichloro-benzyl)oxy)-2,3-dihydro-1-benzo-thiophen-3-yl)acetic acid | 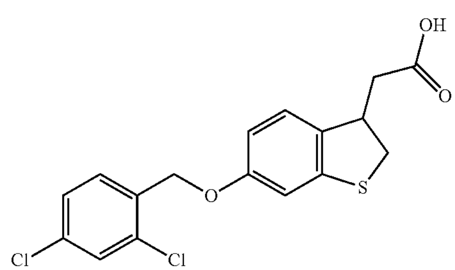 [SMILES: O=C(O)CC1CSc2cc(OCc3ccc(Cl)cc3Cl)ccc21] | 367.0 | | |

TABLE 6

| Ex. No. | Name | Structure | MS (ESI+): [M + H]+ | MS (ESI−): [M − H]− | 1H NMR |
|---|---|---|---|---|---|
| 51 | Ethyl (6-((2,4-dichlorobenzyl)oxy)-1,1-dioxido-2,3-dihydro-1-benzothiophen-3-yl)acetate | 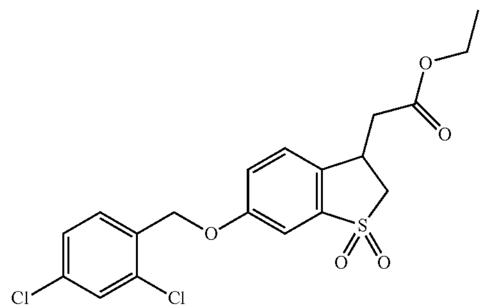 [SMILES: CCOC(=O)CC1CS(=O)(=O)c2cc(OCc3ccc(Cl)cc3Cl)ccc21] | | | 1H NMR (400 MHz, DMSO-d$_6$) δ 1.19 (3H, t, J = 7.2 Hz), 2.67-2.82 (1H, m), 2.94-3.05 (1H, m), 3.40-3.50 (1H, m), 3.73-3.93 (2H, m), 4.00-4.20 (2H, m), 5.23 (2H, s), 7.33 (1H, dd, J = 8.4, 2.4 Hz), 7.40 (1H, d, J = 2.4 Hz), 7.45-7.56 (2H, m), 7.60-7.72 (2H, m). |
| 52 | (6-((2,4-Dichlorobenzyl)oxy)-1,1-dioxido-2,3-dihydro-1-benzothiophen-3-yl)acetic acid | 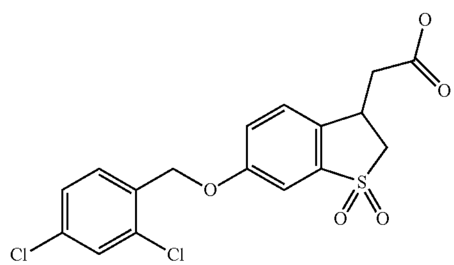 [SMILES: O=C(O)CC1CS(=O)(=O)c2cc(OCc3ccc(Cl)cc3Cl)ccc21] | | | 1H NMR (300 MHz, MeOD) δ 2.64-2.82 (1H, m), 2.88-3.05 (1H, m), 3.37-3.48 (1H, m), 3.70-3.85 (1H, m), 3.85-4.02 (1H, m), 5.23 (2H, s), 7.12-7.42 (3H, m), 7.42-7.65 (3H, m) |
| 53 | Ethyl N-((6-((2,4-dichlorobenzyl)oxy)-1-benzothiophen-3-yl)acetyl)glycinate | 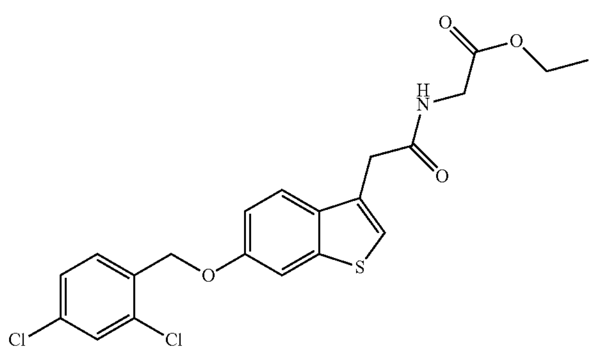 [SMILES: CCOC(=O)CNC(=O)Cc1csc2cc(OCc3ccc(Cl)cc3Cl)ccc12] | 449.9 | | |
| 54 | Methyl N-((6-((2,4-dichlorobenzyl)oxy)-1-benzothiophen-3-yl)acetyl)serinate | 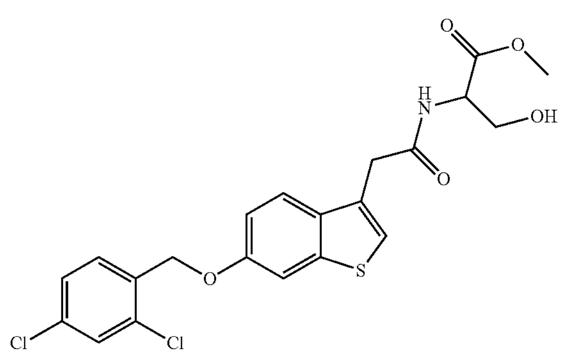 [SMILES: COC(=O)C(CO)NC(=O)Cc1csc2cc(OCc3ccc(Cl)cc3Cl)ccc12] | 466.0 | | |

TABLE 6-continued

| Ex. No. | Name | Structure | MS (ESI+): [M + H]+ | MS (ESI−): [M − H]− | 1H NMR |
|---|---|---|---|---|---|
| 55 | N-((6-((2,4-Dichlorobenzyl)oxy)-1-benzothiophen-3-yl)acetyl)glycine | 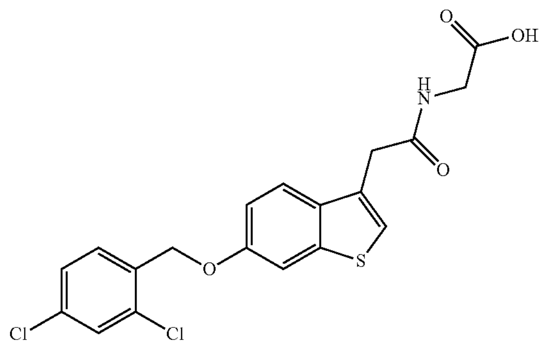 [SMILES: O=C(O)CNC(=O)Cc1csc2cc(OCc3ccc(Cl)cc3Cl)ccc12] | 422.0 | | |
| 56 | N-((6-((2,4-Dichlorobenzyl)oxy)-1-benzothiophen-3-yl)acetyl)serine | 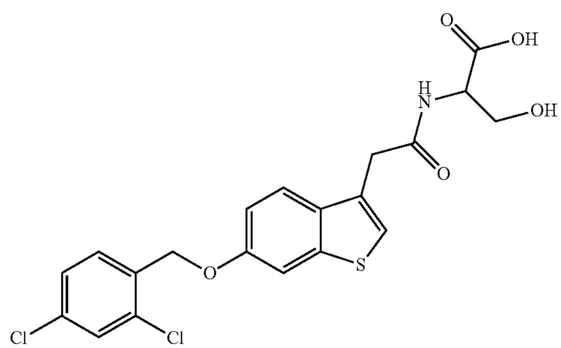 [SMILES: O=C(Cc1csc2cc(OCc3ccc(Cl)cc3Cl)ccc12)NC(CO)C(=O)O] | 452.0 | | |
| 57 | 2-(6-((2,4-Dichlorobenzyl)oxy)-1-benzothiophen-3-yl)-N-methyl-acetamide | 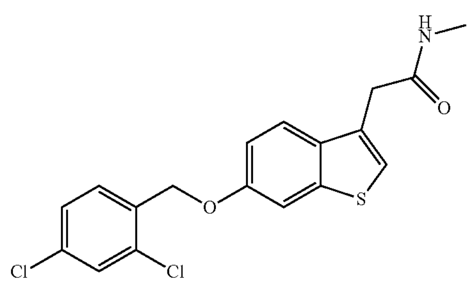 [SMILES: CNC(=O)Cc1csc2cc(OCc3ccc(Cl)cc3Cl)ccc12] | 380.2 | | |
| 58 | 2-(6-((2,4-Dichlorobenzyl)oxy)-1-benzothiophen-3-yl)-1-(morpholin-4-yl)ethanone | 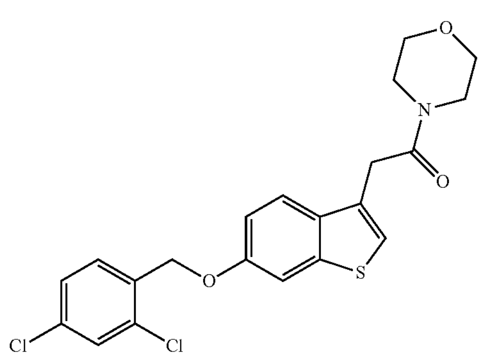 [SMILES: O=C(Cc1csc2cc(OCc3ccc(Cl)cc3Cl)ccc12)N1CCOCC1] | 436.3 | | |

TABLE 6-continued

| Ex. No. | Name | Structure | MS (ESI+): [M + H]+ | MS (ESI−): [M − H]− | 1H NMR |
|---|---|---|---|---|---|
| 59 | Ethyl (6-((2,4-dimethyl-1,3-thiazol-5-yl)methoxy)-1-benzothiophen-3-yl)acetate | 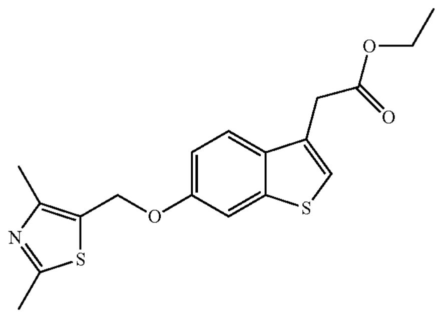 [SMILES: CCOC(=O)Cc1csc2cc(OCc3sc(C)nc3C)ccc12] | 362.2 | | |
| 60 | (6-((2,4-Dimethyl-1,3-thiazol-5-yl)methoxy)-1-benzothiophen-3-yl)acetic acid | 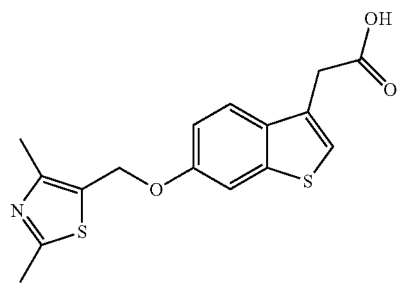 [SMILES: Cc1nc(C)c(COc2ccc3c(CC(=O)O)csc3c2)s1] | 334.0 | | |

TABLE 7

| Ex. No. | Name | Structure | MS (ESI+): [M + H]+ | MS (ESI−): [M − H]− | 1H NMR |
|---|---|---|---|---|---|
| 61 | Ethyl (6-((2-chloro-4-(trifluoromethyl)benzyl)oxy)-1-benzothiophen-3-yl)acetate | 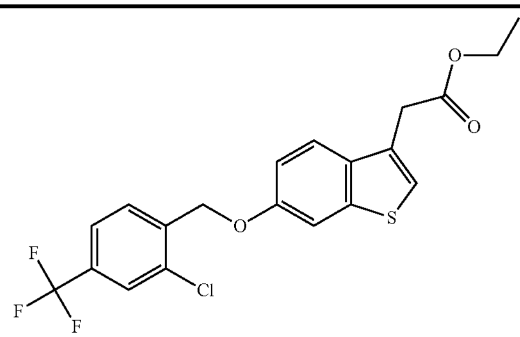 | 427.1 | | |
| 62 | (6-((2-Chloro-4-(trifluoromethyl)benzyl)oxy)-1-benzothiophen-3-yl)acetic acid | 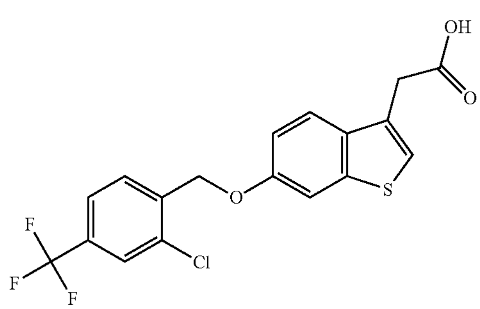 [SMILES: O=C(O)Cc1csc2cc(OCc3ccc(C(F)(F)F)cc3Cl)ccc12] | 399.1 | | |

TABLE 7-continued

| Ex. No. | Name | Structure | MS (ESI+): [M + H]+ | MS (ESI−): [M − H]− | 1H NMR |
|---|---|---|---|---|---|
| 63 | Ethyl 6-((2,4-dichlorobenzyl)oxy)-3-(2-ethoxy-2-oxoethoxy)-1-benzothiophene-2-carboxylate | 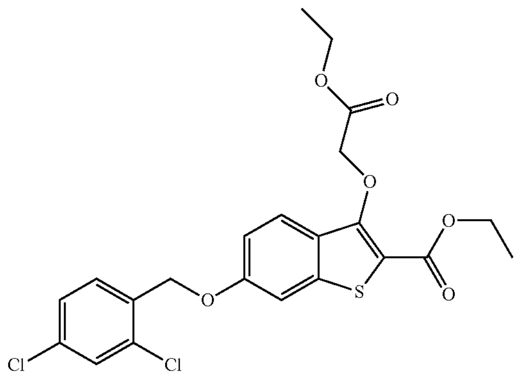 [SMILES: CCOC(=O)COc1c(C(=O)OCC)sc2cc(OCc3ccc(Cl)cc3Cl)ccc12] | 480.8 | | |
| 64 | ((6-((2,4-Dichlorobenzyl)oxy)-1-benzothiophen-3-yl)oxy)acetic acid | 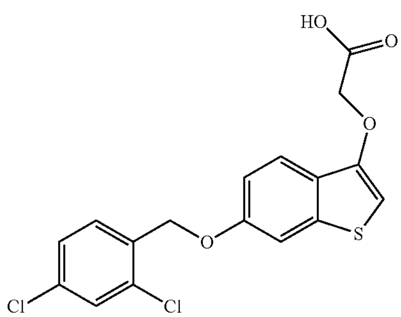 [SMILES: O=C(O)COc1csc2cc(OCc3ccc(Cl)cc3Cl)ccc12] | 380.9 | | |
| 65 | Ethyl ((2-carbamoyl-6-((2,4-dichlorobenzyl)oxy)-1-benzothiophen-3-yl)sulfanyl)acetate | 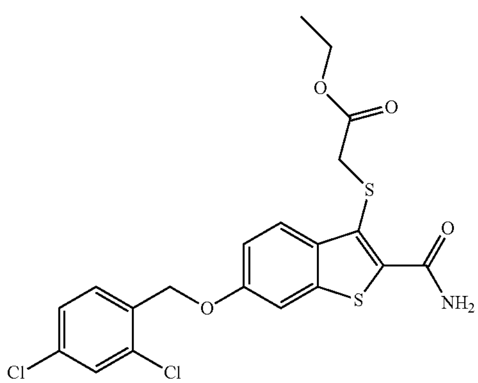 [SMILES: CCOC(=O)CSc1c(C(N)=O)sc2cc(OCc3ccc(Cl)cc3Cl)ccc12] | 469.7 | | |
| 66 | ((2-Carbamoyl-6-((2,4-dichlorobenzyl)oxy)-1-benzothiophen-3-yl)sulfanyl)acetic acid | 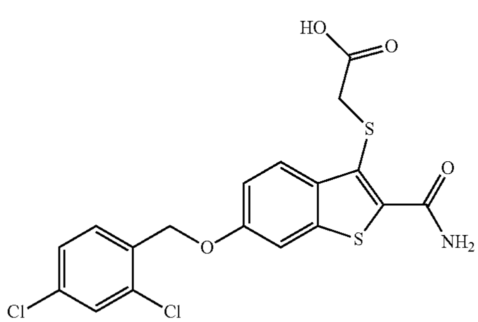 [SMILES: NC(=O)c1sc2cc(OCc3ccc(Cl)cc3Cl)ccc2c1SCC(=O)O] | 439.9 | | |

TABLE 7-continued

| Ex. No. | Name | Structure | MS (ESI+): [M + H]+ | MS (ESI−): [M − H]− | ¹H NMR |
|---|---|---|---|---|---|
| 67 | Ethyl 3-(2-tert-butoxy-2-oxoethoxy)-6-((2,4-dichlorobenzyl)oxy)-1-benzothiophene-2-carboxylate | 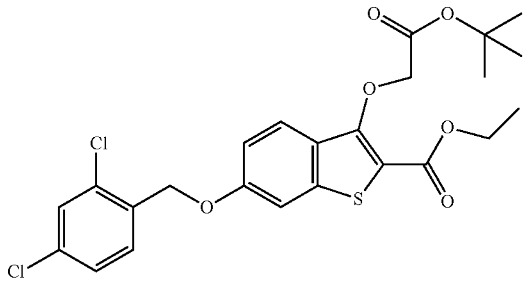 [SMILES: CCOC(=O)c1sc2cc(OCc3ccc(Cl)cc3Cl)ccc2c1OCC(=O)OC(C)(C)C] | | | ¹H NMR (300 MHz, CDCl₃) δ 1.39 (3H, t, J = 7.19 Hz), 1.46 (9H, s), 4.36 (2H, q, J = 7.19 Hz), 4.90 (2H, s), 5.19 (2H, s), 7.10 (1H, dd, J = 9.09, 2.27 Hz), 7.19 (1H, d, J = 2.27 Hz), 7.25-7.32 (1H, m), 7.45 (1H, d, J = 2.27 Hz), 7.50 (1H, d, J = 8.33 Hz), 8.00 (1H, d, J = 8.71 Hz). |
| 68 | Ethyl (6-((4-methoxy-2-methylpyrimidin-5-yl)methoxy)-1-benzothiophen-3-yl)acetate | 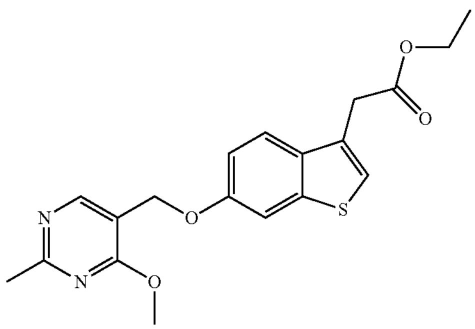 [SMILES: CCOC(=O)Cc1csc2cc(OCc3cnc(C)nc3OC)ccc12] | 373.3 | | |
| 69 | (6-((4-Methoxy-2-methylpyrimidin-5-yl)methoxy)-1-benzothiophen-3-yl)acetic acid | 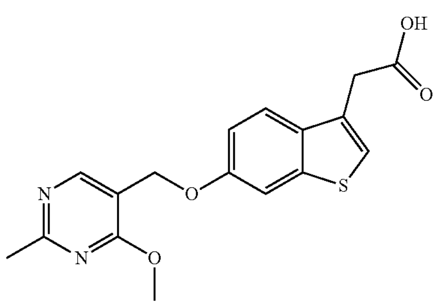 [SMILES: COc1nc(C)ncc1COc1ccc2c(CC(=O)O)csc2c1] | 345.1 | | |
| 70 | 3-(Carboxymethoxy)-6-((2,4-dichlorobenzyl)oxy)-1-benzothipohene-2-carboxylic acid | 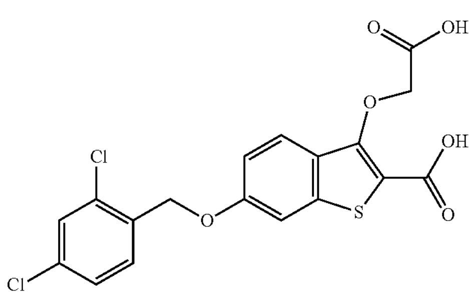 [SMILES: O=C(O)COc1c(C(=O)O)sc2cc(OCc3ccc(Cl)cc3Cl)ccc12] | | | ¹H NMR (300 MHz, DMSO-d₆) δ 4.97 (2H, s), 5.24 (2H, s), 7.17 (1H, dd, J = 9.09, 2.27 Hz), 7.50 (1H, dd, J = 8.33, 1.89 Hz), 7.58-7.78 (3H, m), 7.89 (1H, d, J = 8.71 Hz), 13.08 (2H, brs.). |

TABLE 8

| Ex. No. | Name | Structure | MS (ESI+): [M + H]+ | MS (ESI−): [M − H]− | ¹H NMR |
|---|---|---|---|---|---|
| 71 | Ethyl (6-((4-chloro-2-methylpyrimidin-5-yl)methoxy)-1-benzothiophen-3-yl)acetate | 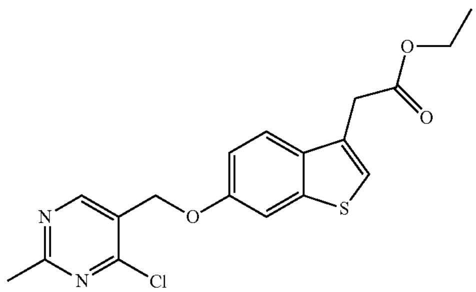 [SMILES: CCOC(=O)Cc1csc2cc(OCc3cnc(C)nc3Cl)ccc12] | 377.2 | | |
| 72 | (6-((4-Chloro-2-methylpyrimidin-5-yl)methoxy)-1-benzothiophen-3-yl)acetic acid | 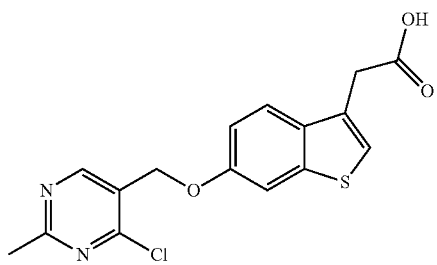 [SMILES: Cc1ncc(COc2ccc3c(CC(=O)O)csc3c2)c(Cl)n1] | 349.3 | | |
| 73 | (6-((4-Ethoxy-2-methylpyrimidin-5-yl)methoxy)-1-benzothiophen-3-yl)acetic acid | 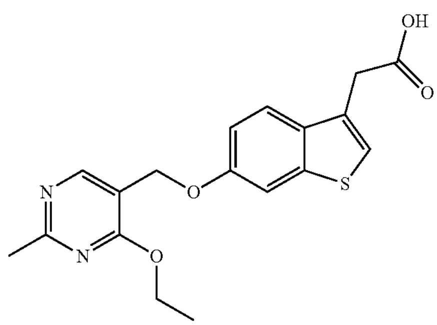 [SMILES: CCOc1nc(C)ncc1COc1ccc2c(CC(=O)O)csc2c1] | 359.0 | | |
| 74 | 2-(6-((2,4-Dichlorobenzyl)oxy)-1-benzothiophen-3-yl)acetamide | 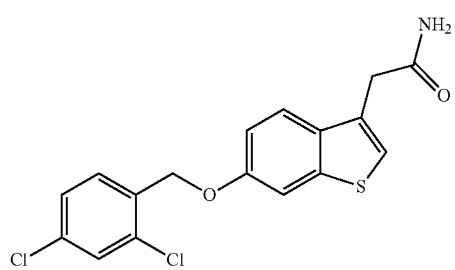 [SMILES: NC(=O)Cc1csc2cc(OCc3ccc(Cl)cc3Cl)ccc12] | 363.8 | | |
| 75 | Ethyl (6-((2,4-dimethyl-1,3-oxazol-5-yl)methoxy)-1-benzothiophen-3-yl)acetate | 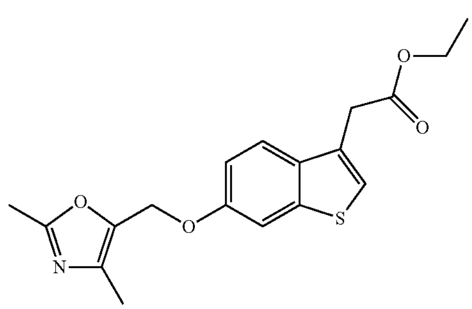 [SMILES: CCOC(=O)Cc1csc2cc(OCc3oc(C)nc3C)ccc12] | 346.4 | | |

TABLE 8-continued

| Ex. No. | Name | Structure | MS (ESI+): [M + H]+ | MS (ESI−): [M − H]− | 1H NMR |
|---|---|---|---|---|---|
| 76 | (6-((2,4-Dimethyl-1,3-oxazol-5-yl)methoxy)-1-benzothiophen-3-yl)acetic acid | 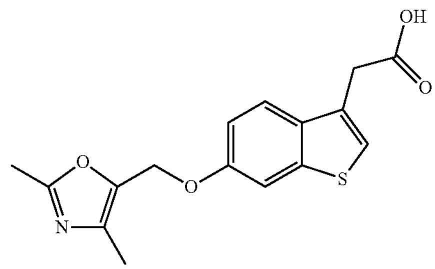 [SMILES: Cc1nc(C)c(COc2ccc3c(CC(=O)O)csc3c2)o1] | 318.2 | | |
| 77 | Ethyl (6-((2,5-dimethyl-1,3-oxazol-4-yl)methoxy)-1-benzothiophen-3-yl)acetate | 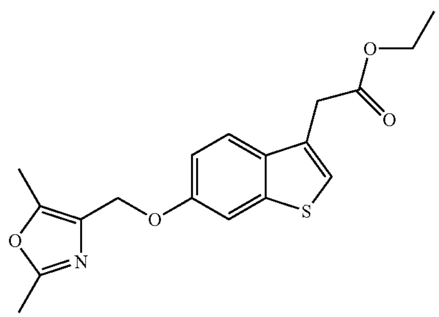 [SMILES: CCOC(=O)Cc1csc2cc(OCc3nc(C)oc3C)ccc12] | 346.1 | | |
| 78 | (6-((2,5-Dimethyl-1,3-oxazol-4-yl)methoxy)-1-benzothiophen-3-yl)acetic acid | 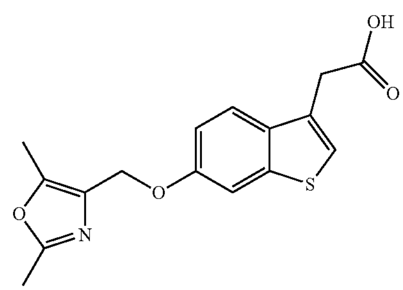 [SMILES: Cc1nc(COc2ccc3c(CC(=O)O)csc3c2)c(C)o1] | 318.2 | | |
| 79 | Ethyl (6-((2,4-dichlorobenzyl)sulfanyl)-1-benzothiophen-3-yl)acetate | 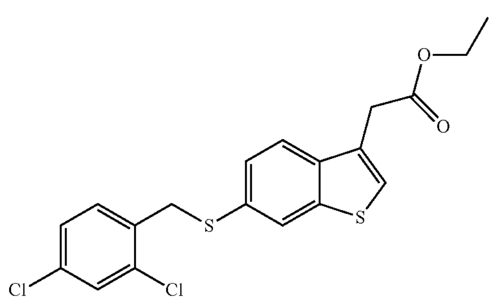 [SMILES: CCOC(=O)Cc1csc2cc(SCc3ccc(Cl)cc3Cl)ccc12] | | | 1H NMR (300 MHz, CDCl3) δ 1.25 (3H, t, J = 7.2 Hz), 3.82 (2H, s), 4.10-4.22 (4H, m), 7.06-7.13 (2H, m), 7.32-7.44 (3H, m), 7.66 (1H, d, J = 8.7 Hz), 7.80 (1H, d, J = 1.9 Hz). |
| 80 | (6-((2,4-Dichlorobenzyl)sulfanyl)-1-benzothiophen-3-yl)acetic acid | 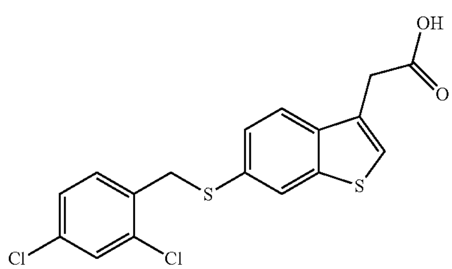 | | | 1H NMR (300 MHz, DMSO-d6) δ 3.81 (2H, s), 4.33 (2H, s), 7.29-7.34 (1H, m), 7.34-7.41 (2H, m), 7.56 (1H, s), 7.62 (1H, d, J = 1.9 Hz), 7.70 (1H, d, J = 8.3 Hz), 8.01 (1H, d, J = 1.9 Hz). |

TABLE 9

| Ex. No. | Name | Structure | MS (ESI+): [M + H]+ | MS (ESI−): [M − H]− | ¹H NMR |
|---|---|---|---|---|---|
| 81 | Ethyl (6-((2,4-dichlorobenzyl)sulfonyl)-1-benzothiophen-3-yl)acetate | 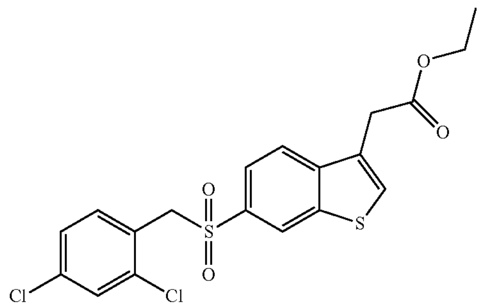 [SMILES: CCOC(=O)Cc1csc2cc(S(=O)(=O)Cc3ccc(Cl)cc3Cl)ccc12] | | | ¹H NMR (300 MHz, DMSO-d₆) δ 1.18 (3H, t), 4.02 (2H, s), 4.11 (2H, q, J = 7.2 Hz), 4.85 (2H, s), 7.37 (1H, d, J = 8.3 Hz), 7.45 (1H, dd), 7.58 (1H, d, J = 1.9 Hz), 7.68 (1H, dd, J = 8.5, 1.7 Hz), 7.94-8.01 (2H, m), 8.46 (1H, s). |
| 82 | Ethyl (6-((2,4-dichlorobenzyl)sulfinyl)-1-benzothiophen-3-yl)acetate | 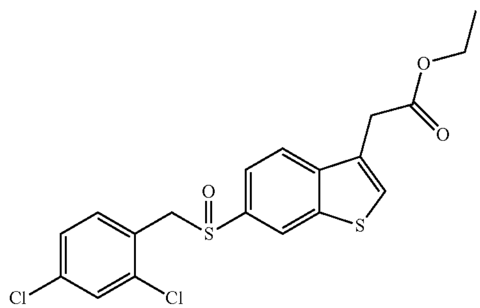 [SMILES: CCOC(=O)Cc1csc2cc(S(=O)Cc3ccc(Cl)cc3Cl)ccc12] | | | ¹H NMR (300 MHz, DMSO-d₆) δ 1.19 (3H, t, J = 7.2 Hz), 4.00 (2H, s), 4.11 (2H, q, J = 7.2 Hz), 4.37 (2H, dd), 7.24 (1H, d, J = 8.3 Hz, 7.39 (1H, dd, J = 8.3, 2.3 Hz), 7.55 (1H, dd, J = 8.3, 1.5 Hz), 7.60 (1H, d, J = 2.3 Hz), 7.81 (1H, s), 7.93 (1H, d, J = 8.3 Hz), 8.18 (1H, s). |
| 83 | (6-((2,4-Dichlorobenzyl)sulfonyl)-1-benzothiophen-3-yl)acetic acid | 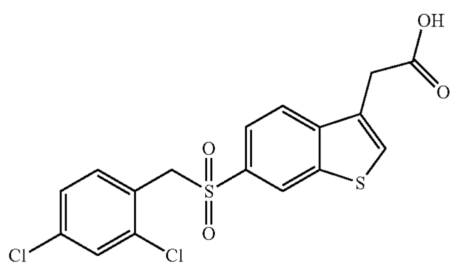 [SMILES: O=C(O)Cc1csc2cc(S(=O)(=O)Cc3ccc(Cl)cc3Cl)ccc12] | | | ¹H NMR (300 MHz, DMSO-d₆) δ 3.92 (2H, s), 4.84 (2H, s), 7.36 (1H, d, J = 8.3 Hz), 7.45 (1H, dd, J = 8.3, 2.3 Hz), 7.60 (1H, d, J = 2.3 Hz), 7.70 (1H, dd, J = 8.5, 1.7 Hz), 7.96 (1H, s), 7.99 (1H, d, J = 8.7 Hz), 8.45 (1H, d, J = 1.5 Hz). |
| 84 | (6-((2,4-Dichlorobenzyl)sulfinyl)-1-benzothiophen-3-yl)acetic acid | 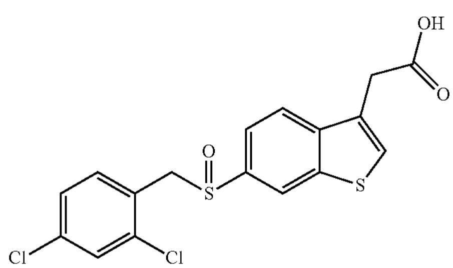 [SMILES: O=C(O)Cc1csc2cc(S(=O)Cc3ccc(Cl)cc3Cl)ccc12] | | | |
| 85 | Ethyl ((6-((2,4-dichlorobenzyl)oxy)-2-((2-methoxyethyl)carbamoyl)-1-benzothiophen-3-yl)oxy)acetate | 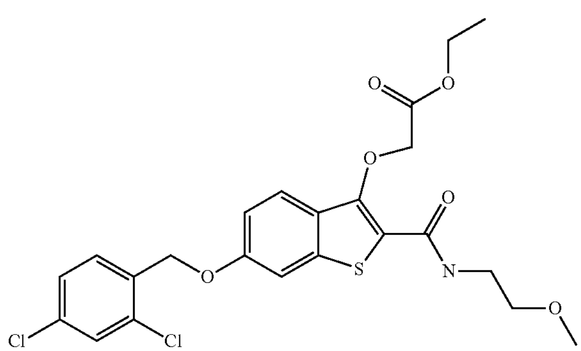 [SMILES: CCOC(=O)COc1c(C(=O)NCCOC)sc2cc(OCc3ccc(Cl)cc3Cl)ccc12] | 512.1 | | ¹H NMR (300 MHz, DMSO-d₆) δ 3.90 (2H, s), 4.37 (2H, dd), 7.25 (1H, d, J = 8.3 Hz), 7.39 (1H, dd, J = 8.3, 1.9 Hz), 7.57 (1H, dd, J = 8.5, 1.7 Hz), 7.61 (1H, d, J = 2.3 Hz), 7.79 (1H, s), 7.94 (1H, d, J = 8.3 Hz), 8.18 (1H, s), 12.53 (1H, brs). |

TABLE 9-continued

| Ex. No. | Name | Structure | MS (ESI+): [M + H]+ | MS (ESI−): [M − H]− | 1H NMR |
|---|---|---|---|---|---|
| 86 | ((6-((2,4-Dichlorobenzyl)oxy)-2-((2-methoxyethyl)carbamoyl)-1-benzothiophen-3-yl)oxy)acetic acid | 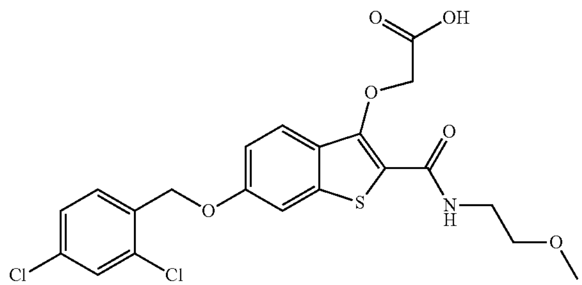 [SMILES: COCCNC(=O)c1sc2cc(OCc3ccc(Cl)cc3Cl)ccc2c1OCC(=O)O] | 484.1 | | |
| 87 | ((2-Carbamoyl-6-((2,4-dichlorobenzyl)oxy)-1-benzothiophen-3-yl)oxy)acetic acid | 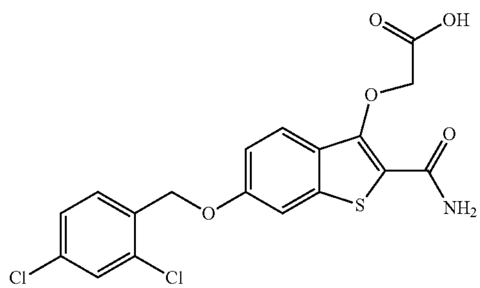 [SMILES: NC(=O)c1sc2cc(OCc3ccc(Cl)cc3Cl)ccc2c1OCC(=O)O] | 425.9 | | |
| 88 | Ethyl (6-((2-chloro-4-iodobenzyl)oxy)-1-benzothiophen-3-yl)acetate | 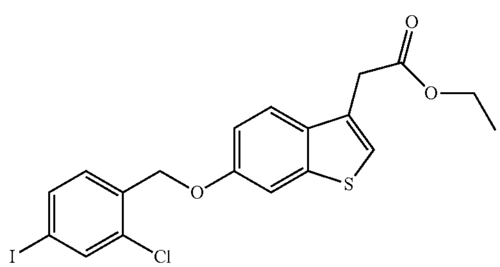 [SMILES: CCOC(=O)Cc1csc2cc(OCc3ccc(I)cc3Cl)ccc12] | 484.7 | | |
| 89 | (6-((2-Chloro-4-iodobenzyl)oxy)-1-benzothiophen-3-yl)acetic acid | 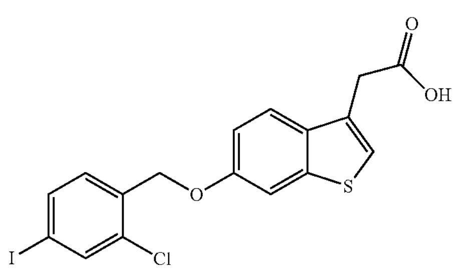 [SMILES: O=C(O)Cc1csc2cc(OCc3ccc(I)cc3Cl)ccc12] | | | 1H NMR (300 MHz, DMSO-d6) δ 3.79 (2H, s), 5.19 (2H, s), 7.05-7.16 (1H, m), 7.33-7.45 (2H, m), 7.64-7.70 (2H, m), 7.76 (1H, dd, J = 8.14, 1.70 Hz), 7.91 (1H, d, J = 1.51 Hz), 12.41 (1H, brs.). |
| 90 | Ethyl (6-((2,4-dimethylbenzyl)oxy)-1-benzothiophen-3-yl)acetate | 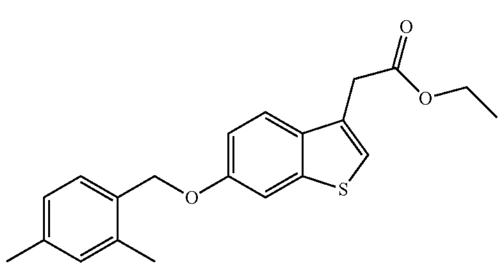 [SMILES: CCOC(=O)Cc1csc2cc(OCc3ccc(C)cc3C)ccc12] | | | 1H NMR (300 MHz, CDCl3) δ 1.25 (3H, t, J = 7.19 Hz), 2.33 (3H, s), 2.35 (3H, s), 3.81 (2H, s), 4.17 (2H, q, J = 7.07 Hz), 5.05 (2H, s), 7.00-7.12 (3H, m), 7.17 (1H, s), 7.30 (1H, d, J = 7.57 Hz), 7.41 (1H, d, J = 2.27 Hz), 7.65 (1H, d, J = 8.71 Hz). |

TABLE 10

| Ex. No. | Name | Structure | MS (ESI+): [M + H]+ | MS (ESI−): [M − H]− | ¹H NMR |
|---|---|---|---|---|---|
| 91 | (6-((2,4-Di-methylbenzyl)oxy)-1-benzothiophen-3-yl)acetic acid | 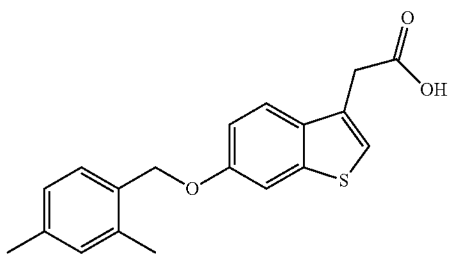 [SMILES: Cc1ccc(COc2ccc3c(CC(=O)O)csc3c2)c(C)c1] | | | ¹H NMR (300 MHz, DMSO-d₆) δ 2.27 (3H, s), 2.30 (3H, s), 3.79 (2H, s), 5.10 (2H, s), 6.96-7.13 (3H, m), 7.31 (1H, d, J = 7.95 Hz), 7.36 (1H, s), 7.61-7.71 (2H, m), 12.43 (1H, brs.). |
| 92 | Ethyl (6-((2-ethyl-6-methylpyridin-3-yl)methoxy)-1-benzothiophen-3-yl)acetate | 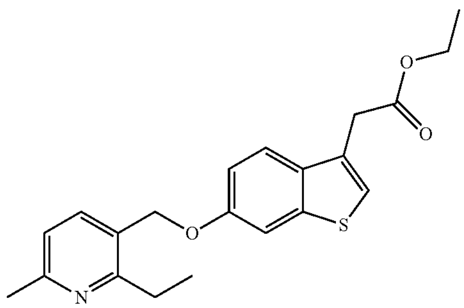 | 370.1 | | |
| 93 | (6-((2-Ethyl-6-methylpyridin-3-yl)methoxy)-1-benzothiophen-3-yl)acetic acid | 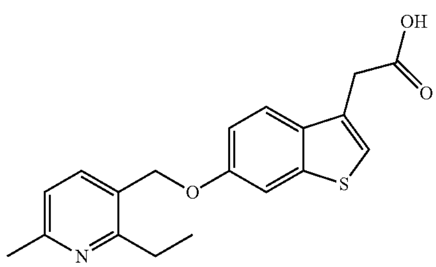 [SMILES: CCc1nc(C)ccc1COc1ccc2c(CC(=O)O)csc2c1] | 342.1 | | |
| 94 | Ethyl (6-((4-amino-2-methylpyrimidin-5-yl)methoxy)-1-benzothiophen-3-yl)acetate | 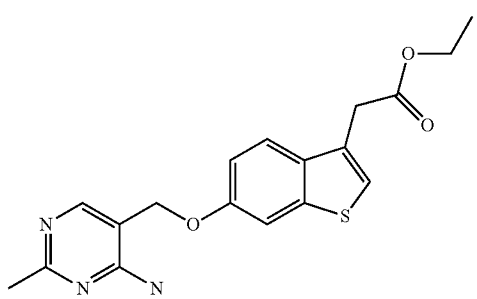 [SMILES: CCOC(=O)Cc1csc2cc(OCc3cnc(C)nc3N)ccc12] | 358.1 | | |
| 95 | (6-((4-Amino-2-methylpyrimidin-5-yl)methoxy)-1-benzothiophen-3-yl)acetic acid | 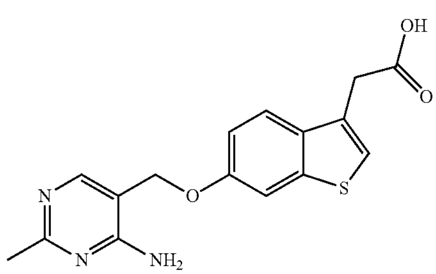 [SMILES: Cc1ncc(COc2ccc3c(CC(=O)O)csc3c2)c(N)n1] | | | ¹H NMR (300 MHz, DMSO-d₆) δ 2.38 (3H, s), 3.79 (2H, s), 5.01 (2H, s), 7.10 (1H, dd, J = 8.69, 2.27 Hz), 7.38 (1H, s), 7.58 (2H, br. s.), 7.63-7.70 (2H, m), 8.23 (1H, s), 12.40 (1H, br. s.) |

TABLE 10-continued

| Ex. No. | Name | Structure | MS (ESI+): [M + H]+ | MS (ESI−): [M − H]− | 1H NMR |
|---|---|---|---|---|---|
| 96 | Ethyl (6-((2,4-dimethylpyrimidin-5-yl)methoxy)-1-benzothiophen-3-yl)acetate | 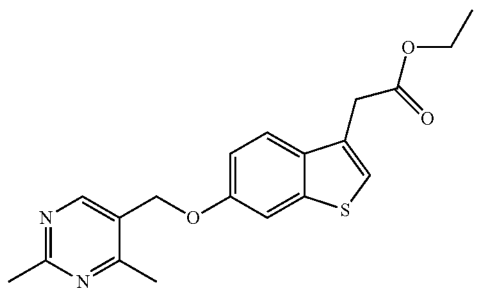 [SMILES: CCOC(=O)Cc1csc2cc(OCc3cnc(C)nc3C)ccc12] | 357.1 | | |
| 97 | (6-((2,4-Dimethylpyrimidin-5-yl)methoxy)-1-benzothiophen-3-yl)acetic acid | 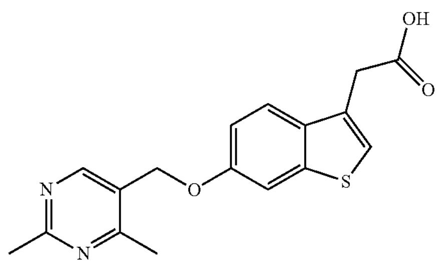 [SMILES: Cc1ncc(COc2ccc3c(CC(=O)O)csc3c2)c(C)n1] | 329.2 | | |
| 98 | Ethyl (6-((1,3-dimethyl-1H-pyrazol-5-yl)methoxy)-1-benzothiophen-3-yl)acetate | 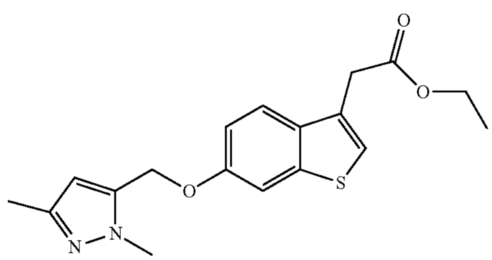 [SMILES: CCOC(=O)Cc1csc2cc(OCc3cc(C)nn3C)ccc12] | 345.1 | | |
| 99 | (6-((1,3-Dimethyl-1H-pyrazol-5-yl)methoxy)-1-benzothiophen-3-yl)acetic acid | 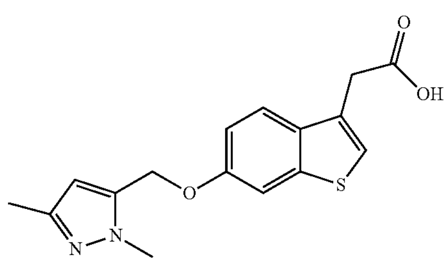 [SMILES: Cc1cc(COc2ccc3c(CC(=O)O)csc3c2)n(C)n1] | 317.0 | | |
| 100 | Ethyl (6-((2-isopropyl-4-methyl-1,3-thiazol-5-yl)methoxy)-1-benzothiophen-3-yl)acetate | 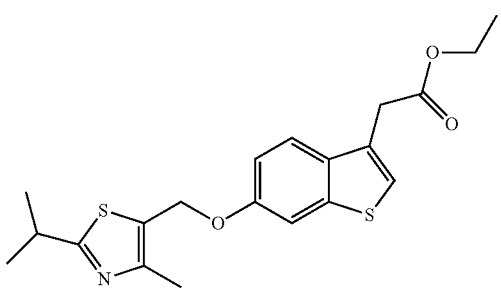 [SMILES: CCOC(=O)Cc1csc2cc(OCc3sc(C(C)C)nc3C)ccc12] | 390.1 | | |

TABLE 11

| Ex. No. | Name | Structure | MS (ESI+): [M + H]+ | MS (ESI−): [M − H]− | 1H NMR |
|---|---|---|---|---|---|
| 101 | (6-((2-Isopropyl-4-methyl-1,3-thiazol-5-yl)methoxy)-1-benzothiophen-3-yl)acetic acid | 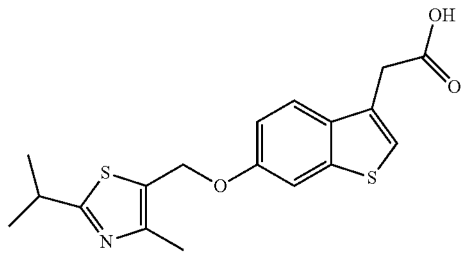 [SMILES: Cc1nc(C(C)C)sc1COc1ccc2c(CC(=O)O)csc2c1] | 362.0 | | |
| 102 | Ethyl (6-((6-methyl-2-(trifluoromethyl)pyridin-3-yl)methoxy)-1-benzothiophen-3-yl)acetate | 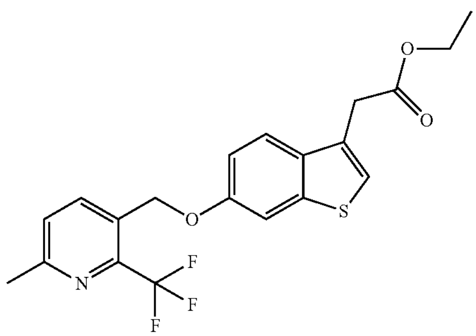 [SMILES: CCOC(=O)Cc1csc2cc(OCc3ccc(C)nc3C(F)(F)F)ccc12] | 410.0 | | |
| 103 | (6-((6-Methyl-2-(trifluoromethyl)pyridin-3-yl)methoxy)-1-benzothiophen-3-yl)acetic acid | 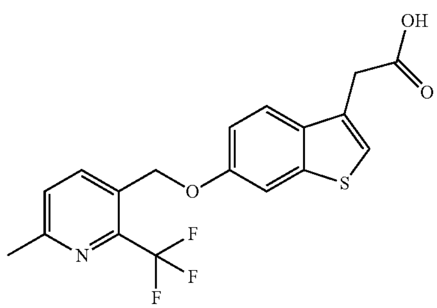 [SMILES: Cc1ccc(COc2ccc3c(CC(=O)O)csc3c2)c(C(F)(F)F)n1] | 382.1 | | |
| 104 | Ethyl (6-((6-ethyl-2-methylpyridin-3-yl)methoxy)-1-benzothiophen-3-yl)acetate | 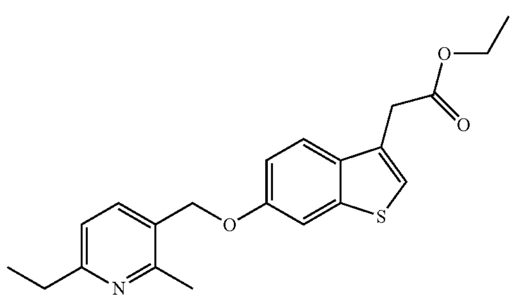 [SMILES: CCOC(=O)Cc1csc2cc(OCc3ccc(CC)nc3C)ccc12] | 370.1 | | |
| 105 | (6-((6-Ethyl-2-methylpyridin-3-yl)methoxy)-1-benzothiophen-3-yl)acetic acid | 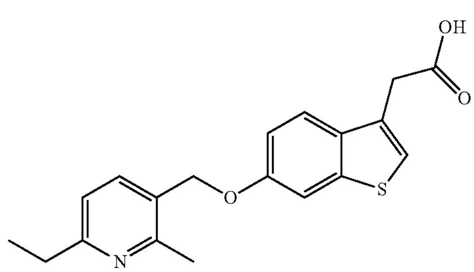 [SMILES: CCc1ccc(COc2ccc3c(CC(=O)O)csc3c2)c(C)n1] | 342.2 | | |

TABLE 11-continued

| Ex. No. Name | Structure | MS (ESI+): [M + H]+ | MS (ESI−): [M − H]− | 1H NMR |
|---|---|---|---|---|
| 106 Ethyl (6-((6-methoxy-2-methylpyridin-3-yl)methoxy)-1-benzothiophen-3-yl)acetate | | 372.1 | | |
| 107 (6-((6-Methoxy-2-methylpyridin-3-yl)methoxy)-1-benzothiophen-3-yl)acetic acid | | 344.2 | | |
| 108 Ethyl (6-((2-ethyl-4-methyl-1,3-thiazol-5-yl)methoxy)-1-benzothiophen-3-yl)acetate | | 376.1 | | |
| 109 (6-((2-Ethyl-4-methyl-1,3-thiazol-5-yl)methoxy)-1-benzothiophen-3-yl)acetic acid | | 348.1 | | |
| 110 Ethyl (6-((4-ethyl-2-methyl-1,3-thiazol-5-yl)methoxy)-1-benzothiophen-3-yl)acetate | | 376.1 | | |

TABLE 12

| Ex. No. | Name | Structure | MS (ESI+): [M + H]+ | MS (ESI−): [M − H]− | ¹H NMR |
|---|---|---|---|---|---|
| 111 | (6-((4-Ethyl-2-methyl-1,3-thiazol-5-yl)methoxy)-1-benzothiophen-3-yl) acetic acid | 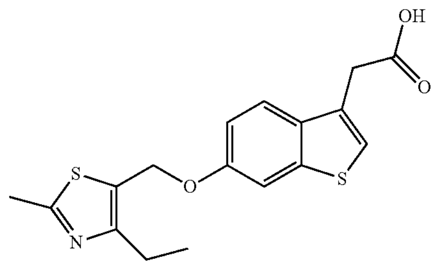 [SMILES: CCc1nc(C)sc1COc1ccc2c(CC(=O)O)csc2c1] | 348.1 | | |
| 112 | Methyl (6-((2,4-dichlorobenzyl)oxy)-7-methyl-1-benzothiophen-3-yl)acetate | 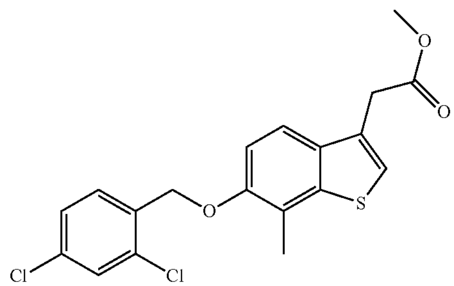 [SMILES: COC(=O)Cc1csc2c(C)c(OCc3ccc(Cl)cc3Cl)ccc12] | 392.9 | | |
| 113 | (6-((2,4-Dichlorobenzyl)oxy)-7-methyl-1-benzothiophen-3-yl)acetic acid | 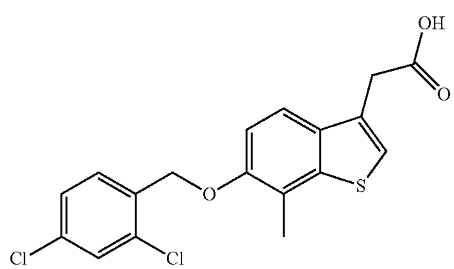 | | 379.0 | |
| 114 | Methyl (6-((2,6-dimethylpyridin-3-yl)methoxy)-7-methyl-1-benzothiophen-3-yl)acetate | 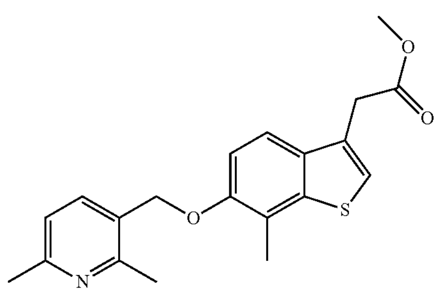 [SMILES: COC(=O)Cc1csc2c(C)c(OCc3ccc(C)nc3C)ccc12] | 356.2 | | |
| 115 | (6-((2,6-Dimethyl-pyridin-3-yl)methoxy)-7-methyl-1-benzothiophen-3-yl) acetic acid | 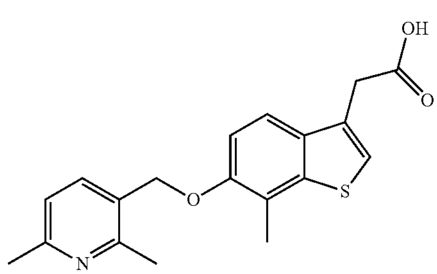 [SMILES: Cc1ccc(COc2ccc3c(CC(=O)O)csc3c2C)c(C)n1] | 342.1 | | |

TABLE 12-continued

| Ex. No. | Name | Structure | MS (ESI+): [M + H]+ | MS (ESI−): [M − H]− | 1H NMR |
|---|---|---|---|---|---|
| 116 | Methyl (6-((2,6-dimethylpyriidn-3-yl)methoxy)-4-methyl-1-benzothiophen-3-yl)acetate | 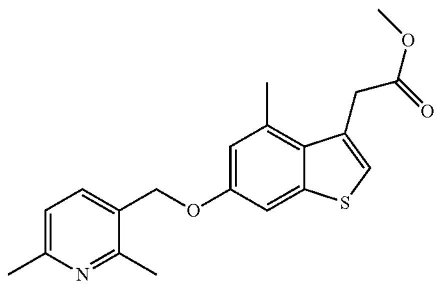 [SMILES: COC(=O)Cc1csc2cc(OCc3ccc(C)nc3C)cc(C)c12] | 356.2 | | |
| 117 | (6-((2,6-Dimethyl-pyridin-3-yl)methoxy)-4-methyl-1-benzothiophen-3-yl) acetic acid | 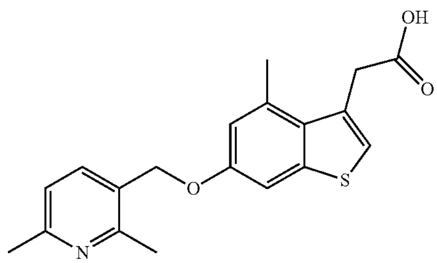 [SMILES: Cc1ccc(COc2cc(C)c3c(CC(=O)O)csc3c2)c(C)n1] | 342.1 | | |
| 118 | Ethyl (6-((2-methyl-4-(trifluoromethyl)-1,3-thiazol-5-yl)methoxy)-1-benzothiophen-3-yl)acetate | 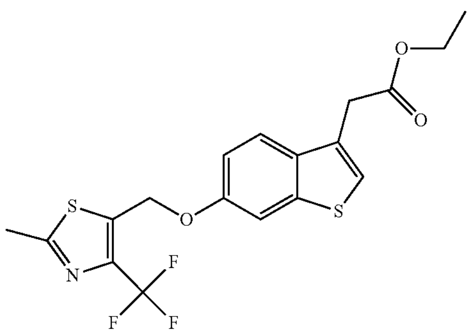 [SMILES: CCOC(=O)Cc1csc2cc(OCc3sc(C)nc3C(F)(F)F)ccc12] | | | $^1$H NMR (300 MHz, CDCl$_3$) δ 1.25 (3H, t, J = 7.19 Hz), 2.71 (3H, s), 3.81 (2H, d, J = 1.14 Hz), 4.17 (2H, q, J = 7.07 Hz), 5.40 (2H, d, J = 1.51 Hz), 7.06 (1H, dd, J = 8.71, 2.27 Hz), 7.22 (1H, s), 7.38 (1H, d, J = 2.27 Hz), 7.68 (1H, d, J = 8.71 Hz) |
| 119 | (6-((2-Methyl-4-(trifluoromethyl)-1,3-thiazol-5-yl)methoxy)-1-benzothiophen-3-yl) acetic acid | 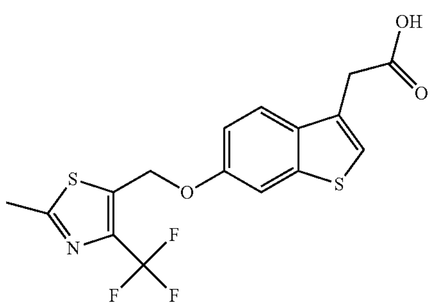 [SMILES: Cc1nc(C(F)(F)F)c(COc2ccc3c(CC(=O)O)csc3c2)s1] | 388.0 | | |
| 120 | Ethyl (6-((4-methyl-2-(tri-fluoromethyl)-1,3-thiazol-5-yl)methoxy)-1-benzothiophen-3-yl)acetate | 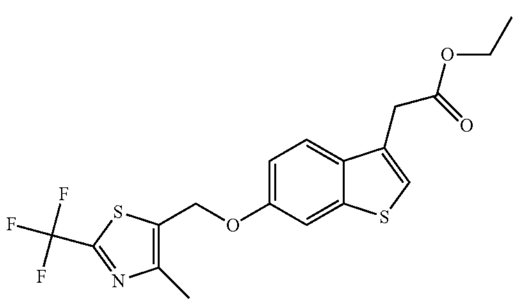 [SMILES: CCOC(=O)Cc1csc2cc(OCc3sc(C(F)(F)F)nc3C)ccc12] | 416.0 | | |

TABLE 13

| Ex. No. | Name | Structure | MS (ESI+): [M + H]+ | MS (ESI−): [M − H]− | 1H NMR |
|---|---|---|---|---|---|
| 121 | (6-((4-Methyl-2-(trifluoromethyl)-1,3-thiazol-5-yl)methoxy)-1-benzothiophen-3-yl)acetic acid | 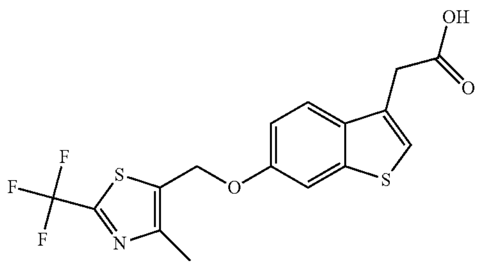 [SMILES: Cc1nc(C(F)(F)F)sc1COc1ccc2c(CC(=O)O)csc2c1] | 386.0 | | |
| 122 | Ethyl (6-((2-methoxy-6-methylpyridin-3-yl)methoxy)-1-benzothiophen-3-yl)acetate | 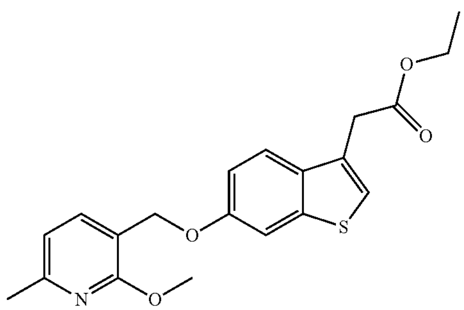 [SMILES: CCOC(=O)Cc1csc2cc(OCc3ccc(C)nc3OC)ccc12] | 372.2 | | |
| 123 | (6-((2-Methoxy-6-methylpyridin-3-yl)methoxy)-1-benzothiophen-3-yl)acetic acid | 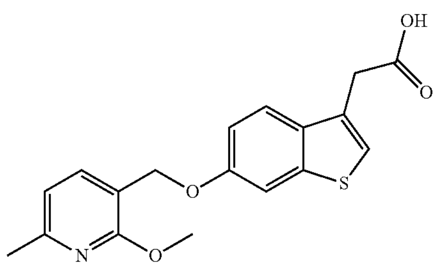 [SMILES: COc1nc(C)ccc1COc1ccc2c(CC(=O)O)csc2c1] | 344.0 | | |
| 124 | Ethyl (6-((3,5-dimethylpyrazin-2-yl)methoxy)-1-benzothiophen-3-yl)acetate | 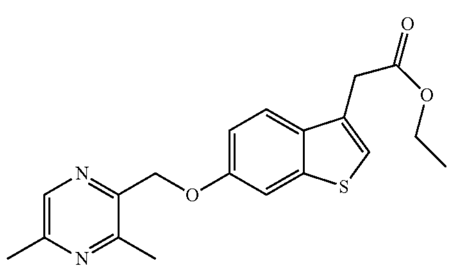 [SMILES: CCOC(=O)Cc1csc2cc(OCc3ncc(C)nc3C)ccc12] | 357.1 | | |
| 125 | (6-((3,5-Dimethylpyrazin-2-yl)methoxy)-1-benzothiophen-3-yl)acetic acid | 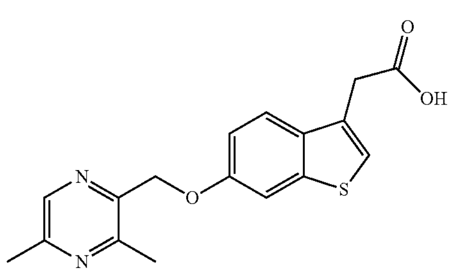 [SMILES: Cc1cnc(COc2ccc3c(CC(=O)O)csc3c2)c(C)n1] | 329.0 | | |

TABLE 13-continued

| Ex. No. Name | Structure | MS (ESI+): [M + H]+ | MS (ESI−): [M − H]− | 1H NMR |
|---|---|---|---|---|
| 126 Methyl (6-((3,5-dimethylpyrazin-2-yl)methoxy)-7-methyl-1-benzothiophen-3-yl)acetate | | 357.1 | | |
| 127 (6-((3,5-Dimethylpyrazin-2-yl)methoxy)-7-methyl-1-benzothiophen-3-yl)acetic acid | | | | 1H NMR (300 MHz, DMSO-d$_6$) δ 2.31 (3H, s), 2.46 (3H, s), 2.59 (3H, s), 3.78 (2H, s), 5.31 (2H, s), 7.29 (1H, d, J = 8.7 Hz), 7.39 (1H, s), 7.57 (1H, d, J = 8.7 Hz), 8.34 (1H, s), 12.39 (1H, brs). |
| 128 2-(6-((2,6-Dimethypyridin-3-yl)methoxy)-1-benzothiophen-3-yl)acetamide | | 327.1 | | |
| 129 2-(6-((2,4-Dichlorobenzyl)oxy)-1-benzothiophen-3-yl)-N-(methylsulfonyl)acetamide | | 442.0 | | |
| 130 Methyl (6-((2,4-dichlorobenzyl)oxy)-4-methoxy-1-benzothiophen-3-yl)acetate | | | | 1H NMR (300 MHz, CDCl$_3$) δ 3.66-3.73 (3H, m), 3.80-3.87 (3H, m), 3.95 (2H, s), 5.15 (2H, s), 6.46 (1H, d, J = 2.3 Hz), 6.88-6.94 (2H, m), 7.21-7.31 (1H, m), 7.44 (1H, d, J = 2.3 Hz), 7.51 (1H, d, J = 8.3 Hz). |

TABLE 14

| Ex. No. | Name | Structure | MS (ESI+): [M + H]+ | MS (ESI−): [M − H]− | 1H NMR |
|---|---|---|---|---|---|
| 131 | (6-((2,4-Dichlorobenzyl)oxy)-4-methoxy-1-benzothiophen-3-yl)acetic acid | 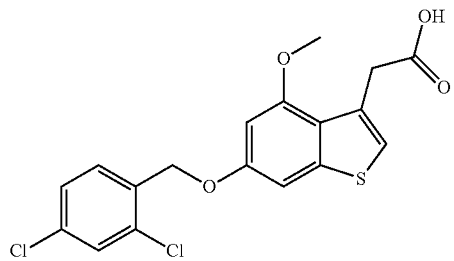 [SMILES: COc1cc(OCc2ccc(Cl)cc2Cl)cc2scc(CC(=O)O)c12] | | 394.9 | |
| 132 | Ethyl (6-((4-chloro-2-methylbenzyl)oxy)-1-benzothiophen-3-yl)acetate | 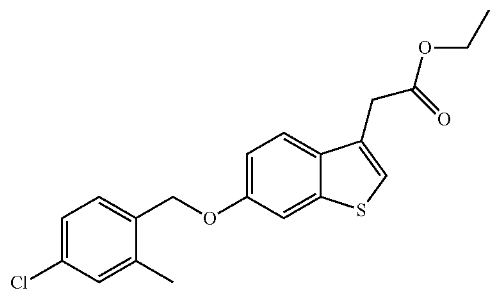 [SMILES: CCOC(=O)Cc1csc2cc(OCc3ccc(Cl)cc3C)ccc12] | | | 1H NMR (300 MHz, CDCl3) δ 1.25 (3H, t, J = 6.99 Hz), 2.37 (3H, s), 3.81 (2H, d, J = 0.76 Hz), 4.17 (2H, q, J = 7.68 Hz), 5.05 (2H, s), 7.08 (1H, dd, J = 8.69, 2.27 Hz), 7.16-7.24 (3H, m), 7.36 (1H, d, J = 8.31 Hz), 7.39 (1H, d, J = 2.27 Hz), 7.66 (1H, d, J = 8.69 Hz) |
| 133 | (6-((4-Chloro-2-methylbenzyl)oxy)-1-benzothiophen-3-yl)acetic acid | 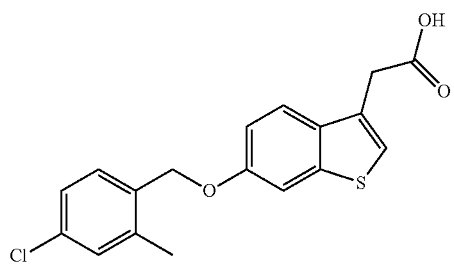 | | 345.1 | |
| 134 | Ethyl (6-((2-methyl-6-(trifluoromethyl)pyridin-3-yl)methoxy)-1-benzothiophen-3-yl)acetate | 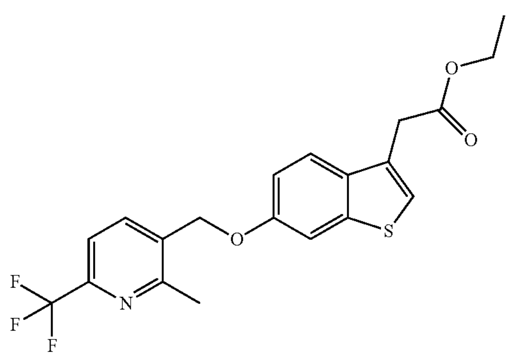 [SMILES: CCOC(=O)Cc1csc2cc(OCc3ccc(C(F)(F)F)nc3C)ccc12] | | 408.1 | |
| 135 | (6-((2-Methyl-6-(trifluoromethyl)pyridin-3-yl)methoxy)-1-benzothiophen-3-yl)acetic acid | 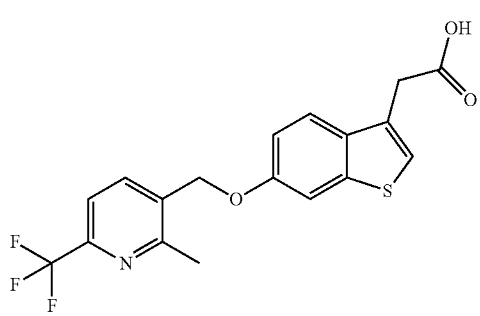 [SMILES: Cc1nc(C(F)(F)F)ccc1COc1ccc2c(CC(=O)O)csc2c1] | | 382.1 | |

TABLE 14-continued

| Ex. No. | Name | Structure | MS (ESI+): [M + H]+ | MS (ESI−): [M − H]− | 1H NMR |
|---|---|---|---|---|---|
| 136 | Ethyl (6-((4-methyl-2-(trifluoromethyl)pyrimidin-5-yl)methoxy)-1-benzothiophen-3-yl)acetate | 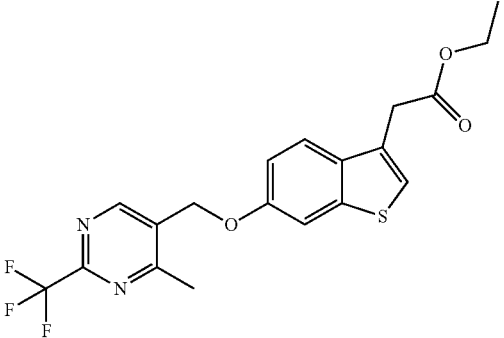 [SMILES: CCOC(=O)Cc1csc2cc(OCc3cnc(C(F)(F)F)nc3C)ccc12] | 409.1 | | |
| 137 | (6-((4-Methyl-2-(trifluoromethyl)pyrimidin-5-yl)methoxy)-1-benzothiophen-3-yl)acetic acid | 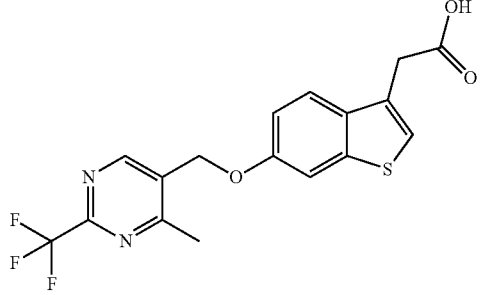 [SMILES: Cc1nc(C(F)(F)F)ncc1COc1ccc2c(CC(=O)O)csc2c1] | 380.9 | | |
| 138 | 2-(6-((2,4-Dichlorobenzyl)oxy)-1-benzothiophen-3-yl)-N-(ethylsulfonyl)acetamide | 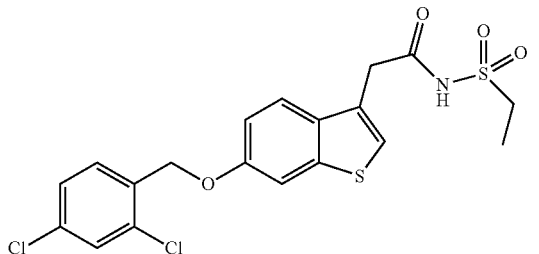 [SMILES: CCS(=O)(=O)NC(=O)Cc1csc2cc(OCc3ccc(Cl)cc3Cl)ccc12] | 457.9 | | |
| 139 | Methyl (4-methyl-6-((4-methyl-2-(trifluoromethyl)pyrimidin-5-yl)methoxy)-1-benzothiophen-3-yl)acetate | 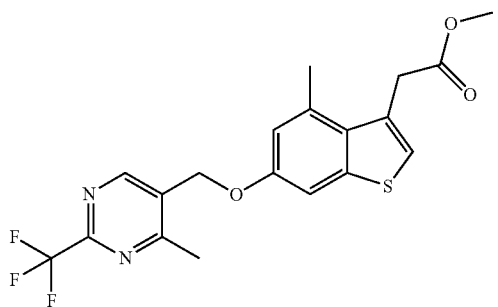 [SMILES: COC(=O)Cc1csc2cc(OCc3cnc(C(F)(F)F)nc3C)cc(C)c12] | 408.8 | | |

TABLE 14-continued

| Ex. No. | Name | Structure | MS (ESI+): [M + H]+ | MS (ESI−): [M − H]− | 1H NMR |
|---|---|---|---|---|---|
| 140 | (4-Methyl-6-((4-methyl-2-(trifluoromethyl)pyrimidin-5-yl)methoxy)-1-benzothiophen-3-yl)acetic acid | 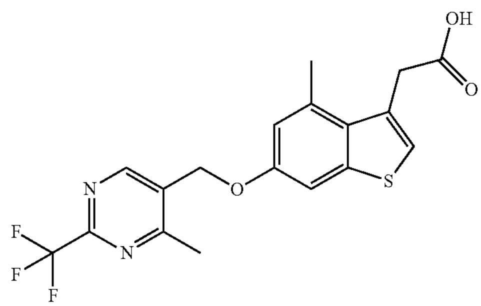 [SMILES: Cc1nc(C(F)(F)F)ncc1COc1cc(C)c2c(CC(=O)O)csc2c1] | 395.0 | | |

TABLE 15

| Ex. No. | Name | Structure | MS (ESI+): [M + H]+ | MS (ESI−): [M − H]− | 1H NMR |
|---|---|---|---|---|---|
| 141 | Ethyl 2-(6-((2,6-dimethylpyridin-3-yl)methoxy)-1-benzothiophen-3-yl)propanoate | 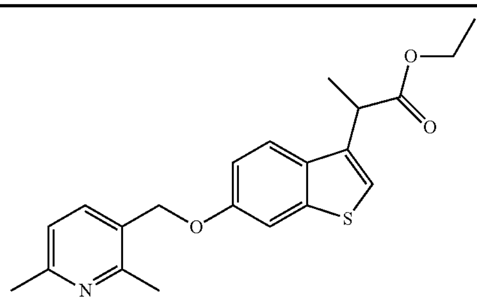 | 370.1 | | |
| 142 | 2-(6-((2,6-Dimethylpyridin-3-yl)methoxy)-1-benzothiophen-3-yl)propanoic acid | 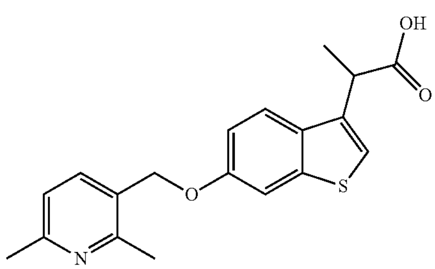 [SMILES: Cc1ccc(COc2ccc3c(C(C)C(=O)O)csc3c2)c(C)n1] | 342.1 | | |
| 143 | Ethyl (6-((2-methyl-4-(trifluoromethyl)benzyl)oxy)-1-benzothiophen-3-yl)acetate | 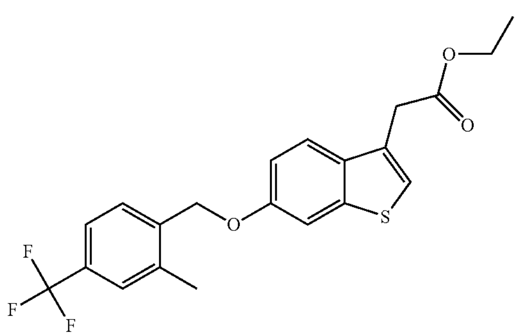 [SMILES: CCOC(=O)Cc1csc2cc(OCc3ccc(C(F)(F)F)cc3C)ccc12] | 407.0 | | |

TABLE 15-continued

| Ex. No. | Name | Structure | MS (ESI+): [M + H]+ | MS (ESI−): [M − H]− | ¹H NMR |
|---|---|---|---|---|---|
| 144 | (6-((2-Methyl-4-(trifluoromethyl)benzyl)oxy)-1-benzothiophen-3-yl)acetic acid | 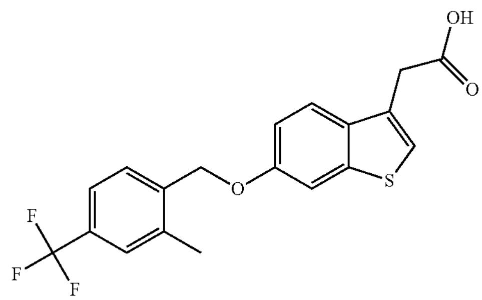 [SMILES: Cc1cc(C(F)(F)F)ccc1COc1ccc2c(CC(=O)O)csc2c1] | 379.0 | | |
| 145 | Methyl (6-((2,6-dimethylpyridin-3-yl)methoxy)-4-methoxy-1-benzothiophen-3-yl)acetate | 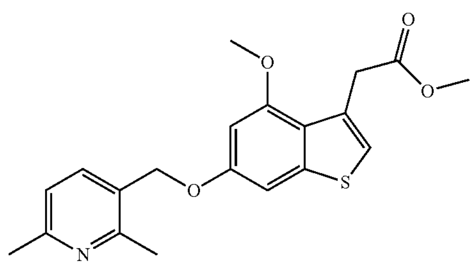 | 372.2 | | |
| 146 | (6-((2,6-Dimethylpyridin-3-yl)methoxy)-4-methoxy-1-benzothiophen-3-yl)acetic acid | 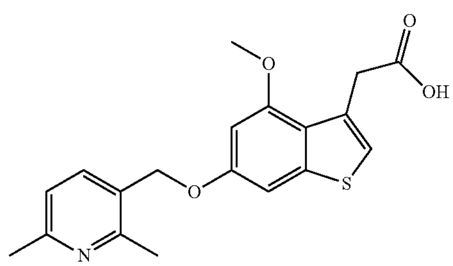 | 358.1 | | |
| 147 | Methyl (6-((2,4-dichlorobenzyl)oxy)-4-vinyl-1-benzothiophen-3-yl)acetate | 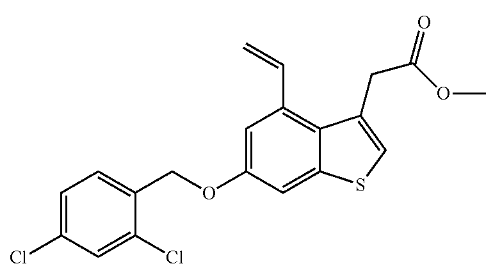 [SMILES: C=Cc1cc(OCc2ccc(Cl)cc2Cl)cc2scc(CC(=O)OC)c12] | | | ¹H NMR (300 MHz, CDCl₃) δ 3.68-3.73 (3H, m), 3.98 (2H, s), 5.37-5.44 (1H, m), 5.54-5.61 (2H, m), 7.05 (1H, d, J = 2.6 Hz), 7.13 (1H, s), 7.27 (1H, s), 7.28-7.40 (3H, m), 7.44 (1H, d, J = 2.3 Hz), 7.53 (1H, d, J = 8.3 Hz). |
| 148 | (6-((2,4-Dichlorobenzyl)oxy)-4-vinyl-1-benzothiophen-3-yl)acetic acid | 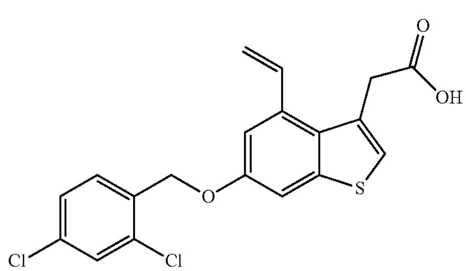 [SMILES: C=Cc1cc(OCc2ccc(Cl)cc2Cl)cc2scc(CC(=O)O)c12] | 391.0 | | |

TABLE 15-continued

| Ex. No. | Name | Structure | MS (ESI+): [M + H]+ | MS (ESI−): [M − H]− | 1H NMR |
|---|---|---|---|---|---|
| 149 | Methyl (4-cyclopropyl-6-((2,6-dimethylpyridin-3-yl)methoxy)-1-benzothiophen-3-yl)acetate | 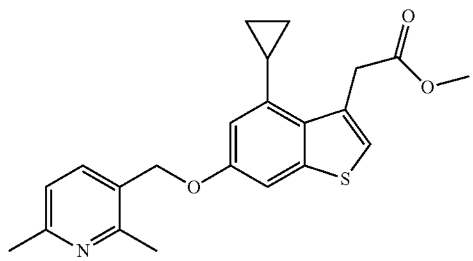 | 382.1 | | |
| 150 | (4-Cyclopropyl-6-((2,6-dimethylpyridin-3-yl)methoxy)-1-benzothiophen-3-yl)acetic acid | 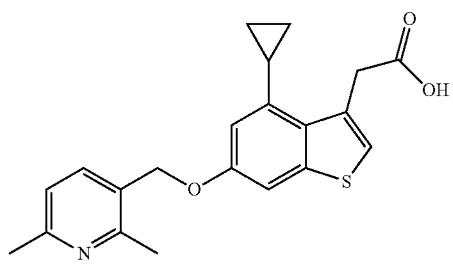 [SMILES: Cc1ccc(COc2cc(C3CC3)c3c(CC(=O)O)csc3c2)c(C)n1] | 368.2 | | |

TABLE 16

| Ex. No. | Name | Structure | MS (ESI+): [M + H]+ | MS (ESI−): [M − H]− | 1H NMR |
|---|---|---|---|---|---|
| 151 | Methyl (4-cyclopropyl-6-((2,4-dichlorobenzyl)oxy)-1-benzothiophen-3-yl)acetate | 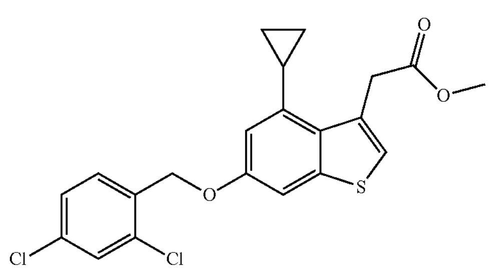 [SMILES: COC(=O)Cc1csc2cc(OCc3ccc(Cl)cc3Cl)cc(C3CC3)c12] | 418.9 | | |
| 152 | (4-Cyclopropyl-6-((2,4-dichlorobenzyl)oxy)-1-benzothiophen-3-yl)acetic acid | 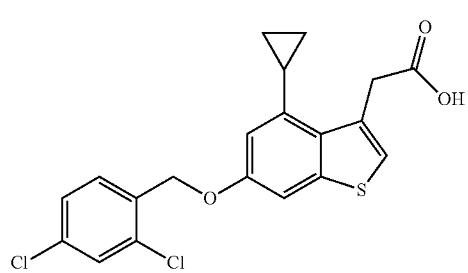 [SMILES: O=C(O)Cc1csc2cc(OCc3ccc(Cl)cc3Cl)cc(C3CC3)c12] | 404.9 | | |

TABLE 16-continued

| Ex. No. | Name | Structure | MS (ESI+): [M + H]+ | MS (ESI−): [M − H]− | ¹H NMR |
|---|---|---|---|---|---|
| 153 | Methyl (6-((2,6-dimethylpyridin-3-yl)methoxy)-4-ethyl-1-benzothiophen-3-yl)acetate | 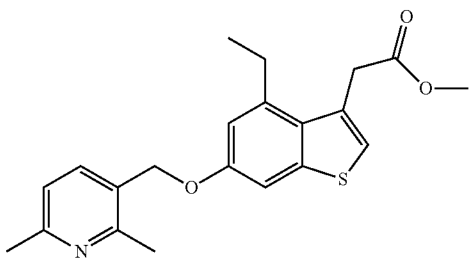 | | | ¹H NMR (300 MHz, CDCl$_3$) δ 1.29 (3H, t, J = 7.3 Hz), 2.54 (3H, s), 2.58 (3H, s), 3.00 (2H, q, J = 7.3 Hz), 3.72 (3H, s), 4.00 (2H, s), 5.05 (2H, s), 6.88 (1H, d, J = 2.6 Hz), 7.02 (1H, d, J = 7.9 Hz), 7.11 (1H, s), 7.23 (1H, d, J = 2.3 Hz), 7.61 (1H, d, J = 7.9 Hz). |
| 154 | (6-((2,6-Dimethyl-pyridin-3-yl)methoxy)-4-ethyl-1-benzothiophen-3-yl)acetic acid | 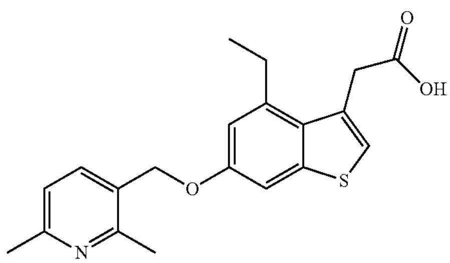 [SMILES: CCc1cc(OCc2ccc(C)nc2C)cc2scc(CC(=O)O)c12] | | 356.2 | |
| 155 | Methyl (6-((2,6-dimethylpyridin-3-yl)methoxy)-4,7-dimethyl-1-benzothiophen-3-yl)acetate | 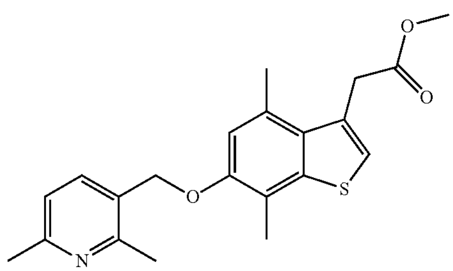 | 370.3 | | |
| 156 | (6-((2,6-Dimethyl-pyridin-3-yl)methoxy)-4,7-dimethyl-1-benzo-thiophen-3-yl)acetic acid | 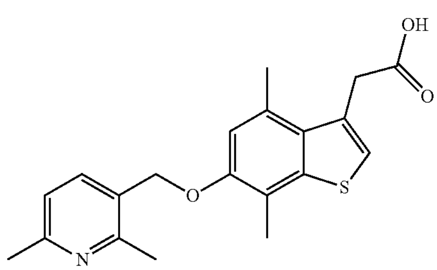 | | 356.2 | |
| 157 | Methyl (6-((2,4-dichlorobenzyl)oxy)-4,7-dimethyl-1-benzothiophen-3-yl)acetate | 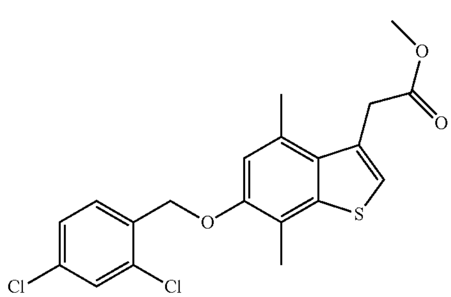 | 406.9 | | |

TABLE 16-continued

| Ex. No. | Name | Structure | MS (ESI+): [M + H]+ | MS (ESI−): [M − H]− | 1H NMR |
|---|---|---|---|---|---|
| 158 | (6-((2,4-Dichloro-benzyl)oxy)-4,7-dimethyl-1-benzo-thiophen-3-yl)acetic acid | 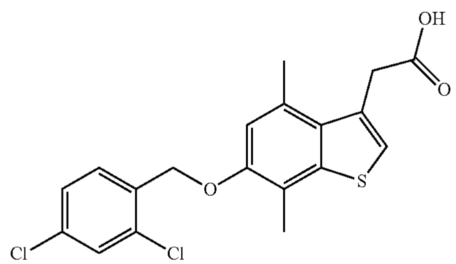 | 392.9 | | |
| 159 | Methyl (6-((2,4-dimethylpyrimidin-5-yl)methoxy)-4-methyl-1-benzothiophen-3-yl)acetate | 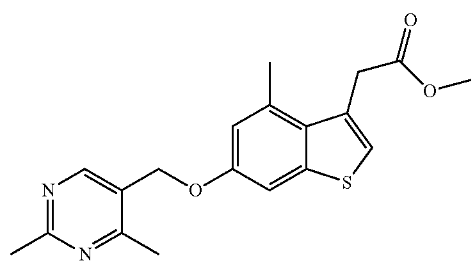 | 357.2 | | |
| 160 | (6-((2,4-Dimethylpyrimidin-5-yl)methoxy)-4-methyl-1-benzo-thiophen-3-yl)acetic acid | 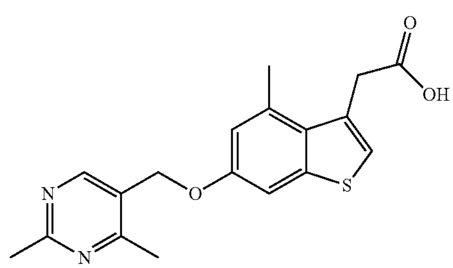 [SMILES: Cc1ncc(COc2cc(C)c3c(CC(=O)O)csc3c2)c(C)n1] | 343.1 | | |

TABLE 17

| Ex. No. | Name | Structure | MS (ESI+): [M + H]+ | MS (ESI−): [M − H]− | 1H NMR |
|---|---|---|---|---|---|
| 161 | Methyl (6-((2,6-dimethylpyridin-3-yl)methoxy)-4-(hydroxymethyl)-1-benzothiophen-3-yl)acetate | 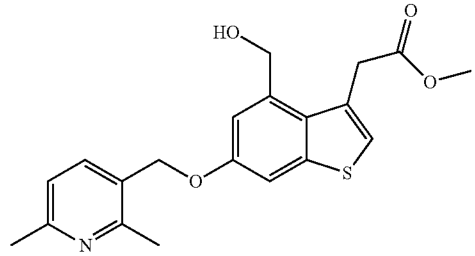 | | | 1H NMR (300 MHz, CDCl$_3$) δ 2.54 (3H, d, J = 1.9 Hz), 2.57 (3H, s), 3.72 (3H, s), 4.13-4.17 (2H, m), 4.96 (2H, s), 5.07 (2H, d, J = 1.9 Hz), 5.48 (1H, brs), 7.02 (1H, dd, J = 7.8, 2.8 Hz), 7.06-7.11 (1H, m), 7.19 (1H, s), 7.32-7.37 (1H, m), 7.57-7.62 (1H, m). |

TABLE 17-continued

| Ex. No. Name | Structure | MS (ESI+): [M + H]+ | MS (ESI−): [M − H]− | ¹H NMR |
|---|---|---|---|---|
| 162 (6-((2,6-Dimethyl-pyridin-3-yl)methoxy)-4-(hydroxymethyl)-1-benzothiophen-3-yl)acetic acid | | 358.1 | | |
| 163 Ethyl (6-((4-chloro-2,6-dimethylpyridin-3-yl)methoxy)-1-benzothiophen-3-yl)acetate | | | | ¹H NMR (300 MHz, CDCl₃) δ 1.25 (3H, t, J = 6.99 Hz), 2.52 (3H, s), 2.64 (3H, s), 3.81 (2H, s), 4.13-4.21 (2H, m), 5.23 (2H, s), 7.04-7.13 (2H, m), 7.20 (1H, s), 7.47 (1H, d, J = 2.27 Hz), 7.67 (1H, d, J = 9.06 Hz). |
| 164 (6-((4-Chloro-2,6-dimethylpyridin-3-yl)methoxy)-1-benzothiophen-3-yl)acetic acid | | 362.0 | | |
| 165 Methyl (6-((4-chloro-2,6-dimethylpyridin-3-yl)methoxy)-4-methyl-1-benzothiophen-3-yl)acetate | | 390.1 | | |
| 166 (6-((4-Chloro-2,6-dimethylpyridin-3-yl)methoxy)-1-benzothiophen-3-yl)acetic acid | | 376.1 | | |

TABLE 17-continued

| Ex. No. | Name | Structure | MS (ESI+): [M + H]+ | MS (ESI−): [M − H]− | 1H NMR |
|---|---|---|---|---|---|
| 167 | Methyl (6-((4,6-dimethylpyridin-3-yl)methoxy)-4-methyl-1-benzothiophen-3-yl)acetate | 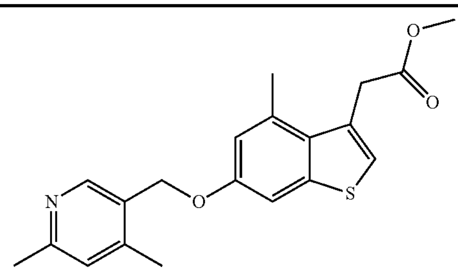 | 356.2 | | |
| 168 | (6-((4,6-Dimethyl-pyridin-3-yl)methoxy)-4-methyl-1-benzo-thiophen-3-yl)acetic acid | 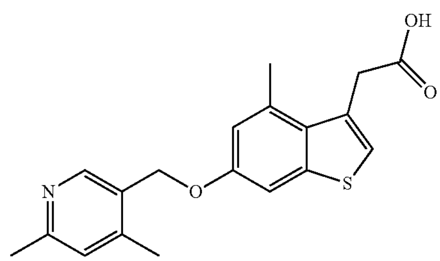 [SMILES: Cc1cc(C)c(COc2cc(C)c3c(CC(=O)O)csc3c2)cn1] | 342.1 | | |
| 169 | Methyl (4-(dimethyl-carbamoyl)-6-((2-methyl-6-(trifluoromethyl)pyridin-3-yl)methoxy)-1-benzothiophen-3-yl)acetate | 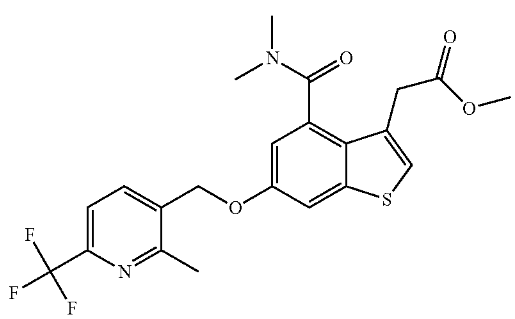 [SMILES: COC(=O)Cc1csc2cc(OCc3ccc(C(F)(F)F)nc3C)cc(C(=O)N(C)C)c12] | | | 1H NMR (300 MHz, CDCl3) δ 2.67 (3H, s), 2.83 (3H, s), 3.14 (3H, s), 3.70 (3H, s), 3.72-3.81 (1H, m), 3.93-4.04 (1H, m), 5.16 (2H, s), 6.94 (1H, d, J = 2.3 Hz), 7.24 (1H, s), 7.42 (1H, d, J = 2.5 Hz), 7.56 (1H, d, J = 8.0 Hz), 7.93 (1H, d, J = 7.8 Hz). |
| 170 | (4-(Dimethyl-carbamoyl)-6-((2-methyl-6-(trifluoromethyl)pyridin-3-yl)methoxy)-1-benzothiophen-3-yl)acetic acid | 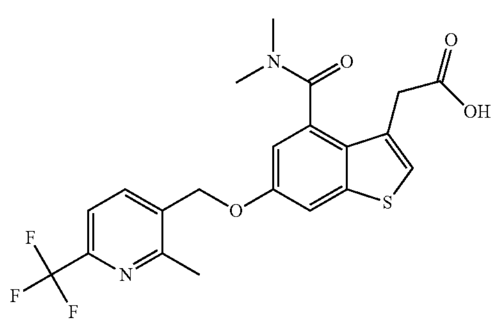 [SMILES: Cc1nc(C(F)(F)F)ccc1COc1cc(C(=O)N(C)C)c2c(CC(=O)O)csc2c1] | 453.1 | | |

TABLE 18

| Ex. No. | Name | Structure | MS (ESI+): [M + H]+ | MS (ESI−): [M − H]− | ¹H NMR |
|---|---|---|---|---|---|
| 171 | Methyl (4-(dimethyl-carbamoyl)-6-((2,6-dimethyl-pyridin-3-yl)methoxy)-1-benzothiophen-3-yl)acetate | 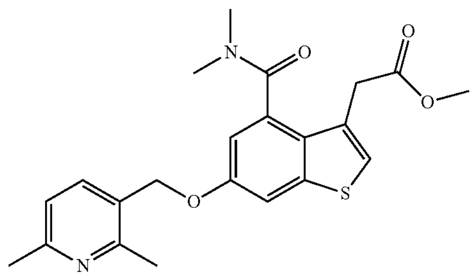 | 413.2 | | |
| 172 | (4-(Dimethyl-carbamoyl)-6-((2,6-dimethyl-pyridin-3-yl)methoxy)-1-benzothiophen-3-yl)acetic acid | 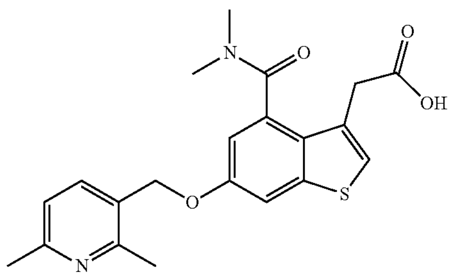 [SMILES: Cc1ccc(COc2cc(C(=O)N(C)C)c3c(CC(=O)O)csc3c2)c(C)n1] | 399.1 | | |
| 173 | Ethyl (6-((2-chloro-6-(trifluoromethyl)pyridin-3-yl)methoxy)-1-benzothiophen-3-yl)acetate | 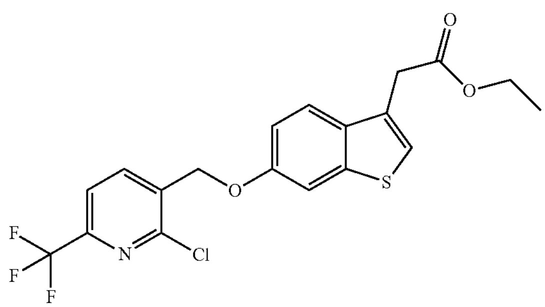 [SMILES: CCOC(=O)Cc1csc2cc(OCc3ccc(C(F)(F)F)nc3Cl)ccc12] | 428.0 | | |
| 174 | (6-((2-Chloro-6-(trifluoromethyl)pyridin-3-yl)methoxy)-1-benzothiophen-3-yl)acetic acid | 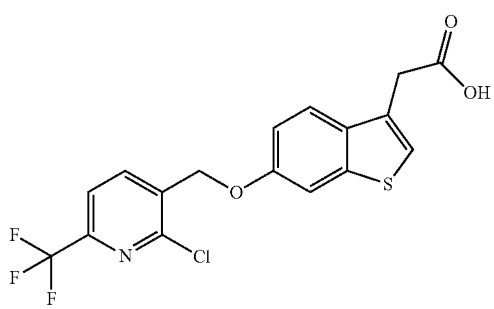 [SMILES: O=C(O)Cc1csc2cc(OCc3ccc(C(F)(F)F)nc3Cl)ccc12] | 400.0 | | |
| 175 | Ethyl (6-((2-(pyrrolidin-1-yl)-6-(trifluoro-methyl)pyridin-3-yl)methoxy)-1-benzothiophen-3-yl)acetate | 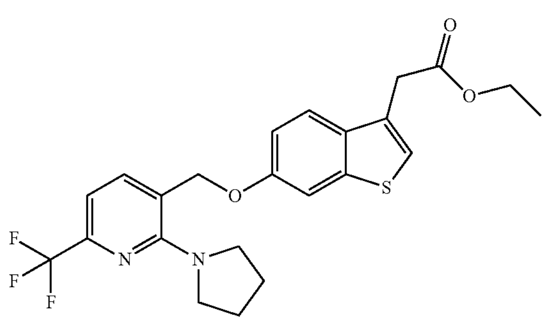 [SMILES: CCOC(=O)Cc1csc2cc(OCc3ccc(C(F)(F)F)nc3N3CCCC3)ccc12] | 465.2 | | |

TABLE 18-continued

| Ex. No. | Name | Structure | MS (ESI+): [M + H]+ | MS (ESI−): [M − H]− | 1H NMR |
|---|---|---|---|---|---|
| 176 | (6-((2-(Pyrrolidin-1-yl)-6-(trifluoromethyl)pyridin-3-yl)methoxy)-1-benzothiophen-3-yl)acetic acid | 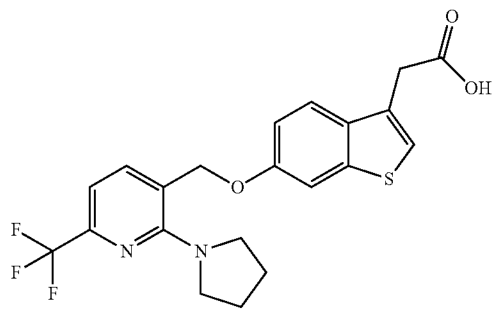 [SMILES: O=C(O)Cc1csc2cc(OCc3ccc(C(F)(F)F)nc3N3CCCC3)ccc12] | 437.0 | | |
| 177 | (4-Chloro-6-((4-methyl-2-(trifluoromethyl)pyrimidin-5-yl)methoxy)-1-benzothiophen-3-yl)acetic acid | 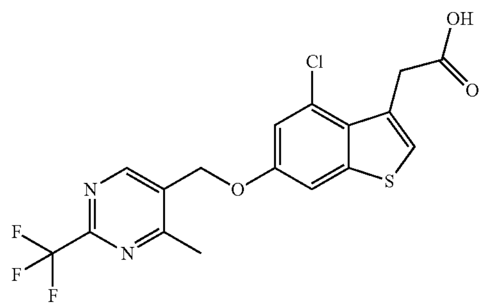 [SMILES: Cc1nc(C(F)(F)F)ncc1COc1cc(Cl)c2c(CC(=O)O)csc2c1] | | 415.0 | |
| 178 | 2-(4-Chloro-6-((1-methyl-3-(trifluoromethyl)-1H-pyrazol-5-yl)methoxy)-1-benzothiophen-3-yl)acetamide | 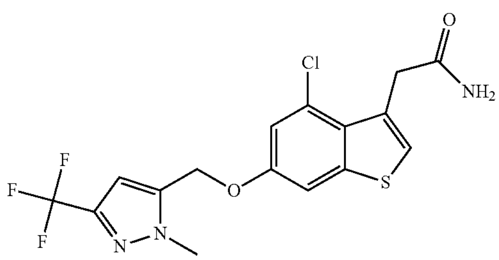 [SMILES: Cn1nc(C(F)(F)F)cc1COc1cc(Cl)c2c(CC(N)=O)csc2c1] | 404.2 | | |
| 179 | Ethyl (6-((E)-2-(2,6-dimethylpyridin-3-yl)vinyl)-1-benzothiophen-3-yl)acetate | 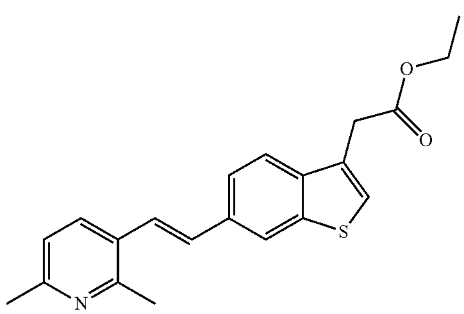 [SMILES: CCOC(=O)Cc1csc2cc(/C=C/c3ccc(C)nc3C)ccc12] | | | 1H NMR (300 MHz, CDCl3) δ 1.22-1.29 (3H, m), 2.54 (3H, s), 2.66 (3H, s), 3.86 (2H, s), 4.19 (2H, q, J = 7.07 Hz), 7.03 (1H, d, J = 7.95 Hz), 7.05 (1H, d, J = 15.90 Hz), 7.31 (1H, d, J = 16.28 Hz), 7.36 (1H, s), 7.59 (1H, dd, J = 8.33, 1.51 Hz), 7.71-7.82 (2H, m), 7.95 (1H, d, J = 0.76 Hz) |
| 180 | Ethyl (6-((Z)-2-(2,6-dimethylpyridin-3-yl)vinyl)-1-benzothiophen-3-yl)acetate | 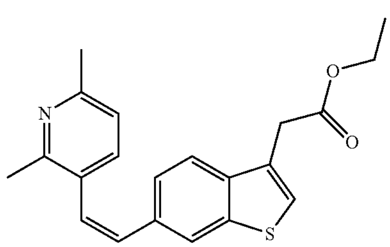 [SMILES: CCOC(=O)Cc1csc2cc(/C=C\c3ccc(C)nc3C)ccc12] | | | 1H NMR (300 MHz, CDCl3) δ 1.24 (3H, t, J = 7.19 Hz), 2.51 (3H, s), 2.52 (3H, s), 3.79 (2H, d, J = 0.76 Hz), 4.16 (2H, q, J = 7.19 Hz), 6.61 (1H, d, J = 12.12 Hz), 6.77 (1H, d, J = 12.49 Hz), 6.82 (1H, d, J = 7.95 Hz), 7.12 (1H, dd, J = 8.33, 1.51 Hz), 7.27-7.33 (2H, m), 7.54 (1H, d, J = 8.33 Hz), 7.61 (1H, s) |

TABLE 19

| Ex. No. | Name | Structure | MS (ESI+): [M + H]+ | MS (ESI−): [M − H]− | ¹H NMR |
|---|---|---|---|---|---|
| 181 | Ethyl (6-(2-(2,6-dimethylpyridin-3-yl)ethyl)-1-benzothiophen-3-yl)acetate | 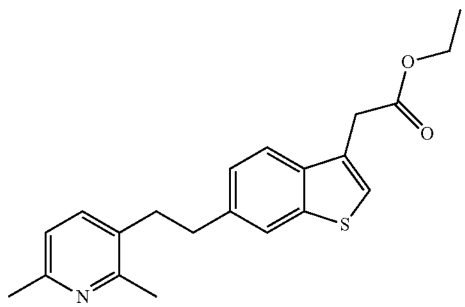 [SMILES: CCOC(=O)Cc1csc2cc(CCc3ccc(C)nc3C)ccc12] | 354.2 | | |
| 182 | (6-(2-(2,6-Dimethylpyridin-3-yl)ethyl)-1-benzothiophen-3-yl)acetic acid | 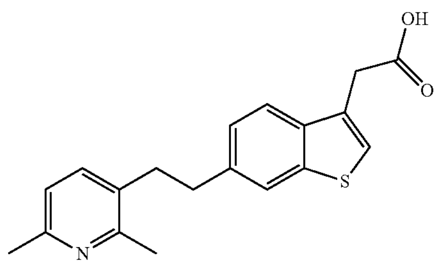 [SMILES: Cc1ccc(CCc2ccc3c(CC(=O)O)csc3c2)c(C)n1] | 326.2 | | |
| 183 | (6-((E)-2-(2,6-Dimethylpyridin-3-yl)vinyl)-1-benzothiophen-3-yl)acetic acid | 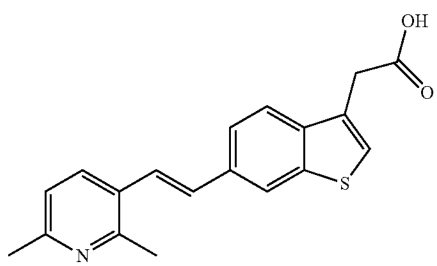 [SMILES: Cc1ccc(/C=C/c2ccc3c(CC(=O)O)csc3c2)c(C)n1] | 324.1 | | |
| 184 | (4-(Difluoromethyl)-6-((2,6-dimethylpyridin-3-yl)methoxy)-1-benzothiophen-3-yl)acetic acid | 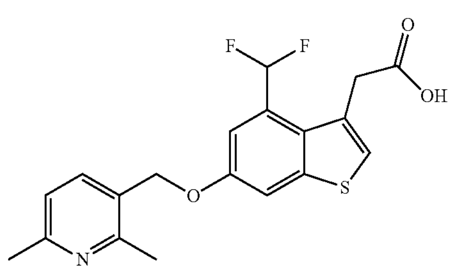 [SMILES: Cc1ccc(COc2cc(C(F)F)c3c(CC(=O)O)csc3c2)c(C)n1] | 378.1 | | |
| 185 | (4-(Difluoromethyl)-6-((1-methyl-3-(trifluoromethyl)-1H-pyrazol-5-yl)methoxy)-1-benzothiophen-3-yl)acetic acid | 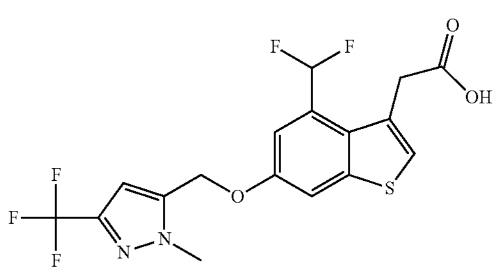 [SMILES: Cn1nc(C(F)(F)F)cc1COc1cc(C(F)F)c2c(CC(=O)O)csc2c1] | 419.0 | | |

TABLE 19-continued

| Ex. No. | Name | Structure | MS (ESI+): [M + H]+ | MS (ESI−): [M − H]− | 1H NMR |
|---|---|---|---|---|---|
| 186 | Methyl (4-chloro-6-((2-methyl-5-(trifluoromethyl)-3-furyl)methoxy)-1-benzothiophen-3-yl)acetate | 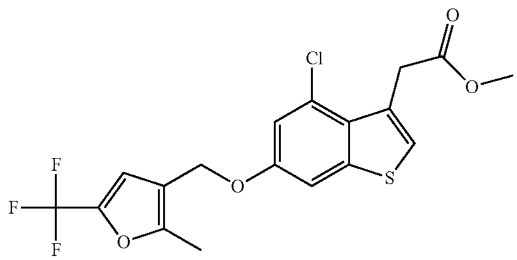 [SMILES: COC(=O)Cc1csc2cc(OCc3cc(C(F)(F)F)oc3C)cc(Cl)c12] | 416.9 | | |
| 187 | (4-Chloro-6-((2-methyl-5-(trifluoromethyl)-3-furyl)methoxy)-1-benzothiophen-3-yl)acetic acid | 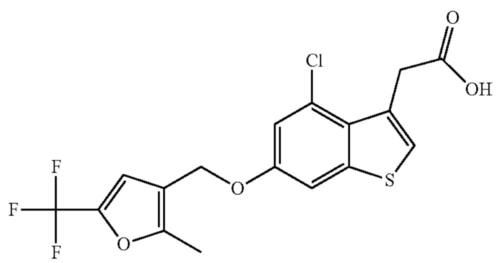 [SMILES: Cc1oc(C(F)(F)F)cc1COc1cc(Cl)c2c(CC(=O)O)csc2c1] | | | 1H NMR (300 MHz, DMSO-d6) δ 2.38 (3H, s), 4.00 (2H, s), 5.03 (2H, s), 7.07-7.12 (1H, m), 7.48 (1H, s), 7.68 (1H, d, J = 2.3 Hz), 8.26-8.31 (1H, m), 12.36(1H, brs) |
| 188 | Methyl (4-chloro-6-((1,3-dimethyl-1H-pyrazol-4-yl)methoxy)-1-benzothiophen-3-yl)acetate | 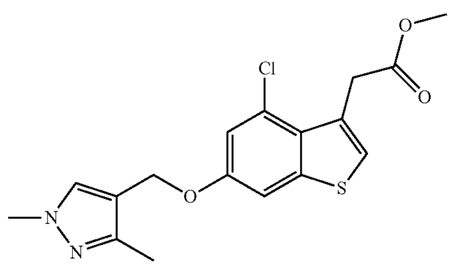 | 365.0 | | |
| 189 | (4-Chloro-6-((1,3-dimethyl-1H-pyrazol-4-yl)methoxy)-1-benzothiophen-3-yl)acetic acid | 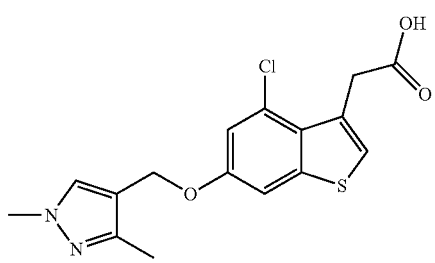 [SMILES: Cc1nn(C)cc1COc1cc(Cl)c2c(CC(=O)O)csc2c1] | 351.1 | | |
| 190 | 1-((4-Chloro-6-((1-methyl-3-(trifluoromethyl)-1H-pyrazol-5-yl)methoxy)-1-benzothiophen-3-yl)methyl)urea | 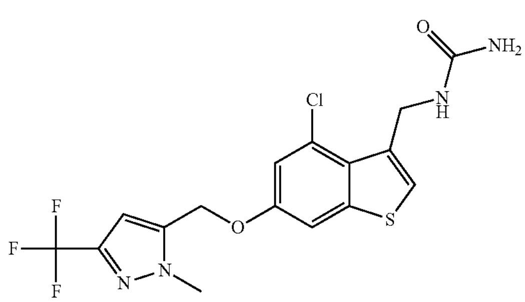 [SMILES: Cn1nc(C(F)(F)F)cc1COc1cc(Cl)c2c(CNC(N)=O)csc2c1] | 419.0 | | |

TABLE 20

| Ex. No. | Name | Structure | MS (ESI+): [M + H]+ | MS (ESI−): [M − H]− | ¹H NMR |
|---|---|---|---|---|---|
| 191 | Methyl 6-((2,4-dichlorobenzyl)oxy)-1-benzofuran-3-carboxylate | 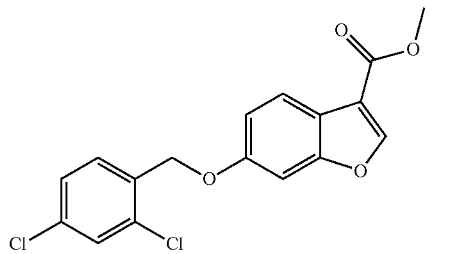 [SMILES: COC(=O)c1coc2cc(OCc3ccc(Cl)cc3Cl)ccc12] | | 349.3 | |
| 192 | 6-((2,4-Dichlorobenzyl)oxy)-1-benzofuran-3-carboxylic acid | 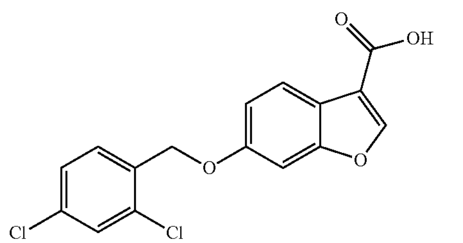 [SMILES: O=C(O)c1coc2cc(OCc3ccc(Cl)cc3Cl)ccc12] | | 335.2 | |
| 193 | Methyl ((3S)-6-((2,4-dichlorobenzyl)oxy)-2,3-dihydro-1-benzofuran-3-yl)acetate | 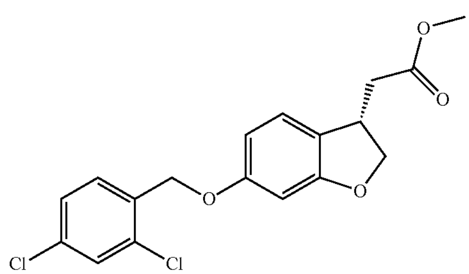 [SMILES: COC(=O)C[C@@H]1COc2cc(OCc3ccc(Cl)cc3Cl)ccc21] | | | ¹H NMR (300 MHz, DMSO-d₆) δ 2.55-2.67 (1H, m), 2.73-2.85 (1H, m), 3.63 (3H, s), 3.66-3.79 (1H, m), 4.22 (1H, dd, J = 9.0, 6.8 Hz), 4.69 (1H, t, J = 9.0 Hz), 5.08 (2H, s), 6.44-6.52 (2H, m), 7.07-7.14 (1H, m), 7.44-7.50 (1H, m), 7.55-7.62 (1H, m), 7.68 (1H, d, J = 2.3 Hz). |
| 194 | Methyl (6-((2,4-dichlorobenzyl)oxy)-1-benzofuran-3-yl)acetate | 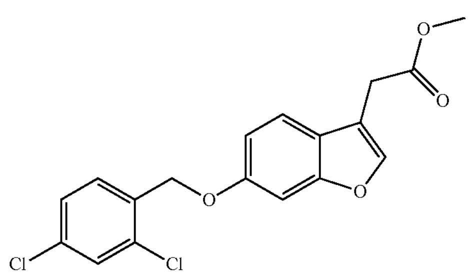 [SMILES: COC(=O)Cc1coc2cc(OCc3ccc(Cl)cc3Cl)ccc12] | 365.2 | | |
| 195 | (6-((2,4-Dichlorobenzyl)oxy)-1-benzofuran-3-yl)acetic acid | 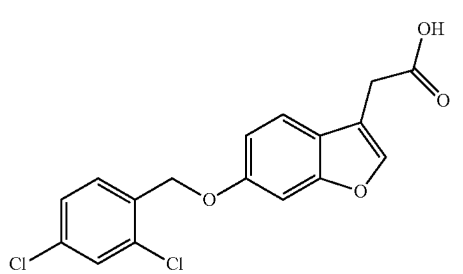 [SMILES: O=C(O)Cc1coc2cc(OCc3ccc(Cl)cc3Cl)ccc12] | | 349.0 | |

TABLE 20-continued

| Ex. No. | Name | Structure | MS (ESI+): [M + H]+ | MS (ESI−): [M − H]− | ¹H NMR |
|---|---|---|---|---|---|
| 196 | N-(2-(6-(2,4-Dichlorobenzyloxy)-1-benzofuran-3-yl)ethyl)acetamide | 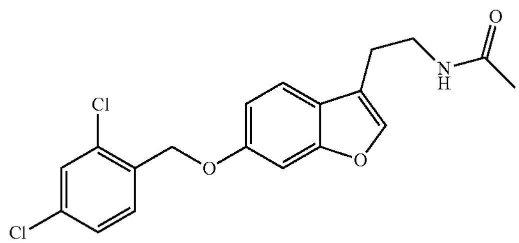 [SMILES: CC(=O)NCCc1coc2cc(OCc3ccc(Cl)cc3Cl)ccc12] | 376.0 | | |
| 197 | N-(2-((3S)-6-(2,4-Dichlorobenzyloxy)-2,3-dihydro-1-benzofuran-3-yl)ethyl)acetamide | 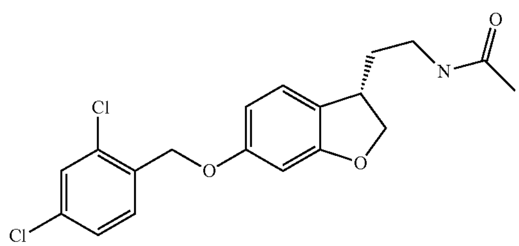 [SMILES: CC(=O)NCC[C@@H]1COc2cc(OCc3ccc(Cl)cc3Cl)ccc21] | 380.0 | | |
| 198 | N-(2-((3S)-6-(2,4-Dichlorobenzyloxy)-2,3-dihydro-1-benzofuran-3-yl)ethyl)propanamide | 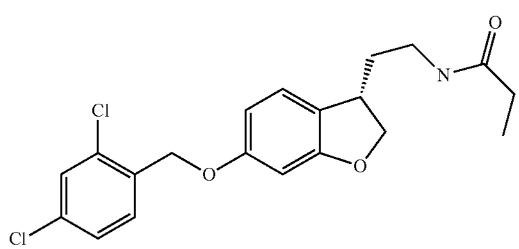 [SMILES: CCC(=O)NCC[C@@H]1COc2cc(OCc3ccc(Cl)cc3Cl)ccc21] | 394.0 | | |
| 199 | N-(2-((3S)-6-(2,4-Dichlorobenzyloxy)-2,3-dihydro-1-benzofuran-3-yl)ethyl)-2-hydroxy-3-methylbutanamide | 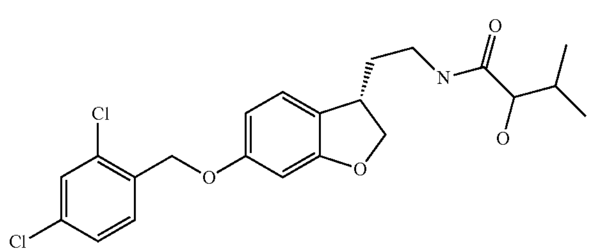 [SMILES: CC(C)C(O)C(=O)NCC[C@@H]1COc2cc(OCc3ccc(Cl)cc3Cl)ccc21] | 437.9 | | |
| 200 | N-(2-((3S)-6-(2,4-Dichlorobenzyloxy)-2,3-dihydro-1-benzofuran-3-yl)ethyl)-2,2,2-trifluoroacetamide | 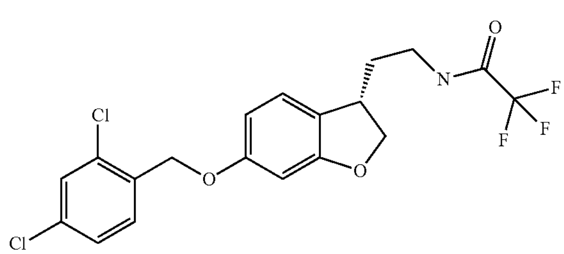 [SMILES: O=C(NCC[C@@H]1COc2cc(OCc3ccc(Cl)cc3Cl)ccc21)C(F)(F)F] | 432.1 | | |

TABLE 21

| Ex. No. | Name | Structure | MS (ESI+): [M + H]+ | MS (ESI−): [M − H]− | ¹H NMR |
|---|---|---|---|---|---|
| 201 | Ethyl ((2-((3S)-6-((2,4-dichloro-benzyl)oxy)-2,3-dihydro-1-benzofuran-3-yl)ethyl)sulfanyl) acetate | 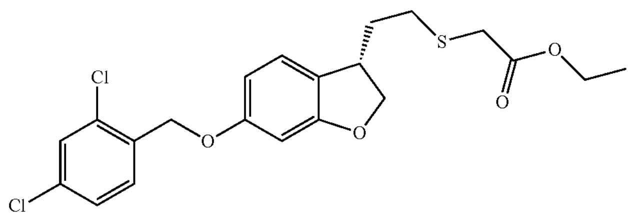 [SMILES: CCOC(=O)CSCC[C@@H]1COc2cc(OCc3ccc(Cl)cc3Cl)ccc21] | 440.9 | | |
| 202 | ((2-((3S)-6-((2,4-Dichlorobenzyl) oxy)-2,3-dihydro-1-benzofuran-3-yl)ethyl)sulfanyl) acetic acid | 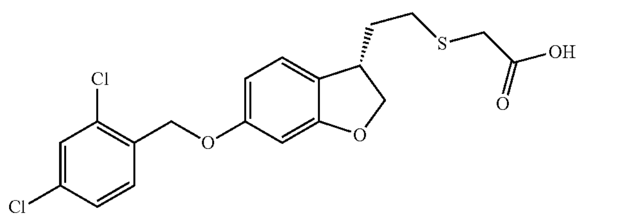 [SMILES: O=C(O)CSCC[C@@H]1COc2cc(OCc3ccc(Cl)cc3Cl)ccc21] | | 410.9 | |
| 203 | Ethyl ((2-(6-((2,4-dichlorobenzyl) oxy)-1-benzofuran-3-yl)ethyl)sulfanyl) acetate | 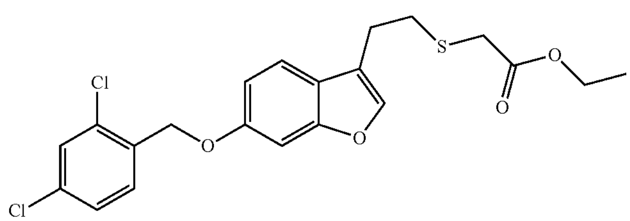 [SMILES: CCOC(=O)CSCCc1coc2cc(OCc3ccc(Cl)cc3Cl)ccc12] | 439.0 | | |
| 204 | 2-(2-(6-(2,4-Dichlorobenzyloxy)-1-benzofuran-3-yl)ethylsulfanyl) acetic acid | 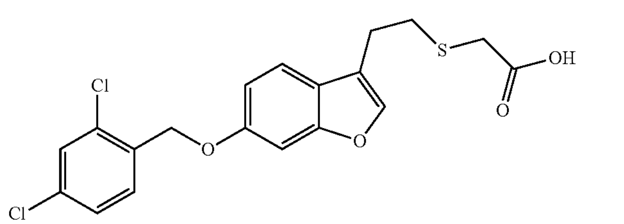 [SMILES: O=C(O)CSCCc1coc2cc(OCc3ccc(Cl)cc3Cl)ccc12] | | 409.0 | |
| 205 | Ethyl 2-(2-(6-(2,4-dichlorobenzyloxy)-1-benzofuran-3-yl)ethylsulfonyl) acetate | 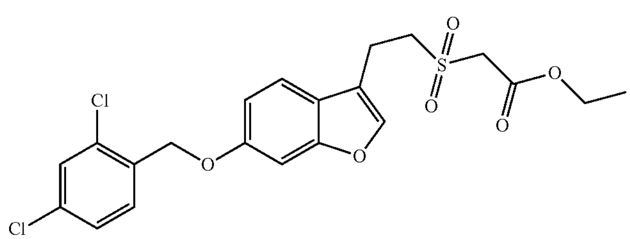 [SMILES: CCOC(=O)CS(=O)(=O)CCc1coc2cc(OCc3ccc(Cl)cc3Cl)ccc12] | 471.1 | | |
| 206 | 2-(2-(6-(2,4-Dichlorobenzyloxy)-1-benzofuran-3-yl)ethylsulfonyl) acetic acid | 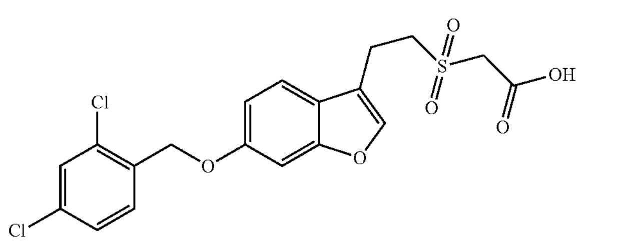 [SMILES: O=C(O)CS(=O)(=O)CCc1coc2cc(OCc3ccc(Cl)cc3Cl)ccc12] | | | ¹H NMR (300 MHz, DMSO-d₆) δ 3.05-3.14 (2H, m), 3.61-3.70 (2H, m), 4.30 (2H, s), 5.20 (2H, s), 7.00 (1H, dd, J = 8.7, 2.3 Hz), 7.31 (1H, d, J = 2.3 Hz), 7.49 (1H, dd, J = 8.3, 2.3 Hz), 7.59 (1H, d, J = 8.7 Hz), 7.65 (1H, d, J = 8.3 Hz), 7.70 (1H, d, J = 1.9 Hz), 7.80 (1H, s). |

TABLE 21-continued

| Ex. No. | Name | Structure | MS (ESI+): [M + H]+ | MS (ESI−): [M − H]− | ¹H NMR |
|---|---|---|---|---|---|
| 207 | Methyl N-((6-((2,4-dichlorobenzyl)oxy)-1-benzofuran-3-yl)acetyl)serinate | 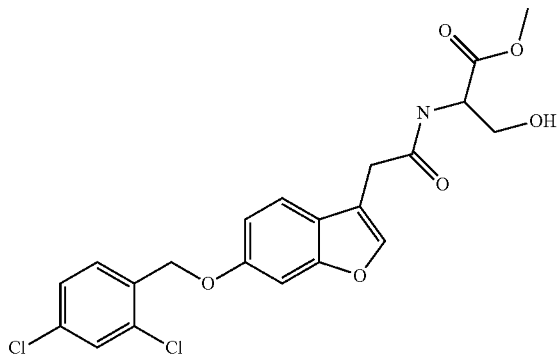 [SMILES: COC(=O)C(CO)NC(=O)Cc1coc2cc(OCc3ccc(Cl)cc3Cl)ccc12] | 450.1 | | |
| 208 | N-((6-((2,4-Dichlorobenzyl)oxy)-1-benzofuran-3-yl)acetyl)serine | 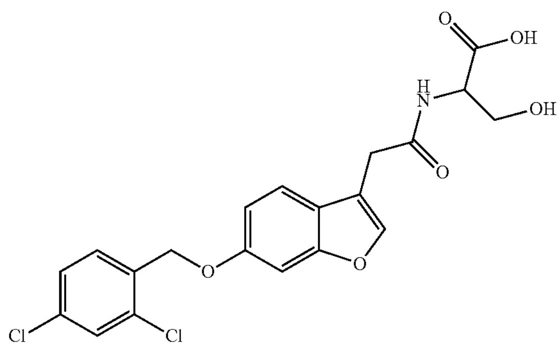 [SMILES: O=C(Cc1coc2cc(OCc3ccc(Cl)cc3Cl)ccc12)NC(CO)C(=O)O] | 436.1 | | |
| 209 | Methyl ((3S)-5-chloro-6-((2,4-dichlorobenzyl)oxy)-2,3-dihydro-1-benzofuran-3-yl)acetate | 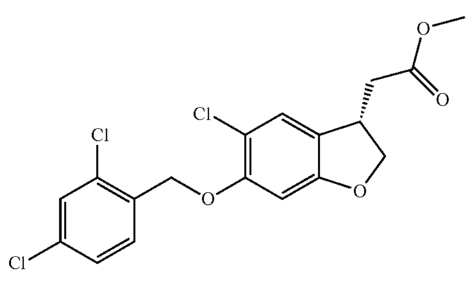 | | | ¹H NMR (300 MHz, DMSO-d₆) δ 2.63 (1H, dd, J = 17.0, 9.1 Hz), 2.87 (1H, dd, J = 16.8, 5.5 Hz), 3.63 (3H, s), 3.69-3.82 (1H, m), 4.26 (1H, dd, J = 9.1, 6.8 Hz), 4.73 (1H, t, J = 9.1 Hz), 5.17 (2H, s), 6.78 (1H, s), 7.30 (1H, s), 7.48-7.55 (1H, m), 7.60-7.66 (1H, m), 7.70 (1H, d, J = 2.3 Hz). |
| 210 | ((3S)-5-Chloro-6-((2,4-dichlorobenzyl)oxy)-2,3-dihydro-1-benzofuran-3-yl)acetic acid | 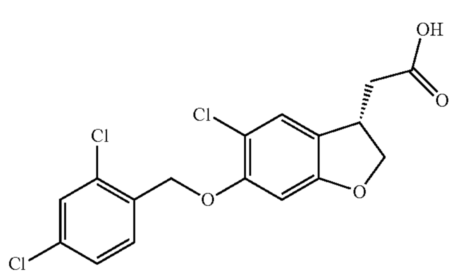 [SMILES: O=C(O)C[C@@H]1COc2cc(OCc3ccc(Cl)cc3Cl)c(Cl)cc21] | | 385.0 | |

TABLE 22

| Ex. No. | Name | Structure | MS (ESI+): [M + H]+ | MS (ESI−): [M − H]− | 1H NMR |
|---|---|---|---|---|---|
| 211 | Methyl (5-chloro-6-((2,4-dichlorobenzyl)oxy)-1-benzofuran-3-yl)acetate | 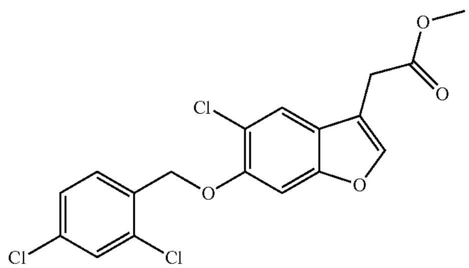 [SMILES: COC(=O)Cc1coc2cc(OCc3ccc(Cl)cc3Cl)c(Cl)cc12] | 397.0 | | |
| 212 | (5-Chloro-6-((2,4-dichlorobenzyl)oxy)-1-benzofuran-3-yl)acetic acid | 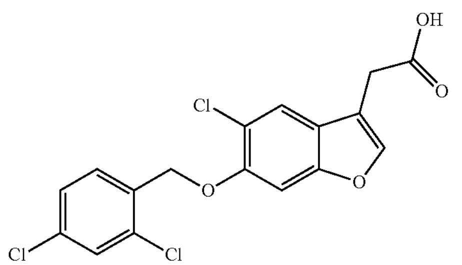 [SMILES: O=C(O)Cc1coc2cc(OCc3ccc(Cl)cc3Cl)c(Cl)cc12] | 383.0 | | |
| 213 | Methyl ((3S)-5-bromo-6-((2,4-dichlorobenzyl)oxy)-2,3-dihydro-1-benzofuran-3-yl)acetate | 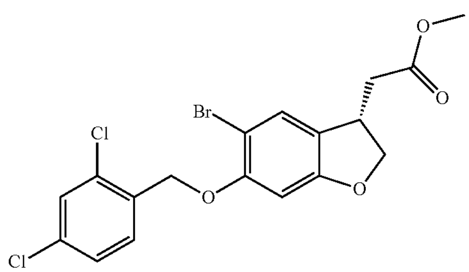 [SMILES: COC(=O)C[C@@H]1COc2cc(OCc3ccc(Cl)cc3Cl)c(Br)cc21] | 442.9 | | |
| 214 | Methyl (5-bromo-6-((2,4-dichlorobenzyl)oxy)-1-benzofuran-3-yl)acetate | 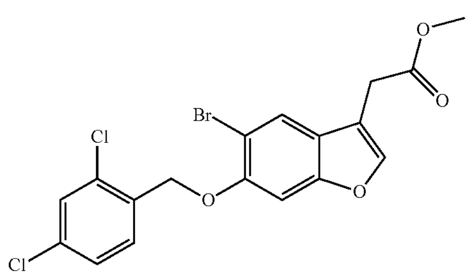 [SMILES: COC(=O)Cc1coc2cc(OCc3ccc(Cl)cc3Cl)c(Br)cc12] | | | 1H NMR (300 MHz, CDCl$_3$) δ 3.66 (2H, s), 3.75 (3H, s), 5.21 (2H, s), 7.09 (1H, s), 7.29-7.35 (1H, m), 7.43 (1H, d, J = 2.3 Hz), 7.56 (1H, s), 7.69 (1H, d, J = 8.3 Hz), 7.76 (1H, s). |
| 215 | Methyl (6-((2,4-dichlorobenzyl)oxy)-5-methyl-1-benzofuran-3-yl)acetate | 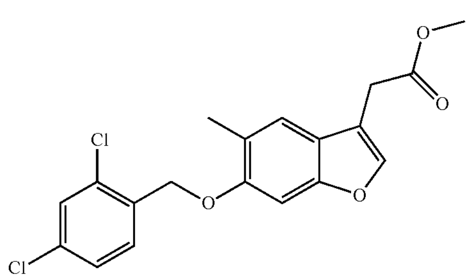 [SMILES: COC(=O)Cc1coc2cc(OCc3ccc(Cl)cc3Cl)c(C)cc12] | 377.2 | | |

TABLE 22-continued

| Ex. No. | Name | Structure | MS (ESI+): [M + H]+ | MS (ESI−): [M − H]− | ¹H NMR |
|---|---|---|---|---|---|
| 216 | (6-((2,4-Dichlorobenzyl)oxy)-5-methyl-1-benzofuran-3-yl)acetic acid | 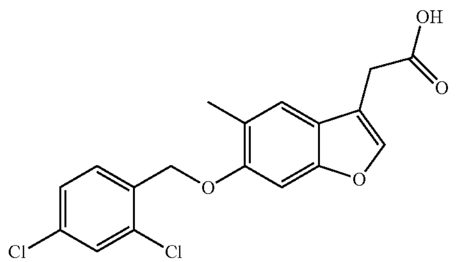 [SMILES: Cc1cc2c(CC(=O)O)coc2cc1OCc1ccc(Cl)cc1Cl] | | 363.1 | |
| 217 | Methyl (5-cyclopropyl-6-((2,4-dichlorobenzyl)oxy)-1-benzofuran-3-yl)acetate | 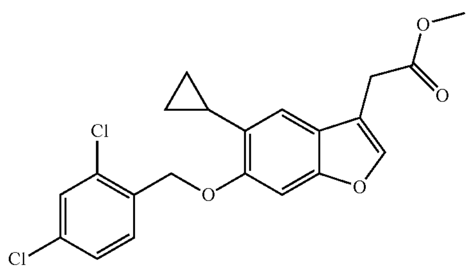 [SMILES: COC(=O)Cc1coc2cc(OCc3ccc(Cl)cc3Cl)c(C3CC3)cc12] | 403.1 | | |
| 218 | (5-Cyclopropyl-6-((2,4-dichlorobenzyl)oxy)-1-benzofuran-3-yl)acetic acid | 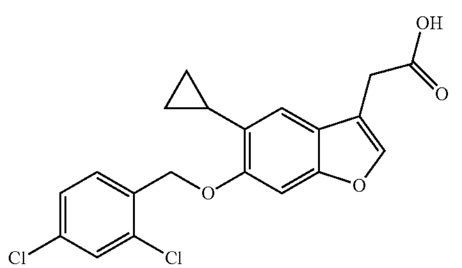 [SMILES: O=C(O)Cc1coc2cc(OCc3ccc(Cl)cc3Cl)c(C3CC3)cc12] | | 389.0 | |
| 219 | Methyl (5-(4-chlorophenyl)-6-((2,4-dichlorobenzyl)oxy)-1-benzofuran-3-yl)acetate | 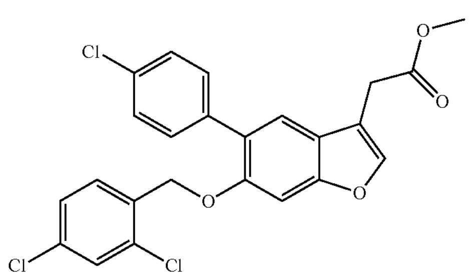 [SMILES: COC(=O)Cc1coc2cc(OCc3ccc(Cl)cc3Cl)c(-c3ccc(Cl)cc3)cc12] | 472.9 | | |
| 220 | Methyl (6-((2,4-dichlorobenzyl)oxy)-5-(1-methyl-1H-pyrazol-4-yl)-1-benzofuran-3-yl)acetate | 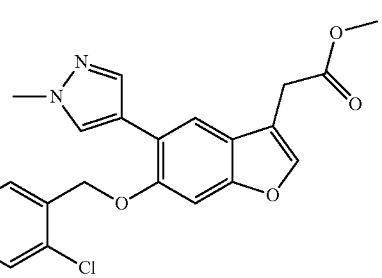 | 445.3 | | |

TABLE 23

| Ex. No. | Name | Structure | MS (ESI+): [M + H]+ | MS (ESI−): [M − H]− | 1H NMR |
|---|---|---|---|---|---|
| 221 | (6-((2,4-Dichlorobenzyl)oxy)-5-(1-methyl-1H-pyrazol-4-yl)-1-benzofuran-3-yl)acetic acid | 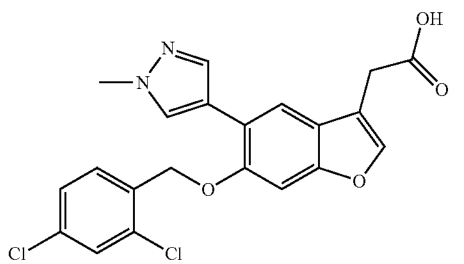 [SMILES: Cn1cc(-c2cc3c(CC(=O)O)coc3cc2OCc2ccc(Cl)cc2Cl)cn1] | 431.0 | | |
| 222 | (5-(4-Chlorophenyl)-6-((2,4-dichlorobenzyl)oxy)-1-benzofuran-3-yl)acetic acid | 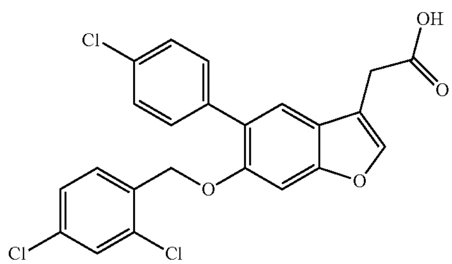 [SMILES: O=C(O)Cc1coc2cc(OCc3ccc(Cl)cc3Cl)c(-c3ccc(Cl)cc3)cc12] | 459.1 | | |
| 223 | Methyl (6-((2,4-dichlorobenzyl)oxy)-5-(1,3,5-trimethyl-1H-pyrazol-4-yl)-1-benzofuran-3-yl)acetate | 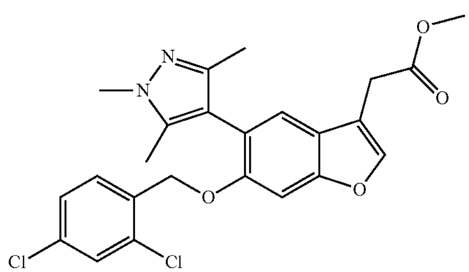 [SMILES: COC(=O)Cc1coc2cc(OCc3ccc(Cl)cc3Cl)c(-c3c(C)nn(C)c3C)cc12] | 473.0 | | |
| 224 | (6-((2,4-Dichlorobenzyl)oxy)-5-(1,3,5-trimethyl-1H-pyrazol-4-yl)-1-benzofuran-3-yl)acetic acid | 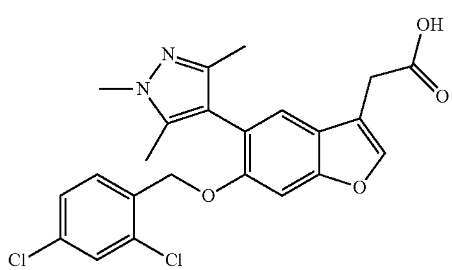 [SMILES: Cc1nn(C)c(C)c1-c1cc2c(CC(=O)O)coc2cc1OCc1ccc(Cl)cc1Cl] | 459.1 | | |
| 225 | Methyl ((3S)-7-bromo-5-chloro-6-((2,4-dichlorobenzyl)oxy)-2,3-dihydro-1-benzofuran-3-yl)acetate | 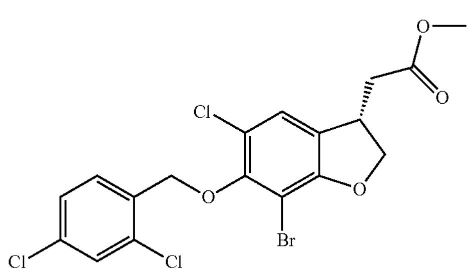 [SMILES: COC(=O)C[C@@H]1COc2c1cc(Cl)c(OCc1ccc(Cl)cc1Cl)c2Br] | | | 1HNMR (300 MHz, CDCl3) δ 2.57-2.71 (1H, m), 2.72-2.85 (1H, m), 3.74 (3H, s), 3.90-4.07 (1H, m), 4.33-4.45 (1H, m), 4.90 (1H, t, J = 9.2 Hz), 5.09 (2H, s), 7.15 (1H, d, J = 1.1 Hz), 7.32 (1H, dd, J = 8.5, 2.1 Hz), 7.39-7.45 (1H, m), 7.75 (1H, d, J = 8.3 Hz). |

TABLE 23-continued

| Ex. No. | Name | Structure | MS (ESI+): [M + H]+ | MS (ESI−): [M − H]− | ¹H NMR |
|---|---|---|---|---|---|
| 226 | ((3S)-7-Bromo-5-chloro-6-((2,4-dichlorobenzyl)oxy)-2,3 dihydro-1-benzofuran-3-yl)acetic acid | 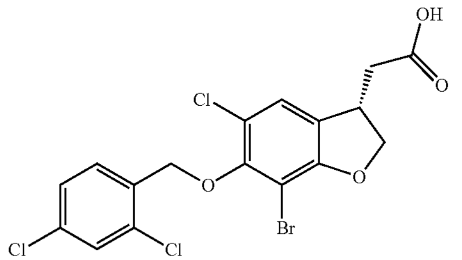 [SMILES: O=C(O)C[C@@H]1COc2c1cc(Cl)c(OCc1ccc(Cl)cc1Cl)c2Br] | | | ¹H NMR (400 MHz, DMSO-d₆) δ 2.62 (1H, dd, J = 16.6, 9.1 Hz), 2.85 (1H, dd, J = 16.8, 5.1 Hz), 3.82-3.98 (1H, m), 4.37 (1H, dd, J = 9.3, 7.4 Hz), 4.86 (1H, t, J = 9.3 Hz), 5.05 (2H, s), 7.43 (1H, d, J = 1.1 Hz), 7.52 (1H, dd, J = 8.3, 1.9 Hz), 7.70 (1H, d, J = 1.9 Hz), 7.72 (1H, d, J = 8.3 Hz), 12.54 (1H, s). |
| 227 | Methyl (7-bromo-5-chloro-6-((2,4-dichlorobenzyl)oxy)-1-benzofuran-3-yl)acetate | 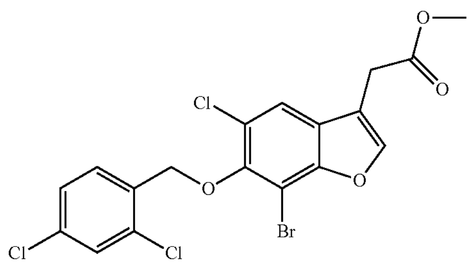 [SMILES: COC(=O)Cc1coc2c(Br)c(OCc3ccc(Cl)cc3Cl)c(Cl)cc12] | | | ¹H NMR (300 MHz, CDCl₃) δ 3.67 (2H, s), 3.76 (3H, s), 5.15 (2H, s), 7.34 (1H, dd, J = 8.3, 2.3 Hz), 7.43 (1H, d, J = 2.3 Hz), 7.58 (1H, s), 7.72 (1H, s), 7.79 (1H, d, J = 8.3 Hz). |
| 228 | (7-Bromo-5-chloro-6-((2,4-dichlorobenzyl)oxy)-1-benzofuran-3-yl)acetic acid | 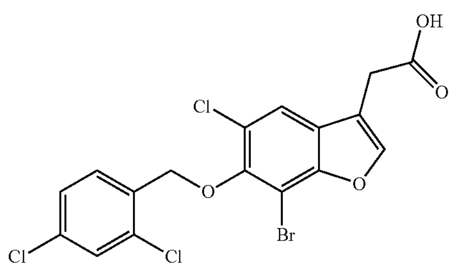 [SMILES: O=C(O)Cc1coc2c(Br)c(OCc3ccc(Cl)cc3Cl)c(Cl)cc12] | | 460.9 | |
| 229 | Methyl ((3S)-6-(1-(2,4 dichlorophenyl)ethoxy)-2,3-dihydro-1-benzofuran-3-yl)acetate | 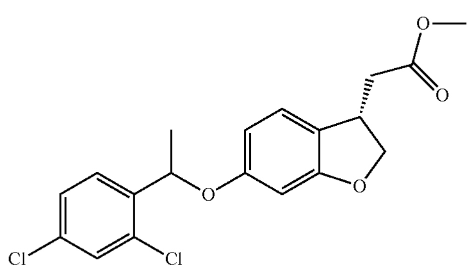 [SMILES: COC(=O)C[C@@H]1COc2cc(OC(C)c3ccc(Cl)cc3Cl)ccc21] | | | ¹H NMR (300 MHz, CDCl₃) δ 1.56 (6H, s), 2.51 (1H, dd, J = 16.47, 9.28 Hz), 2.70 (1H, dd, J = 16.47, 5.49 Hz), 3.70-3.81 (1H, m), 4.21 (1H, ddd, J = 9.18, 6.15, 1.70 Hz), 4.71 (1H, td, J = 9.09, 2.27 Hz), 5.56 (1H, q, J = 6.18 Hz), 6.22-6.33 (2H, m), 6.94 (1H, d, J = 8.33 Hz), 7.19 (1H, dd, J = 8.52, 2.08 Hz), 7.34-7.43 (2H, m) |
| 230 | ((3S)-6-(1-(2,4-Dichlorophenyl)ethoxy)-2,3-dihydro-1-benzofuran-3-yl)acetic acid | 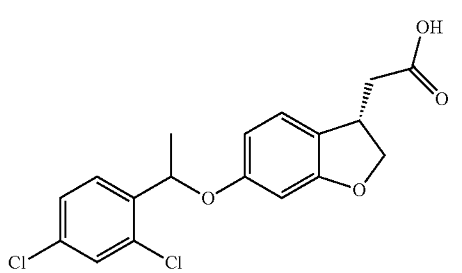 [SMILES: CC(Oc1ccc2c(c1)OC[C@H]2CC(=O)O)c1ccc(Cl)cc1Cl] | | 365.0 | |

TABLE 24

| Ex. No. | Name | Structure | MS (ESI+): [M + H]+ | MS (ESI−): [M − H]− | 1H NMR |
|---|---|---|---|---|---|
| 231 | Methyl (6-(1-(2,4-dichlorophenyl)ethoxy)-1-benzofuran-3-yl)acetate | 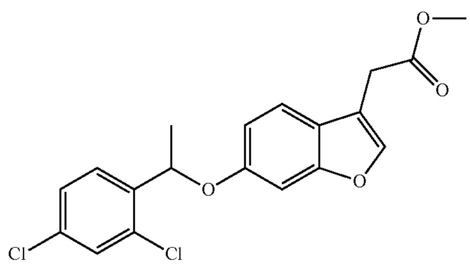 [SMILES: COC(=O)Cc1coc2cc(OC(C)c3ccc(Cl)cc3Cl)ccc12] | 377.0 | | |
| 232 | (6-(1-(2,4-Dichlorophenyl)ethoxy)-1-benzofuran-3-yl)acetic acid | 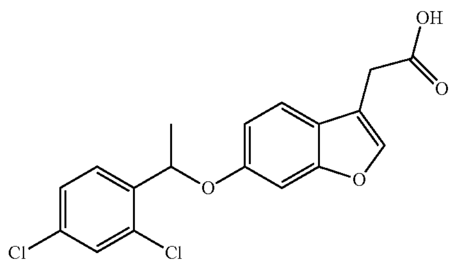 [SMILES: CC(Oc1ccc2c(CC(=O)O)coc2c1)c1ccc(Cl)cc1Cl] | | | 1H NMR (300 MHz, DMSO-d6) δ 1.58 (3H, d, J = 6.42 Hz), 3.55-3.67 (2H, m), 5.74 (1H, q, J = 6.29 Hz), 6.86 (1H, dd, J = 8.69, 2.27 Hz), 6.95 (1H, d, J = 1.89 Hz), 7.37-7.45 (2H, m), 7.52 (1H, d, J = 9.00 Hz), 7.65 (1H, d, J = 1.89 Hz), 7.73 (1H, s), 12.42 (1H, brs.) |
| 233 | Methyl (6-((2,4-dichlorobenzyl)oxy)-7-methyl-1-benzofuran-3-yl)acetate | 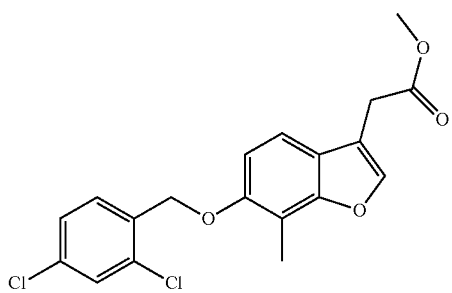 [SMILES: COC(=O)Cc1coc2c(C)c(OCc3ccc(Cl)cc3Cl)ccc12] | 377.0 | | |
| 234 | (6-((2,4-Dichlorobenzyl)oxy)-7-methyl-1-benzofuran-3-yl)acetic acid | 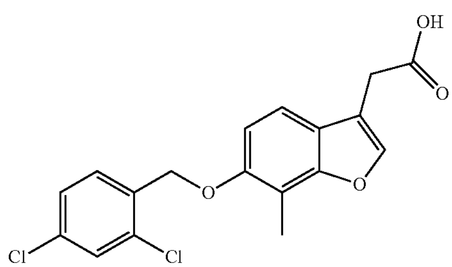 [SMILES: Cc1c(OCc2ccc(Cl)cc2Cl)ccc2c(CC(=O)O)coc12] | | 363.1 | |
| 235 | Methyl (6-((2,6-dimethylpyridin-3-yl)methoxy)-7-methyl-1-benzofuran-3-yl)acetate | 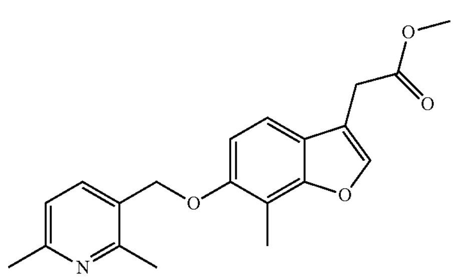 | 340.1 | | |

TABLE 24-continued

| Ex. No. | Name | Structure | MS (ESI+): [M + H]+ | MS (ESI−): [M − H]− | ¹H NMR |
|---|---|---|---|---|---|
| 236 | (6-((2,6-Dimethylpyridin-3-yl)methoxy)-7-methyl-1-benzofuran-3-yl)acetic acid | 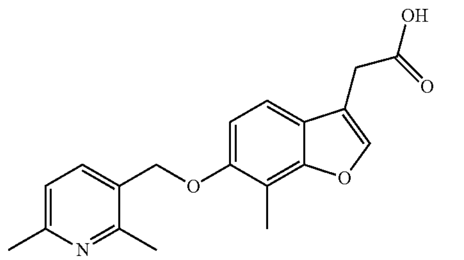 | 326.2 | | |
| 237 | Methyl (6-((2,6-dimethylpyridin-3-yl)methoxy)-1-benzofuran-3-yl)acetate | 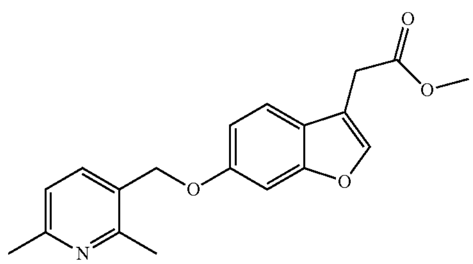 | 326.2 | | |
| 238 | (6-((2,6-Dimethylpyridin-3-yl)methoxy)-1-benzofuran-3-yl)acetic acid | 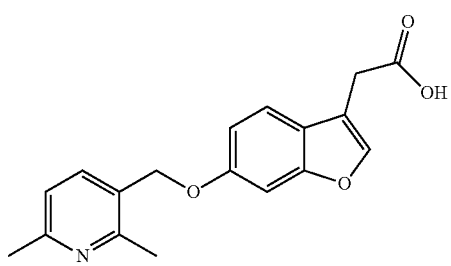 [SMILES: Cc1ccc(COc2ccc3c(CC(=O)O)coc3c2)c(C)n1] | 312.1 | | |
| 239 | Methyl (6-((2,6-dimethylpyridin-3-yl)methoxy)-7-propyl-1-benzofuran-3-yl)acetate | 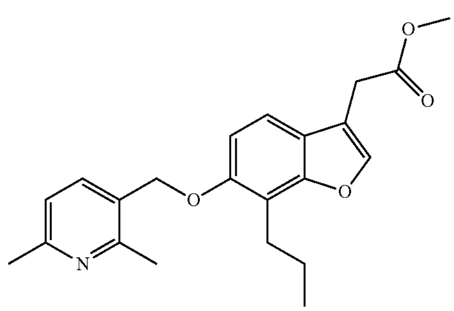 | 368.2 | | |
| 240 | (6-((2,6-Dimethylpyridin-3-yl)methoxy)-7-propyl-1-benzofuran-3-yl)acetic acid | 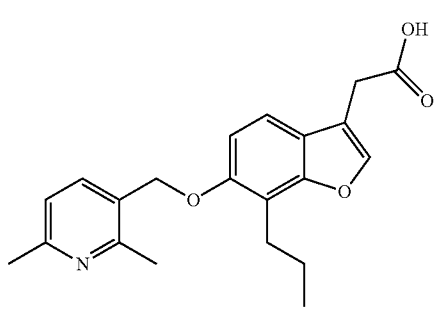 [SMILES: CCCc1c(OCc2ccc(C)nc2C)ccc2c(CC(=O)O)coc12] | 354.2 | | |

TABLE 25

| Ex. No. | Name | Structure | MS (ESI+): [M + H]+ | MS (ESI−): [M − H]− | ¹H NMR |
|---|---|---|---|---|---|
| 241 | Methyl (6-((2,4-dichlorobenzyl)oxy)-7-propyl-1-benzofuran-3-yl)acetate | 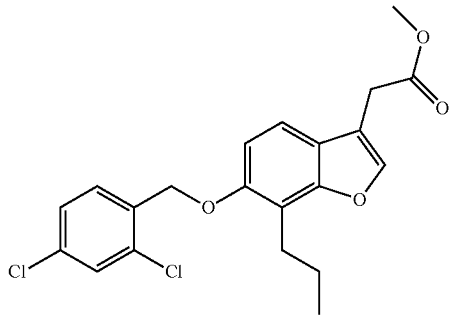 [SMILES: CCCc1c(OCc2ccc(Cl)cc2Cl)ccc2c(CC(=O)OC)coc12] | | 405.1 | |
| 242 | (6-((2,4-Dichlorobenzyl)oxy)-7-propyl-1-benzofuran-3-yl)acetic acid | 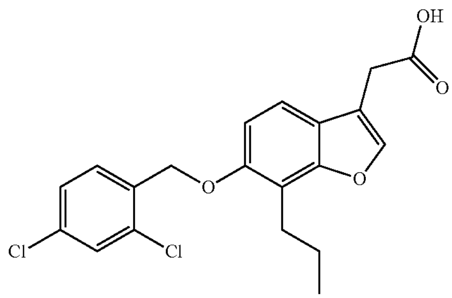 [SMILES: CCCc1c(OCc2ccc(Cl)cc2Cl)ccc2c(CC(=O)O)coc12] | | 391.0 | |
| 243 | Methyl (6-((1,3-dimethyl-1H-pyrazol-5-yl)methoxy)-7-methyl-1-benzofuran-3-yl)acetate | 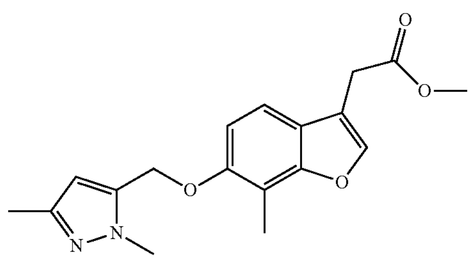 | 329.2 | | |
| 244 | (6-((1,3-Dimethyl-1H-pyrazol-5-yl)methoxy)-7-methyl-1-benzofuran-3-yl)acetic acid | 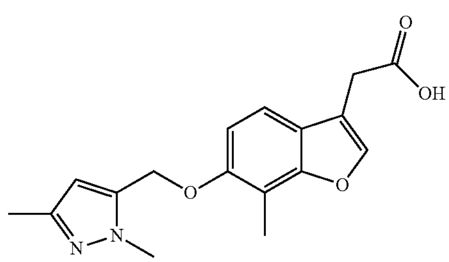 [SMILES: Cc1cc(COc2ccc3c(CC(=O)O)coc3c2C)n(C)n1] | | 315.1 | |
| 245 | Methyl (6-((2,4-dichlorobenzyl)oxy)-7-methoxy-1-benzofuran-3-yl)acetate | 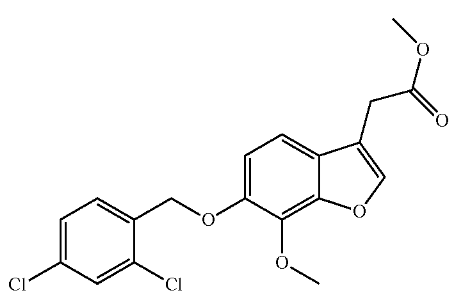 [SMILES: COC(=O)Cc1coc2c(OC)c(OCc3ccc(Cl)cc3Cl)ccc12] | 393.1 | | |

TABLE 25-continued

| Ex. No. | Name | Structure | MS (ESI+): [M + H]+ | MS (ESI−): [M − H]− | ¹H NMR |
|---|---|---|---|---|---|
| 246 | (6-((2,4-Dichlorobenzyl)oxy)-7-methoxy-1-benzofuran-3-yl)acetic acid | 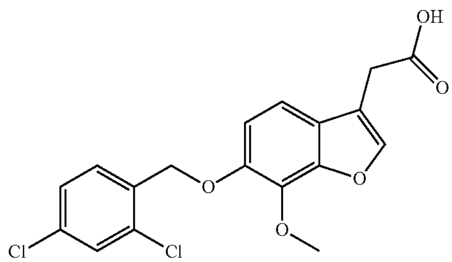 [SMILES: COc1c(OCc2ccc(Cl)cc2Cl)ccc2c(CC(=O)O)coc12] | | 379.0 | |
| 247 | Methyl (6-((2,6-dimethylpyridin-3-yl)methoxy)-7-methoxy-1-benzofuran-3-yl)acetate | 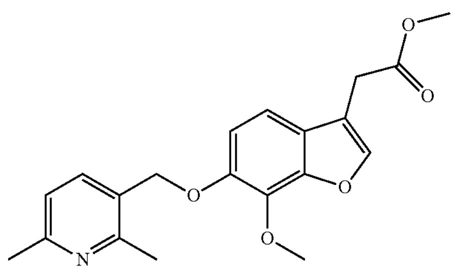 | 356.2 | | |
| 248 | (6-((2,6-Dimethylpyridin-3-yl)methoxy)-7-methoxy-1-benzofuran-3-yl)acetic acid | 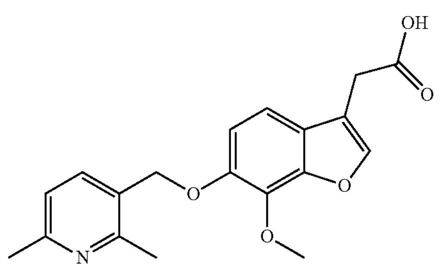 [SMILES: COc1c(OCc2ccc(C)nc2C)ccc2c(CC(=O)O)coc12] | | 342.1 | |
| 249 | Methyl (6-((3,5-dimethylpyrazin-2-yl)methoxy)-1-benzofuran-3-yl)acetate | 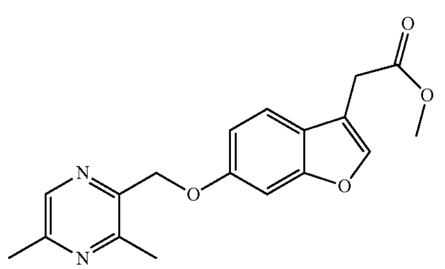 [SMILES: COC(=O)Cc1coc2cc(OCc3ncc(C)nc3C)ccc12] | | | ¹H NMR (300 MHz, CDCl₃) δ 2.54 (3H, s), 2.65 (3H, s), 3.66 (2H, s), 3.72 (3H, s), 5.23 (2H, s), 6.93-7.02 (1H, m), 7.15 (1H, d, J = 2.3 Hz), 7.42 (1H, d, J = 8.7 Hz), 7.53 (1H, s), 8.28 (1H, s). |
| 250 | (6-((3,5-Dimethylpyrazin-2-yl)methoxy)-1-benzofuran-3-yl)acetic acid | 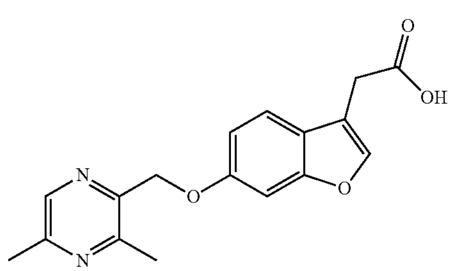 [SMILES: Cc1cnc(COc2ccc3c(CC(=O)O)coc3c2)c(C)n1] | | 313.1 | |

TABLE 26

| Ex. No. | Name | Structure | MS (ESI+): [M + H]+ | MS (ESI−): [M − H]− | ¹H NMR |
|---|---|---|---|---|---|
| 251 | Methyl (7-acetyl-6-((2,4-dichlorobenzyl)oxy)-1-benzofuran-3-yl)acetate | 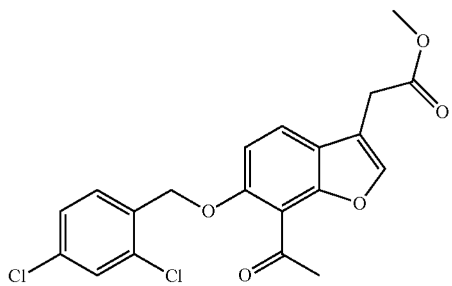 [SMILES: COC(=O)Cc1coc2c(C(C)=O)c(OCc3ccc(Cl)cc3Cl)ccc12] | 406.9 | | |
| 252 | (7-Acetyl-6-((2,4-dichlorobenzyl)oxy)-1-benzofuran-3-yl)acetic acid | 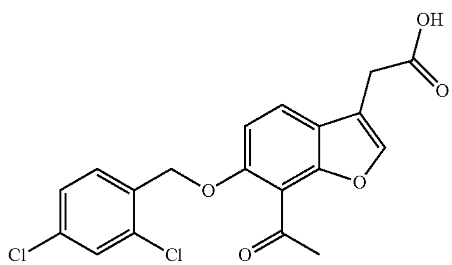 [SMILES: CC(=O)c1c(OCc2ccc(Cl)cc2Cl)ccc2c(CC(=O)O)coc12] | | 391.0 | |
| 253 | Methyl (6-((2,4-dichlorobenzyl)oxy)-7-(1-hydroxyethyl)-1-benzofuran-3-yl)acetate | 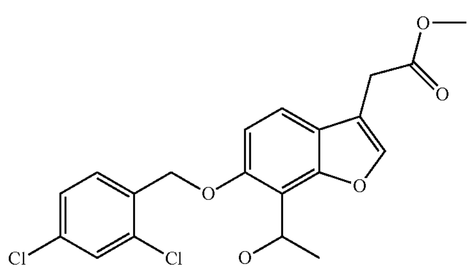 [SMILES: COC(=O)Cc1coc2c(C(C)O)c(OCc3ccc(Cl)cc3Cl)ccc12] | 407.0 | | |
| 254 | (6-((2,4-Dichlorobenzyl)oxy)-7-(1-hydroxyethyl)-1-benzofuran-3-yl)acetic acid | 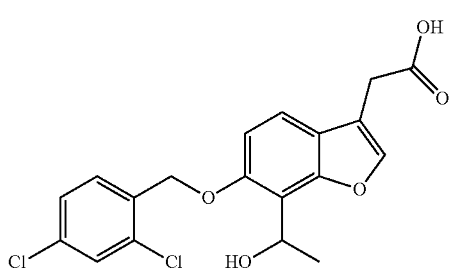 [SMILES: CC(O)c1c(OCc2ccc(Cl)cc2Cl)ccc2c(CC(=O)O)coc12] | | 392.9 | |
| 255 | Methyl (7-acetyl-6-((2,6-dimethylpyridin-3-yl)methoxy)-1-benzofuran-3-yl)acetate | 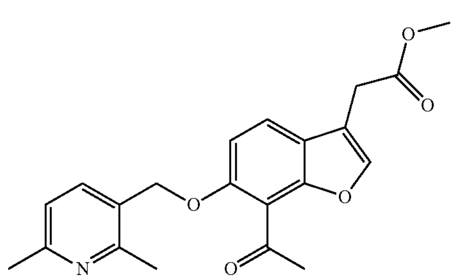 | 368.3 | | |

TABLE 26-continued

| Ex. No. | Name | Structure | MS (ESI+): [M + H]+ | MS (ESI−): [M − H]− | ¹H NMR |
|---|---|---|---|---|---|
| 256 | (7-Acetyl-6-((2,6-dimethylpyridin-3-yl)methoxy)-1-benzofuran-3-yl)acetic acid | 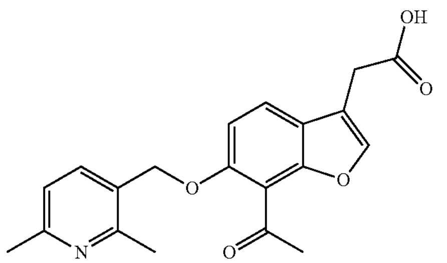 [SMILES: CC(=O)c1c(OCc2ccc(C)nc2C)ccc2c(CC(=O)O)coc12] | 354.2 | | |
| 257 | Methyl (6-((2,6-dimethylpyridin-3-yl)methoxy)-7-(1-hydroxyethyl)-1-benzofuran-3-yl)acetate | 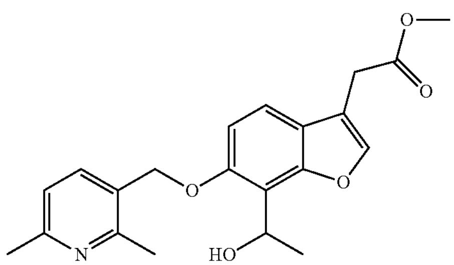 | 370.3 | | |
| 258 | (6-((2,6-Dimethylpyridin-3-yl)methoxy)-7-(1-hydroxyethyl)-1-benzofuran-3-yl)acetic acid | 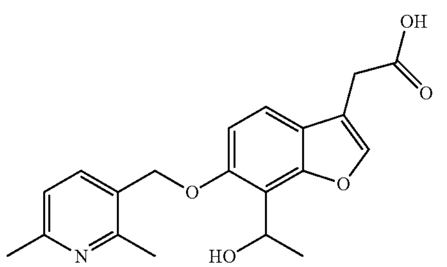 [SMILES: Cc1ccc(COc2ccc3c(CC(=O)O)coc3c2C(C)O)c(C)n1] | 356.2 | | |
| 259 | Methyl (7-chloro-6-((2,6-dimethylpyridin-3-yl)methoxy)-1-benzofuran-3-yl)acetate | 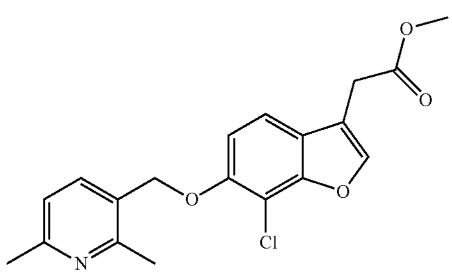 | 360.1 | | |
| 260 | (7-Chloro-6-((2,6-dimethylpyridin-3-yl)methoxy)-1-benzofuran-3-yl)acetic acid | 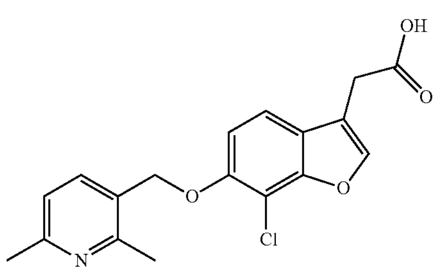 | 346.0 | | |

TABLE 27

| Ex. No. | Name | Structure | MS (ESI+): [M + H]+ | MS (ESI−): [M − H]− | 1H NMR |
|---|---|---|---|---|---|
| 261 | (6-((2,4-Dichlorobenzyl)oxy)-2,3-dihydro-1-benzofuran-3-yl)acetic acid | 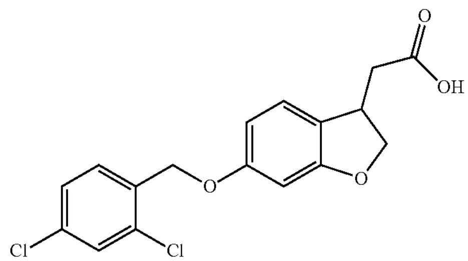 [SMILES: O=C(O)CC1COc2cc(OCc3ccc(Cl)cc3Cl)ccc21] | | 351.1 | |
| 262 | ((3S)-6-((2,4-Dichlorobenzyl)oxy)-2,3-dihydro-1-benzofuran-3-yl)acetic acid | 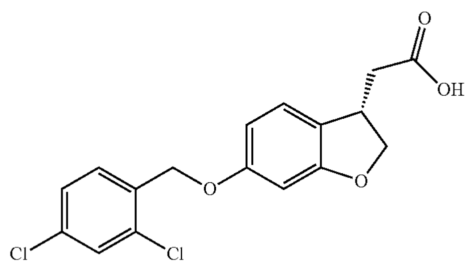 [SMILES: O=C(O)C[C@@H]1COc2cc(OCc3ccc(Cl)cc3Cl)ccc21] | | 351.2 | |
| 263 | ((3R)-6-((2,4-Dichlorobenzyl)oxy)-2,3-dihydro-1-benzofuran-3-yl)acetic acid | 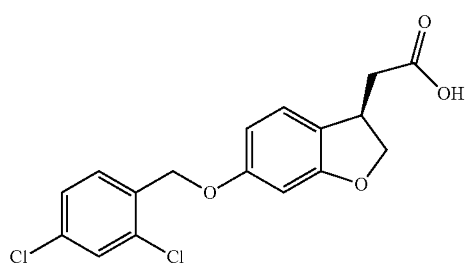 [SMILES: O=C(O)C[C@H]1COc2cc(OCc3ccc(Cl)cc3Cl)ccc21] | | 351.2 | |
| 264 | Methyl 6-((2,4-dichlorobenzyl)oxy)-2,3-dihydro-1-benzofuran-3-carboxylate | 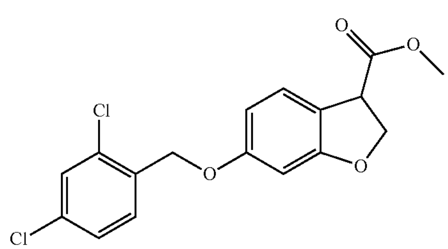 [SMILES: COC(=O)C1COc2cc(OCc3ccc(Cl)cc3Cl)ccc21] | | 350.8 | |
| 265 | 6-((2,4-Dichlorobenzyl)oxy)-2,3-dihydro-1-benzofuran-3-carboxylic acid | 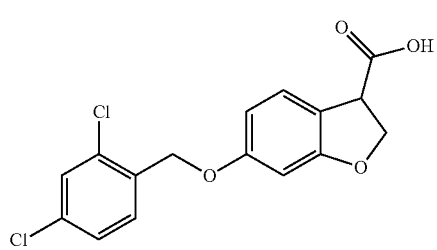 [SMILES: O=C(O)C1COc2cc(OCc3ccc(Cl)cc3Cl)ccc21] | | 337.0 | |

| Ex. No. | Name | Structure | MS (ESI+): [M + H]+ | MS (ESI−): [M − H]− | 1H NMR |
|---|---|---|---|---|---|
| 266 | (6-((2,4-Dichlorobenzyl)oxy)-2,3-dihydro-1-benzofuran-3-yl)(pyrrolidin-1-yl)methanone | 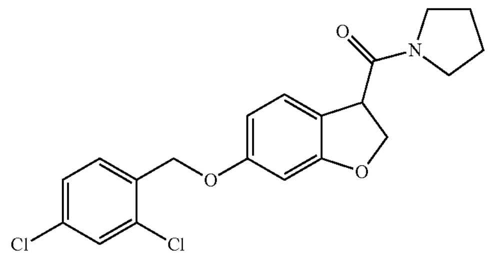 [SMILES: O=C(C1COc2cc(OCc3ccc(Cl)cc3Cl)ccc21)N1CCCC1] | 392.3 | | |
| 267 | (6-((2,4-Dichlorobenzyl)oxy)-2,3-dihydro-1-benzofuran-3-carboxamide | 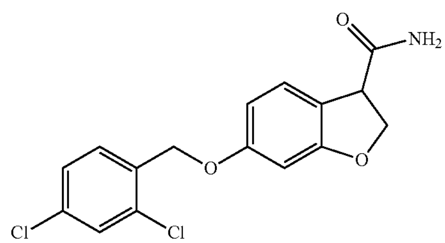 [SMILES: NC(=O)C1COc2cc(OCc3ccc(Cl)cc3Cl)ccc21] | 338.2 | | |
| 268 | (6-((2,4-Dichlorobenzyl)oxy)-2,3-dihydro-1-benzofuran-3-yl)(morpholin-4-yl)methanone | 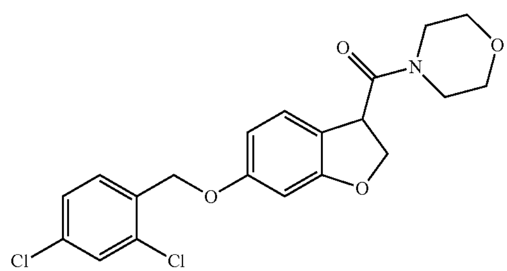 [SMILES: O=C(C1COc2cc(OCc3ccc(Cl)cc3Cl)ccc21)N1CCOCC1] | 408.2 | | |
| 269 | 6-((2,4-Dichlorobenzyl)oxy)-N-methyl-2,3-dihydro-1-benzofuran-3-carboxamide | 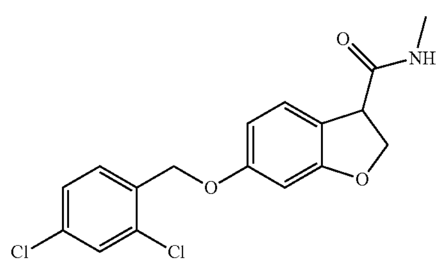 [SMILES: CNC(=O)C1COc2cc(OCc3ccc(Cl)cc3Cl)ccc21] | 352.2 | | |
| 270 | Methyl 6-((2,4-dichlorobenzyl)oxy)-3-hydroxy-2,3-dihydro-1-benzofuran-3-carboxylate | 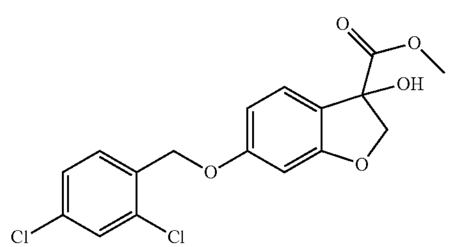 [SMILES: COC(=O)C1(O)COc2cc(OCc3ccc(Cl)cc3Cl)ccc21] | | | $^1$HNMR (300 MHz, CDCl$_3$) δ 3.88 (3H, s), 5.11 (2H, s), 5.87 (1H, d, J = 1.5 Hz), 6.38 (1H, d, J = 1.5 Hz), 6.51-6.60 (2H, m), 7.07 (1H, d, J = 8.7 Hz), 7.25-7.31 (1H, m), 7.43 (1H, d, J = 2.3 Hz), 7.49 (1H, d, J = 8.3 Hz), 8.06 (1H, brs). |

TABLE 28

| Ex. No. | Name | Structure | MS (ESI+): [M + H]+ | MS (ESI−): [M − H]− | 1H NMR |
|---|---|---|---|---|---|
| 271 | 6-((2,4-Dichlorobenzyl)oxy)-N-(methylsulfonyl)-2,3-dihydro-1-benzofuran-3-carboxamide | 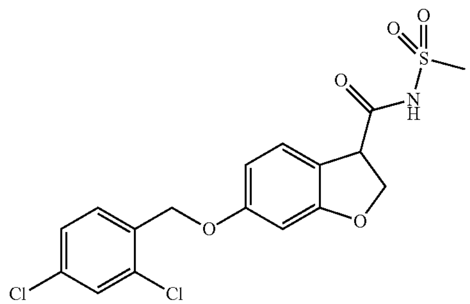 [SMILES: CS(=O)(=O)NC(=O)C1COc2cc(OCc3ccc(Cl)cc3Cl)ccc21] | | 414.2 | |
| 272 | 2-((3S)-6-((2,4-Dichlorobenzyl)oxy)-2,3-dihydro-1-benzofuran-3-yl)-N-methylacetamide | 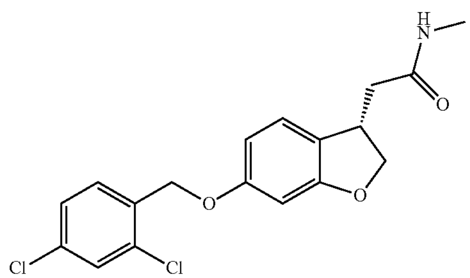 [SMILES: CNC(=O)C[C@@H]1COc2cc(OCc3ccc(Cl)cc3Cl)ccc21] | 366.2 | | |
| 273 | 2-((3S)-6-((2,4-Dichlorobenzyl)oxy)-2,3-dihydro-1-benzofuran-3-yl)-1-(pyrrolidin-1-yl)ethanone | 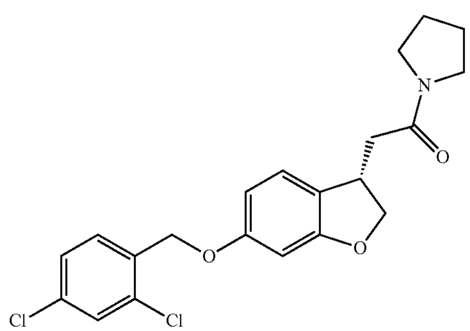 [SMILES: O=C(C[C@@H]1COc2cc(OCc3ccc(Cl)cc3Cl)ccc21)N1CCCC1] | 406.0 | | |
| 274 | 2-((3S)-6-((2,4-Dichlorobenzyl)oxy)-2,3-dihydro-1-benzofuran-3-yl)acetamide | 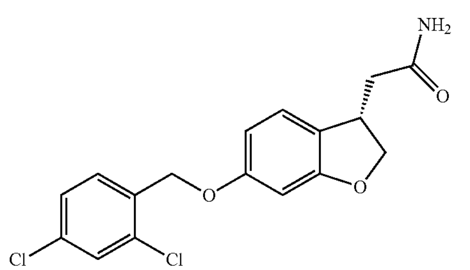 [SMILES: NC(=O)C[C@@H]1COc2cc(OCc3ccc(Cl)cc3Cl)ccc21] | 352.2 | | |
| 275 | Methyl 6-((2,4-dichlorobenzyl)oxy)-3-methyl-2,3-dihydro-1-benzofuran-3-carboxylate | 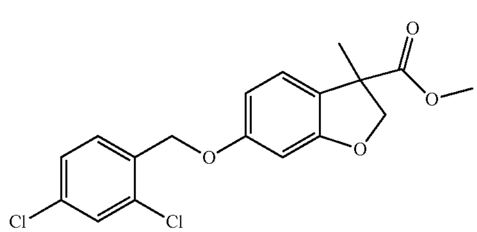 [SMILES: COC(=O)C1(C)COc2cc(OCc3ccc(Cl)cc3Cl)ccc21] | 364.9 | | |

TABLE 28-continued

| Ex. No. | Name | Structure | MS (ESI+): [M + H]+ | MS (ESI−): [M − H]− | 1H NMR |
|---|---|---|---|---|---|
| 276 | 6-((2,4-Dichlorobenzyl)oxy)-3-methyl-2,3-dihydro-1-benzofuran-3-carboxylic acid | 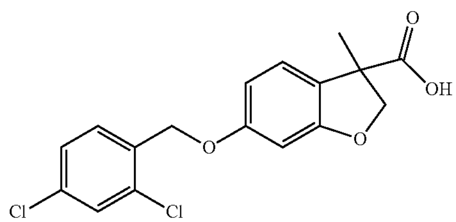 [SMILES: CC1(C(=O)O)COc2cc(OCc3ccc(Cl)cc3Cl)ccc21] | 353.0 | | |
| 277 | 1-(6-((2,4-Dichlorobenzyl)oxy)-2,3-dihydro-1-benzofuran-3-yl)-3-ethylurea | 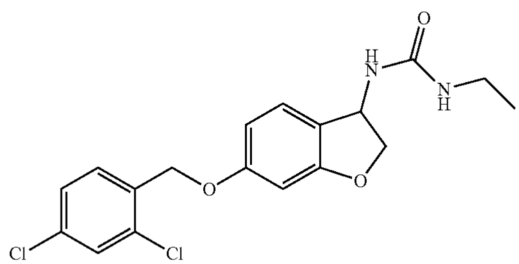 [SMILES: CCNC(=O)NC1COc2cc(OCc3ccc(Cl)cc3Cl)ccc21] | | | 1H NMR (300 MHz, DMSO-$d_6$) δ 0.98 (3H, t, J = 7.0 Hz), 2.97-3.07 (2H, m), 4.13-4.23 (1H, m), 4.61 (1H, dd, J = 9.8, 7.9 Hz), 5.11 (2H, s), 5.15-5.25 (1H, m), 5.74 (1H, t, J = 5.5 Hz), 6.32 (1H, d, J = 7.2 Hz), 6.52-6.57 (2H, m), 7.17-7.23 (1H, m), 7.48 (1H, dd, J = 8.3, 1.9 Hz), 7.59 (1H, d, J = 8.3 Hz), 7.69 (1H, d, J = 2.3 Hz). |
| 278 | Methyl 6-((2,4-dichlorobenzyl)oxy)-3-(hydroxymethyl)-2,3-dihydro-1-benzofuran-3-carboxylate | 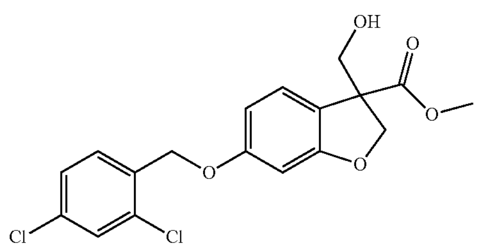 [SMILES: COC(=O)C1(CO)COc2cc(OCc3ccc(Cl)cc3Cl)ccc21] | | | 1HNMR (300 MHz, $CDCl_3$) δ 3.52-3.60 (1H, m), 3.69 (3H, s), 3.94 (1H, dd, J = 10.0, 5.9 Hz), 4.58 (1H, d, J = 9.5 Hz), 4.93 (1H, d, J = 9.5 Hz), 5.09 (2H, s), 5.33 (1H, t, J = 5.3 Hz), 6.48-6.56 (2H, m), 7.17-7.22 (1H, m), 7.48 (1H, dd, J = 8.3, 1.9 Hz), 7.59 (1H, d, J = 8.3 Hz), 7.68 (1H, d, J = 1.9 Hz). |
| 279 | 6-((2,4-Dichlorobenzyl)oxy)-3-(hydroxymethyl)-2,3-dihydro-1-benzofuran-3-carboxylic acid | 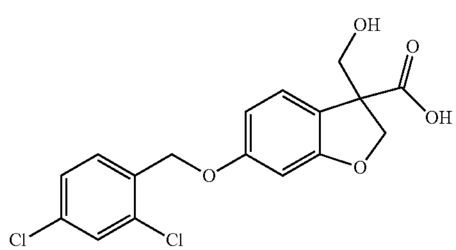 [SMILES: O=C(O)C1(CO)COc2cc(OCc3ccc(Cl)cc3Cl)ccc21] | 367.3 | | |
| 280 | Methyl 6-((2,4-dichlorobenzyl)oxy)-3-(methoxymethyl)-2,3-dihydro-1-benzofuran-3-carboxylate | 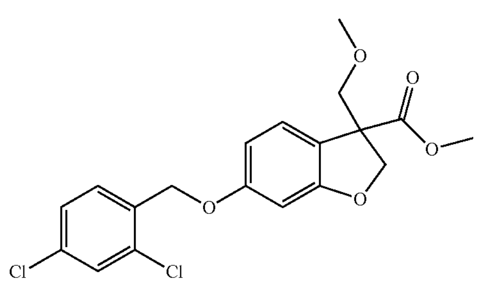 [SMILES: COCC1(C(=O)OC)COc2cc(OCc3ccc(Cl)cc3Cl)ccc21] | | | 1HNMR (300 MHz, $CDCl_3$) δ 3.35 (3H, s), 3.49 (1H, d, J = 9.1 Hz), 3.78 (3H, s), 3.94 (1H, d, J = 8.7 Hz), 4.60 (1H, d, J = 9.4 Hz), 5.07 (2H, s), 5.10 (1H, dd, J = 9.4, 1.1 Hz), 6.45 (16, d, J = 2.3 Hz), 6.49 (1H, dd, J = 8.3, 2.3 Hz), 7.22 (1H, d, J = 8.3 Hz), 7.27 (1H, dd, J = 8.3, 1.9 Hz), 7.41 (1H, d, J = 1.9 Hz), 7.46 (1H, d, 3 = 8.3 Hz). |

TABLE 29

| Ex. No. | Name | Structure | MS (ESI+): [M + H]+ | MS (ESI−): [M − H]− | ¹H NMR |
|---|---|---|---|---|---|
| 281 | 6-((2,4-Dichlorobenzyl)oxy)-3-(methoxymethyl)-2,3-dihydro-1-benzofuran-3-carboxylic acid | 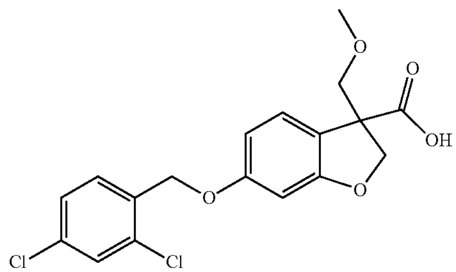 [SMILES: COCC1(C(=O)O)COc2cc(OCc3ccc(Cl)cc3Cl)ccc21] | | 381.1 | |
| 282 | Ethyl N-((6-((2,4-dichlorobenzyl)oxy)-2,3-dihydro-1-benzofuran-3-yl)carbonyl)glycinate | 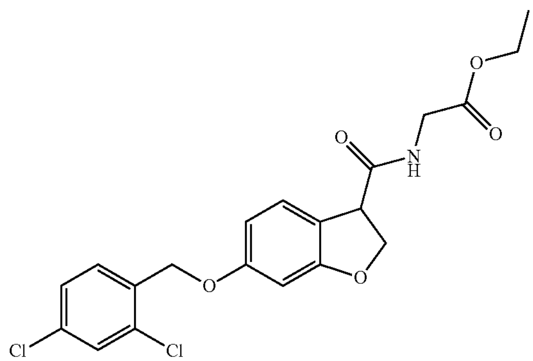 [SMILES: CCOC(=O)CNC(=O)C1COc2cc(OCc3ccc(Cl)cc3Cl)ccc21] | | 422.2 | |
| 283 | N-((6-((2,4-Dichlorobenzyl)oxy)-2,3-dihydro-1-benzofuran-3-yl)carbonyl)glycine | 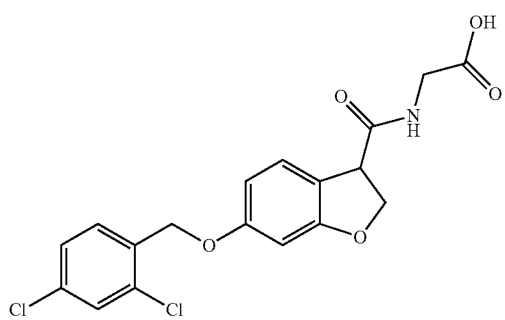 [SMILES: O=C(O)CNC(=O)C1COc2cc(OCc3ccc(Cl)cc3Cl)ccc21] | | 394.0 | |
| 284 | Methyl 2-(6-((2,4-dichlorobenzyl)oxy)-2,3-dihydro-1-benzofuran-3-yl)-3-hydroxypropanoate | 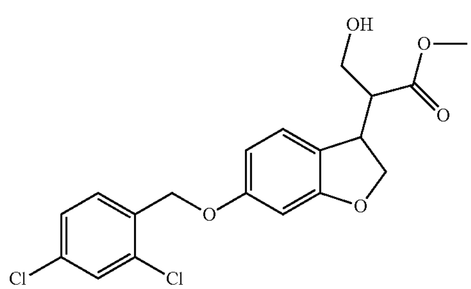 [SMILES: COC(=O)C(CO)C1COc2cc(OCc3ccc(Cl)cc3Cl)ccc21] | | 397.0 | |
| 285 | 2-(6-((2,4-Dichlorobenzyl)oxy)-2,3-dihydro-1-benzofuran-3-yl)-3-hydroxypropanoic acid | 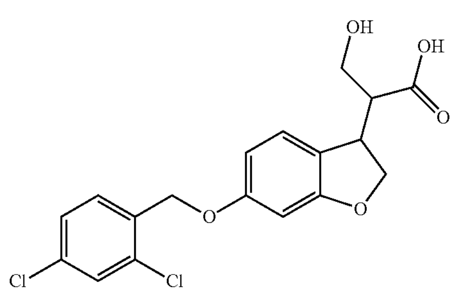 [SMILES: O=C(O)C(CO)C1COc2cc(OCc3ccc(Cl)cc3Cl)ccc21] | | 381.1 | |

TABLE 29-continued

| Ex. No. | Name | Structure | MS (ESI+): [M + H]+ | MS (ESI−): [M − H]− | 1H NMR |
|---|---|---|---|---|---|
| 286 | Ethyl N-(6-((2,4-dichlorobenzyl)oxy)-2,3-dihydro-1-benzofuran-3-yl)glycinate | 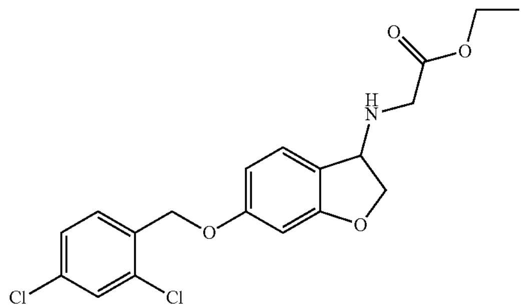 [SMILES: CCOC(=O)CNC1COc2cc(OCc3ccc(Cl)cc3Cl)ccc21] | | | 1HNMR (300 MHz, CDCl3) δ 1.27 (3H, t, J = 7.2 Hz), 3.30-3.51 (2H, m), 4.18 (2H, q, J = 7.2 Hz), 4.37-4.58 (3H, m), 5.09 (2H, s), 6.47 (1H, d, J = 2.3 Hz), 6.52 (1H, dd, J = 7.9, 2.3 Hz), 7.22 (1H, d, J = 8.3 Hz), 7.27 (1H, dd, J = 8.3, 2.3 Hz), 7.42 (1H, d, J = 1.9 Hz), 7.47 (1H, d, J = 8.3 Hz). |
| 287 | N-(6-((2,4-Dichlorobenzyl)oxy)-2,3-dihydro-1-benzofuran-3-yl)glycine | 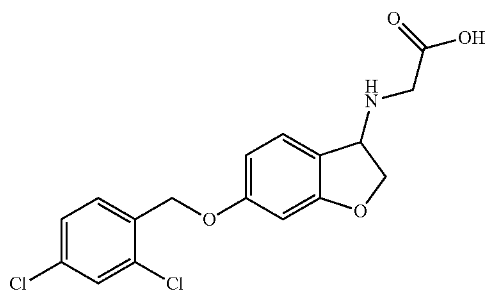 [SMILES: O=C(O)CNC1COc2cc(OCc3ccc(Cl)cc3Cl)ccc21] | 366.1 | | |
| 288 | Methyl (6-((2,6-dimethylpyridin-3-yl)methoxy)-4,7-dimethyl-2,3-dihydro-1-benzofuran-3-yl)acetate | 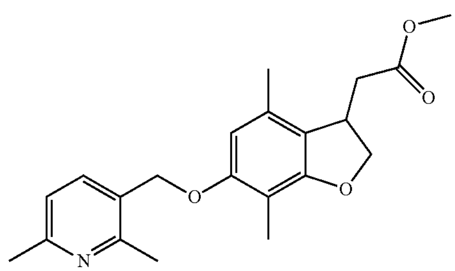 | 356.2 | | |
| 289 | (6-((2,6-Dimethylpyridin-3-yl)methoxy)-4,7-dimethyl-2,3-dihydro-1-benzofuran-3-yl)acetic acid | 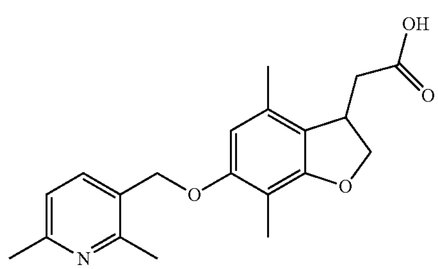 [SMILES: Cc1ccc(COc2cc(C)c3c(c2C)OCC3CC(=O)O)c(C)n1] | 342.2 | | |
| 290 | Methyl (6-((2,4-dichlorobenzyl)oxy)-4,7-dimethyl-2,3-dihydro-1-benzofuran-3-yl)acetate | 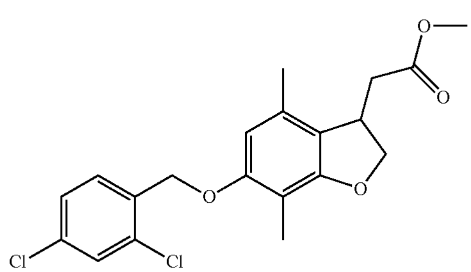 [SMILES: COC(=O)CC1COc2c(C)c(OCc3ccc(Cl)cc3Cl)cc(C)c21] | 395.0 | | |

TABLE 30

| Ex. No. | Name | Structure | MS (ESI+): [M + H]+ | MS (ESI−): [M − H]− | 1H NMR |
|---|---|---|---|---|---|
| 291 | (6-((2,4-Dichlorobenzyl)oxy)-4,7-dimethyl-2,3-dihydro-1-benzofuran-3-yl)acetic acid | 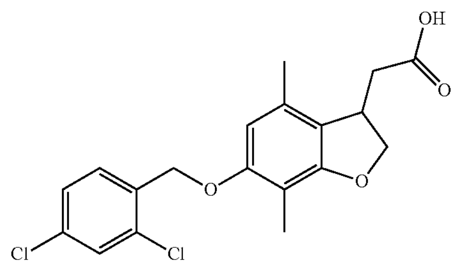 [SMILES: Cc1cc(OCc2ccc(Cl)cc2Cl)c(C)c2c1C(CC(=O)O)CO2] | 379.0 | | |
| 292 | Methyl 6-((2,4-dichlorobenzyl)sulfanyl)-3-(2-ethoxy-2-oxoethoxy)thieno[2,3-b]pyridine-2-carboxylate | 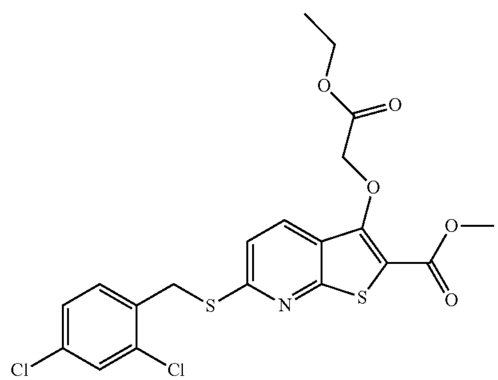 [SMILES: CCOC(=O)COc1c(C(=O)OC)sc2nc(SCc3ccc(Cl)cc3Cl)ccc12] | 485.9 | | |
| 293 | 3-(Carboxymethoxy)-6-((2,4-dichlorobenzyl)sulfanyl)thieno[2,3-b]pyridine-2-carboxylic acid | 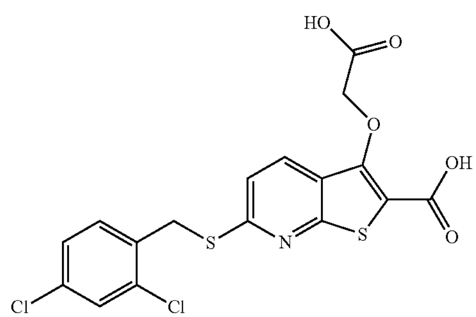 [SMILES: O=C(O)COc1c(C(=O)O)sc2nc(SCc3ccc(Cl)cc3Cl)ccc12] | 444.1 | | |
| 294 | ((6-((2,4-Dichlorobenzyl)sulfanyl)thieno[2,3-b]pyridin-3-yl)oxy)acetic acid | 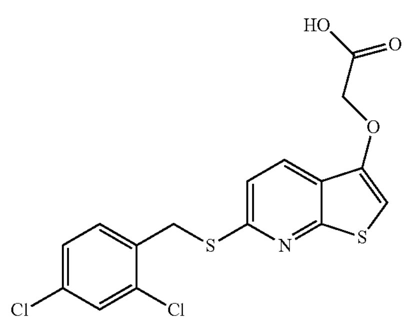 [SMILES: O=C(O)COc1csc2nc(SCc3ccc(Cl)cc3Cl)ccc12] | 400.1 | | |

TABLE 30-continued

| Ex. No. | Name | Structure | MS (ESI+): [M + H]+ | MS (ESI−): [M − H]− | ¹H NMR |
|---|---|---|---|---|---|
| 295 | Methyl 6-((2,4-dichlorobenzyl)oxy)-3-(2-ethoxy-2-oxoethoxy)thieno[2,3-b]pyridine-2-carboxylate | 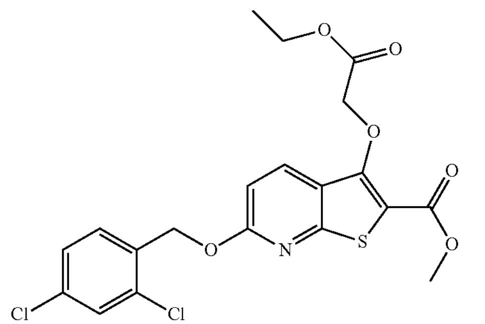 [SMILES: CCOC(=O)COc1c(C(=O)OC)sc2nc(OCc3ccc(Cl)cc3Cl)ccc12] | | | ¹HNMR (300 MHz, CDCl₃) δ 1.27 (3H, t, J = 7.2 Hz), 3.91 (3H, s), 4.22 (2H, q, J = 7.3 Hz), 5.02 (2H, s), 5.53 (2H, s), 6.88 (1H, d, J = 8.7 Hz), 7.24-7.29 (1H, m), 7.44 (1H, d, J = 2.3 Hz), 7.50 (1H, d, J = 8.3 Hz), 8.24 (1H, d, J = 8.7 Hz). |
| 296 | 3-(Carboxymethoxy)-6-((2,4-dichlorobenzyl)oxy)thieno[2,3-b]pyridine-2-carboxylic acid | 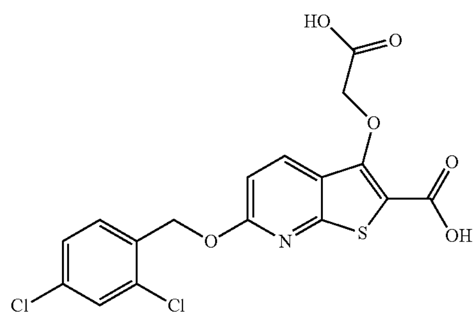 [SMILES: O=C(O)COc1c(C(=O)O)sc2nc(OCc3ccc(Cl)cc3Cl)ccc12] | 428.0 | | |
| 297 | ((6-((2,4-Dichlorobenzyl)oxy)thieno[2,3-b]pyridin-3-yl)oxy)acetic acid | 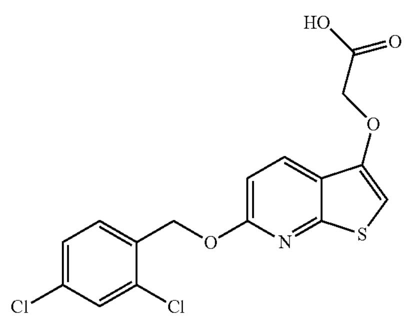 [SMILES: O=C(O)COc1csc2nc(OCc3ccc(Cl)cc3Cl)ccc12] | 383.9 | | |
| 298 | Methyl (4-cyano-6-((2,4-dichlorobenzyl)oxy)-1-benzothiophen-3-yl)acetate | 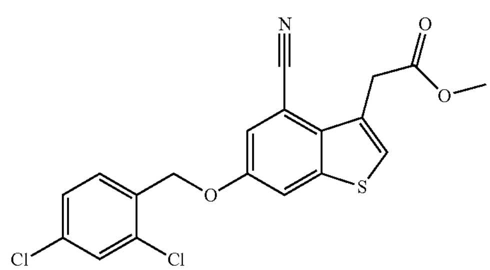 [SMILES: COC(=O)Cc1csc2cc(OCc3ccc(Cl)cc3Cl)cc(C#N)c12] | | | ¹H NMR (300 MHz, DMSO-d₆) δ 3.65 (3H, s), 4.05-4.20 (2H, m), 5.29 (2H, s), 7.50 (1H, dd, J = 8.3, 2.2 Hz), 7.63-7.75 (4H, m), 8.15 (1H, d, J = 2.5 Hz). |
| 299 | (4-Cyano-6-((2,4-dichlorobenzyl)oxy)-1-benzothiophen-3-yl)acetic acid | 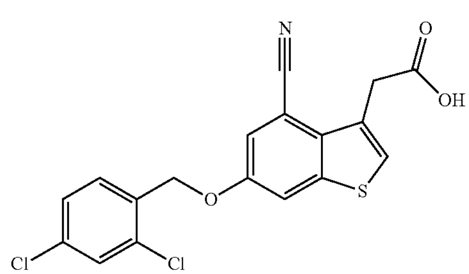 [SMILES: N#Cc1cc(OCc2ccc(Cl)cc2Cl)cc2scc(CC(=O)O)c12] | 390.1 | | |

TABLE 30-continued

| Ex. No. | Name | Structure | MS (ESI+): [M + H]+ | MS (ESI−): [M − H]− | ¹H NMR |
|---|---|---|---|---|---|
| 300 | Methyl (6-((2-chloro-4-fluorobenzyl)oxy)-4-cyano-1-benzothiophen-3-yl)acetate | 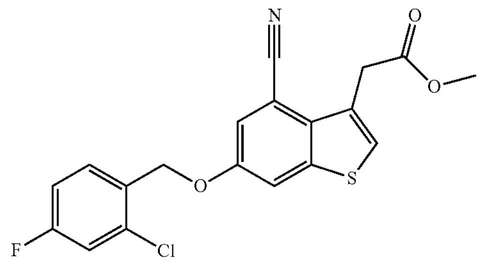 [SMILES: COC(=O)Cc1csc2cc(OCc3ccc(F)cc3Cl)cc(C#N)c12] | | | ¹H NMR (300 MHz, DMSO-$d_6$) δ 3.65 (3H, s), 4.04-4.20 (2H, m), 5.27 (2H, s), 7.30 (1H, td, J = 8.5, 2.6 Hz), 7.55 (1H, dd, J = 8.9, 2.6 Hz), 7.66-7.76 (3H, m), 8.16 (1H, d, J = 2.5 Hz). |

TABLE 31

| Ex. No. | Name | Structure | MS (ESI+): [M + H]+ | MS (ESI−): [M − H]− | ¹H NMR |
|---|---|---|---|---|---|
| 301 | (6-((2-Chloro-4-fluorobenzyl)oxy)-4-cyano-1-benzothiophen-3-yl)acetic acid | 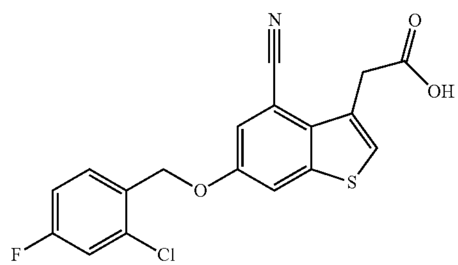 [SMILES: N#Cc1cc(OCc2ccc(F)cc2Cl)cc2scc(CC(=O)O)c12] | | | ¹H NMR (300 MHz, DMSO-$d_6$) δ 3.98-4.11 (2H, m), 5.27 (2H, s), 7.29 (1H, td, J = 8.5, 2.6 Hz), 7.54 (1H, dd, J = 8.8, 2.6 Hz), 7.63-7.77 (3H, m), 8.14 (1H, d, J = 2.5 Hz), 11.80-13.23 (1H, m). |
| 302 | Methyl (4-fluoro-6-((1-methyl-3-(trifluoromethyl)-1H-pyrazol-5-yl)methoxy)-1-benzothiophen-3-yl)acetate | 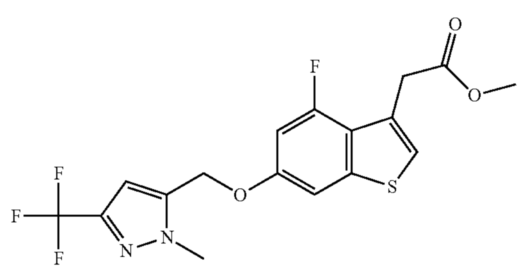 [SMILES: COC(=O)Cc1csc2cc(OCc3cc(C(F)(F)F)nn3C)cc(F)c12] | 403.0 | | |
| 303 | (4-Fluoro-6-((1-methyl-3-(trifluoromethyl)-1H-pyrazol-5-yl)methoxy)-1-benzothiophen-3-yl)acetic acid | 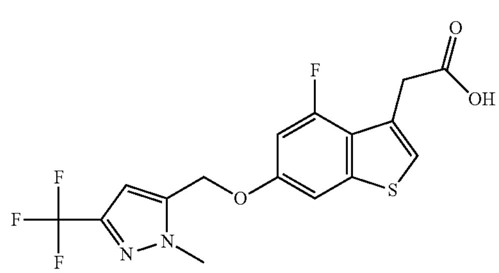 [SMILES: Cn1nc(C(F)(F)F)cc1COc1cc(F)c2c(CC(=O)O)csc2c1] | | 389.2 | |

TABLE 31-continued

| Ex. No. | Name | Structure | MS (ESI+): [M + H]+ | MS (ESI−): [M − H]− | ¹H NMR |
|---|---|---|---|---|---|
| 304 | Methyl (4-fluoro-6-((2-methyl-6-(trifluoromethyl)pyridin-3-yl)methoxy)-1-benzothiophen-3-yl)acetate | 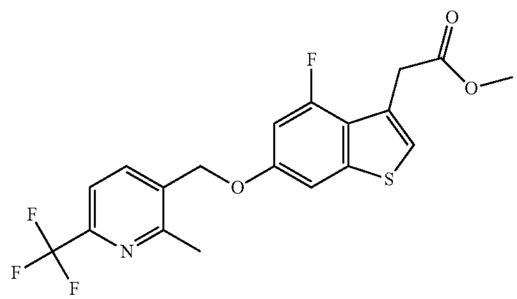 [SMILES: COC(=O)Cc1csc2cc(OCc3ccc(C(F)(F)F)nc3C)cc(F)c12] | 414.2 | | |
| 305 | (4-Fluoro-6-((2-methyl-6-(trifluoromethyl)pyridin-3-yl)methoxy)-1-benzothiophen-3-yl)acetic acid | 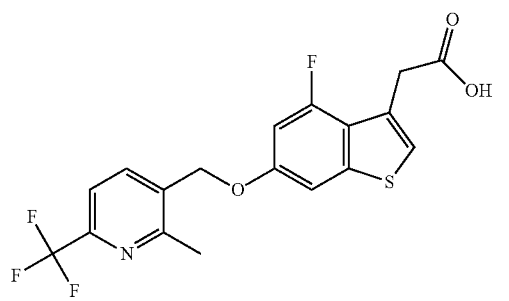 [SMILES: Cc1nc(C(F)(F)F)ccc1COc1cc(F)c2c(CC(=O)O)csc2c1] | 400.2 | | |
| 306 | Methyl (4-chloro-2-methyl-6-((1-methyl-3-(trifluoromethyl)-1H-pyrazol-5-yl)methoxy)-1-benzothiophen-3-yl)acetate | 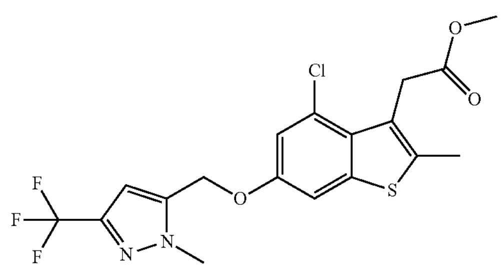 [SMILES: COC(=O)Cc1c(C)sc2cc(OCc3cc(C(F)(F)F)nn3C)cc(Cl)c12] | 433.1 | | |
| 307 | (4-Chloro-2-methyl-6-((1-methyl-3-(trifluoromethyl)-1H-pyrazol-5-yl)methoxy)-1-benzothiophen-3-yl)acetic acid | 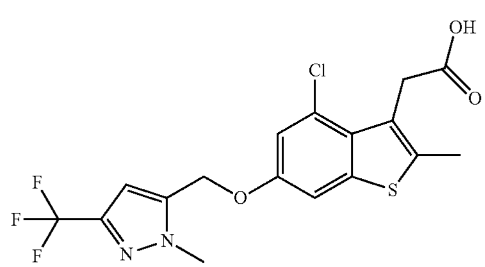 [SMILES: Cc1sc2cc(OCc3cc(C(F)(F)F)nn3C)cc(Cl)c2c1CC(=O)O] | 419.0 | | |
| 308 | Methyl (4-chloro-2-methyl-6-((2-methyl-6-(trifluoromethyl)pyridin-3-yl)methoxy)-1-benzothiophen-3-yl)acetate | 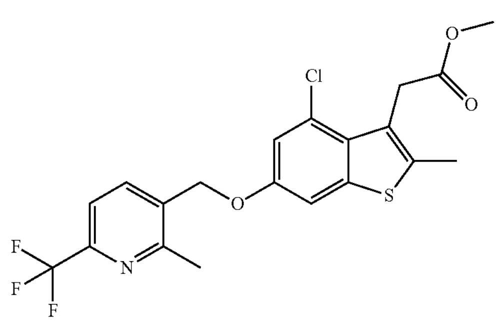 [SMILES: COC(=O)Cc1c(C)sc2cc(OCc3ccc(C(F)(F)F)nc3C)cc(Cl)c12] | 444.0 | | |

TABLE 31-continued

| Ex. No. | Name | Structure | MS (ESI+): [M + H]+ | MS (ESI−): [M − H]− | ¹H NMR |
|---|---|---|---|---|---|
| 309 | (4-Chloro-2-methyl-6-((2-methyl-6-(trifluoromethyl)pyridin-3-yl)methoxy)-1-benzothiophen-3-yl)acetic acid | 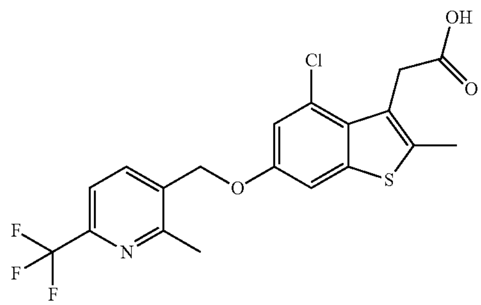 [SMILES: Cc1nc(C(F)(F)F)ccc1COc1cc(Cl)c2c(CC(=O)O)c(C)sc2c1] | 430.1 | | |
| 310 | (6-((2-Chloro-4-(3-methoxypropoxy)benzyl)oxy)-2,3-dihydro-1-benzofuran-3-yl)acetic acid | 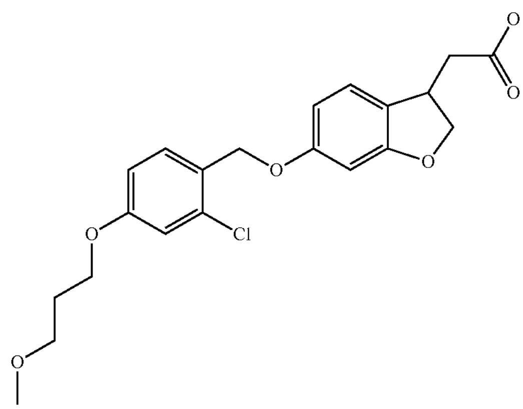 [SMILES: COCCCOc1ccc(COc2ccc3c(c2)OCC3CC(=O)O)c(Cl)c1] | 405.1 | | |

TABLE 32

| Ex. No. | Name | Structure | MS (ESI+): [M + H]+ | MS (ESI−): [M − H]− | ¹H NMR |
|---|---|---|---|---|---|
| 311 | (6-((4-(Benzyloxy)-2-chlorobenzyl)oxy)-2,3-dihydro-1-benzofuran-3-yl)acetic acid | 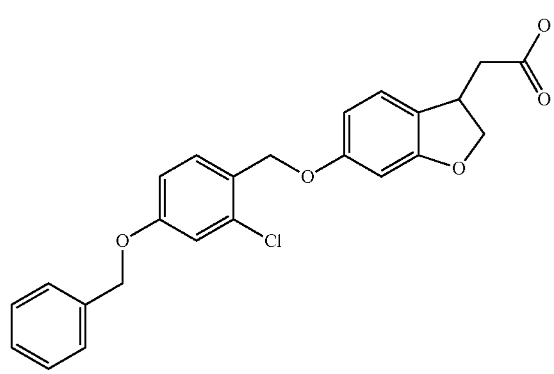 [SMILES: O=C(O)CC1COc2cc(OCc3ccc(OCc4ccccc4)cc3Cl)ccc21] | 423.1 | | |

TABLE 32-continued

| Ex. No. | Name | Structure | MS (ESI+): [M + H]+ | MS (ESI−): [M − H]− | ¹H NMR |
|---|---|---|---|---|---|
| 312 | (6-((2-Chloro-4-(pyridin-3-ylmethoxy)benzyl)oxy)-2,3-dihydro-1-benzofuran-3-yl)acetic acid | 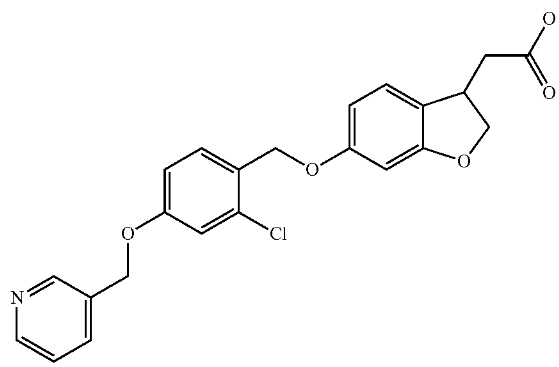 [SMILES: O=C(O)CC1COc2cc(OCc3ccc(OCc4cccnc4)cc3Cl)ccc21] | 424.1 | | |
| 313 | (6-((2-Chloro-4-(2-phenylethoxy)benzyl)oxy)-2,3-dihydro-1-benzofuran-3-yl)acetic acid | 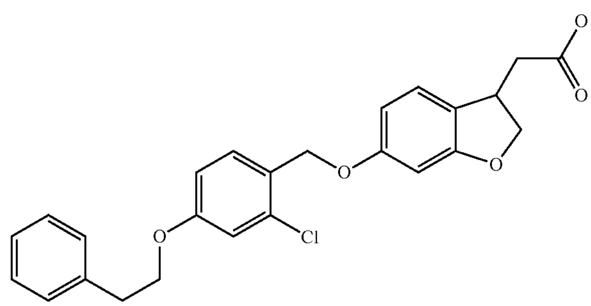 [SMILES: O=C(O)CC1COc2cc(OCc3ccc(OCCc4ccccc4)cc3Cl)ccc21] | 437.1 | | |
| 314 | (6-((2-Chloro-4-((2,5-dimethylhexan-3-yl)oxy)benzyl)oxy)-2,3-dihydro-1-benzofuran-3-yl)acetic acid | 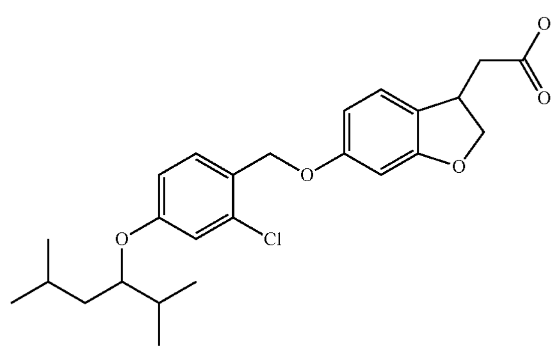 [SMILES: CC(C)CC(Oc1ccc(COc2ccc3c(c2)OCC3CC(=O)O)c(Cl)c1)C(C)C] | 445.2 | | |
| 315 | (6-((2-Chloro-4-(cyclopropyl(phenyl)methoxy)benzyl)oxy)-2,3-dihydro-1-benzofuran-3-yl)acetic acid | 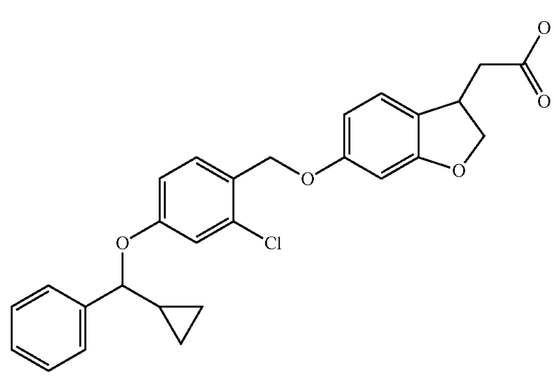 [SMILES: O=C(O)CC1COc2cc(OCc3ccc(OC(c4ccccc4)C4CC4)cc3Cl)ccc21] | 463.1 | | |

TABLE 32-continued

| Ex. No. | Name | Structure | MS (ESI+): [M + H]+ | MS (ESI−): [M − H]− | 1H NMR |
|---|---|---|---|---|---|
| 316 | (6-((4-Butoxy-2-chlorobenzyl)oxy)-2,3-dihydro-1-benzofuran-3-yl)acetic acid | 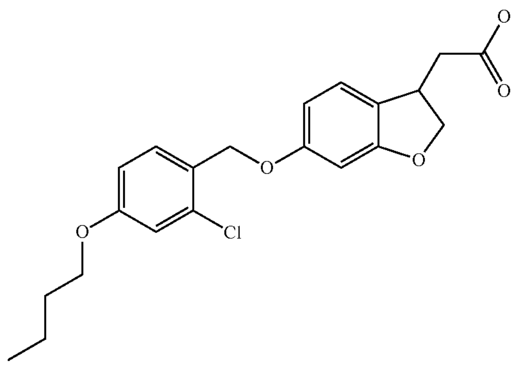 [SMILES: CCCCOc1ccc(COc2ccc3c(c2)OCC3CC(=O)O)c(Cl)c1] | | 389.1 | |
| 317 | ((3S)-6-((2,4-Difluorobenzyl)oxy)-2,3-dihydro-1-benzofuran-3-yl)acetic acid | 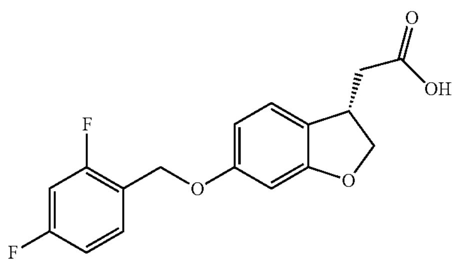 [SMILES: O=C(O)C[C@@H]1COc2cc(OCc3ccc(F)cc3F)ccc21] | | 321.0 | |
| 318 | ((3S)-6-[(2,4-Dichloro-5-fluorobenzyl)oxy]-2,3-dihydro-1-benzofuran-3-yl)acetic acid | 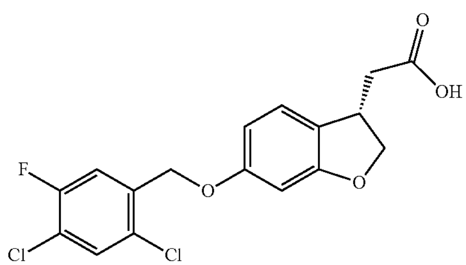 [SMILES: O=C(O)C[C@@H]1COc2cc(OCc3cc(F)c(Cl)cc3Cl)ccc21] | | 369.1 | |
| 319 | Methyl (4-cyano-6-((2,6-dimethylpyridin-3-yl)methoxy)-1-benzothiophen-3-yl)acetate | 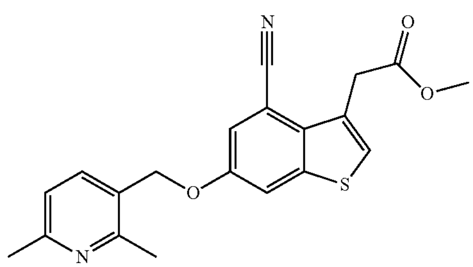 | | 367.1 | |
| 320 | (4-Cyano-6-((2,6-dimethylpyridin-3-yl)methoxy)-1-benzothiophen-3-yl)acetic acid | 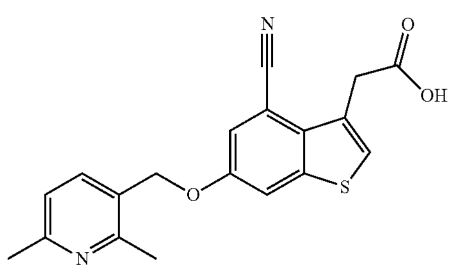 [SMILES: Cc1ccc(COc2cc(C#N)c3c(CC(=O)O)csc3c2)c(C)n1] | | 353.2 | |

TABLE 33

| Ex. No. | Name | Structure | MS (ESI+): [M + H]+ | MS (ESI−): [M − H]− | ¹H NMR |
|---|---|---|---|---|---|
| 321 | (6-((2,6-Dimethylpyridin-3-yl)methoxy)-4-fluoro-1-benzothiophen-3-yl)acetic acid | 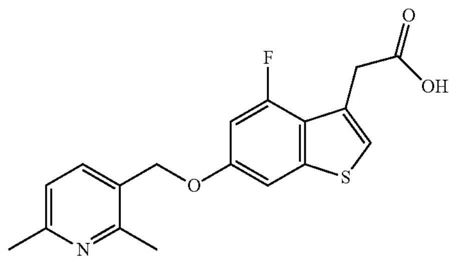 [SMILES: Cc1ccc(COc2cc(F)c3c(CC(=O)O)csc3c2)c(C)n1] | 346.2 | | |

Experimental Example 1

Construction of GOAT-Expressing Plasmid

Human GOAT (Accession NO: EU518495) cDNA was amplified by PCR including reaction of (1) 98° C., 1 min, (2) 35 repeats of 98° C., 10 sec·65° C., 15 sec·72° C., 80 sec, and (3) 72° C., 5 min, using human stomach cDNA library (Takara Bio) as a template and Pyrobest DNA Polymerase (Takara Bio). The amplified fragment was treated with restriction enzymes, inserted into Stu I/Not I sites of pFast-Bacl (Invitrogen) by using Ligation High (TOYOBO), and transfected into ECOS JM109 (Nippon Gene) to construct pFB/hGOAT.

Production of Baculovirus and Preparation of Insect Cell Microsome Fraction For preparation of baculovirus from pFB/hGOAT, BacTo-Bac baculovirus expression system (Invitrogen) was used. The virus titer was measured by Real-Time PCR using SYBR Green (Takara Bio). Sf9 cells were infected with the obtained baculovirus at Multiplicity of Infection (MOI)=0.2, and cultured for 70 hr. The Sf9 cells were recovered, suspended in a suspension buffer (TBS (0.3 M NaCl), 1 mM DTT, 1 mM EDTA, Complete (Roche) (1 tablet/50 mL)), and the cells were disrupted twice on ice at 20000 rpm, 30 sec using a polytron homogenizer. The cell disruption solution was centrifuged at 1000 rpm for 10 min at 4° C., the supernatant was further ultracentrifuged at 40000 rpm for 30 min at 4° C. and the precipitate was recovered. The obtained precipitate was suspended in the suspension buffer used above to give a human GOAT-expressing microsome fraction. The protein level was measured using BCA Protein assay Reagent (PIERCE).

Enzyme Activity Measurement by HTRF Method

A compound solution (2 μL) diluted with an assay buffer containing 50 mM Tris-HCl (pH 7.5), 0.5% TWEEN20, and Complete to 15% DMSO and 90 μg/mL human GOAT-expressing microsome fraction (2 μL) were incubated at room temperature for 20 min, after which a substrate mixed solution (2 μL) containing 30 μM octanoyl-CoA (CHEM-IMPLEX) and 3 μM Ghrelin-biotin (Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-epsilon aminocaproic acid-biotin (Greiner Coutom synthesis)) was added to 384 white small volume plate (Greiner). After reaction for 20 min, 2 μL of citrate buffer (pH3) (mixed solution of 0.1 M citric acid (39.8 mL) and 0.2 M Na₂HPO₄ (10.2 mL)), 2 μL of 25 nM anti-active ghrelin antibody (produced in mouse), 5 μL of Eu(K)-Anti Mouse IgG Pab (Cis Bio) 100-fold diluted with HTRF detection buffer (Cis Bio) and 5 μL of streptavidin-Xlent (Cis Bio) 66.6-fold diluted with HTRF detection buffer (Cis Bio) were added. After incubation at room temperature for 1 hr or longer, the fluorescence values at 620 nm and 665 nm were measured by Envision (PerkinElmer). The data was calculated [(665 nm signal/620 nm signal)×10⁴], and the inhibitory activity against human GOAT was shown by the data where 0% control was without compound, and 100% control was without enzyme. The results are shown in Table 34.

TABLE 34

| Ex. No. | GOAT inhibition (%) at 10 μM |
|---|---|
| 1 | 69 |
| 2 | 99.2 |
| 3 | 92.8 |
| 4 | 99 |
| 5 | 84.4 |
| 6 | 103 |
| 7 | 94.7 |
| 8 | 95.6 |
| 9 | 93.8 |
| 10 | 99.2 |
| 11 | 95.2 |
| 12 | 104 |
| 13 | 96.5 |
| 14 | 107 |
| 15 | 91.6 |
| 16 | 101 |
| 17 | 88.9 |
| 18 | 98.2 |
| 21 | 100 |
| 22 | 105 |
| 23 | 62.8 |
| 24 | 105 |
| 25 | 97.4 |
| 26 | 105 |
| 27 | 92.7 |
| 28 | 105 |
| 29 | 88.1 |
| 30 | 106 |
| 31 | 103 |
| 32 | 103 |
| 33 | 96.1 |
| 34 | 104 |
| 35 | 94 |
| 36 | 106 |
| 37 | 98.9 |
| 38 | 107 |
| 39 | 88.6 |
| 40 | 106 |
| 42 | 100 |

TABLE 34-continued

| Ex. No. | GOAT inhibition (%) at 10 μM |
|---|---|
| 43 | 92.7 |
| 44 | 102 |
| 45 | 68.7 |
| 46 | 103 |
| 50 | 99 |
| 52 | 79 |
| 53 | 56 |
| 54 | 86 |
| 55 | 95 |
| 56 | 97 |
| 80 | 99.3 |
| 83 | 83 |
| 84 | 67 |
| 135 | 93.1 |
| 137 | 97.3 |
| 138 | 83.2 |
| 140 | 100 |
| 182 | 97.3 |
| 183 | 83.1 |
| 196 | 73 |
| 197 | 69 |
| 198 | 59 |
| 262 | 93 |
| 263 | 86 |
| 279 | 81 |
| 281 | 85 |
| 289 | 94.8 |
| 291 | 96.2 |
| 302 | 99.9 |
| 303 | 104 |
| 304 | 94.9 |
| 305 | 102 |
| 306 | 99.5 |
| 307 | 106 |
| 308 | 51.5 |
| 309 | 103 |

| Formulation Example 1 (production of capsule) | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablets) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is pinched by a tableting machine, whereby 1000 tablets containing 30 mg of the compound of Example 1 per tablet are obtained.

INDUSTRIAL APPLICABILITY

The compound of the present invention has a GOAT inhibitory activity, which is useful for the prophylaxis or treatment of obesity, diabetes, hyperlipidemia, metabolic syndrome, non-alcoholic fatty liver, steatohepatitis, sarcopenia, appetite control, alcohol/narcotic dependence, Alzheimer's disease, Parkinson's disease, cerebrovascular dementia, cerebral apoplexy, cerebral infarction, cardiac disease, some kind of tumors (e.g., prostate cancer, breast cancer etc.) and the like.

This application is based on patent application No. 61/602,888 filed in USA, the contents of which are hereby incorporated by reference.

The invention claimed is:

1. A compound represented by the formula (I):

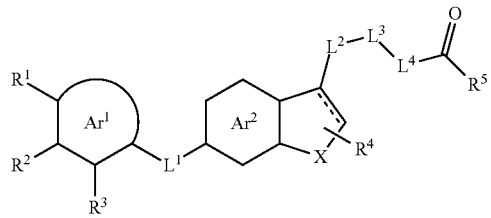

wherein ring $Ar^1$ is a 5- or 6-membered aromatic ring optionally further substituted by 1 or 2 substituents selected from a halogen atom, an optionally substituted $C_{1-6}$ alkyl group and an optionally substituted $C_{1-6}$ alkoxy group;

ring $Ar^1$ is an optionally further substituted 6-membered aromatic ring;

------ is a double bond;

$L^1$ is a group represented by the formula: $-L^{1A}-L^{1B}-$ (wherein $L^{1A}$ is optionally substituted $CH_2$; and $L^{1B}$ is O, S, SO, $SO_2$ or optionally substituted $CH_2$), optionally substituted $-CH=CH-$, or $-C\equiv C-$;

$L^2$ and $L^4$ are each independently a bond or an optionally substituted $C_{1-3}$ alkylene group;

$L^3$ is a bond, O, S, SO, $SO_2$ or $NR^6$;

X is O, S, SO or $SO_2$;

$R^1$ and $R^3$ are each independently a halogen atom, an optionally substituted $C_{1-6}$ alkyl group, an optionally substituted $C_{1-10}$ alkoxy group, an optionally substituted amino group, an optionally substituted $C_{3-10}$ cycloalkyl group, or an optionally substituted nitrogen-containing heterocyclic group which is bonded to ring $Ar^1$ via a nitrogen atom thereof;

$R^2$ is a hydrogen atom, or absent;

$R^4$ is a hydrogen atom, a halogen atom, a cyano group, an optionally substituted $C_{1-6}$ alkyl group, an optionally substituted hydroxy group or $-CO-R^7$;

$R^5$ is $-OR^{8A}$ or $-NR^{8B}R^{8C}$;

$R^6$ is a hydrogen atom or an optionally substituted $C_{1-6}$ alkyl group;

$R^7$ is an optionally substituted hydroxy group, an optionally substituted amino group, or an optionally substituted nitrogen-containing heterocyclic group which is bonded to $-CO-$ via a nitrogen atom thereof;

$R^{8A}$ is a hydrogen atom or an optionally substituted $C_{1-6}$ alkyl group;

$R^{8B}$ is a hydrogen atom, an optionally substituted $C_{1-6}$ alkyl group or $-SO_2-R^9$;

$R^{8C}$ is a hydrogen atom or an optionally substituted $C_{1-6}$ alkyl group, or $R^{8B}$ and $R^{8C}$ in combination optionally form, together with the adjacent nitrogen atom, an optionally substituted ring; and $R^9$ is an optionally substituted $C_{1-6}$ alkyl group, or a salt thereof.

2. The compound or salt of claim 1, wherein $L^1$ is a group represented by the formula: $-L^{1A}-L^{1B}-$ (wherein each symbol is as defined above), and $R^1$ and $R^3$ are each independently a halogen atom, an optionally substituted $C_{1-6}$ alkyl group, an optionally substituted $C_{1-10}$ alkoxy group or an optionally substituted amino group.

3. A composition comprising the compound or salt of claim 1, and a pharmacologically acceptable carrier.

4. (4-Chloro-6-((1-methyl-3-(trifluoromethyl)-1H-pyrazol-5-yl)methoxy)-1-benzothiophen-3-yl)acetic acid or a salt thereof.

5. (4,7-Dichloro-6-((2-methyl-6-(trifluoromethyl)pyridin-3-yl)methoxy)-1-benzothiophen-3-yl)acetic acid or a salt thereof.

6. A method for inhibiting ghrelin O-acyltransferase in a mammal, comprising administering an effective amount of the compound or salt of claim 1 to the mammal.

7. A method for lowering body weight in a mammal, comprising administering an effective amount of the compound or salt of claim 1 to the mammal.

8. A method for the prophylaxis or treatment of obesity in a mammal, comprising administering an effective amount of the compound or salt of claim 1 to the mammal.

\* \* \* \* \*

UNITED STATES PATENT AND TRADEMARK OFFICE
CERTIFICATE OF CORRECTION

| | | |
|---|---|---|
| PATENT NO. | : 9,238,639 B2 | |
| APPLICATION NO. | : 14/380215 | |
| DATED | : January 19, 2016 | |
| INVENTOR(S) | : Nobuyuki Takakura | |

It is certified that error appears in the above-identified patent and that said Letters Patent is hereby corrected as shown below:

In column 294, replace Claim 1 with the following corrected claim.

1. A compound represented by the formula (I):

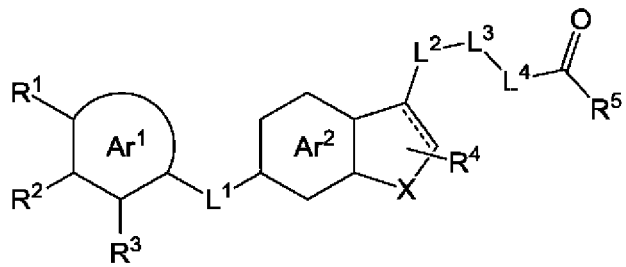

wherein ring $Ar^1$ is a 5- or 6-membered aromatic ring optionally further substituted by 1 or 2 substituents selected from a halogen atom, an optionally substituted $C_{1-6}$ alkyl group and an optionally substituted $C_{1-6}$ alkoxy group;

ring $Ar^2$ is an optionally further substituted 6-membered aromatic ring;

------ is a double bond;

$L^1$ is a group represented by the formula: $-L^{1A}-L^{1B}-$ (wherein $L^{1A}$ is optionally substituted $CH_2$; and $L^{1B}$ is O, S, SO, $SO_2$ or optionally substituted $CH_2$), optionally substituted -CH=CH-, or -C≡C-;

$L^2$ and $L^4$ are each independently a bond or an optionally substituted $C_{1-3}$ alkylene group;

$L^3$ is a bond, O, S, SO, $SO_2$ or $NR^6$;

X is O, S, SO or $SO_2$;

$R^1$ and $R^3$ are each independently a halogen atom, an optionally substituted $C_{1-6}$ alkyl group, an Signed and Sealed this
Twenty-third Day of August, 2016

Michelle K. Lee
*Director of the United States Patent and Trademark Office* optionally substituted $C_{1-10}$ alkoxy group, an optionally substituted amino group, an optionally substituted $C_{3-10}$ cycloalkyl group, or an optionally substituted nitrogen-containing heterocyclic group which is bonded to ring $Ar^1$ via a nitrogen atom thereof;

$R^2$ is a hydrogen atom, or absent;

$R^4$ is a hydrogen atom, a halogen atom, a cyano group, an optionally substituted $C_{1-6}$ alkyl group, an optionally substituted hydroxy group or $-CO-R^7$;

$R^5$ is $-OR^{8A}$ or $-NR^{8B}R^{8C}$;

$R^6$ is a hydrogen atom or an optionally substituted $C_{1-6}$ alkyl group;

$R^7$ is an optionally substituted hydroxy group, an optionally substituted amino group, or an optionally substituted nitrogen-containing heterocyclic group which is bonded to $-CO-$ via a nitrogen atom thereof;

$R^{8A}$ is a hydrogen atom or an optionally substituted $C_{1-6}$ alkyl group;

$R^{8B}$ is a hydrogen atom, an optionally substituted $C_{1-6}$ alkyl group or $-SO_2-R^9$;

$R^{8C}$ is a hydrogen atom or an optionally substituted $C_{1-6}$ alkyl group, or $R^{8B}$ and $R^{8C}$ in combination optionally form, together with the adjacent nitrogen atom, an optionally substituted ring; and $R^9$ is an optionally substituted $C_{1-6}$ alkyl group, or a salt thereof.